(12) United States Patent
Garcez Lopes et al.

(10) Patent No.: US 10,059,963 B2
(45) Date of Patent: Aug. 28, 2018

(54) MODIFIED MICROORGANISMS AND METHODS OF MAKING BUTADIENE USING SAME

(71) Applicant: Braskem S.A., Camacari-BA (BR)

(72) Inventors: Mateus Schreiner Garcez Lopes, Camacari (BR); Avram Michael Slovic, Camacari (BR); Iuri Estrada Gouvea, Camacari (BR); Johana Rincones Perez, Camacari (BR); Lucas Pedersen Parizzi, Camacari (BR)

(73) Assignee: BRASKEM S.A., Camacari (BR)

( * ) Notice: Subject to any disclaimer, the term of this patent is extended or adjusted under 35 U.S.C. 154(b) by 43 days.

(21) Appl. No.: 14/885,311

(22) Filed: Oct. 16, 2015

(65) Prior Publication Data

US 2016/0032325 A1  Feb. 4, 2016

Related U.S. Application Data

(63) Continuation of application No. 14/365,441, filed as application No. PCT/US2012/070161 on Dec. 7, 2012, now Pat. No. 9,518,273.

(60) Provisional application No. 61/606,035, filed on Mar. 2, 2012, provisional application No. 61/576,788, filed on Dec. 16, 2011.

(51) Int. Cl.
*C12P 5/02* (2006.01)
*C12N 15/52* (2006.01)
*C12N 9/88* (2006.01)

(52) U.S. Cl.
CPC ............... *C12P 5/026* (2013.01); *C12N 9/88* (2013.01); *C12N 15/52* (2013.01); *C12P 5/02* (2013.01); *C12Y 402/01127* (2013.01)

(58) Field of Classification Search
None
See application file for complete search history.

(56) References Cited

U.S. PATENT DOCUMENTS

| | | |
|---|---|---|
| 2009/0155869 A1 | 6/2009 | Buelter et al. |
| 2011/0165644 A1 | 7/2011 | Marliere |
| 2011/0172476 A1 | 7/2011 | Dumesic et al. |
| 2011/0262975 A1 | 10/2011 | Berry et al. |
| 2011/0300597 A1 | 12/2011 | Burk et al. |
| 2012/0021478 A1 | 1/2012 | Osterhout et al. |
| 2013/0189753 A1* | 7/2013 | Pearlman .............. C12P 5/02 435/167 |

OTHER PUBLICATIONS

Slater et al., "Multiple beta-Ketothiolases Mediate Poly(beta-Hydroxyalkanoate) Copolymer Synthesis in Ralstonia eutropha," Journal of Bacteriology, American Society for Microbiology, US, vol. 180, No. 8, Apr. 1, 1998, pp. 1979-1987.
Tseng et al., "Controlled biosynthesis of odd-chain fuels and chemicals via engineered modular metabolic pathways," Proceedings of the National Academy of Sciences, vol. 109,No. 44, Oct. 30, 2012, pp. 17925-17930.
Office Action issued in corresponding Canadian Patent Application No. 2,859,556 dated Aug. 7, 2017.
Office Action issued in corresponding European Patent Application No. 12857162.7 dated Aug. 24, 2017.
Office Action issued in corresponding Chinese Patent Application No. 201280069265.6 dated Jul. 31, 2017 and English translation of same.

* cited by examiner

*Primary Examiner* — Suzanne Marie Noakes
*Assistant Examiner* — Jae W Lee
(74) *Attorney, Agent, or Firm* — K&L Gates LLP

(57) ABSTRACT

The present disclosure generally relates to microorganisms that comprise one or more polynucleotides coding for enzymes in one or more pathways that catalyze a conversion of a fermentable carbon source to butadiene. Also provided are methods of using the microorganisms in industrial processes including, for use in the production of butadiene and products derived therefrom.

14 Claims, 3 Drawing Sheets

Specification includes a Sequence Listing.

SEQUENCE LISTING

```
<160> NUMBER OF SEQ ID NOS: 139

<210> SEQ ID NO 1
<211> LENGTH: 651
<212> TYPE: DNA
<213> ORGANISM: Escherichia coli K12

<400> SEQUENCE: 1
atggatgcga aacaacgtat tgcgcgccgt gtggcgcaag agcttcgtga tggtgacatc      60
gttaacttag ggatcggttt acccacaatg gtcgccaatt atttaccgga gggtattcat     120
atcactctgc aatcggaaaa cggcttcctc ggtttaggcc cggtcacgac agcgcatcca     180
gatctggtga acgctggcgg gcaaccgtgc ggtgttttac ccggtgcagc catgtttgat     240
agcgccatgt catttgcgct aatccgtggc ggtcatattg atgcctgcgt gctcggcggt     300
ttgcaagtag acgaagaagc aaacctcgcg aactgggtag tgcctgggaa aatggtgccc     360
ggtatgggtg gcgcgatgga tctggtgacc gggtcgcgca aagtgatcat cgccatggaa     420
cattgcgcca aagatggttc agcaaaaatt ttgcgccgct gcaccatgcc actcactgcg     480
caacatgcgg tgcatatgct ggttactgaa ctggctgtct ttcgttttat tgacggcaaa     540
atgtggctca ccgaaattgc cgacgggtgt gatttagcca ccgtgcgtgc caaaacagaa     600
gctcggtttg aagtcgccgc cgatctgaat acgcaacggg gtgatttatg a             651
```

<210> SEQ ID NO 2
<211> LENGTH: 663
<212> TYPE: DNA
<213> ORGANISM: Escherichia coli K12

<400> SEQUENCE: 2

| | | |
|---|---|---|
| atgaaaacaa aattgatgac attacaagac gccaccggct tctttcgtga cggcatgacc | 60 |
| atcatggtgg gcggatttat ggggattggc actccatccc gcctggttga agcattactg | 120 |
| gaatctggtg ttcgcgacct gacattgata gccaatgata ccgcgtttgt tgataccggc | 180 |
| atcggtccgc tcatcgtcaa tggtcgagtc cgcaaagtga ttgcttcaca tatcggcacc | 240 |
| aacccggaaa caggtcggcg catgatatct ggtgagatgg acgtcgttct ggtgccgcaa | 300 |
| ggtacgctaa tcgagcaaat cgctgtggt ggagctggac ttggtggttt tctcacccca | 360 |
| acgggtgtcg gcaccgtcgt agaggaaggc aaacagacac tgacactcga cggtaaaacc | 420 |
| tggctgctcg aacgcccact gcgcgccgac ctggcgctaa ttcgcgctca tcgttgcgac | 480 |
| acacttggca acctgaccta tcaacttagc gcccgcaact ttaaccccct gatagccctt | 540 |
| gcggctgata tcacgctggt agagccagat gaactggtcg aaaccggcga gctgcaacct | 600 |
| gaccatattg tcacccctgg tgccgttatc gaccacatca tcgtttcaca ggagagcaaa | 660 |
| taa | 663 |

<210> SEQ ID NO 3
<211> LENGTH: 1509
<212> TYPE: DNA
<213> ORGANISM: Corynebacterium glutamicum ATCC 13032

<400> SEQUENCE: 3

| | | |
|---|---|---|
| atgtctgatc gcattgcttc agaaaagctg cgctccaagc tcatgtccgc cgacgaggcg | 60 |
| gcacagtttg ttaaccacgg tgacaaggtt ggtttctccg gcttcaccgg cgctggctac | 120 |
| ccaaaggcac tgcctacggc aatcgctaac cgggctaaag aagcacacgg tgcaggcaac | 180 |
| gactacgcaa tcgacctgtt cactggcgca tcgaccgccc ctgactgcga tggcgtactt | 240 |
| gcagaagctg acgctatccg ctggcgcatg ccatacgcat ctgatccaat catgcgtaac | 300 |
| aagatcaact ccggctccat gggatactcc gatatccacc tgtcccactc cggccagcag | 360 |
| gttgaagagg gcttcttcgg ccagctcaac gtagctgtca ttgaaatcac ccgcatcact | 420 |
| gaagagggct acatcatccc ttcttcctcc gtgggtaaca acgttgagtg gctcaacgct | 480 |
| gcagagaagg tcatcctcga ggttaactct tggcagtctg aagacctcga aggtatgcac | 540 |
| gacatctggt ctgttcctgc cctgccaaac cgcattgccg tgccaatcaa caagccaggc | 600 |
| gaccgcatcg gtaagaccta catcgagttc gacaccgaca aggttgttgc tgttgttgag | 660 |
| accaacaccg cagaccgcaa cgcaccattc aagcctgtcg acgacatctc taagaagatc | 720 |
| gctggcaact tcctcgactt cctggaaagc gaagttgctg caggtcgcct gtcctacgac | 780 |
| ggctacatca tgcagtccgg cgtgggcaac gtgccaaacg cggtgatggc aggcctgctg | 840 |
| gaatccaagt ttgagaacat ccaggcctac accgaagtta tccaggacgg catggtggac | 900 |
| ctcatcgacg ccggcaagat gaccgttgca tccgcaactt ccttctccct gtctcctgag | 960 |
| tacgcagaga agatgaacaa cgaggctaag cgttaccgcg agtccattat cctgcgccca | 1020 |
| cagcagatct ctaaccaccc agaggtcatc cgccgcgttg gcctgatcgc accaacggt | 1080 |
| ctcatcgagg ctgacattta cggcaacgtc aactccacca acgttctgg ctcccgcgtc | 1140 |
| atgaacggca tcggcggctc cggcgacttc acccgtaacg gctacatctc cagcttcatc | 1200 |

```
acccettcag aggcaaaggg cggcgcaatc tctgcgatcg ttcctttcgc atcccacatc    1260
gaccacaccg agcacgatgt catggttgtt atctctgagt acggttacgc agaccttcgt    1320
ggtctggctc cacgtgagcg cgttgccaag atgatcggcc tggctcaccc tgattaccgc    1380
ccactgctcg aggagtacta cgctcgcgca acctccggtg acaacaagta catgcagacc    1440
cctcatgatc ttgcaaccgc gtttgatttc cacatcaacc tggctaagaa cggctccatg    1500
aaggcataa                                                            1509

<210> SEQ ID NO 4
<211> LENGTH: 378
<212> TYPE: DNA
<213> ORGANISM: Corynebacterium glutamicum ATCC 13032

<400> SEQUENCE: 4
atgaatggta tcggcggctc gggcgatttc acgcgtaacg cctttgcttc cacatttatc     60
tctccctcgg cagccaaagt tgatgcgatt tccgcgattg tgcctttcgc gtcccatatc    120
gatcacacgg aacatgatgc gatggttgtc attactgaat atggctacgc agacctgcgc    180
gggctatcgc caaacaacg agtccccaaa atgattgcca tcgccaccc ggactatcga    240 ccactgctgg aagcatactt tgaccgggcg ctgaacagtg ctgattccta tcagcacacc    300
ctgcatgatc tgcgcaccgc cttcgatttc cataatcgct tgaactcaca aggaaccatg    360
aaaatcgaaa aagcatag                                                  378

<210> SEQ ID NO 5
<211> LENGTH: 657
<212> TYPE: DNA
<213> ORGANISM: Clostridium acetobutylicum

<400> SEQUENCE: 5
atgaactcta aaataattag atttgaaaat ttaaggtcat tctttaaaga tgggatgaca     60
attatgattg gaggtttttt aaactgtggc actccaacca aattaattga tttttttagtt    120 aatttaaata taaagaattt aacgattata agtaatgata catgttatcc taatacaggt    180
attggtaagt taatatcaaa taatcaagta aaaaagctta ttgcttcata taggcagc      240 aacccagata ctggcaaaaa acttttttaat aatgaacttg aagtagagct ctctccccaa    300
ggaactctag tggaaagaat acgtgcaggc ggatctggct taggtggtgt actaactaaa    360
acaggtttag gaactttgat tgaaaaagga agaaaaaaaa tatctataaa tggaacggaa    420
tatttgttag agctacctct tacagccgat gtagcattaa ttaaaggtag tattgtagat    480
gaggccggaa acaccttcta taaaggtact actaaaaact ttaatcccta tatggcaatg    540
gcagctaaaa ccgtaatagt tgaagctgaa aatttagtta gctgtgaaaa actagaaaag    600
gaaaaagcaa tgacccccgg agttcttata aattatatag taaaggagcc tgcataa      657

<210> SEQ ID NO 6
<211> LENGTH: 666
<212> TYPE: DNA
<213> ORGANISM: Clostridium acetobutylicum

<400> SEQUENCE: 6
atgattaatg ataaaaacct agcgaaagaa ataatagcca aaagagttgc aagagaatta     60
aaaaatggtc aacttgtaaa cttaggtgta ggtcttccta ccatggttgc agattatata    120
ccaaaaaatt tcaaaattac tttccaatca gaaaacggaa tagttggaat gggcgctagt    180
```

-continued

| | |
|---|---|
| cctaaaataa atgaggcaga taaagatgta gtaaatgcag gaggagacta tacaacagta | 240 |
| cttcctgacg gcacattttt cgatagctca gtttcgtttt cactaatccg tggtggtcac | 300 |
| gtagatgtta ctgttttagg ggctctccag gtagatgaaa agggtaatat agccaattgg | 360 |
| attgttcctg gaaaaatgct ctctggtatg ggtggagcta tggatttagt aaatggagct | 420 |
| aagaaagtaa taattgcaat gagacataca aataaaggtc aacctaaaat tttaaaaaaa | 480 |
| tgtacacttc ccctcacggc aaagtctcaa gcaaatctaa ttgtaacaga acttggagta | 540 |
| attgaggtta ttaatgatgg tttacttctc actgaaatta ataaaaacac aaccattgat | 600 |
| gaaataaggt cttttaactgc tgcagattta ctcatatcca atgaacttag acccatggct | 660 |
| gtttag | 666 |

<210> SEQ ID NO 7
<211> LENGTH: 1753
<212> TYPE: DNA
<213> ORGANISM: Roseburia sp. A2-183

<400> SEQUENCE: 7

| | |
|---|---|
| agaaatctgc tacgaactgg gaacctattt tgtgggacag cgcgactacg cggaagcggt | 60 |
| tctctggttc tacaatgccg cctatgagac ggaaagcatc ctggacgttc acacaagcgg | 120 |
| ggatcttccg ctgctcggtc ttgtcgaatg ttacgagacg ctcctcgccg gggaggaagc | 180 |
| caaaattcct tccgacacag cgcttaccat ccagtacgaa atgatgctcg acaaataccg | 240 |
| ggaggcttcc agagactggc ggatgccgga ggagacctga tcttacaaat ctccggaaat | 300 |
| acgctccggc agggcttgta aaatacgaca taaagtgata ggatgaaact atggtaaaat | 360 |
| tttaacaatc ttttgtgtgg gaggtatttg agatggattt tcgtgaagaa tacaaacaga | 420 |
| agcttgtctc cgcagatgag gcggtaaagc tcatcaaatc cggagactgg gtagattacg | 480 |
| gctggtgcac caacaccgtt gacgcactgg atcaggctct cgcaaagcgc accgacgaac | 540 |
| tgacagacgt caagctgcgc ggcggtatcc tgatgaagcc gctggctgtt tttgcacgtg | 600 |
| aggatgcagg tgagcatttc tgctggaact cctggcatat gtccggtatc gagcgcaaga | 660 |
| tgataaacag aggcgtggct tactactgtc cgatccgcta ctccgagctg ccgcgctact | 720 |
| accgcgagct tgactgcccg gatgacgttg ccatgttcca ggttgctccg atggatgcgc | 780 |
| acggctactt taacttcggt ccgagtgcct cacatctggg tgcaatgtgc gagcgcgcaa | 840 |
| agcacatcat cgtagaagtc aatgaaaata tgccacgctg cctcggcggt accgagtgtg | 900 |
| gcatccacat ttccgatgtc acctacatcg tggaaggctc caacccgcca atcggtgaac | 960 |
| tgggtgcagg cggtcctgct acagatgtgg ataaggctgt cgcaaagctg atcgtcgatg | 1020 |
| agattccgaa cggtgcctgc ttacagctcg gtatcggcgg catgccaaac gctgtcggtt | 1080 |
| ccctgattgc agagtccgac ttgaaggatc tcggcgttca cactgagatg tacgtggatg | 1140 |
| catttgtcga tattgcaaag gcaggtaaga tcaacggttc caaaaagaat atcgaccgtt | 1200 |
| accgccagac ctacgctttc ggcgccggca ccaagaaaat gtacgattat ctggacgaca | 1260 |
| acccggaact gatgagcgct ccggtcgact acacgaacga catccgctcg atctccgcac | 1320 |
| tggataactt tatttccatc aacaatgccg tggatattga tctctatggt caggtaaatg | 1380 |
| cagagtctgc aggcatcaag cagatcagcg gcgcaggcgg acagcttgac ttcgtgctcg | 1440 |
| gagcttatct gtccaagggc ggcaagagct ttatctgctt atcctctacc ttcaagacca | 1500 |
| aggacggtca ggtgcagtcc cgtatccgcc cgacgctggc aaacggttcc atcgttaccg | 1560 |
| acgcaagacc gaatacacac tatgttgtaa ccgaatacgg caaggtgaac ttaaagggtc | 1620 |

| | |
|---|---:|
| tgtctacctg gcagagagcc gaggctctga tctcgatcgc gcatcccgat ttccgcgacg | 1680 |
| acctcatcaa agaggcggag cagatgcaca tctggagaag aagcaaccgc tagtaccgga | 1740 |
| ggacgactga cgg | 1753 |

<210> SEQ ID NO 8
<211> LENGTH: 1000
<212> TYPE: DNA
<213> ORGANISM: Clostridium propionicum

<400> SEQUENCE: 8

| | |
|---|---:|
| gaattcaaaa ttgctatcgt tgatgacgat ttggctcagg aatccagaca gattcgtgtt | 60 |
| gacgttctgg atggcgaagg tggccctctt tatagaatgg caaaagcttg gcagcaaatg | 120 |
| tacggttgct ctcttgcaac tgatacaaag aaaggccgcg gcagaatgct gatcaacaag | 180 |
| acaattcaga caggtgcaga tgctatcgtt gttgcgatga tgaaattctg tgatcctgaa | 240 |
| gaatgggatt accctgtaat gtacagagaa tttgaagaaa aaggcgttaa gagtctgatg | 300 |
| atcgaagttg atcaggaagt ttcttccttc gaacagatca agacaagact gcagtctttc | 360 |
| gtagaaatgc tgtaatttga acaatcgttt gctgaaaaac tgtacactgg ggtgggtgac | 420 |
| tgctccagtg tattgtaata agcaaataag caaaaatcga taagatttag gaggattttc | 480 |
| gacaatgaga aaggttccca ttattaccgc agatgaggct gcaaagctta ttaaagacgg | 540 |
| tgatacagtt acaacaagtg gtttcgttgg aaatgcaatc cctgaggctc ttgatagagc | 600 |
| tgtagaaaaa agattcttag aaacaggcga acccaaaaac attacatatg tttattgtgg | 660 |
| ttctcaaggt aacagagacg gaagaggtgc tgagcacttt gctcatgaag gcctttttaaa | 720 |
| acgttacatc gctggtcact gggctacagt tcctgctttg ggtaaaatgg ctatggaaaa | 780 |
| taaaatggaa gcatataatg tatctcaggg tgcattgtgt catttgttcc gtgatatagc | 840 |
| ttctcataag ccaggcgtat ttacaaaggt aggtatcggt actttcattg accccagaaa | 900 |
| tggcggcggt aaagtaaatg atattaccaa agaagatatt gttgaattgg tagagattaa | 960 |
| gggtcaggaa tatttattct accctgcttt tcctattcat | 1000 |

<210> SEQ ID NO 9
<211> LENGTH: 1554
<212> TYPE: DNA
<213> ORGANISM: Clostridium beijerinchii

<400> SEQUENCE: 9

| | |
|---|---:|
| gtgagaaaag taaagttttt aacaagtcgc gaagcagtac aaatagtgaa ggatggagat | 60 |
| gtgttagtaa ctggcggatt tgttggtagt tgtgcacctg aaactcttag ttgtgcttta | 120 |
| gaaaaacgtt tcattgaaac aaatcatccg caaaatataa ctttatttca tgcagcagga | 180 |
| caaggcgata gtaaggggaa aggttcagat cattatgccc acgaaggctt acttaagaga | 240 |
| gtggttgcag gtcattataa tttagcaccg aaaattggaa agttaattaa tgaaaataaa | 300 |
| atagaagctt ataatctacc acaagggaca atttctcaat tatttagaga tattgcggga | 360 |
| aaaagaattg ggacaataac tcacgttgga ttgaatacat tgtggatcc aagaattagt | 420 |
| ggtggaaaat aaatgaaaaa aacaaaagaa gatctagtaa agctaataaa tatagaaggt | 480 |
| gaagaaaaat tattatacaa atcaattcca gttaatgtct gcttcttaag aggatctttt | 540 |
| gcagatgaat acggtaatgt atcattgaaa aaagaaatag ctacacttga ggatacgtca | 600 |
| atagcccaag cttgtaagaa taatggcgga aaagtaatag ttcaagtaga aaagtagtt | 660 |

```
gaagcaggat ctttagaccc acgtcttata aaaattccag gtatatatgt agatgcggtt    720
gtaatctcaa ctcccgaaga gcatgaacaa tccttcgaat gcccatttaa tccagcagta    780
acaggtgaaa tgagaattcc attaaacagt gtagaaaaag ctccattaaa tgagagaaag    840
ataattgcga gaagagcagc tatggaatta agaaagata cggtagtaaa tttaggtata    900
gggataccag aagttatttc tttagttgcg aatgaagaag gaattggtga atatatgaca    960
ttaactgtag aagccggtcc aataggaggt ataccacaag gatgcacagc ttttggagcg   1020
agtataaatc cagaagctat tatagatcag ccatatcaat ttgattttta tgatggtgga   1080
ggcgtcgata tagcattttt aggactagct caggttgatg aacatggaaa tttgaatgta   1140
agtaagtttg ggcctagaat tgctggatgt ggtggattca taaatataac tcaaaatgct   1200
aagaaagtgt tattttgtgg aacattcact gcaggaggct aaaagtagt aacaggagat   1260 ggcaaattag aaattaaaca agaaggaaaa gctaaaaaat tcattaagga tgtagagcaa   1320
attacattta gtggagatta tgcaagaagg atggatcaac aagttatgta taactgag   1380 agagcagtat ttgagttaag gaaagatgga ttataccctta cagaaatagc gcctgggata   1440
gatctaaaaa aggatgtatt ggatttaatg gatttcaaac ctaaaatgga tggagtacct   1500
agactaatga atgaagaat attttatgat aagttgatgg gattaaggga gtaa          1554

<210> SEQ ID NO 10
<211> LENGTH: 687
<212> TYPE: DNA
<213> ORGANISM: Acinetobacter sp. ADP1

<400> SEQUENCE: 10
atgatagata aaagtgcagc gaccctaacg gaagcgctct cccagatcca cgacggtgcc     60
accatcctga ttggtggttt tggaacagcc ggccaacccg ccgagctgat tgacggactg    120
attgaactag gtcgcaagaa cctaaccatc gtcagcaaca acgccggcaa tggagactat    180
ggactggcca agctgctaaa aactggcgcc gtcaaaaaga tcatctgttc cttcccacgt    240
caggccgact cctacgtatt tgacgagcta taccgtgcgg gcaaaattga acttgaaatc    300
gtgccgcagg gcaatctggc ctgtcgtata caggccgccg gcatggggct ggggccgatc    360
tacaccccaa ccggttttgg cactttactc gcagaaggta aacctaccct gaactttgat    420
ggcaaagact acgtactgga aaacccgatc aaggccgact ttgccctgat caaagcctac    480
aagggcgacc gctggggcaa tctggtctat cgcaaatcag cacgaaactt cggcccgatc    540
atggccatgg ccgccaacgt gaccatcgca caagtgagcg aagtggtggc actaggagaa    600
ctcgacccgg aaaacgtggt gaccccaggc atctttgttc aacacgttgt accagtccaa    660
tctaccccag caagcgctgc accataa                                        687

<210> SEQ ID NO 11
<211> LENGTH: 654
<212> TYPE: DNA
<213> ORGANISM: Acinetobacter sp. ADP1

<400> SEQUENCE: 11
atgagttatc acaaactgac ccgtgaccag atcgcccagc gcgttgccca agacattccg     60
gaaggctcct atgtcaatct tggcattggc ctgccgacca gattgccag ctatctgcct    120 gccgacaaag acgtatttct acattcagaa aacggactgc tggcctttgg cccaccacca    180
gcggccggcg aagaagatcc ggaactgatc aacgcaggca agaatacgt aaccatgctc    240 gaaggcggtt gcttctttca ccatggcgac tccttcgcca tgatgcgcgg tggacatctg    300
```

-continued

| gatatctgcg tattaggcgc attccagatc gccgccaatg gagacctggc caactggcac | 360 |
| accggtgcac cggatgccat accgtcggtc ggtggagcca tggatcttgc ggttggggca | 420 |
| aaaaaagttt ttgtaaccac cgatcatgtc accaaaaaag gtgagccgaa gattgtagct | 480 |
| gaactgacgt atccagccac gggtcagaaa tgtgtcgacc ggatctacac cgacctgtgc | 540 |
| atcatcgatg tggtgccaga aggactgaaa gtgatcgaga agtcgaagg cttaagcttt | 600 |
| gaagaactac aacgcctgac cggtgcaaca ctgatcgatg cgacacaagg ctaa | 654 |

<210> SEQ ID NO 12
<211> LENGTH: 696
<212> TYPE: DNA
<213> ORGANISM: Pseudomonas putida

<400> SEQUENCE: 12

| ttgatcaata aaacgtacga gtccatcgcc agcgcggtgg aagggattac cgacggttcg | 60 |
| accatcatgg tcggtggctt cggcacggct ggcatgccgt ccgagctgat cgatggcctc | 120 |
| attgccaccg gtgcccgcga cctgaccatc atcagcaaca cgccggcaa cggcgagatc | 180 |
| ggcctggccg ccctgctcat ggcaggcagc gtgcgcaagg tggtctgctc gttcccgcgc | 240 |
| cagtccgact cctacgtgtt cgacgaactg taccgcgccg gcaagatcga gctggaagtg | 300 |
| gtcccgcagg gcaacctggc cgagcgtatc cgcgccgcag gctccggcat tggtgcgttc | 360 |
| ttctcgccaa ccggctacgg caccctgctg gccgagggca aggaaacccg tgagatcgat | 420 |
| ggccgcatgt acgtgctgga aatgccgctg cacgccgact tcgcactgat caaggcgcac | 480 |
| aagggtgacc gttggggcaa cctgacctac cgcaaggccg cccgcaactt cggcccgatc | 540 |
| atggccatgg ctgccaagac cgccatcgcc caggtcgacc aggtcgtcga actcggtgaa | 600 |
| ctggacccgg aacacatcat cacccgggt atcttcgtcc agcgcgtggt cgccgtcacc | 660 |
| ggtgctgccg cttcttcgat tgccaaagct gtctga | 696 |

<210> SEQ ID NO 13
<211> LENGTH: 642
<212> TYPE: DNA
<213> ORGANISM: Pseudomonas putida

<400> SEQUENCE: 13

| atgaccatca ccaaaaagct ctcccgcacc gagatggccc aacgcgtggc cgcagacatc | 60 |
| caggaaggcg cgtatgtaaa cctgggtatc ggcgcaccaa ccctggtggc caactacctg | 120 |
| ggcgacaagg aagtgttcct gcacagcgaa acggcctgc tgggcatggg cccaagccct | 180 |
| gcgccgggcg aggaagacga tgacctgatc aacgccggca agcagcacgt caccctgctg | 240 |
| accggtggtc ccttcttcca ccatgccgat tcgttctcga tgatgcgtgg cggccacctg | 300 |
| gacatcgccg tactgggtgc cttccaggtg tcggtcaagg gcgacctggc caactggcac | 360 |
| acgggtgcca aggttcgat cccggccgta ggcgcgcaa tggacctggc caccggcgcc | 420 |
| cgccaggtgt tcgtgatgat ggaccacctg accaagaccg gcgaaagcaa gctggtgccc | 480 |
| gagtgcacct acccgctgac cggtatcgcg tgcgtcagcc gcatctacac cgacctggcc | 540 |
| gtgctggaag tgacaccgga agggctgaaa gtggtcgaaa tctgcgcgga catcgacttt | 600 |
| gacgaactgc agaaactcag tggcgtgccg ctgatcaagt aa | 642 |

<210> SEQ ID NO 14
<211> LENGTH: 717
<212> TYPE: DNA

<213> ORGANISM: Bacillus subtilis

<400> SEQUENCE: 14

| | | | | | |
|---|---|---|---|---|---|
| atgggaaaag | tgctgtcatc | aagcaaggaa | gctgcgaaac | tgattcatga | tggggatacg | 60 |
| ctgatcgcgg | gagggtttgg | gctgtgcggc | atccctgaac | agctcatttt | gtctataaga | 120 |
| gatcaggag | taaaggattt | aaccgttgtc | agcaataact | gcggagtcga | tgactggggg | 180 |
| cttggtttgc | ttctggctaa | caagcaaatc | aagaaaatga | tcgcttccta | tgtcggtgaa | 240 |
| aataaaattt | ttgagcggca | gtttttaagc | ggagagcttg | aggtagagct | tgttccccaa | 300 |
| ggaacgctcg | ctgagagaat | tcgtgcaggc | ggtgcaggca | taccgggatt | ttatacggcg | 360 |
| acaggcgtcg | gcacctccat | agccgaggga | aaagaacata | aacattcgg | cggccggact | 420 |
| tatgtgctgg | agcgaggcat | taccggcgat | gtggcgatcg | tcaaagcgtg | gaaagcggac | 480 |
| accatgggca | atttgatttt | taggaaaacg | gcgagaaatt | tcaatcccat | tgccgccatg | 540 |
| gcaggcaaga | tcacgattgc | cgaggcggaa | gaaatcgtgg | aagcaggaga | gctcgatcca | 600 |
| gatcacatcc | atacgccggg | aatttacgta | cagcatgtcg | tgcttggcgc | gagccaagaa | 660 |
| aaacggattg | aaaaacgaac | agttcagcaa | gcatcgggaa | agggtgaggc | caagtga | 717 |

<210> SEQ ID NO 15
<211> LENGTH: 651
<212> TYPE: DNA
<213> ORGANISM: Bacillus subtilis

<400> SEQUENCE: 15

| | | | | | |
|---|---|---|---|---|---|
| gtgaaggaag | cgagaaaacg | aatggtcaaa | cgggctgtac | aagaaatcaa | ggacggcatg | 60 |
| aatgtgaatc | tcgggattgg | aatgccgacg | cttgtcgcaa | atgagatacc | cgatggcgtt | 120 |
| cacgtcatgc | ttcagtcgga | aaacggcttg | ctcggaattg | gccctatcc | tctggaagga | 180 |
| acggaagacg | cggatttgat | caatgcggga | aaggaaacga | tcactgaagt | gacaggcgcc | 240 |
| tcttattttg | acagcgctga | gtcattcgcg | atgataagag | gcgggcatat | cgatttagct | 300 |
| attctcggcg | gaatggaggt | tcggagcag | ggggatttgg | ccaattggat | gatcccgggc | 360 |
| aaaatggtaa | aagggatggg | cggcgccatg | gatctcgtca | acggggcgaa | acgaatcgtt | 420 |
| gtcatcatgg | agcacgtcaa | taagcatggt | gaatcaaagg | tgaaaaaaac | atgctccctt | 480 |
| ccgctgacag | gccagaaagt | cgtacacagg | ctgattacgg | attggctgt | atttgatttt | 540 |
| gtgaacggcc | gcatgacact | gacggagctt | caggatggtg | tcacaattga | agaggtttat | 600 |
| gaaaaaacag | aagctgattt | cgctgtaagc | cagtctgtac | tcaattctta | a | 651 |

<210> SEQ ID NO 16
<211> LENGTH: 1617
<212> TYPE: DNA
<213> ORGANISM: Clostridium kluyveri

<400> SEQUENCE: 16

| | | | | | |
|---|---|---|---|---|---|
| atgagtaaag | ggataaagaa | ttcacaattg | aaaaaaaaga | atgtaaaggc | tagtaatgtg | 60 |
| gcagaaaaga | ttgaagagaa | agttgaaaaa | acagataagg | ttgttgaaaa | ggcagctgag | 120 |
| gttacagaaa | aacgaattag | aaacttgaag | cttcaggaaa | aagttgtaac | agcagatgtg | 180 |
| gcagctgata | tgatagaaaa | cggtatgatt | gttgcaatta | gcggatttac | tccttccggg | 240 |
| tatcctaaag | aagtacctaa | agcattgact | aaaaagtta | atgccttaga | ggaagaattc | 300 |
| aaggtaacac | tttatacagg | ttcatctaca | ggagccgata | tagacggaga | atgggcaaaa | 360 |
| gcaggaataa | tagaaagaag | aattccatat | cagacaaatt | ctgatatgag | gaaaaaaata | 420 |

```
aatgatggtt ctattaagta tgctgatatg catttaagcc atatggctca atatattaat      480
tattctgtaa ttcctaaagt agatatagct ataatagagg cagtagctat tacagaagaa      540
ggggatatta ttccttcaac aggaattgga aatacagcta cttttgtgga aaatgcagat      600
aaggtaatag tggaaattaa tgaggctcaa ccgcttgaat tggaaggtat ggcagatata      660
tatacattaa aaaccctcc aagaagagag cccataccta tagttaatgc aggcaatagg       720
atagggacca catatgtgac ctgtggttct gaaaaaatat gcgctatagt gatgacaaat      780
acccaggata aacaagacc tcttacagaa gtgtctcctg tatctcaggc tatatccgat       840
aatcttatag gatttttaaa taagagggtt gaagagggaa aattacctaa gaacctgctt      900
cctatacagt caggagttgg aagtgtagca aatgcagttt tggccggact ttgtgaatca      960
aattttaaaa atttgagttg ttatacagaa gttatacagg attctatgct gaagcttata     1020
aaatgtggta agcagatgt ggtgtcaggc acttccataa gtccttcacc ggagatgttg      1080
cctgagttca taaaggacat aaatttctt agagaaaaga tagtattaag accacaggaa      1140
ataagtaata atccagagat agcaagaaga ataggagtta tatccataaa cactgctttg     1200
gaagtagata tatatggtaa tgtaaactcc actcatgtta tgggaagcaa aatgatgaat     1260
ggtataggcg ttctggaga ctttgccaga aatgcatatt tgactatatt cactacagag     1320
tctatcgcca aaaaggaga tatatcatct atagttccta tggtatccca tgtggatcat     1380
acagaacatg atgtaatggt aattgttaca gaacagggag tagcagattt aagaggtctt     1440
tctcctaggg aaaaggccgt ggctataata gaaaattgtg ttcatcctga ttacaaggat     1500
atgcttatgg aatattttga agaggcttgt aagtcatcag gtggaaatac accacataat     1560
cttgaaaaag ctctttcctg gcatacaaaa tttataaaaa ctggtagtat gaaataa       1617

<210> SEQ ID NO 17
<211> LENGTH: 1290
<212> TYPE: DNA
<213> ORGANISM: Clostridium kluyveri

<400> SEQUENCE: 17
atggagtggg aagagatata taagagaaaa ctggtaactg cagaaaaagc tgtttcaaaa       60
atagaaaacc atagcagggt agttttttgca catgcagtag agaacccgt agatttagta      120 aatgcactag ttaaaaataa ggataattat ataggactag aaatagttca catggtagct      180
atgggcaaag gtaatatac aaaagagggt atgcaaagac attttagaca taatgcttta      240
tttgtaggcg gatgtactag agatgcagta aattcaggaa gagcagatta tacaccttgt      300
tttttctatg aagtgccaag tttgtttaaa gaaaaacgtt tgcctgtaga gtagcacttt       360
attcaggtaa gtgagccaga taatatggc tactgcagtt ttggagtttc caatgactat       420
accaagccag cagcagaaag tgctaagctt gtaattgcag aagtgaataa aaacatgcca      480
agaactcttg gagattcttt tatacatgta tcagatattg attatatagt ggaagcttca      540
cacccattgt tagaattgca gcctcctaaa ttgggagatg tagaaaaagc cataggagaa      600
aactgtgcat cttaattga agatggagct actcttcagc ttggaatagg tgctatacca      660
gatgcggtac ttttattctt aaagaacaaa agaatttag gaatacattc tgagatgata      720
tcagatggtg tgatggaact ggtgaaggca ggggttatca ataacaagaa aaagacccctc     780 catccaggca aaatagttgt aacatttta atgggaacaa aaaaattata tgattttgta       840
aacaataatc caatggtaga aacttattct gtagattatg taaataatcc actggtaatt      900
```

| | |
|---|---|
| atgaaaaatg acaatatggt ttcaataaat tcttgtgttc aagtagactt aatgggacaa | 960 |
| gtatgttctg aaagtatagg attgaaacag ataagtggag tgggaggcca ggtagatttt | 1020 |
| attagaggag ctaatctatc aaagggtgga aaggctatta tagctatacc ttccacagct | 1080 |
| ggaaaaggaa aagtttcaag aataactcca cttctagata ctggtgctgc agttacaact | 1140 |
| tctagaaatg aagtagatta tgtagttact gaatatggtg ttgctcatct taagggcaaa | 1200 |
| actttaagaa atagggcaag agctctaata aatatcgctc atccaaaatt cagagaatca | 1260 |
| ttaatgaatg aatttaaaaa gagattttag | 1290 |

<210> SEQ ID NO 18
<211> LENGTH: 1314
<212> TYPE: DNA
<213> ORGANISM: Clostridium kluyveri

<400> SEQUENCE: 18

| | |
|---|---|
| atggttttta aaaattggca ggatctttat aaaagtaaaa ttgttagtgc agacgaagct | 60 |
| gtatctaaag taagctgtgg agatagcata atttttaggca atgcttgtgg agcatctctt | 120 |
| acacttttag atgccttggc tgcaaataag gaaaagtata agagtgtaaa gatacacaat | 180 |
| cttatactta attataaaaa tgatatatat actgatccgg aatcagaaaa gtatattcat | 240 |
| ggaaatactt tctttgtaag tggaggtaca aaggaagcag ttaattgtaa tagaacagat | 300 |
| tatactccat gctttttta tgaaatacca aaattattaa acaaaagta tataaatgca | 360 |
| gatgtagctt ttattcaagt aagtaagcct gatagccatg gatactgtag ctttggagta | 420 |
| tcaaccgatt attcacaggc aatggtacag tctgcaaagc ttataattgc agaagtaaac | 480 |
| gatcagatgc caagagtttt aggagacaat tttatacaca tttctgatat ggattacata | 540 |
| gtagaaagtt cacgtccaat tctagaattg actcctccta aaataggaga agtagagaag | 600 |
| acaataggaa atactgtgc atctcttgta gaagatggtt ctacacttca gcttggaata | 660 |
| ggagctattc cagatgcagt actttattc ttgaaggata aaaaggattt gggtatacat | 720 |
| tcagaaatga tatccgatgg tgttgttgaa ttagttgaag cagggggtaat tacaaataag | 780 |
| aaaaagtccc ttcatccagg aaaaataatt attacattct taatgggaac taagaaatta | 840 |
| tatgatttca taaatgataa tcctatggta gaaggatacc ctgtagatta tgtaaatgat | 900 |
| cctaaggtta ttatgcaaaa ttctaagatg gtatgtataa actcctgtgt agaagtggat | 960 |
| ttcacaggac aagtgtgtgc tgaaagtgta ggatttaaac aaataagcgg tgtaggtgga | 1020 |
| caagttgatt acatgagagg agctagcatg gctgatggag aaaatcaat tcttgctata | 1080 |
| ccatctactg cagctggcgg caaaatttca agaatagttc ctatttaac tgaaggagcg | 1140 |
| ggggttacta cttcaagata tgatgttcaa tatgttgtta cagaatatgg tattgcactt | 1200 |
| ctcaagggca aatccataag agaaagagct aaggagctta taaaaattgc acatcctaaa | 1260 |
| tttagggaag aattaacagc tcaatttgaa aaaagattca gttgtaagct ttaa | 1314 |

<210> SEQ ID NO 19
<211> LENGTH: 963
<212> TYPE: DNA
<213> ORGANISM: Acidaminococcus fermentans

<400> SEQUENCE: 19

| | |
|---|---|
| ttgagtaaag taatgacgtt aaaagacgca atcgccaagt atgtgcacag tggtgatcac | 60 |
| attgctctgg gtggttttac gacgaccgt aaacccctatg cggctgtgtt cgaaatcctg | 120 |
| agacagggta tcacggatct gaccggtctg ggcggcgctg ccggcggcga ctgggatatg | 180 |

```
ctgatcggca acggccgtgt gaaagcctac atcaactgct acaccgccaa ctccggtgtg    240
accaacgttt ccagacggtt cagaaaatgg ttcgaagccg gcaaactgac catggaagac    300
tattcccagg atgttatcta catgatgtgg catgccgccg ctctgggcct gcccttcctg    360
cctgtaaccc tgatgcaggg ctccggcctg accgatgaat ggggcatcag caaggaagtc    420
cgtaaaaccc tggacaaagt tcctgatgac aaattcaaat acatcgacaa ccccttcaaa    480
ccgggtgaaa aagtcgtggc tgttcctgtt ccgcaggttg atgtggccat catccatgcc    540
cagcaggctt ctcccgatgg caccgttcgc atctggggcg gcaaattcca ggatgtggat    600
attgctgaag cagccaaata caccatcgtt acctgcgaag aaatcatttc tgatgaagaa    660
atcagaagag atcccaccaa gaacgatatc cccggcatgt gcgtagatgc tgttgtcctg    720
gctccttacg gtgcacatcc ttctcagtgc tatggcctgt acgactacga caatccgttc    780
ctgaaagtct atgacaaggt ctccaagacc caggaagact cgatgccctt ctgcaaggaa    840
tgggtgttcg acctgaagga tcatgacgaa tacctgaaca aactgggtgc cactcgtctg    900
atcaacctga aggttgttcc tggtctgggc taccacatcg acatgacgaa ggaggacaaa    960
taa                                                                   963

<210> SEQ ID NO 20
<211> LENGTH: 963
<212> TYPE: DNA
<213> ORGANISM: Acidaminococcus fermentans

<400> SEQUENCE: 20
ttgagtaaag taatgacgtt aaaagacgca atcgccaagt atgtgcacag tggtgatcac     60
attgctctgg gtggttttac gacggaccgt aaaccctatg cggctgtgtt cgaaatcctg    120
agacagggta tcacggatct gaccggtctg ggcggcgctg ccggcggcga ctgggatatg    180
ctgatcggca acggccgtgt gaaagcctac atcaactgct acaccgccaa ctccggtgtg    240
accaacgttt ccagacggtt cagaaaatgg ttcgaagccg gcaaactgac catggaagac    300
tattcccagg atgttatcta catgatgtgg catgccgccg ctctgggcct gcccttcctg    360
cctgtaaccc tgatgcaggg ctccggcctg accgatgaat ggggcatcag caaggaagtc    420
cgtaaaaccc tggacaaagt tcctgatgac aaattcaaat acatcgacaa ccccttcaaa    480
ccgggtgaaa aagtcgtggc tgttcctgtt ccgcaggttg atgtggccat catccatgcc    540
cagcaggctt ctcccgatgg caccgttcgc atctggggcg gcaaattcca ggatgtggat    600
attgctgaag cagccaaata caccatcgtt acctgcgaag aaatcatttc tgatgaagaa    660
atcagaagag atcccaccaa gaacgatatc cccggcatgt gcgtagatgc tgttgtcctg    720
gctccttacg gtgcacatcc ttctcagtgc tatggcctgt acgactacga caatccgttc    780
ctgaaagtct atgacaaggt ctccaagacc caggaagact cgatgccctt ctgcaaggaa    840
tgggtgttcg acctgaagga tcatgacgaa tacctgaaca aactgggtgc cactcgtctg    900
atcaacctga aggttgttcc tggtctgggc taccacatcg acatgacgaa ggaggacaaa    960
taa                                                                   963

<210> SEQ ID NO 21
<211> LENGTH: 1251
<212> TYPE: DNA
<213> ORGANISM: Escherichia coli

<400> SEQUENCE: 21
```

| | |
|---|---:|
| atgtcaactc cacttcaagg aattaaagtt ctcgatttca ccggtgtgca atctggccca | 60 |
| tcttgtactc aaatgctggc ctggtttggc gctgacgtta ttaaaattga acgtcccggc | 120 |
| gttggtgacg taacgcgtca ccagctgcga gatattcctg atatcgatgc gctttacttc | 180 |
| accatgctta acagtaacaa acgttctatt gagttaaata ccaaaacagc ggaaggcaaa | 240 |
| gaggtaatgg aaaagctgat ccgcgaagct gatatcttag tcgagaactt tcatccaggg | 300 |
| gccattgatc acatgggctt cacctgggag catattcaag aaatcaatcc acgtctgatt | 360 |
| tttggttcga tcaaagggtt tgatgagtgt tcgccttatg tgaatgtaaa agcctatgaa | 420 |
| aacgttgctc aggcagcggg tggcgcggca tccactacgg ttttttggga tggtccgccg | 480 |
| ctggtaagcg ctgcagcgtt gggtgacagc aacaccggaa tgcatttgct gatcggttta | 540 |
| cttgctgctt tgctgcatcg cgaaaaaacg gggcgtgggc aacgagtcac catgtcaatg | 600 |
| caggatgccg tattgaacct tgccgcgtg aaattacgtg accagcagcg tctcgataaa | 660 |
| ttgggttatc tggaagaata cccgcagtat ccgaatggta catttggtga tgcagttccc | 720 |
| cgcggtggta atgcaggtgg tggcggtcag cctggctgga tcctgaaatg taaaggctgg | 780 |
| gaaaccgatc ctaacgccta tatttatttc actattcagg agcaaaactg ggaaaacacc | 840 |
| tgtaaagcca tcggcaaacc agaatggatt accgatccgg catacagtac agcccatgca | 900 |
| cgacagccac atattttcga tattttttgct gaaatcgaaa aatacactgt cactattgat | 960 |
| aaacatgaag cggtggccta tttgactcag tttgatattc cttgtgcacc ggttttaagt | 1020 |
| atgaaagaaa tttcacttga tccctctttg cgccaaagtg gcagtgttgt tgaagtggaa | 1080 |
| caaccgttgc gtgaaaaata tctgaccgtt ggttgtccaa tgaaattctc tgcctttacg | 1140 |
| ccggatatta agctgcgcc gctattaggt gaacataccg ctgctgtatt gcaggagctg | 1200 |
| ggttatagcg acgatgaaat tgctgcaatg aagcaaaacc acgccatctg a | 1251 |

<210> SEQ ID NO 22
<211> LENGTH: 1278
<212> TYPE: DNA
<213> ORGANISM: Bradyrhizobium sp.

<400> SEQUENCE: 22

| | |
|---|---:|
| atgaccaagg cgctcgaggg cgttcgcatt ctcgacttca cccacgtcca gtccggaccg | 60 |
| acctgcaccc agctgctggc ctggttcggc gccgacgtga tcaaggtcga gcggccgggc | 120 |
| gtgggtgaca tcacccgcgg ccagctgcag gacattccca acgtggacag cctgtatttc | 180 |
| acgatgctga accacaacaa gcggtcgatc acgctcgaca ccaagaaccc caagggcaag | 240 |
| gaggttctga ccgagctgat caagaagtgc gacgtgctgg tcgagaattt cggccccggc | 300 |
| gtgcttgacc gcatgggctt ccctgggag aagatccagg ccatcaaccc gaagatgatc | 360 |
| gtcgcctcga tcaagggttt cggccctggc ccttacgagg actgcaaggt ctacgagaac | 420 |
| gtcgcgcagt gcaccggcgg cgccgcctcg accaccggct ccgtgacgg cctgccgctg | 480 |
| gtcaccggcg cgcagatcgg cgattccggc accggcctgc acctcgcgct cggcatcgtc | 540 |
| accgcgctct atcagcgcac ccataccggc aagggccagc gcgtcacggc tgcgatgcag | 600 |
| gacggcgtgc tcaacctctg ccgtgtcaag ctgcgcgacc agcagcgcct ggagcgcggc | 660 |
| ccgctcaagg aatacagcca gttcggtgag ggcgttccgt tcggcgacgc cgtgccgcgc | 720 |
| gccgcaacg attccggcgg tggccagccg ggccgcatcc tgaagtgcaa gggctgggag | 780 |
| accgacccga acgcctacat ctacttcatc acccaggccc cggtctggga agatctgc | 840 |
| gacgtgatcg gcgagcccac ctggaagacc gatccgaact acgccaagcc ggccgcccgc | 900 |

```
ctgccgcgcc tgaacgagat cttcggccgc atcgagcagt ggaccatgac caagaccaag    960
ttcgaggcca tggacatcct caacgagttc gacatcccct gcggcccgat cctgtcgatg   1020
aaggagatcg ccgaggacga gtcgctgcgc aagaccggca ccctggtcga ggtcgaccac   1080
ccgacccgcg gcaaatatct ctcggtcggc aacccgatca agctgtcgga cagcccggcc   1140
gaggtgaccc gctcgccttt gctcggcgag cacaccgatg agatcctgcg ccaggtgctt   1200
ggcttcagcg accaccaggt cgccgagatc acgactccg gcgcgctcga tccaccgcgt    1260
aaggaagctg cggagtaa                                                 1278
```

```
<210> SEQ ID NO 23
<211> LENGTH: 1326
<212> TYPE: DNA
<213> ORGANISM: Rhodopseudomonas palustris

<400> SEQUENCE: 23
```

```
atgggagaga tgccgcttcg gcgcgcaaga gacaacagga gcacgaccat gaccaaggcg     60
ctcgacggcg ttcgcgttct cgacttcacc cacgtccaat ccggcccgac ctgcacgcag    120
ctcttggcgt ggttcggtgc cgacgtgatc aaggtggagc gccccggcag cggcgacatc    180
acccgcggtc agctgcagga catcccgaag gtggacagcc tgtatttcac catgctgaac    240
cacaacaagc ggtcgatcac gctcgacacc aagaacccga agggcaagga ggtgctgacc    300
gcgctgatcc gcacctgcga cgtgctggta gagaatttcg ccccggtgt gctcgaccgg     360 atgggcttca cctgggagaa gatccaggag atcaacccgc ggatgatcgt cgcctcgatc    420
aagggcttcg gtcccggccc gtatgaagac tgcaaggtgt acgagaacgt tgcgcagtgc    480
accggcggcg ccgcctcgac caccggattc gcgcaaggcc tgccgctggt caccggcgcg    540
cagatcggcg atagcggcac cggcctgcat ctcgcgctcg gcatcgtcac cgcgctgtat    600
cagcgccacc acaccggccg cggccagcgc gtcaccgcgg cgatgcagga cggcgtgctg    660
aacctctgcc gcgtcaagct gcgcgatcag cagcgcctcg accatggtcc gctgaaggaa    720
tacagccagt tcggcgaagg catcccgttc ggcgatgcgg tgccgcgtgc cggcaacgat    780
tccggtggcg gccagcccgg ccgcatcctg aagtgcaagg gctgggagca ggatccgaac    840
gcctacatct acgtcatcac ccaggcgccg gtgtgggaga agatctgcga cgtgatcggc    900
gagaccggct ggaagacgca ccccgactac gccacgccgc cggcgcggct gtcgcggctc    960
aacgagatct tcgcgcgcat tgagcaatgg accatgacca agaccaagtt cgaggccatg   1020
gagatcctca cgccgacga catcccctgc ggcccgatcc tgtcgatgaa ggaactcgcc    1080
gaagatcagt cgctgcgcgc caccggcacc atcgtcgagg tcgatcaccc gacccgcggc   1140
aagtatctgt cggtcggcaa cccgatcaag ctgtcggact cccgaccga ggtgaagcgc    1200 tcgccgctac tcggtgaaca caccgacgaa atcctgcgcg acgtcctcgg ctacagcgac   1260
gcgcacgtcg cagagatcca cgactccggc gcgaccgctc cgccgcgcaa gcaagcggcg    1320
gagtaa                                                              1326
```

```
<210> SEQ ID NO 24
<211> LENGTH: 1251
<212> TYPE: DNA
<213> ORGANISM: Shigella dysenteriae

<400> SEQUENCE: 24
```

```
atgtcaactc cacttcaagg aattaaagtt ctcgatttca ccggtgtgca atctggccca     60
```

```
tcttgtactc aaatgctggc ctggtttggc gctgacgtca ttaaaattga acgccccggc    120
gttggtgacg taacgcgtca ccagctgcga gatattcctg atatcgatgc gctttacttc    180
accatgctta acagtaacaa acgttctatt gagttaaata ccaaaacagc ggaaggcaaa    240
gaggtaatgg aaaagctgat ccgcgaagct gatatcttag tcgagaactt tcatccaggg    300
gccattgatc acatgggctt cacctgggag catattcaag aaatcaatcc acgtctgatt    360
tttggttcga tcaagggtt tgacgagtgt tcgccttatg tgaatgtaaa agcctatgaa    420
aacgttgctc aggcagcggg tggcgcggca tccactacgg ttttggga cggtccgccg    480 ctggtaagcg ctgcagcgtt aggagacagc aacaccggaa tgcatttgct gatcggttta    540
cttgctgctt tgctgcatcg cgaaaaaacg gggcgtgggc aacgagtcac catgtcaatg    600
caggatgccg tattgaacct tgccgcgtg aaattacgcg accagcagcg tctcgataaa    660
ttgggttatc tggaagaata cccgcagtat ccgaatggta catttggtga tgcagttccc    720
cgcggaggta atgcgggtgg tggcggtcaa cctggatgga tcctgaaatg taaaggctgg    780
gaaacagatc ctaacgccta tatttatttc actattcagg agcaaaactg ggaaaacacc    840
tgtaaagcca tcggcaaacc agattggatt accgatccgg catacagtac agcccatgcc    900
cgacagccac atattttcga tattttgct gaaatcgaaa aatacactgt cactattgat    960
aaacatgaag cggtggccta tttgactcag tttgatattc cttgtgcacc ggttttaagt   1020
atgaaagaaa tttcacttga tccctcttta cgccaaagtg gcagtgttgt cgaagtggaa   1080
caaccgttgc gtggaaaata tctgacagtt ggttgtccaa tgaaattctc tgcctttacg   1140
ccagatatta aagctgcgcc gctattaggt gaacataccg ctgctgtatt acaggagctg   1200
ggttatagcg acgatgaaat tgctgcaatg aagcaaaacc acgccatctg a            1251
```

<210> SEQ ID NO 25
<211> LENGTH: 1278
<212> TYPE: DNA
<213> ORGANISM: Rhodopseudomonas palustris

<400> SEQUENCE: 25

```
atgaccaagg cgctcgacgg cgttcgcatt ctcgatttca cccacgtcca gtccggcccg     60
acctgcaccc agttgctggc gtggttcggc gccgacgtca tcaaggtcga gcgtcccggc    120
accggcgaca tcacccgcgg gcagttgcag gacatcccga aggtggacag cctgtatttc    180
accatgctga accacaacaa gcgctcgatc acgctcgaca ccaagaaccc caagggcaag    240
gaggtgctga ccgcgctgat ccgctcctgc gacgtgctgg tggagaattt cggccccggc    300
gtgctcgatc gcatgggctt cacctgggac aagatccagg agatcaaccc gcggatgatc    360
gtcgcctcga tcaagggttt cggcccgggt ccctatgaag actgcaaggt ctacgagaac    420
gtcgcgcaat gcaccggcgg cgccgcctcg accaccggct tccgcgacgg ccgccgctg    480 gtcaccggcg cacagatcgg cgactcgggc accgggctgc atctcgcgct cggcatcgtc    540
accgcgctgt atcagcgcca tcacccggcc gcggccagc gcgtcaccgc cgcgatgcag    600
gacggcgtgc tcaatttgtc gcgcgtcaag ctgcgcgatc agcagcgcct cgcccacggc    660
ccgctcaagg aatacagcca gttcggcgaa ggcattccgt tcggcgacgc ggtgccgcgc    720
gccggcaatg attccggcgg cggccagccc ggccgcatcc tgaaatgcaa gggctgggag    780
accgatccca acgcctacat ctacttcatc gcgcaggccc cggtgtggga agatctgc    840 gacgtgatcg gcgagaccgg ctggaagacc catccggact acgcgacgcc gccggcgcgg    900
ctgaagcacc tcaacgacat cttcgcccgc atcgaacaat ggaccatgac caagaccaag    960
```

```
ttcgaggcga tggacatcct caacagggac gacattccct gcgggccgat cctgtcgatg     1020
aaggaactcg ccgaggacgc ctcgctgcgc gccaccggca cgatcgtcga ggtcgatcat     1080
ccgacccgcg gcaaatatct gtcggtcggc aacccgatca aactgtcgga ctcgccgacc     1140
catgtcgagc gctcgccgct tctcggcgag cacaccgacg aaattctgcg cgacgtcctc     1200
ggcttcaacg atcatcaggt cgctgaaatc cacgattccg gcgcactcgc tccgccgcgc     1260
aagcaggccg cagagtaa                                                   1278
```

<210> SEQ ID NO 26
<211> LENGTH: 1290
<212> TYPE: DNA
<213> ORGANISM: Methylobacterium extorquens

<400> SEQUENCE: 26

```
atgagcaagg caccgggcaa ggccctcgag ggcgttcgca tcctcgattt cacccatgtt      60
caatcggggc cgacctgcac gcaattgctc gcgtggttcg gggccgacgt catcaaggtc     120
gagcggccgg gtgcgggcga cgcgacgcgc cagcagcttc aggaccttcc cggcgtggac     180
agcctctatt tcacgatgct gaaccacaac aagcgttcga tcacgctcga cggcaagaac     240
cccaagggca acgcgatcct ctggcggctc attgccgagt gcgacgtgct ggtcgagaac     300 ttcgccccg gtgcgctcga ccgcatgggg ctgacctggg agaagctgca ggccgccaat     360
ccgggcctga tcctggcctc ggtgaagggc ttcgggcccg gccgctacca ggattgcaag     420
gtctacgaga acgtcgccca atgcgtcggc ggcgcggcct ccaccaccgg ctggcgcgac     480
ggcgtgccga tggtgtcggg ggcgcagatc ggcgattccg gcaccggcct gcatctggcg     540
ctcggcatcg tcacggccct ctaccagcgc acccagacgg ggcagggcca gcgcgtcgat     600
tgtgccatgc aggacggggt gctcaacctc tgccgggtga agctgcggga ccagcagcgc     660
ctcgcccacg gcccgctgat ggaatacagc cagtacggcg agggcgtccc cttcggcgag     720
gcggtgccgc gggccggcaa cgattccggc gggggcagc ccggccgcat cctcaagtgc     780
aagggctggg agcaggatcc caacgcttac atctacttca tcacgcaggg cgcggtctgg     840
gggccgatct gcgacatcat cggcgagccg gactggaaga ccgatccggc ctacgcgacg     900
ccgaaagccc gcctgccgca tctcaacgag atcttcacgc gcatcgaagc gtggacgatg     960
aagcacgaca agctcgaggc gatggagatc ctcaacgcct acgagatccc gtgcggaccg    1020
atcctgtcga tgcgggagat cgccgaggat ccgatgctgc gggcgaacgg cacggtggtc    1080
gaggtcgagc acccgacccg cggggcctat ctgacggtgg caacccgat caagctgtcg    1140 gcgagcccca ccgagatcac ccgcgcgccg ctgctcggcg agcataccga cgagatcctg    1200
cgcgaggtgc tgggctgcac cgatacggaa atcagcgaca tcctcggttc gggtgcggtg    1260
ggcggcgtcc accgcatcgc cgcggagtag                                     1290
```

<210> SEQ ID NO 27
<211> LENGTH: 1251
<212> TYPE: DNA
<213> ORGANISM: Ralstonia eutropha H16

<400> SEQUENCE: 27

```
gtgaacctcc cactcaacgg catcaagatc atcgacttca cgcacgtcca ggccggtccc      60
gcctgcacgc agcttctcgc gtggttcggt gcggacgtga tcaaggtcga gcgccccggt     120
tccggcgacg tgacgcgcac ccagctgcgc gacatcccgg atgtcgatgc cctgtacttc     180
```

| | |
|---|---|
| accatgctca acagcaacaa gcgcagcctg acgctggata ccaagaagcc ggaaggcaag | 240 |
| aagatcctgg agcagctgat ccgcgagtcg gacgtgctgg tcgagaactt cggcccgggc | 300 |
| gcgctggacc gcatggggtt ctcgtgggaa cgcatcaacg aactgaaccc gaagatgatc | 360 |
| gtggcttcgg tcaagggctt cagcgacggc caccactatg aagacctgaa ggtctacgag | 420 |
| aacgtggccc agtgcgccgg cggcgcggcc tcgaccaccg gcttctggga tggcccgccg | 480 |
| acggtgtccg ccgcggcgct gggcgattcc aacaccggca tgcacctggc catcggcatc | 540 |
| ctcaccgcgc tgatcggccg cgacaagacc ggcaagggcc agaaggtggc tgtgtcgatg | 600 |
| caggatgcgg tgctgaacct gtgccgggtc aagctgcgcg accagcagcg cctggaccgc | 660 |
| ctgggctacc tggaggagta cccgcagtat ccgcacggca gcttcagcga cgtggtgccg | 720 |
| cgcggcggca acgcgggcgg cggcggccag ccgggctggg tgctgaagtg caaggggtgg | 780 |
| gaaaccgacc ccaacgccta tatctacttc accatccagg gccatgcctg ggagccgatc | 840 |
| tgcaaggcgc tgggcaagcc ggaatggatt ccgatcccca actacgccac cgccaaggct | 900 |
| cgccagccgc atatcttcga tatcttcaac accatcgagg aatggctggc cgacaagacc | 960 |
| aagtacgagg ccgtggacat cctgcgcaag ttcgacatcc cgtgctcgcc ggtgctgtcg | 1020 |
| atgaaggaaa tcgccgccga tccgtcgctg cgcgccagcg gcagcatcac cgaggtgccg | 1080 |
| cacaaggagc gcggtaccta cctgacggtg ggcagcccga tcaagttctc cgacctcaag | 1140 |
| ccggagatca ccgggtcgcc actgctgggc gagcatagcc aagaggtgct ggccggcctg | 1200 |
| ggctacggcg cggacgacat caagcgcctg cgcgagtccc aggtgatctg a | 1251 |

<210> SEQ ID NO 28
<211> LENGTH: 1251
<212> TYPE: DNA
<213> ORGANISM: Burkholderia xenovorans

<400> SEQUENCE: 28

| | |
|---|---|
| atgaccaaac ctctcgaagg catccggatc atcgacttca cccatgttca agccggccct | 60 |
| gcatgcaccc agttgctcgc ctggttcggc gcggacgtca tcaaggttga acggccgggt | 120 |
| tcgggcgacg tgacgcgcaa ccagttgcgc gatattcccg acgccgacgc gttgtacttc | 180 |
| acgatgctca acagcaacaa gaaatcgctg acgttggaca caaaaaaacc cgaaggcaag | 240 |
| gaagtactcg aaaagctgat cgcgaatccc gacgtgctgg tggagaattt cggcccgggc | 300 |
| gcgttggacc gcatgggctt ttcgtgggaa cggctgaatg aactcaatcc gaagatgatc | 360 |
| gtcgcctcgg tgaaaggctt cagcgacggc caccactacg acgacctgaa ggtctacgaa | 420 |
| aacgtggcgc aatgcgcggg cggtgcggcc tccaccaccg gcttctggga cggtccgccc | 480 |
| accatcagcg ccgccgcgct cggcgacagc aataccggta tgcatctggc catcggcatt | 540 |
| ctgaccgcgc tgctcggtcg cgacaaaacc ggcaaaggcc agaaggtcgc agtgtccatg | 600 |
| caggacagcg tgctgaatct gtgccgcgtg aagcttcgtg accagcagcg gctggaacgc | 660 |
| gttggctatc tcgaggagta cccgcaatat ccgcacggca attcagcga cgtggtaccg | 720 |
| cgcggcggca atgcaggcgg cggcggccag ccgggttggg tgctcaaatg caaaggctgg | 780 |
| gaaacggatc cgaacgccta catctacttc acgattcagg gccatgcgtg ggagcccatc | 840 |
| tgcaaggcgc tcggcaagcc cgagtggatc gacgacccgg cctacaagac tgcggaagcg | 900 |
| cgtcaaccgc atatcttcga tatcttccag accatcgaaa cctggctcgc ggacaaaacc | 960 |
| aagttcgaag cggtcgacat cttgcgcaag ttcgacattc cgtgcgcacc ggtgctgacc | 1020 |
| atgaaggaac tggccaacga tccgtcgttg cgcgcgagcg gcacgatcgt cgaagtaccg | 1080 |

```
cacaagaaac gcggcacgta tctgactgtc ggcagcccga tcaagttttc ggatctgaag    1140
ccggaagtca ccgcgtcgcc gctgctcggc gaacacaccg acgaggtgct ggcgagcctt    1200
ggctacagcc agcagcaaat cttcaacctg cgcgaagtca aggcagttta a             1251

<210> SEQ ID NO 29
<211> LENGTH: 423
<212> TYPE: DNA
<213> ORGANISM: Azoarcus evansii

<400> SEQUENCE: 29
tcagtccttc ggcggttcca gatagcgccc gaagcgctcg cgccattcgt cgtcgatcaa      60
ggtcgcgcgc ggggcgccgc cgaggtcggc ccacacgacc gtctgcttcg cgcggaagcg     120
cacctgctcg cccatcgacg cggtcgtgac gatgtccatc gagctgccgc cgatgcgcgc     180
gacgtagagc gtgaaggtga gctcatcgcc gtgcatgctc ggtgcgaaaa agtcgacttc     240
gaggtggcgc atcggcacgc gcggcggat ctccgcgtgc agcttgtaga agtccacgcc      300
gatgccgcgg tcgaaccagt cctcgaccac ctcattgcac agcaccaggc actgcgggta     360
gaagacgatg ccggccgggt cgcagtggtg gaaacggatg gatttcttgc attcgaagat     420
cat                                                                  423

<210> SEQ ID NO 30
<211> LENGTH: 432
<212> TYPE: DNA
<213> ORGANISM: Magnetospirillum magnetotacticum

<400> SEQUENCE: 30 tcatgggcc gcaacctcca ccagccgggt gcgataggct tccaggcgtt cgcgcatggg       60
accgggcatg ggaaccgcct tcaccttttc ctgatcggcg acgacacaga cgaaactggt     120
ctcgaaggcc accacgccgt caccccgcgc gccgatggtg cggaaatgaa tggaagagcc     180 ccccacccctg tccaccagga ccgagatatc cacccggtcg ccgggccgaa gcggcgattt    240
gatctccatg ccgatcttga cgaagggcgt gccgaagccg tgttccttgt tgatggtgta    300
ccagtcatag ccgatgacat cggccatgaa gacctccagc gcctccatgg cgtattccag    360
gaagcggggc gtatagacga tgcgcgccgc gtcggaatcg ccgaaatgga cccggcggcg    420
gtgaatgaac ac                                                        432

<210> SEQ ID NO 31
<211> LENGTH: 411
<212> TYPE: DNA
<213> ORGANISM: Jannaschia sp. CCS1

<400> SEQUENCE: 31
atgacccacc tctggcccct gcgcgtctac tatgaagacg tcgatctggc ggggatcgtc     60
tactacgcca actacctgaa atacctggag cgggggcgct ctgaaatggt gcgtgaggcc    120
ggcatttccc agctcgacat gaaagctgcg gggctggtct ttgccgtgcg gcgggtggag    180
gcggaatacc tcaaacccgc caaatacgat gatgagctgg tcgtggagac gcagctggac    240
cgcctgaaag gggccagttt cgacatgccc cagcgggtcc tgcgcggcga tgacgtgctg    300
ctggacgcgc ggatcaaggt tgtgatcctc aacgcggacg gccgggcggc gcgacttccg    360
gcggatattc gcgcaaaagt cacagccgtc gcggcaagtg atggcccgta a              411

<210> SEQ ID NO 32
```

```
<211> LENGTH: 432
<212> TYPE: DNA
<213> ORGANISM: Sagittula stellata

<400> SEQUENCE: 32
atgtcgcagg aggaagccgt ggggcagccg ttcgagcatg agatccgggt gacctggggg    60
gactgcgatc ccgcgcggat cgcctatacg gcgcgcatcc cctggttcgc gctggatgcg   120
atcaacgcct ggtgggagga gaagctgggc ggcggctggt tccagatgga gctgaccgc    180
ggtgtcggca cgccgttcgt caacatgacc atcgatttcc gcagtccggt cacgccgcgc   240
caccggctgc tctgcgccgt gcgcccggtg cggctgggcg agacctcggt cagtttcgaa   300
gtgctgggac ggcaggacgg tgtgctgtgt ttcgaggggc ggttcacctg cgtgttcatc   360
gccgtgccgc gttttcgcaa ggcgccgccg ccggaggata tccgggcggt ggtggaggcg   420
catctgaact ag                                                       432

<210> SEQ ID NO 33
<211> LENGTH: 414
<212> TYPE: DNA
<213> ORGANISM: Escherichia coli

<400> SEQUENCE: 33
atgatctgga aacgccattt aacgctcgac gaactgaacg ccaccagcga taacacaatg    60
gtggcgcatc tggaattgt gtatacccgt ctgggcgatg atgtgctgga agccgaaatg   120
ccggttgata cccgtactca tcagccgttc ggtttactac atggcggcgc gtcggcggcg   180
ctggcggaaa cgctgggatc gatggccgga tttatgatga cccgcgacgg acagtgtgtg   240
gtaggcacag aacttaatgc aacacaccat cgcccggtgt ctgagggaaa ggtacgcggc   300
gtctgccagc cgctgcatct tggtcggcaa aatcagagct gggaaatcgt cgttttcgat   360
gaacagggc ggcgttgctg cacttgtcgg ctgggtacgg cagttttggg atga          414

<210> SEQ ID NO 34
<211> LENGTH: 1989
<212> TYPE: DNA
<213> ORGANISM: Acetobacter pasteurianus

<400> SEQUENCE: 34
atgtcggaaa acatcactat cctgcctaca cagtatgcag attacccggc tctgatgcca    60
cctgcggaac tggccgccat gcagcgctat gcacgccgag acccggatgg tttttggctg   120
caacaggccc ggcgtgtgca ctggcaccgc aagcctaggc gaggctttac gggcagcttt   180
acgggtgatg tgtccataag ctggtttgaa gatggcctta tcaacgcatc cgtatgctgt   240
attgataagc atctgacaga caaggctgat cagattgccc ttatcagcca ccgtgaaggc   300
cgggccgagg cagaaaaaat tacatatgcc atgctgcatg aacgggtttg ccgcctgtct   360
aacgcgctgg tgcatttggg ggtggaggaa gggcaccgcg ttgccatttg cctgcccatg   420
atttcagaag ccgtggtggc catgctggcc tgtgcgcgta ttggcgcggt gcatgtggtg   480
ctgtttggtg gttttcggc agaaggtatt gcagaacgta ttatagatag cggcgcagtt   540
gcggtaatta ccgccagcga aagcatgcgc ggcaacaaga tcgtgccctt taaagcgatt   600
atggatgaag ccctgtgcaa ggcaggtgca gaaagtggcg tgcgggctgt tctagttgtg   660
cgcacgtctg atgcacctgt tcccatgctg cctggtaggg attacgattt tcatgatttt   720
gtagattcgt ttgaggcaga ttttgtgccc gttgtcatgc gggcagaagc accattattt   780
atgctctaca catctggcag cacaggcaag cccaaagcag ttgtgcatgc cactggtggc   840
```

| | |
|---|---:|
| tatatggtgt gggcagctta cactatggac atggtgtacc atcatcaacc tggtgatgtg | 900 |
| ctgtggtgca cggcagatgt ggcatggata accgggcata catccgttgt gtatggcccg | 960 |
| ctggccaatg gcggaaccac catgatttcc gatagcctgc cttcataccc cgctccgggc | 1020 |
| agatggttgg atctgataga tgagcataag gtgaccatgc tgtttaccgc ccccacagcc | 1080 |
| gtgcgcgcca tgatggccga tggtgatgat gtggtgaacg cccgcaatct ggagtctctg | 1140 |
| cgtttgctgg gtgtggcggg ggagcccata agcccggatg cgtggctatg gtatcacgat | 1200 |
| gttgtgggta aaagcgttg ccccgtggtg gatacatggt ggcagacaga aaccgccggc | 1260 |
| attgtgctgg ggccagtgcc gggtgtgcaa ccgcttaaac ccggctctgc cagcacgccg | 1320 |
| ctgccggggt tggaaatggt catagccgat acgcagggca ggccggtgca ggggcctgca | 1380 |
| gaaggtagcc tgtgcattgc gcgttcatgg ccggggcagg cccgcacaat ctggaaagat | 1440 |
| catgctcgct tctgccagac atattttggt atggttccgg ggcattattt cacgggtgat | 1500 |
| ggcgcacggc gagatgccga tggctattac tggattacgg ggcgcatgga cgatgttatc | 1560 |
| aatattgcag ggcaccgttt gggtacagca gaagtggaag atgcgttggc agcagatcat | 1620 |
| cgtattgtgg aatctgctgc agtgggcatc ccgcacccgg taaaggggca ggcgctggcg | 1680 |
| gtatttgtta ccagcgcca gaacgtggct acggaactga cagaaaaagg cataagccgc | 1740 |
| cttatctccg gtatgttggg gcgttatgcc acgccagagg ccgtttatct ggtgccagat | 1800 |
| ctgcctcgca cgcgctctgg caagattgta cgccgcctgc tgcgcaaaat tgccagtggg | 1860 |
| gaaatggata atctgggaga tctttcatcg ctgaatgatc cttccatcgt gcgtatgctg | 1920 |
| tgtgacagag tatggagcca catggctttt gatgaggaat ctgcacctcg cacacaggca | 1980 |
| agggcctga | 1989 |

<210> SEQ ID NO 35
<211> LENGTH: 1890
<212> TYPE: DNA
<213> ORGANISM: Azotobacter vinelandii

<400> SEQUENCE: 35

| | |
|---|---:|
| atgaactatc agcactacca tgaacgctcc atcgccgatc ccgccggttt ctgggccgaa | 60 |
| caggcgcagg ccgtgcgctg gttccgccag ccgacggaaa ttctccgcgc cctggcggac | 120 |
| ggcacgcacc agtggttcgc cgacggccgg ttgaacagtt gctatctggc cctggatcat | 180 |
| cagatcgaac agggccgtgg cgagcagacg gccctgatcc acgactcgcc ggtcaccggc | 240 |
| ggcaaggccc gctacagcta ccgcgaactg cgcgacgaag tggcgcgcct ggccggcgcc | 300 |
| ctgcgcgagc tgggcgtgga aaagggcgac cgggtcatca tctacatgcc gatggtgccg | 360 |
| caagcggcca tggccatgct cgcctgcgcg cggatcggcg cggtgcactc ggtggtgttc | 420 |
| ggcggcttcg cccctcacga actggcgctg cgcatcgacg acgcccggcc caaactgctg | 480 |
| ctcaccgcgt cctgcggcct ggagttcgac cgggtcatcg aatacaaacc gctggtcgac | 540 |
| aaggccctgg aactggccag ccaccagccc gggcacgtac tggtgctgca acggccacaa | 600 |
| gcgagcgccg cgctgctccc agggcgcgac ctgactggc aggccagggt cccgctggcc | 660 |
| gcgccggtgg agcccgtgcc cctggacagc ggcgatccgc tgtacatcat gtacacctcc | 720 |
| ggcaccaccg gaaaacccaa gggcgtcgtg cgcgacaacg gcggcaacgc ggtggccctg | 780 |
| agcttcgcca tgccatgt ctacgccatg cgggccggcg acgtctggtg ggcatctcc | 840 |
| gacgtcggct gggtggtcgg ccattcgctg atcgtctacg gcccgctgat gaacggatgc | 900 |

| | |
|---|---|
| accagcatcc tctacgaagg caagccggtc cgcacgcccg acgccggcgc ctactggcgg | 960 |
| gtgatcgagg aataccggcgt caacggcctg ttctgcgcgc cgacggcgat ccgcgccatg | 1020 |
| cgcaaggaag atccttcggg cgaactgagc gggcgccacg acctgggctc gctgcggcac | 1080 |
| ctgttcctgg ccggcgagaa gctcgattcg agcacccacc ggtggctgga ggaactgacc | 1140 |
| gggaagccgg tgcacgacca ctggtggcag accgagaccg gctggccggt caccgctccc | 1200 |
| tgcgccgggc tggagggcca caccgcacgc cacggttcga gcaaccgccc ggtgcccggc | 1260 |
| tatcgcgtcc aggtgatgga cgaacagggt cacctgctcg gagcgaaccg gcagggctcg | 1320 |
| atcgtcatcg ccctgcccct gccgccgggc tgcgcgcaga ccctgtggaa cgaccacgag | 1380 |
| cgctatctgc gctcttatct gagctcctat cccggctact accacaccgg cgacggcggc | 1440 |
| tacctggacg acgagggctt cgtctacatc atgggccgca ccgacgacgt gataaacgtg | 1500 |
| gccggccacc gcctctccac cggagaaatg gaagacctgg tggcccggca tccggcggtg | 1560 |
| gccgaatgcg cggtgatcgg catccccgac gcgatcaagg acaggtgcc gctgggcctg | 1620 |
| atcgtcctca aggacggcag ccgaatccgc gaggagcaac tgcagcggga gttgaccgcc | 1680 |
| tcgatccgcg agcagatcgg cgcgctggcc tgcttccagc ggatagcgac ggtcaagcgc | 1740 |
| ctgccgaaga cccgttcggg caaaatcctc cgggcggtgc tgcgcaagat cgccaacggc | 1800 |
| gaggaggtgg ccacgcccat gaccatcgac gatccggcga tactcgggga aatcggcgcc | 1860 |
| gccctggcgt tgtacacgcg cgccagttga | 1890 |

<210> SEQ ID NO 36
<211> LENGTH: 1959
<212> TYPE: DNA
<213> ORGANISM: Dehalococcoides sp.

<400> SEQUENCE: 36

| | |
|---|---|
| atgagtaccg aagaaaagaa gtttgacacg caaaacctgc ctaccaagac ttatttctgg | 60 |
| ccgctgaaaa gataccagga cctttataac agctcactgg ctgacccgga ggctttctgg | 120 |
| gccaaacact cagacgtgct ttcatgggaa aagccttggg aaaaagtact ggactggaat | 180 |
| ccgccttatg cccgctggtt tgtaggcggc aagctgaata tgtcttacca atgcgtagac | 240 |
| cgccatgcca aaagctggcg taagagcaag gtagctatct attgggaagg cgaaaacggg | 300 |
| gatacccaga ccataagcta ttcagacctt tacgaaaatg taaaccgtta tgcatccgtc | 360 |
| ctgaaaaagc tgggcatatg caagggtgac agggtaactg tctacctgcc catgatacct | 420 |
| gaaatggtct atattctatt agcctgcaac cgggttggag ccgtccataa cgtaatattc | 480 |
| tcaggtttct cttcccagtc tatcgcagac agggtaaatg actccggttc aaaaatggtt | 540 |
| gttaccgcca gcggcggaca ccgccgcggt aagatactgc ctcttaaaga aatcgtagat | 600 |
| gaggctgtaa atccacccc gactatagaa catgtactgg ttattaaata taccggccac | 660 |
| gaagtagcca tggaccccac cagagacgta tgggcacatg atctgctgaa agatgcagat | 720 |
| aaatacgtag cccctgaagc tatggaatcc accgacccgc ttttatcct gtacacctca | 780 |
| ggcactaccg gtaaaccgaa gggtattctg catggtaccg gcggctacgg cgtctgggcg | 840 |
| tgcaataccc ttaagtgggc tttcaaaccc acggacgaat cagtcttctg gtgcacggca | 900 |
| gacgtaggct ggattaccgg gcacacatat gttgtatatg ccccgctggc gctgggactt | 960 |
| acccaggtta tttacgaggg agctccggat tatccttcag tagaccgctg gtgggagatt | 1020 |
| attgataaat acggggtaag catattctat acctcgccta ccgccatacg catgtttatg | 1080 |
| cgccacggcg aggagttgcc tgccagacac gaccttggca ctctggaaat gctgggaagc | 1140 |

```
gtgggcgaac ccattaaccc tgaagcctgg gaatggtatt acaagaatat aggccatgag    1200
aactgcccca tttccgatac ttggtggcag accgaaacag gcggttttat gattacccc     1260 tgccccggca tacaatcctt cccgctcaaa ccgggctcag ccactttgcc tctaccggga    1320
gttgacccgg tagtggtaga tgctgaaggc aaggaactgc cggctaatga aaccgggttt    1380
attgccatcc gcaaaccttg gccgggcata atgctgggta tatataacgg tgatgaactt    1440 tataaaaga cctactggag ccgtttcccc ggctggtatt gtccgggaga cttttcaatg     1500
aaagattctg acggatatct gtggctgctg ggacgggctg acgaagttat caaggtagcc    1560
ggtcaccgca taagcaccgc cgaattggag catgctctgg taggccatag ttcagttgcc    1620
gaagcggcag tagcctcccg ccctgacgaa gtaaagggtg aagctattgt ggttttcgtc    1680
accctgaaaa aaggtgtaga agcctctgcg gaagtaaaga gagagcttac ccatcacctc    1740
cgctctgcta tcggcactat agccaccccg gaagagatca ttttcgtgga gaaactgccc    1800
aaaacccgtt cggcaagat tatgcgccgc ctgctgaagg ccgttgccaa cgaagtaccc     1860
attggtgata ccactacact tgatgatgag acttcggtaa atgaggccag agcggctttt    1920
gatgaactgc tggcagcacg caaacaccac aaacactaa                          1959

<210> SEQ ID NO 37
<211> LENGTH: 810
<212> TYPE: DNA
<213> ORGANISM: Escherichia coli

<400> SEQUENCE: 37
atgacgaagc atactcttga gcaactggcg gcggatttac gccgcgccgc agagcagggc    60
gaagcgattg caccgctgcg cgatctgatt ggtatcgata cgctgaagc ggcttacgcc     120 attcagcaca taaatgtgca acatgacgtt gcgcaggggc gtcgcgtggt agggcgtaaa    180
gtgggcctga cacatccgaa agtgcaacaa caactgggcg ttgatcaacc ggattttggg    240
acgttatttg ccgacatgtg ttatggcgat aacgaaatca ttcctttttc ccgtgttctg    300
caaccccgca ttgaagcgga gatcgcactg gtgttgaacc gcgatttgcc cgcaaccgat    360
atcaccttcg acgaattgta taacgccatt gaatgggtac ttccggcgct ggaagtggtg    420
gggagccgca ttcgcgactg gtcgattcag tttgtcgata ccgtggcaga taacgcctcc    480
tgtggggtgt atgtcatcgg cggtccggcg caacgtccgg cggggttaga cctgaaaaac    540
tgcgccatga agatgacgcg taataacgaa gaggtttcta gcgggcgcgg cagcgaatgc    600
ctgggacatc cgcttaatgc ggccgtctgg ctggcacgca aaatggccag tctgggtgaa    660
ccgctgcgca ccggagatat cattcttacc ggggcattag gtccgatggt ggcggtgaat    720
gcgggcgatc gttttgaagc ccatattgaa ggcataggtt cagttgctgc gacattttca    780
agcgcagccc caaaaggaag tctgtcatga                                     810

<210> SEQ ID NO 38
<211> LENGTH: 789
<212> TYPE: DNA
<213> ORGANISM: Pseudomonas putida

<400> SEQUENCE: 38
atgaatgaag ccaacgtgat tgcgaacctg ttatgggatg cgcagcggca aaagctgccc    60
tgtgcaccgg tgcgggaata tttcgagggg aagagcgagg ttgaccaggc gctattggcc    120
tatgccgtac agcaggtgaa tgttcagcgc caggtggagg gcggccgacg tatcgtcggt    180
```

```
cgcaagatcg gccttacctc tccggcagtg cagaagcaat tgggtgtaga tcggccggac      240
ttcggcacgt tgctggacga catggcgatc gtcgatggcg agccgatcaa cactgcgcgt      300
cttctgcagc ccaaggtcga agctgagatc gccctggtac tcgagcgtga cctcgatcgg      360
gagcgtcata cagtcgccga cctgatcgac gcgacagcgt atgcacttgc tgcaatcgag      420
gtggtggata gccgtatcac cggttggaac atccgctttg ttgacaccgt ggcagacaac      480
gcctcatcgg gcttgttcgt actcggtact cagcctgttg gcctgtcgaa gcttgatctg      540
gccggtatgt cgatgcgcat ggcgcgtggc gaagagcttg tatcgcaagg ggctggagct      600
gcctgccttg gcaacccgtt gaacgcgcgc cgttggcttg ctgacacgtt ggtccaagtg      660
ggcacgccat tgcgtgccgg cgatgtggtt ctgaccggcg ctctggggcc aatggtcgcg      720
gtcgagtccg gtcacaccta tacggcatgg atcgatggct cgccccggt acgagcaatt      780 ttctcctga                                                              789
```

`<210> SEQ ID NO 39`
`<211> LENGTH: 807`
`<212> TYPE: DNA`
`<213> ORGANISM: Pseudomonas putida`

`<400> SEQUENCE: 39`

```
atgagcgaac tagataccgc gcggacaggt gccgtgcgta aagctgccga cctgctgtac       60
gaagccaccc ggtccggtgt ggccgtggtg ccggtgcgca atctgatcgg cgagacggat      120
ttggaggcag cctatgcagt acaggaggtt aatacacaga gagcattggt tgccgggcgg      180
cgcctggttg acgcaagat tgggctgacc tctgtcgctg tacagaagca gctcggagtg       240
gaacagcccg actatggcat gttgttcgca gacatggcgc gtaccgaggg ggaggaaatc      300
gcccttgatg acgtgctcca acctaaagtc gaagccgaga tcgcctttgt cctgggacgt      360
gacctcgatg gcgatcaatt gacggtggcc gacctctttc gcgccatcga gttcgccgtt      420
ccggcgatcg agatcgtggg ttcgcggata accaattggg atatccgtat cacggacacc      480
attgctgaca atgcttcgtc tggcctgtat gtgctgggct ccacgccgaa gcgcttgtgc      540
gattttgact cgcgccaggc aggcatggtg atggagcggc aaggcatacc ggtgtcttcc      600
ggggtagggg ccgcctgcct tggagcgcct ctcaacgcag tcctttggtt ggccagggtc      660
atggctcgag cgggccgtcc gttgcgcact ggcgacacgg tgctttccgg tgcgctgggc      720
cccatggtgc cagtggcagg aggagatgta ttcgatgtgc ggatagccgg gcttggatcg      780
gtgaccgccg cttttgcaaa ggcataa                                          807
```

`<210> SEQ ID NO 40`
`<211> LENGTH: 804`
`<212> TYPE: DNA`
`<213> ORGANISM: Klebsiella pneumoniae`

`<400> SEQUENCE: 40`

```
atgctcgata aacagacccg taccctgatt gcccagcggc tgaaccaggc cgaaaagcag       60
cgtgaacaga tccgcgcgat ctcgctggat tatccgtcga tcaccattga ggacgcctac      120
gccgtccagc gcgagtgggt cgagatgaag atcgccgaag gcgcgtgct caaaggccac      180 aagatcggcc tgacctctaa agcgatgcag gccagttcgc agatcagcga gccggactac      240
ggcgcgctgc tcgacgatat gttcttccac gacggcagcg atattcccac cgaccgcttt      300
atcgttccgc gtatcgaagt cgagctgcc ttcgtgctgg ccaaaccgct gcgcggcccg      360
aactgtacgc tgtttgatgt ctacaacgcc accgactacg ttatcccggc gctggagctt      420
```

```
atcgacgcgc gctgccacaa catcgacccg gaaacccagc gtccgcgcaa agtgttcgac    480
accatctccg acaacgccgc caacgccggg gtgatcctcg gcggccggcc gattaaaccg    540
gacgagctcg acctgcgctg gatctccgcc ctgctgtatc gcaacggcgt aattgaagag    600
accggcgtcg ccgcgggcgt actcaatcat ccggccaacg gcgtggcctg gctggccaac    660
aagctggcgc gtacgatgt ccagctcgaa gccgggcaga ttatcctcgg cggctccttc     720 accccgcccgg tcccggcgcg caagggcgat accttccacg tcgactacgg caacatgggc   780
gtcatcagct gccggtttgt ctag                                           804
```

<210> SEQ ID NO 41
<211> LENGTH: 804
<212> TYPE: DNA
<213> ORGANISM: Escherichia coli

<400> SEQUENCE: 41

```
atgttcgaca acacaccca cccctgatc gcccagcgtc tggatcaggc agaaaaacag      60
cgcgaacaga tccgcgcgat ctcgctggat tacccggaga tcaccatcga agacgcttac   120
gcggtgcagc gtgaatgggt tcgactgaaa atcgccgaag gtcgcacgct gaaaggccac   180
aaaatcggcc tgacttcgaa agcgatgcag gccagctcgc agatcagcga accggattac   240
ggtgcactgc tggacgacat gttcttccac gatggcagcg atatcccgac cgatcgcttt   300
atcgtgccgc gcattgaagt ggagctggct tttgtgctgg caaaaccgct gcgtggacca   360
aactgcacgg tgttcgacgt ttacaacgcc acggactatg tgatcccggc gctggagctg   420
atcgacgctc gctgccacaa catcgatccg gaaacccagc gcccgcgtaa agtgttcgac   480
accatttctg ataacgccgc caatgccggg gtgatcctcg gtggtcgtcc cattaagccc   540
gatgagttgg atctacgttg gatctccgcc ctgatgtatc gcaatggcgt gattgaagaa   600
accggcgtcg ccgctggcgt gctgaatcat ccggcaaacg gcgtggcctg gctggcgaac   660
aaactcgccc cctatgacgt acaactggaa gccgggcaaa tcattctcgg cggttcgttc   720 accccgcccgg ttccggcgcg taagggcgac accttccacg tcgattacgg caacatgggc   780
tccattagct gccgctttgt ttaa                                            804
```

<210> SEQ ID NO 42
<211> LENGTH: 840
<212> TYPE: DNA
<213> ORGANISM: Comamonas testosteroni

<400> SEQUENCE: 42

```
atgaaccgaa cacaagccaa agtagtcgaa ggcaaatttc ccacacagaa caccatggac    60
aactccaaga tccagcacta cggcgacgag ctctaccagt cgctgctcga ccgccaaccc   120
gtcgctccgc tgaccgaccg cgaagcggac atcaccatcg aggacgccta ccagatccag   180
ctgcgcatga tccagcgccg gctggacgcg ggcgagcgcg tggtgggcaa gaaaataggc   240
gtgacgagca aggtcgtgat ggacatgctc aaggtcaacc agcccgactt cggccacctg   300
ctctcgggca tggtctacaa cgaaggccag cccatcccgg tgagcagcat gatcgcgccc   360
aaggccgagg cagaggtcgc cttcatcctg gcgcgcgacc tcgaaggccc cggcgtcacc   420
gcggccgacg tgctgcgcgc caccgactgc gtgatgccgt gcttcgagat cgtcgactcg   480
cgcatcaagg actggaagat caagatccag gacaccgtgg ccgacaacgc ctcctgcggc   540
gtgctcacgc tcggcggcct gcgcaagagc ccgcgcgacc tcgacctcgc gctggccggc   600
```

```
atggtgctgg aaaagaacgg cgaaatcatc agcacgtcct gcggcgcatc ggtgcagggc      660
tcgccggtca acgcgtggc ctggctggcc aacacgctcg gccgtctggg catcggcctc       720
aaggccggcg acatcatcct ctctggctcg cagtcgccgc tggtgccggt ggtcgcgggc      780
gacagcctgt attgcagcgt cggcggcctg ggcggcacgt cggtgcgttt cgtcgcctga      840
```

<210> SEQ ID NO 43
<211> LENGTH: 507
<212> TYPE: DNA
<213> ORGANISM: Methanocaldococcus jannaschii

<400> SEQUENCE: 43

```
atgagaagta taataaaggg aagagtttgg aagtttggaa ataacgtaga tacagatgct      60
atattaccag caaggtattt agtttataca aaaccagagg aattagctca gtttgttatg     120
actggggcag acccagattt tccaaagaag gttaagccag agatataat agttggagga      180 aagaactttg gatgtggttc aagtagagag catgccccat taggattaaa aggagctgga    240
atcagctgtg ttattgctga gagcttcgca agaatatttt atagaaatgc cataaatgtt     300
ggattaccat taattgaatg taagggcatt tcagagaaag tcaatgaagg ggatgagtta     360
gaggttaatt tagagactgg agagattaaa aacttaacca ctggagaggt tttaaaaggt    420
caaaaattac cagaattcat gatggaaatt ttagaggctg gaggattaat gccatactta    480
aagaaaaaga tggctgaaag ccaataa                                         507
```

<210> SEQ ID NO 44
<211> LENGTH: 1263
<212> TYPE: DNA
<213> ORGANISM: Eubacterium limosum

<400> SEQUENCE: 44

```
ttgggtatga caatgactca gaaaatattg gcggcacatg ctggtctgga atccgtaaaa      60
ccgggtgatt tgatcatggc agacctggat ctggtgttgg ggaatgatat tacctcaccg     120
gtagccatca atgttttttaa aaatattaat aaggaaaccg tttttgacaa agacaaggtt   180
gcgctggtcc cagaccattt tgcgccgaac aaggatatta aggctgcgga gcagtgcaaa    240
caggtgcgct gttttgcctg tgagcaggat gtcaccaact attttgaaat cggcgaaatg    300
ggtgtagagc atgctctgct gccggaaaag ggactggtcg ttgccggcga tgtcgtgatt    360
ggggcagatt cgcacacctg tacctatggt gcgcttgggg ctttctcaac cggtgtgggt    420
tctaccgaca tggccgttgg tatggcaacc ggtaaagcct ggtttaaggt accgtctgcc    480
attaaattca atctgactgg cgctttcaaa gaaggtgttt caggaaaaga cctgattctt    540
cacattatcg gaatgattgg tgtggatggt gcgctttata atcaatggga atttgccgga    600
gagggtgtgt caagcctgac gatggatgat cgcttcacca ttgcgaatat ggccattgaa    660
gctggcggta aaatggtat cttccctgtc gacgataaga ccatcgaata tatgaaggag    720
cattctacca aggaatacaa ggcctttgaa gcagacgcag acgccgagta tgacgctgtg    780
tacgatatta atctggcaga tatcaagtct acggtagcat tcccgcactt gcctgaaaac    840
actaaaaccg ttgatgaaat tactgaaccg gttaagattg accaggttgt tatcggctca    900
tgcaccaatg gacgtttctc agactttaaa aaggccgcag atctgatgcg cggtaagcat    960
gttgccaaag gaatccgtgt tttgattatc ccagcaactc agcagattta cctggattgt   1020
atggaagcgg gatatttaaa agactttatt gaagcgggcg caacggtgag cacaccgacc   1080
tgcgggccat gcctgggcgg acatatgggg attctggcag cgggagaacg ctgcgtttcc   1140
```

```
acaacaaacc gtaactttgt cggacgcatg ggccatgtgg actcggaagt ctatctggcg    1200
agccccgagg ttgcggcggc atctgctatc ctgggccgta ttgccggacc agaagaatta    1260
taa                                                                  1263

<210> SEQ ID NO 45
<211> LENGTH: 492
<212> TYPE: DNA
<213> ORGANISM: Eubacterium limosum

<400> SEQUENCE: 45
atgaaagcaa aaggaaaagt atttagatat ggcaacaatg ttgatacaga cgttattatt     60
cccgcaagat acctgaacac cagcgatcct ctggaattag cggagcattg tatggaggat    120
attgacaagg attttataaa acgcgtggag gacggcgata tcatcgtcgc tgatgataat    180
tttggctgcg gctcttcaag agagcatgcg cccattgcca tcaaagcctc aggtgtctcc    240
tgtgtaatcg ccaatagctt tgcgcgtatt ttttatcgca attccatcaa tatcgggctg    300
ccgattctgg aatgtccgga agcggtggca gcgattgaag caggcgacga agtagaagtg    360
gattttgact ctggcgttat cactgacgtg accaagggac agagcttcca gggacaggca    420
ttccctgaat ttatgcagaa gctgatcgca gcaggcggcc tggtaaatta cgtcaacgag    480
aatctcattt ag                                                        492

<210> SEQ ID NO 46
<211> LENGTH: 1770
<212> TYPE: DNA
<213> ORGANISM: Macrococcus caseolyticus

<400> SEQUENCE: 46
atgtactata gtaatggaaa ctatgaagca tttgcaagac cgaagaagcc ggaaggggta     60
gataataagt ctgcatattt agttggttct ggtttagcgt cattagcagc ggcaagtttt    120
ttaatacgag atggtcaaat gaaaggtgaa atattcata tattagaaga actcgatctc    180
cctggaggaa gcttggatgg aatattgaat cctgaacgtg gctatataat gcgtggcggt    240
cgtgagatgg agaatcattt tgaatgttta tgggatttat ttcgttcagt accatcattg    300
gaagtcgaag atgcttctgt tctggatgaa ttttactggt taaataaaga agatccaaac    360
tattcgaagt gccgcgtaat agaaaatcgt ggacaacgcc tagaatcaga tggaaaaatg    420
actctaacaa aaaagcaaa taagaaaatt atccagctgt gcttaatgaa agaagaacag    480
ctgaatgatg tgaagatctc tgatgtcttc agtaaagact tcttagactc aaacttctgg    540
atctactgga aaacgatgtt tgcatttgaa ccttggcatt ctgctatgga gatgcgtcga    600
tatttaatgc gtttcatcca tcatattggt ggacttgcag acttttcagc tctaaaattt    660
acgaagttca atcagttcga atcacttgtt atgcctctga ttgagcatct taaagcgaag    720
aacgttacat ttgaatatgg tgtaactgtt aagaatatac aagttgaatg ttcaaaagag    780
tcaaaagttg caaaggcaat agacatcgtg cgcagaggta acgaggaatc aattccttta    840
actgaaaatg atttagtatt tgtaacaaat ggcagtatca ctgaaagtac tacttatgga    900
gataatgaca caccgtgcacc gcctacatca aaacctggtg gcgcatggca actatgggaa    960
aacttaagta cgcaatgtga ggagtttggt aatccagcta aattctataa agatttacca   1020
gaaaaaagct ggttcgtgtc tgctacagca acaacaaata caaagaagt tatagattat   1080 attcaaaaaa tttgtaaacg cgatccatta tcaggtcgta cagtaactgg cggtatcgtt   1140
```

```
actgtagatg attcaaattg gcagttaagc tttacgctaa atcgacaaca gcagtttaaa   1200
aatcaacctg atgatcaagt gagtgtatgg atttacgcac tttattcaga tgaacgtgga   1260
gaacgtacaa ataaaacaat tgttgagtgt tctggtaaag aaatttgtga agaatggctt   1320
tatcatatgg gtgttcctga agagaagatt tcagcactag cagcagaatg taatacaatt   1380
ccaagctata tgccgtacat taccgcttac tttatgccgc gtaaagaagg agatcgtcct   1440
ttagtagtac cacatggttc aaagaatatt gcatttatag gtaactttgc agaaacagaa   1500
agagataccg tatttacaac agaatattca gtaagaactg ctatggaagc ggtgtataaa   1560
cttctagaag tagaccgtgg agtgcctgaa gtattcgctt cagtatacga tgtgagaatt   1620
ttattacatg cgttatctgt actgaatgat ggcaagaaac tagatgaaat tgatatgcca   1680
ttctatgaaa gattggtaga aaacgcttg ttgaagaaag catctggtac gttcattgaa   1740
gaactgttag aagaagcaaa tttgatataa                                     1770

<210> SEQ ID NO 47
<211> LENGTH: 831
<212> TYPE: DNA
<213> ORGANISM: Pseudomonas putida

<400> SEQUENCE: 47
atgagcaaat acgaaggccg ctggaccacc gtgaaggtcg aactggaagc gggcatcgcc    60
tgggtgaccc tcaatcgccc ggaaaaacgc aatgccatga gccccaccct gaaccgggaa   120
atggtcgacg tgctggaaac ccttgagcag gacgctgacg ctggcgtgct ggtattgacc   180
ggtgccggca gtcctggac cgccggcatg gacctgaagg agtacttccg cgaggtggac   240
gccggcccgg aaatcctcca ggaaaagatt cgtcgcgaag cctcgcaatg caatggaag   300 ttgctgcgtc tgtatgccaa accgaccatc gccatggtca acggctggtg cttcggcggc   360
ggcttcagcc cactggtggc atgcgacctg gcgatctgcg ccaacgaagc gaccttcggc   420
ctgtcggaaa tcaactgggg catcccgcct ggtaacctgg tcagcaaggc catggccgat   480
accgttggcc atcgtcagtc gctgtactac atcatgaccg gcaagacctt cgatggtcgc   540
aaggctgccg agatgggcct ggtgaacgac agtgtgccgc tggccgagct gcgtgaaacc   600
acccgcgagt tggcgctgaa cctgctggaa agaacccgg tggtgctgcg tgccgcgaag   660
aatggcttca gccgttgccg cgagctgacc tgggaacaga acgaggacta cctctacgcc   720
aagctcgacc agtcgcgcct gctggacact accggcggcc gcgagcaggg catgaagcag   780
ttcctcgacg acaagagcat caagccaggc ctgcaggcct acaagcgctg a           831

<210> SEQ ID NO 48
<211> LENGTH: 786
<212> TYPE: DNA
<213> ORGANISM: Clostridium acetobutylicum

<400> SEQUENCE: 48
atggaactaa acaatgtcat ccttgaaaag gaaggtaaag ttgctgtagt taccattaac    60
agacctaaag cattaaatgc gttaaatagt gatacactaa agaaatggga ttatgttata   120
ggtgaaattg aaaatgatag cgaagtactt gcagtaattt taactggagc aggagaaaaa   180
tcatttgtag caggagcaga tatttctgag atgaaggaaa tgaataccat tgaaggtaga   240
aaattcggga tacttggaaa taagtgtttt agaagattag aacttcttga aaagcctgta   300
atagcagctg ttaatggttt tgctttagga ggcggatgcg aaatagctat gtcttgtgat   360
ataagaatag cttcaagcaa cgcaagattt ggtcaaccag aagtaggtct cggaataaca   420
```

```
cctggttttg gtggtacaca aagactttca agattagttg gaatgggcat ggcaaagcag    480
cttatattta ctgcacaaaa tataaaggca gatgaagcat taagaatcgg acttgtaaat    540
aaggtagtag aacctagtga attaatgaat acagcaaaag aaattgcaaa caaaattgtg    600
agcaatgctc cagtagctgt taagttaagc aaacaggcta ttaatagagg aatgcagtgt    660
gatattgata ctgctttagc atttgaatca gaagcatttg gagaatgctt ttcaacagag    720
gatcaaaagg atgcaatgac agctttcata gagaaaagaa aaattgaagg cttcaaaaat    780
agatag                                                               786
```

<210> SEQ ID NO 49
<211> LENGTH: 792
<212> TYPE: DNA
<213> ORGANISM: Pseudomonas putida

<400> SEQUENCE: 49

```
atgactttcc agcacatcct gttttccatc gaggacggcg ttgccttcct ttcattgaac     60
cgccccgagc agctgaacag cttcaatacg gccatgcacc tggaggtgcg cgaagcgctc    120
agacaagtgc gccagagcag tgacgcgcgg gtgctgctgc tgacggctga aggccgcggc    180
ttctgcgccg gccaggacct gtccgaccgc aacgttgccc aggcgccgga gatgccagac    240
ctgggccagt cgatcgacaa gttctacaac ccgctggtgc gcaccctgcg cgacctgcct    300
ttgccggtga tatgtgcggt caacggcgtg gcggccggtg ccggtgccaa cattcccttg    360
gcctgcgacc tggtgctggc cgcccgctcg gccagtttca tccaggcctt ctgcaagatc    420
ggcctggtgc cggactccgg cggtacttgg ctgctgccgc gcttggtcgg catggcccgg    480
gccaaggcgc tggccatgct gggcgagcgc cttggcgccg aacaggccga gcaatggggg    540
ctgatctacc gcgtggtgga tgatgcagcg ctgcgtgatg aagccctcac cctcgcccgc    600
cacctcgccg cccagcccac ctacggcctg acactgatca agcgcagcct caatgccagt    660
ttcgacaatg gttttgaggc gcagctggag ctggagcgcg acctgcagcg cctggcaggg    720
cgcagcgagg actaccgcga aggcgtgaac gccttcatga caaacgcac gccagccttc    780 aagggggcgct ga                                                       792
```

<210> SEQ ID NO 50
<211> LENGTH: 1164
<212> TYPE: DNA
<213> ORGANISM: Escherechia coli

<400> SEQUENCE: 50

```
atggaacagg ttgtcattgt cgatgcaatt cgcaccccga tgggccgttc gaagggcggt     60
gcttttcgta acgtgcgtgc agaagatctc tccgctcatt taatgcgtag cctgctggcg    120
cgtaacccgg cgctggaagc ggcggccctc gacgatattt actggggttg tgtgcagcag    180
acgctggagc agggttttaa tatcgcccgt aacgcggcgc tgctggcaga agtaccacac    240
tctgtcccgg cggttaccgt taatcgcttg tgtggttcat ccatgcaggc actgcatgac    300
gcagcacgaa tgatcatgac tggcgatgcg caggcatgtc tggttggcgg cgtggagcat    360
atgggccatg tgccgatgag tcacggcgtc gattttcacc ccggcctgag ccgcaatgtc    420
gccaaagcgg cgggcatgat gggcttaacg gcagaaatgc tggcgcgtat gcacggtatc    480
agccgtgaaa tgcaggatgc ctttgccgcg gtcacacg cccgcgcctg ggccgccacg    540
cagtcggccg catttaaaaa tgaaatcatc ccgaccggtg gtcacgatgc cgacggcgtc    600
```

```
ctgaagcagt ttaattacga cgaagtgatt cgcccggaaa ccaccgtgga agccctcgcc      660
acgctgcgtc cggcgtttga tccagtaaac ggtatggtaa cggcgggcac atcttctgca      720 cttt ccgatg gcgcagctgc catgctggtg atgagtgaaa gccgcgccca tgaattaggt    780
cttaagccgc gcgctcgtgt gcgttcgatg gcggtcgttg gttgtgaccc atcgattatg      840
ggttacggcc cggttccggc ctcgaaactg gcgctgaaaa agcggggct ttctgccagc       900 gatatcggcg tgtttgaaat gaacgaagcc tttgccgcgc agatcctgcc atgtattaaa      960
gatctgggac taattgagca gattgacgag aagatcaacc tcaacggtgg cgcgatcgcg     1020
ctgggtcatc cgctgggttg ttccggtgcg cgtatcagca ccacgctgct gaatctgatg     1080
gaacgcaaag acgttcagtt tggtctggcg acgatgtgta tcggtctggg tcagggtatt     1140
gcgacggtgt tgagcgggt ttaa                                             1164

<210> SEQ ID NO 51
<211> LENGTH: 2190
<212> TYPE: DNA
<213> ORGANISM: Escherechia coli

<400> SEQUENCE: 51
atgctttaca aaggcgacac cctgtacctt gactggctgg aagatggcat tgccgaactg       60
gtatttgatg ccccaggttc agttaataaa ctcgacactg cgaccgtcgc cagcctcggc      120
gaggccatcg gcgtgctgga acagcaatca gatctaaaag gctgctgct gcgttcgaac       180 aaagcagcct ttatcgtcgg tgctgatatc accgaatttt tgtccctgtt cctcgttcct      240
gaagaacagt taagtcagtg gctgcacttt gccaatagcg tgtttaatcg cctggaagat      300
ctgccggtgc cgaccattgc tgccgtcaat ggctatgcgc tgggcggtgg ctgcgaatgc      360
gtgctggcga ccgattatcg tctggcgacg ccggatctgc gcatcggtct gccggaaacc      420
aaactgggca tcatgcctgg ctttggcggt tctgtacgta tgccacgtat gctgggcgct      480
gacagtgcgc tggaaatcat tgccgccggt aaagatgtcg gcgcggatca ggcgctgaaa      540
atcggtctgg tggatggcgt agtcaaagca gaaaaactgg ttgaaggcgc aaaggcggtt      600
ttacgccagg ccattaacgg cgacctcgac tggaaagcaa acgtcagcc gaagctggaa       660 ccactaaaac tgagcaagat tgaagccacc atgagcttca ccatcgctaa agggatggtc      720
gcacaaacag cggggaaaca ttatccggcc cccatcaccg cagtaaaaac cattgaagct      780
gcggcccgtt ttggtcgtga agaagcctta aacctggaaa acaaaagttt tgtcccgctg      840
gcgcatacca acgaagcccg cgcactggtc ggcattttcc ttaacgatca atatgtaaaa      900
ggcaaagcga agaaactcac caaagacgtt gaaaccccga acaggccgc ggtgctgggt       960 gcaggcatta tgggcggcgg catcgcttac cagtctgcgt ggaaaggcgt gccggttgtc     1020
atgaaagata tcaacgacaa gtcgttaacc ctcggcatga ccgaagccgc gaaactgctg     1080
aacaagcagc ttgagcgcgg caagatcgat ggtctgaaaac tggctggcgt gatctccaca     1140
atccacccaa cgctcgacta cgccggattt gaccgcgtgg atattgtggt agaagcggtt     1200 gttgaaaaacc cgaaagtgaa aaaagccgta ctggcagaaa ccgaacaaaa agtacgccag     1260
gataccgtgc tggcgtctaa cacttcaacc attcctatca gcgaactggc caacgcgctg     1320
gaacgcccgg aaaacttctg cgggatgcac ttctttaacc cggtccaccg aatgccgttg     1380
gtagaaatta ttcgcggcga gaaaagctcc gacgaaaacca tcgcgaaagt tgtcgcctgg     1440
gcgagcaaga tgggcaagac gccgattgtg gttaacgact gccccggctt ctttgttaac     1500
cgcgtgctgt tcccgtattt cgccggtttc agccagctgc tgcgcgacgg cgcggatttc     1560
```

```
cgcaagatcg acaaagtgat ggaaaaacag tttggctggc cgatgggccc ggcatatctg    1620
ctggacgttg tgggcattga taccgcgcat cacgctcagg ctgtcatggc agcaggcttc    1680
ccgcagcgga tgcagaaaga ttaccgcgat gccatcgacg cgctgtttga tgccaaccgc    1740
tttggtcaga gaacggcct cggtttctgg cgttataaag aagacagcaa aggtaagccg    1800
aagaaagaag aagacgccgc cgttgaagac ctgctggcag aagtgagcca gccgaagcgc    1860
gatttcagcg aagaagagat tatcgcccgc atgatgatcc cgatggtcaa cgaagtggtg    1920
cgctgtctgg aggaaggcat tatcgccact ccggcggaag cggatatggc gctggtctac    1980
ggcctgggct tccctccgtt ccacggcggc gcgttccgct ggctggacac cctcggtagc    2040
gcaaaatacc tcgatatggc acagcaatat cagcacctcg gcccgctgta tgaagtgccg    2100
gaaggtctgc gtaataaagc gcgtcataac gaaccgtact atcctccggt tgagccagcc    2160
cgtccggttg gcgacctgaa aacggcttaa                                     2190
```

```
<210> SEQ ID NO 52
<211> LENGTH: 702
<212> TYPE: DNA
<213> ORGANISM: Escherechia coli

<400> SEQUENCE: 52
atgacaacct taagctgtaa agtgacctcg gtagaagcta tcacggatac cgtatatcgt     60
gtccgcatcg tgccagacgc ggccttttct tttcgtgctg gtcagtattt gatggtagtg    120
atggatgagc gcgacaaacg tccgttctca atggcttcga cgccggatga aaagggtt     180 atcgagctgc atattggcgc ttctgaaatc aacctttacg cgaaagcagt catggaccgc    240
atcctcaaag atcatcaaat cgtggtcgac attccccacg gagaagcgtg gctgcgcgat    300
gatgaagagc gtccgatgat tttgattgcg ggcggcaccg ggttctctta tgcccgctcg    360
attttgctga cagcgttggc gcgtaaccca aaccgtgata tcaccattta ctggggcggg    420
cgtgaagagc agcatctgta tgatctctgc gagcttgagg cgctttcgtt gaagcatcct    480
ggtctgcaag tggtgccggt ggttgaacaa ccggaagcgg ctggcgtgg gcgtactggc    540 accgtgttaa cggcggtatt gcaggatcac ggtacgctgg cagagcatga tatctatatt    600
gccggacgtt ttgagatggc gaaaattgcc cgcgatctgt tttgcagtga gcgtaatgcg    660
cgggaagatc gcctgtttgg cgatgcgttt gcatttatct ga                       702
```

```
<210> SEQ ID NO 53
<211> LENGTH: 2145
<212> TYPE: DNA
<213> ORGANISM: Escherechia coli

<400> SEQUENCE: 53
atggaaatga catcagcgtt taccct taat gttcgtctgg acaacattgc cgttatcacc     60
atcgacgtac cgggtgagaa aatgaatacc ctgaaggcgg agtttgcctc gcaggtgcgc    120
gccattatta agcaactccg tgaaaacaaa gagttgcgag gcgtggtgtt tgtctccgct    180
aaaccggaca acttcattgc tggcgcagac atcaacatga tcggcaactg caaaacggcg    240
caagaagcgg aagctctggc gcggcagggc caacagttga tggcggagat tcatgctttg    300
cccattcagg ttatcgcggg tattcatggc gcttgcctgg tggtgggct ggagttggcg    360 ctggcgtgcc acggtcgcgt ttgtactgac gatcctaaaa cggtgctcgg tttgcctgaa    420
gtacaacttg gattgttacc cggttcaggc ggcacccagc gtttaccgcg tctgataggc    480
```

| | |
|---|---|
| gtcagcacag cattagagat gatcctcacc ggaaaacaac ttcgggcgaa acaggcatta | 540 |
| aagctggggc tggtggatga cgttgttccg cactccattc tgctggaagc cgctgttgag | 600 |
| ctggcaaaga aggagcgccc atcttcccgc cctctacctg tacgcgagcg tattctggcg | 660 |
| gggccgttag gtcgtgcgct gctgttcaaa atggtcggca agaaaacaga acacaaaact | 720 |
| caaggcaatt atccggcgac agaacgcatc ctggaggttg ttgaaacggg attagcgcag | 780 |
| ggcaccagca gcggttatga cgccgaagct cgggcgtttg cgaactggc gatgacgcca | 840 |
| caatcgcagg cgctgcgtag tatcttttt gccagtacgg acgtgaagaa agatcccggc | 900 |
| agtgatgcgc cgcctgcgcc attaaacagc gtggggattt taggtggtgg cttgatgggc | 960 |
| ggcggtattg cttatgtcac tgcttgtaaa gcggggattc cggtcagaat taaagatatc | 1020 |
| aacccgcagg gcataaatca tgcgctgaag tacagttggg atcagctgga gggcaaagtt | 1080 |
| cgccgtcgtc atctcaaagc cagcgaacgt gacaaacagc tggcattaat ctccggaacg | 1140 |
| acggactatc gcggctttgc ccatcgcgat ctgattattg aagcggtgtt tgaaaatctc | 1200 |
| gaattgaaac aacagatggt ggcggaagtt gagcaaaatt gcgccgctca taccatcttt | 1260 |
| gcttcgaata cgtcatcttt accgattggt gatatcgccg ctcacgccac gcgacctgag | 1320 |
| caagttatcg gcctgcattt cttcagtccg gtggaaaaaa tgccgctggt ggagattatt | 1380 |
| cctcatgcgg ggacatcggc gcaaaccatc gctaccacag taaaactggc gaaaaaacag | 1440 |
| ggtaaaacgc caattgtcgt gcgtgacaaa gccggttttt acgtcaatcg catcttagcg | 1500 |
| ccttacatta atgaagctat ccgcatgttg acccaaggtg aacgggtaga gcacattgat | 1560 |
| gccgcgctag tgaaatttgg ttttccggta ggcccaatcc aacttttgga tgaggtagga | 1620 |
| atcgacaccg ggactaaaat tattcctgta ctggaagccg cttatggaga acgttttagc | 1680 |
| gcgcctgcaa atgttgtttc ttcaatttg aacgacgatc gcaaaggcag aaaaaatggc | 1740 |
| cggggtttct atctttatgg tcagaagggg cgtaaaagca aaaacaggt cgatcccgcc | 1800 |
| atttacccgc tgattggcac acaagggcag ggcgaatct ccgcaccgca ggttgctgaa | 1860 |
| cggtgtgtga tgttgatgct gaatgaagca gtacgttgtg ttgatgagca ggttatccgt | 1920 |
| agcgtgcgtg acggggatat tggcgcggta tttggcattg gttttccgcc atttctcggt | 1980 |
| ggaccgttcc gctatatcga ttctctcggc gcgggcgaag tggttgcaat aatgcaacga | 2040 |
| cttgccacgc agtatggttc ccgtttacc ccttgcgagc gtttggtcga tgggcgcg | 2100 |
| cgtggggaaa gttttggaa acaactgca actgacctgc aataa | 2145 |

<210> SEQ ID NO 54
<211> LENGTH: 720
<212> TYPE: DNA
<213> ORGANISM: Escherechia coli

<400> SEQUENCE: 54

| | |
|---|---|
| atggtcatta aggcgcaaag cccggcgggt ttcgcggaag agtacattat tgaaagtatc | 60 |
| tggaataacc gcttccctcc cgggactatt ttgcccgcag aacgtgaact ttcagaatta | 120 |
| attggcgtaa cgcgtactac gttacgtgaa gtgttacagc gtctggcacg agatggctgg | 180 |
| ttgaccattc aacatggcaa gccgacgaag gtgaataatt tctgggaaac ttccggttta | 240 |
| aatatccttg aaacactggc gcgactggat cacgaaagtg tgccgcagct tattgataat | 300 |
| ttgctgtcgg tgcgtaccaa tatttccact atttttattc gcaccgcgtt tcgtcagcat | 360 |
| cccgataaag cgcaggaagt gctggctacc gctaatgaag tggccgatca cgccgatgcc | 420 |
| tttgccgagc tggattacaa catattccgc ggcctggcgt ttgcttccgg caacccgatt | 480 |

-continued

| | |
|---|---|
| tacggtctga ttcttaacgg gatgaaaggg ctgtatacgc gtattggtcg tcactatttc | 540 |
| gccaatccgg aagcgcgcag tctggcgctg ggcttctacc acaaactgtc ggcgttgtgc | 600 |
| agtgaaggcg cgcacgatca ggtgtacgaa acagtgcgtc gctatgggca tgagagtggc | 660 |
| gagatttggc accggatgca gaaaaatctg ccgggtgatt tagccattca ggggcgataa | 720 |

<210> SEQ ID NO 55
<211> LENGTH: 1000
<212> TYPE: DNA
<213> ORGANISM: Castellaniella defragrans

<400> SEQUENCE: 55

| | |
|---|---|
| atgcggttca cattgaagac gacggcgatt gtgtcggccg ccgccctgct ggccggtttc | 60 |
| gggccgccgc cccgcgcggc ggaactgccg ccggggcggc tcgccaccac cgaggactat | 120 |
| ttcgcgcagc aggcgaagca ggccgtcacc cccgacgtga tggcccagct ggcctacatg | 180 |
| aactacatcg atttcatctc gcccttctac agcgggggct gctccttcga ggcctgggag | 240 |
| ctcaagcaca cgccgcagcg ggtcatcaag tattcgatcg ccttctatgc gtatggcctg | 300 |
| gccagcgtgg cgctcatcga cccgaagctg cgtgcgctcg ccggccatga cctggacatc | 360 |
| gcggtctcca agatgaagtg caagcgggtc tggggcgact gggaggaaga cgggttcggc | 420 |
| accgacccga tcgagaaaga gaacatcatg tacaagggcc acctgaacct gatgtacggc | 480 |
| ctctatcagc tggtgaccgg cagccgccgg tacgaagccg agcatgccca cctcacccgc | 540 |
| atcatccatg acgagatcgc ggccaacccc tttgccggca tcgtctgcga gccggacaat | 600 |
| tattttgtcc agtgcaattc ggtcgcctac ctgagcctgt gggtctatga ccggctgcat | 660 |
| ggcaccgact accgggcggc caccagggcc tggctggatt tcatccagaa ggacctgatc | 720 |
| gatcccgagc ggggcgcctt ctacctgtcc tatcaccccg agtccggcgc ggtgaagccg | 780 |
| tggatctcgg cgtatacgac agcctggacg ctcgccatgg tgcacggcat ggaccccgcc | 840 |
| tttttccgagc gctactaccc ccggttcaag cagaccttcg tcgaggtcta cgacgagggc | 900 |
| cgcaaggccc gggtgcgcga cacggccggc acggacgacg cggatggcgg ggtgggcctg | 960 |
| gcttcggcgt tcaccctgct gctggcccgc gagatgggcg | 1000 |

<210> SEQ ID NO 56
<211> LENGTH: 1000
<212> TYPE: DNA
<213> ORGANISM: Castellaniella defragrans

<400> SEQUENCE: 56

| | |
|---|---|
| atgcggttca cattgaagac gacggcgatt gtgtcggccg ccgccctgct ggccggtttc | 60 |
| gggccgccgc cccgcgcggc ggaactgccg ccggggcggc tcgccaccac cgaggactat | 120 |
| ttcgcgcagc aggcgaagca ggccgtcacc cccgacgtga tggcccagct ggcctacatg | 180 |
| aactacatcg atttcatctc gcccttctac agcgggggct gctccttcga ggcctgggag | 240 |
| ctcaagcaca cgccgcagcg ggtcatcaag tattcgatcg ccttctatgc gtatggcctg | 300 |
| gccagcgtgg cgctcatcga cccgaagctg cgtgcgctcg ccggccatga cctggacatc | 360 |
| gcggtctcca agatgaagtg caagcgggtc tggggcgact gggaggaaga cgggttcggc | 420 |
| accgacccga tcgagaaaga gaacatcatg tacaagggcc acctgaacct gatgtacggc | 480 |
| ctctatcagc tggtgaccgg cagccgccgg tacgaagccg agcatgccca cctcacccgc | 540 |
| atcatccatg acgagatcgc ggccaacccc tttgccggca tcgtctgcga gccggacaat | 600 |

```
tattttgtcc agtgcaattc ggtcgcctac ctgagcctgt gggtctatga ccggctgcat      660
ggcaccgact accgggcggc caccagggcc tggctggatt tcatccagaa ggacctgatc      720
gatcccgagc ggggcgcctt ctacctgtcc tatcaccccg agtccggcgc ggtgaagccg      780
tggatctcgg cgtatacgac agcctggacg ctcgccatgg tgcacggcat ggaccccgcc      840
ttttccgagc gctactaccc ccggttcaag cagaccttcg tcgaggtcta cgacgagggc      900
cgcaaggccc gggtgcgcga cacggccggc acggacgacg cggatggcgg ggtgggcctg      960
gcttcggcgt tcaccctgct gctggcccgc gagatgggcg                           1000

<210> SEQ ID NO 57
<211> LENGTH: 1392
<212> TYPE: DNA
<213> ORGANISM: Sulfolobus solfataricus

<400> SEQUENCE: 57
atgagatcaa aagaagattt cctaaagtcc ttaaaagatg aagaaatttt gtattatagg      60
gggaagttag tagaagatat aacaacacat cagatcttaa agacagccgc attgcacgca     120
gctaagttat atgaatacgc tgatagagtc tatgaggata taaaatggg aaaaatgagc      180 aagttcttta aggtaccttg acatctcaa gatttgctag atagacataa actaatttac      240
gatttaacga tgtattgtaa tggggtattt aacatttcac aagcaatagg aagtgatgcg      300
atctttgccc ttatgatcac ggcaaaacaa gttgatagaa atacggaac tgattactca      360 aaacgtgttg aaaaatattt tgagagagtt gctaagaaag atttaacgtt agccactgcc      420
cagactgacg ttaagggaga tcgaagtaag aggccttctg aacaagttga tccagatatg      480
tatgttagag tagttgatgt gaaaagcgat ggaatagttg ttagaggagc aaaggctcat      540
acaactcaat ctgcggtatc tgatgagatt attgtcatac caaccagagt aatgaggat      600 agcgataaag attacgcagt agcctttgcg gttccagcta atactaaagg tttgaagatg      660
tatattagac caattgatga aattgagggc aattcctcct cagtactcag tagaaaagat      720
tatgagctag aaacattaac cgtcttcaac gacgttttcg ttccttggga tagggtattt      780
ttatttaagg aatacgacta cgctggaaca ttggctatgc tatttgcaac cttccatagg      840
tttactgcat tatcgtatag gtcagcgacc atgaatctat atttgggagc atctaaagtg      900
gcatctcaag taaatggcat tgagaatgaa agcatgtga gagatgatat agttgatata      960
attctctaca aggaaattat gaggagtagc gcgatagctg cggctgtgta tccagtaaac     1020
atggagggta tagctgtgcc caacccgctt tttactaatg ttggtaaatt atactccaat     1080 atgcattttcc atgatgttgt aagagattta attgacattg ctgggggat aatagctact     1140 atgccctctc aagaagattt ggaaagtgat gaaggaaaga atattgttaa atatttaagg     1200
ggctcagttg atggagagga aagagcaaaa gtgttaaaac tagctaagga attaggggct     1260
agtacgttta ctggctattt gctaactggt atgatacatg cggaaggttc tatggaagct     1320
agcaaaatag agctattcag aagttataat tttaaggagg ccgagaactt agttaaaagg     1380
gtattaagct ag                                                       1392

<210> SEQ ID NO 58
<211> LENGTH: 1206
<212> TYPE: DNA
<213> ORGANISM: Escherichia coli

<400> SEQUENCE: 58
atgcgtgaag cctttattg tgacggaatt cgtacgccaa ttggtcgcta cggcggggca      60
```

```
ttatcaagtg ttcgggctga tgatctggct gctatccctt tgcgggaact gctggtgcga      120
aacccgcgtc tcgatgcgga gtgtatcgat gatgtgatcc tcggctgtgc taatcaggcg      180
ggagaagata accgtaacgt agcccggatg gcgactttac tggcggggct gccgcagagt      240
gtttccggca caaccattaa ccgcttgtgt ggttccgggc tggacgcact ggggtttgcc      300
gcacgggcga ttaaagcggg cgatggcgat ttgctgatcg ccggtggcgt ggagtcaatg      360
tcacgggcac cgtttgttat gggcaaggca gccagtgcat tttctcgtca ggctgagatg      420
ttcgatacca ctattggctg gcgatttgtg aacccgctca tggctcagca atttggaact      480
gacagcatgc cggaaacggc agagaatgta gctgaactgt taaaaatctc acgagaagat      540
caagatagtt ttgcgctacg cagtcagcaa cgtacggcaa aagcgcaatc ctcaggcatt      600
ctggctgagg agattgttcc ggttgtgttg aaaaacaaga aaggtgttgt aacagaaata      660
caacatgatg agcatctgcg cccggaaacg acgctggaac agttacgtgg gttaaaagca      720
ccatttcgtg ccaatggggt gattaccgca ggcaatgctt ccggggtgaa tgacggagcc      780
gctgcgttga ttattgccag tgaacagatg gcagcagcgc aaggactgac accgcgggcg      840
cgtatcgtag ccatggcaac cgccggggtg gaaccgcgcc tgatgggggct tggtccggtg      900 cctgcaactc gccgggtgct ggaacgcgca gggctgagta ttcacgatat ggacgtgatt      960
gaactgaacg aagcgttcgc ggcccaggcg ttgggtgtac tacgcgaatt ggggctgcct     1020
gatgatgccc cacatgttaa ccccaacgga ggcgctatcg ccttaggcca tccgttggga     1080
atgagtggtg cccgcctggc actggctgcc agccatgagc tgcatcggcg taacggtcgt     1140
tacgcattgt gcaccatgtg catcggtgtc ggtcagggca tcgccatgat tctggagcgt     1200
gtttga                                                               1206
```

<210> SEQ ID NO 59
<211> LENGTH: 1221
<212> TYPE: DNA
<213> ORGANISM: Pseudomonas putida

<400> SEQUENCE: 59

```
atgaatgaac cgacccacgc cgatgccttg atcatcgacg ccgtgcgcac gcccattggc       60
cgctatgccg gggccctgag cagcgtgcgc gccgacgacc tggcggccat cccgctcaaa      120
gccttgatcc agcgtcaccc cgaactggac tggaaagcca ttgatgacgt tatcttcggc      180
tgtgccaacc aggctggcga agacaaccgc aacgtggccc acatggcgag cctgctggcc      240
gggctgccac tcgaagtacc agggaccacg atcaaccgcc tgtgcggttc cggtctggat      300
gccatcggta atgcggcacg tgccctgcgc tgcggtgaag cggggctcat gctggccggt      360
ggtgtggagt ccatgtcgcg tgcaccgttt gtgatgggta agtcggagca ggcattcggg      420
cgtgcggccg agctgttcga caccaccatc ggctggcgtt tcgtcaaccc gctgatgaag      480
gccgcctacg gcatcgattc gatgccgaaa acggctgaaa acgtggccga acagttcggc      540
atctcgcgcg ccgaccagga tgcctttgcc ctgcgcagcc agcacaaagc cgcagcagct      600
caggcccgcg ccgcctggc gcgggaaatc gtgccggtcg aaatcccgca acgcaaaggc      660
ccagccaaag tggtcgagca tgacgagcac ccgcgcggcc acgaccct ggagcagctg       720 gctcggctcg ggacgccgtt tcgtgaaggc ggcagcgtaa cggcgggtaa tgcctccggc      780
gtgaatgacg gcgcttgcgc cctgctgctg ccagcagcg ccgcggcccg ccgccatggg      840
ttgaaggccc gcggccgcat cgtcggcatg gcggtggccg gggttgagcc caggctgatg      900
```

```
ggcattggtc cggtgcctgc gacccgcaag gtgctggcgc tcaccggcct ggcactggct      960
gacctggatg tcatcgaact caatgaggcc tttgccgccc aagggctggc cgtgttgcgc     1020
gagctgggcc tggccgacga cgacccgcga gtcaaccgca acggcggcgc catcgccctg     1080
ggccatcccc tgggcatgag cggtgccggt tggtgaccga ctgccttgca cgagcttgaa     1140
gaaacggccg ccgctacgcc cctgtgcacc atgtgcatcg gcgtaggcca aggcattgcc     1200
atgatcatcg agcgcctctg a                                               1221

<210> SEQ ID NO 60
<211> LENGTH: 1203
<212> TYPE: DNA
<213> ORGANISM: Pseudomonas putida

<400> SEQUENCE: 60
atgcacgacg tattcatctg tgacgccatc cgtaccccga tcggccgctt cggcggcgcc       60
ctggccagcg tgcgggccga cgacctggcc gccgtgccgc tgaaggcgct gatcgagcgc      120
aaccctggcg tgcagtggga ccaggtagac gaagtgttct cggctgcgc caaccaggcc      180
ggtgaagaca accgcaacgt ggcccgcatg gcactgctgc tggccggcct gccggaaagc      240
atcccgggcg tcaccctgaa ccgtctgtgc gcgtcgggca tggatgccgt cggcaccgcg      300
ttccgcgcca tcgccagcgg cgagatggac ctggtgattg ccggtggcgt cgagtcgatg      360
tcgcgcgccc cgttcgtcat gggcaaggct gaaagcgcct attcgcgcaa catgaagctg      420
gaagacacca ccattggctg cgttttcatc aacccgctga tgaagagcca gtacggtgtg      480
gattccatgc cggaaaccgc cgacaacgtg gccgacgact atcaggtttc gcgtgctgat      540
caggacgctt cgccctgcg cagccagcag aaggctgccg ctgcgcaggc tgccggcttc      600
tttgccgaag aaatcgtgcc ggtgcgtatc gctcacaaga agggcgaaat catcgtcgaa      660
cgtgacgaac acctgcgccc ggaaaccacg ctggaggcgc tgaccaagct caaaccggtc      720
aacgccccgg acaagacggt caccgccggc aacgcctcgg gcgtgaacga cggtgctgcg      780
gcgatgatcc tggcctcggc cgcagcggtg aagaaacacg gcctgactcc gcgtgcccgc      840
gttctgggca tggccagcgg cggcgttgcg ccacgtgtca tgggcattgg cccggtgccg      900
gcggtgcgca aactgaccga gcgtctgggg atagcggtaa gtgatttcga cgtgatcgag      960
cttaacgaag cgtttgccag ccaaggcctg gcggtgctgc gtgagctggg tgtggctgac     1020
gatgcgcccc aggtaaaccc taatggcggt gccattgccc tgggccaccc cctgggcatg     1080
agcggtgcac gcctggtact gactgcgttg caccagctgg agaagagtgg cggtcgcaag     1140
ggcctggcga ccatgtgtgt gggtgtcggc caaggtctgg cgttggccat cgagcgggtt     1200
tga                                                                   1203

<210> SEQ ID NO 61
<211> LENGTH: 1212
<212> TYPE: DNA
<213> ORGANISM: Acinetobacter calcoaceticus

<400> SEQUENCE: 61
atgacattaa aaacgctta tatcatcgat gccatccgta ctccattcgg tcgttatgcc        60
ggtggccttg cacctgtccg tgcagatgac cttggtgctg tgccgattaa agccctcatg      120
caacgtaacc caagtgtaga ttgggaacag gtcgatgatg tgatctatgg ctgtgccaac      180
caagccggtg aagataaccg taatgtcggt cgtatgtcag cacttcttgc aggttttacca     240
tatcaggtac cggcaaccac tattaaccgt ttatgcggtt cttcactcga tgccattgcc      300
```

-continued

```
attgcagccc gtgctattaa agcaggtgaa gcgaacttgg tgattgcagg tggtgtagaa      360
agcatgagcc gtgcgcctta tgtaatgggt aagtcagaca gtgcttttgg ccgtagccag      420
aagattgaag acaccaccat gggctggcgt tttattaacc caaaacttaa agaattgtat      480
ggtgtagaca ccatgcccca gactgccgaa aacgtggctg aacagtttaa cgtcaatcgt      540
gcagatcagg accagtttgc cttggtgagc caacaacgca ccgcaagcgc gcaagccaaa      600
ggcttttttt ctaaagaaat cgtggcagtt gaaatccctc agcgtaaggg tgatgctgtt      660
gtgattgata ctgatgaaca tccacgtgca tcaaccaccc ttgaaggttt aagcaaactt      720
aaatctgtgg ttaaagcaga tggcacagta acagcaggca atgcttcagg tattaatgat      780
ggtgcagcag ctctactgat tgcttctgat gaagcagttc aggcatacaa cctaaaaccc      840
cgcgccaaga ttattgcttc aacagcggtg ggtgtagaac cacggattat gggctttgct      900
ccagcaccag ccattaaaaa attacttaaa caagctaacc tgactttaga tcagatggat      960
gtaattgagc tcaatgaagc ttttgctgct caggctttgg cagtgacccg tgatttaggt     1020
ttgccagatg attctcacaa ggtaaaccca atggtggtg ccattgcttt gggtcatcca      1080
cttggtgctt caggtgcacg catcgtgact acagccttga accagcttga acaaacaggt     1140
ggtcgctacg ctttgtgttc aatgtgtatt ggggtgggcc aaggcatcgc attgattatt     1200
gagagagtct aa                                                          1212

<210> SEQ ID NO 62
<211> LENGTH: 1164
<212> TYPE: DNA
<213> ORGANISM: Aeromonas hydrophila

<400> SEQUENCE: 62
atgaaagacg tagtcattgt cgactgtatc cggaccccga tgggccggtc caagggcggc       60
gccttccgca acgtgcgtgc agaagacttg tccgcgcacc tgatgaaatc catcctgctg      120 cgcaaccccea acctcgaccc gaacgagatc gaggatatct actggggctg cgtgcagcag      180
accctggagc agggcttcaa catcgcccgc aacgcagcct tgctggccgg cattcccaag      240
caggtggggg cggtcaccgt caaccgcctg tgcggctcca gcatgcaggc gctgcacgat      300
gcctcccgcg ccattcaggt aggtgatggg gatatcttca tcatcggcgg tgtcgagcac      360
atgggccacg tgccgatgag ccacggggtg gacttccacc ccggcatggc caagtcggtg      420
gcgaaagcct ccggcatgat ggggctgacc gccgagatgc tcggcaagct gcacggcatc      480
agtcgtcagc agcaggacga gtttgccgcc gctcccatc gtcgcgctca cgccgccacc      540
gtggaaggac gtttcgccaa ggagatcgtc gggctggaag gcatgacgc cagcggcgcc      600 cgcttcttct acgactacga cgaggtgatc cgccccgaga ccacggtgga aaccctgagc      660
cagctgcgcc cggtgttcga cccggtcaac ggcaccgtca ccgccggcac ctcgtcggcc      720
ctgtccgatg cgccgccgc catgctggtg atgagtgcgg accgcgccaa ggcgctcggc      780
ctcaccccgc gcgccaagat acgtgccatg gccgtcgccg gctgcgatgc cgccatcatg      840
ggttacggcc cggtaccggc cacccagaag gcgctcaagc gggccggcct gaccatcggc      900
gacatcgacc tgttcgagct gaacgaggcg tttgccgccc agtccctgcc ttgcgtgaag      960
gatctgggtc tgcaagacgt ggtggatgag aaggtgaacc tgaacggcgg cgccatcgcc     1020
ctgggtcacc cgctcggctg ctccggcgcc cgcatctcca ccaccctgct caacctgatg     1080
gaagagaagg acgccaccct gggggttgcc accatgtgca tcggcctggg tcagggcatc     1140
```

```
gccaccgtgt tcgaacgagt gtaa                                          1164
```

<210> SEQ ID NO 63
<211> LENGTH: 1005
<212> TYPE: DNA
<213> ORGANISM: Aeromonas salmonicida

<400> SEQUENCE: 63

```
atggatattg tgattgttgc ggccaagcgt accccatgg gggccttcca gggagccttg     60
gccaacctga ctgcccccga gcttggcgct tgcgccattg ctgccgccat agcacaagcc   120
gggctcaagg gggagcagat cgatgaagcc tacatgggca atgtgctcag tgccggggtg   180
gggcaggcac ccgcccgtca ggctgtgttg aaggcaggtt tgccggagag tgtgccatgc   240
accactgtca acaaggtgtg tggttccggc atgaaggcgg tgatgctggc ggcagacagc   300
ttgcgtctgg gtgacaccga catagtgatc gccggtggca tggagagcat gagccgggcg   360
ccttacctgc tcgacaaggc gcgcagcggt tttcgcatgg gcatcagag cgtgctggat    420
catatgttcc tcgatggctt gcaggatgct tacgaaggcc agttgatggg cattatgcc    480
cagttgagtg cggatcgcgc cggtctggcc cgctccgaca tggacgcttt tgccatcgct   540
tccctgacgc gtgcgctggc tgcccagcag agcggtgctt tcaaggccga gctggcccag   600
gttactgtcg gtgacaccct gctgctcgcc gaggatgagc agcctgccaa ggccaggccc   660
gacaagatcc ctcatctgaa accggcattc agcaagcagg gcaccataac ggctgccaat   720
gccagctcca tctcggacgg agcggcggcg ctcatcctga tgcgagccga cacggcggcg   780
cagctgggcc tgcctgtgct ggccatggcg ggttgcaacc tgcctcatga caaggtgaac   840
gtgaacggcg gggcctgcgc actggggcat ccactggggg cgagtggtgc ccgtattctg   900
gttacgctca ttcatgcact gcatgcgcgc agtctgaaac ggggtgtggc aagcctgtgt   960
atcggtggag gggaggcgac tgccgtcgcc atcgagttga gctaa                  1005
```

<210> SEQ ID NO 64
<211> LENGTH: 1206
<212> TYPE: DNA
<213> ORGANISM: Pseudomonas aeroginosa

<400> SEQUENCE: 64

```
atgagccgcg aggtattcat ctgcgatgcc gtgcgcacgc cgatcggccg tttcggcggc    60
agtctttccg cggtgcgcgc cgacgacctc gcggcggtgc cgctgaaggc cctggtcgag   120
cgcaacccgg gggtcgactg gtcggcgctg acgaggtgt tcctcggctg cgccaaccag    180
gccggcgagg acaaccgtaa cgtggcgcgc atggcgctgc tgctggccgg tttgccggag   240
agcgtgcccg cgtcacccct caaccgcctc tgcgcctcgg ggatggacgc catcggcacg   300
gcgttccgcg ccatcgcctg cggcgagatg gagctggcca tcgccggcgg cgtcgagtcg   360
atgtcgcgcg cgccgtacgt gatgggcaag gccgatagcg ccttcgggcg cggccagaag   420
atcgaggaca ccaccatcgg ctggcgcttc gtcaacccgc tgatgaagga gcagtacggc   480
atcgacccga tgccgcagac cgccgacaac gtcgccgacg actatcgcgt gtcgcgtgcc   540
gaccaggatg ccttcgccct gcgcagccag cagcgcgccg gcaggcgca ggcggccggt    600
ttcttcgccg aggaaatcgt cccggtgacg attcgcgggc gcaagggcga cacctggtc    660
gagtacgacg agcatccgcg tcccgacacc accctggagg cgctggcccg gctcaagccg   720
gtcaacgggc cggagaagac cgtcaccgcc ggcaacgcgt ccggggtcaa cgacggcgcc   780
gccgcgctgg tcctggcctc cgccgaggca gtggagaagc acggcctgac tccgcgcgcg   840
```

```
cgggtgctgg gcatggccag cgccggcgtc gccccacgga tcatgggcat cggcccggtg      900
ccggcggtgc gcaagctgct gcggcgcctg gacctggcga tcgacgcctt cgacgtgatc      960
gaactcaacg aagccttcgc cagccagggc ctggcctgcc tgcgcgaact gggcgtggcc     1020
gacgacagtg agaaggtcaa cccgaacggc ggtgccatcg ccctcggcca cccgctgggg     1080
atgagcggtg cgcggctggt cctcaccgcg ctccatcaac ttgagaagag cggcggccgg     1140
cgcggcctgg cgaccatgtg cgtaggcgtc ggccaaggcc tggcgctggc catcgagcgg     1200
gtctga                                                                1206
```

<210> SEQ ID NO 65
<211> LENGTH: 1185
<212> TYPE: DNA
<213> ORGANISM: Ralstonia eutropha

<400> SEQUENCE: 65

```
atgacgcgtg aagtggtagt ggtaagcggt gtccgtaccg cgatcgggac ctttggcggc       60
agcctgaagg atgtggcacc ggcggagctg ggcgcactgg tggtgcgcga ggcgctggcg      120
cgcgcgcagg tgtcgggcga cgatgtcggc cacgtggtat tcggcaacgt gatccagacc      180
gagccgcgcg acatgtatct gggccgcgtc gcggccgtca acggcggggt gacgatcaac      240
gcccccgcgc tgaccgtgaa ccgcctgtgc ggctcgggcc tgcaggccat tgtcagcgcc      300
gcgcagacca tcctgctggg cgataccgac gtcgccatcg gcggcggcgc ggaaagcatg      360
agccgcgcac cgtacctggc gccggcagcg cgctggggcg cacgcatggg cgacgccggc      420
ctggtcgaca tgatgctggg tgcgctgcac gatcccttcc atcgcatcca catgggcgtg      480
accgccgaga atgtcgccaa ggaatacgac atctcgcgcg cgcagcagga cgaggccgcg      540
ctggaatcgc accgccgcgc ttcggcagcg atcaaggccg gctacttcaa ggaccagatc      600
gtcccggtgg tgagcaaggg ccgcaagggc gacgtgacct cgacaccga cgagcacgtg      660 cgccatgacg ccaccatcga cgacatgacc aagctcaggc cggtcttcgt caaggaaaac      720
ggcacggtca cggccggcaa tgcctcgggc ctgaacgacg ccgccgccgc ggtggtgatg      780
atggagcgcg ccgaagccga gcgccgcggc ctgaagccgc tggcccgcct ggtgtcgtac      840
ggccatgccg gcgtggaccc gaaggccatg gcatcggcc cggtgccggc gacgaagatc      900
gcgctggagc gcgccggcct gcaggtgtcg gacctggacg tgatcgaagc caacgaagcc      960
tttgccgcac aggcgtgcgc cgtgaccaag gcgctcggtc tggacccggc caaggttaac     1020 ccgaacgggct cgggcatctc gctgggccac ccgatcggcg ccaccggtgc cctgatcacg     1080
gtgaaggcgc tgcatgagct gaaccgcgtg cagggccgct acgcgctggt gacgatgtgc     1140
atcggcggcg gcagggcat tgccgccatc ttcgagcgta tctga                      1185
```

<210> SEQ ID NO 66
<211> LENGTH: 1188
<212> TYPE: DNA
<213> ORGANISM: Rhodopseudomonas palustris

<400> SEQUENCE: 66

```
atgaccgagg ccgttatcgt ttcaaccgcg cgcacgccga tcggcaaggc gtatcgcggc       60
gccctcaacg ccaccgaggg tgccacactg ctcggccacg ccatcgagca cgcggtgaag      120
cgcgccggta tcgacccgaa ggaggtcgag acgtggtga tgggcgcggc gatgcagcag      180
ggcgccaccg gcggcaacat cgcccgcaag gcgctgctgc gcgccggcct gccggtgact      240
```

```
accgccggca ccaccatcga tcggcagtgc gcctccggcc tgcaggcgat cgcgctcgcc      300
gctcgtcgg tgctgttcga cggcgtcgag atcgcggtcg cggtggcgg cgagtcgatc       360
tcgctcgtcc agaacgacaa gatgaacacc ttccacgccg tcgatccggc gctcgaggcg     420
atcaagggcg acgtctacat ggcgatgctc gacaccgccg aaaccgtggc gaagcgctac     480
ggcatctcgc gcgagcgcca ggacgagtat tcgctggaaa gccagcgccg caccgcggct    540
gcgcagcagg gcggcaagtt caacgacgag atcgcgccga tctcgaccaa gatgggcgtc    600
gtcgacaagg ccaccggcgc ggtgtcgttc aaggatatca cgctgtcgca ggacgaaggc    660
ccgcggccgg aaaccaccgc tgaaggtctc gccggtctta aggccgtgcg tggtgaaggc    720
ttcaccatca ctgccggcaa tgccagccag ctgtcggacg gcgcctcggc cacggtgatc    780
atgagcgaca gacgcggc cgcgaagggc ctcaagccgc tcggcatctt ccgcggcatg     840
gtctcctacg gctgcgagcc ggacgagatg ggcatcggcc cggtgttcgc ggtgccgcgc    900
ctgttgaagc gccatggtct cagcgtcgac gacatcggtc tgtgggagct gaacgaagcc    960
ttcgccgtgc aggtgctgta ctgccgcgac aagctcggca tcgatccgga gaagctcaat   1020
gtcaacggcg cgcgatctc ggtcggccac ccctacggca tgtcgggtgc acgcctcgcc    1080
ggccacgcgc tgatcgaagg ccgtcgccgc aaggcgaagt acgcggtggt cacgatgtgc   1140
gtcggcggcg gcatgggctc cgccggcctg ttcgagatcg tgcactga                1188
```

<210> SEQ ID NO 67
<211> LENGTH: 1293
<212> TYPE: DNA
<213> ORGANISM: Syntrophus aciditrophicus

<400> SEQUENCE: 67

```
atgaaagatg tcgtcatcgt aagcggcgcc agaaccgccg tgggtgcttt tggcggatcg      60
ctgaaaggcg tgagagttac ggatttggga gcgctggtca tcaaagaggc catcaagaga     120
gcggggctgc ggccggccat cagtgaagaa gtgaaaggct gccgttgcga taccttcgga    180
gaattcgaca gaccgaaat caacaagaaa tattatgatt acgatgaatc cctgaccccc      240
gtttatttcg acgagtgcat catggggaac tgcctgatcg ccggcctggg acagaatccc    300
ggccgtcagt ccagcatcta tgccggtctg cccgaagaaa cgaacaccat cacagtgaac    360
aaggtctgcg catccggcat gaaagccatc accctggccg cccagatcat caaagccggc    420
gatgccgaca tcatggtggc cggcggcatg gaaaacatga gcaatgtacc ctacgccctg    480
cccgacgccc gctggggata ccggatgaac atgcctacgg gttccatcat cgacctcatg    540
gttcatgatg gtctctggga aatcttcaac ggctatcaca tgggattcac ggcggaaaat    600
atcgcctccc gttatggaat cagccgtcag gcccaggacg agctggccct catgagccat    660
cagcgcgccc gtgcggccat cgccagcggc gccgtcgccg atgaaatcat ccccgttccg    720
ctgcccgtga agaaaggcgc ggctccgcag ttttttctccg tcgacgagcg tcccatggac    780
accagcctgg aaaagatggc gaagctggcc ccagtcttca agaaggacgg aaccgtcacg    840
gcggccaacg cctcgggtat caatgacggt gcggcggctg tcgtcgtgat gagcgccgac    900
aaggcaaagg aactgggcct caaaccgctg gcgaagatcc tcggctatgc ctccggcggc    960
gtcgatccgg catacatggg tctgggtccg attccggcaa cccgcaaggt cttcaagaaa   1020
ctcggcctga ccatgaagga catggacatc gtggaactga acgaggcctt tgcatcccag   1080
gccctgggct gctccagga atgggtgtg atctgacca aaaccaatct caacggcagc      1140
gggatctcca tcggtcaccc cgtcggctgc accgcgcccc ggatcaccta cagcttggcc   1200
```

```
atgcagctgc agaagaagaa cgcgcacctc ggactcgcca cgctgtgtat cggtggcgga    1260
caggggatgg ccattgtcct ggaaagagtg taa                                 1293
```

<210> SEQ ID NO 68
<211> LENGTH: 1209
<212> TYPE: DNA
<213> ORGANISM: Cupriavidus necator

<400> SEQUENCE: 68

```
atgcgcagag ctgcaatcgt cactcccctc cgcacgcccg tcggcacctt cggcggcagc     60
ctgcgcccgg tgcccgtgga ggagctggcc gccaccgccg tgcgcgccgt ggtggaacgc    120
agcggcatcg atcccgcgcg tatcgatgac gtggtctttg cccagtccta cgccaacagc    180
gaagtgccct cgctcggccg ctgggccgcg ctgcaggccg gctgccggt cgaagtgccg     240 ggcatgcagc tggaccgccg ctgcggcggc ggcctgcagg ccatcgtcac ggcctcgatg    300
atggtgcaaa gcgcgccgc cgacgtggtg atcgcgggcg cgtcgagag catgagcaat     360 atcgagtact acaccaccga catgcgctgg ggcgcgcgct cgggcaatgt gcgcttcttc    420
gaccgcctcg accgcggccg tgaacgctcc cagccggtcg agcgcttcgg caagatctcc    480
gggatgatcg agacggccga gaacctggcg cgcgactacg gcatcagccg cgaagcggcc    540
gatgtcttcg ccgcccgcag ccacgcacgc gccgcggcag cctgggaggc cggccgcttc    600
gatgccgagg tcgtccccgt gcaggtgccc cagcgcaagg gcgatccggt gcggttcgcg    660
cgcgacgaag gtttccgccc ggaaaccacg cgtgaaagcc tgggcaagct cgcacgctg    720 atgccgaacg gtaccgtcac cgccggcaac gccagccagc agaacgacgc ctcggccgcg    780
tgcctgatcg tggccgaaga caagctggcc gaattgggcc tcacccccat ggcctcgctg    840
gtgggctggg cggcggctgg ctgcgagccc tcgcacatgg gcatcggccc ggtgcccgcg    900
gtgaagaagc tgctggcgcg cctgaacctg acgctggacc ggatggacct ggtcgagctg    960
aacgaagcct tcgcctgcca ggtgctggcc gtgctcaagg gctgggaatg gcatgaccag   1020
gacgcgatcg agcagaagct caacgtgaac ggctcgggca tctcgcttgg ccatccgatc   1080
ggcgccaccg gcgtgcgcat cctggccacg ctgctgcacg aactgcagcg ccgcggcggc   1140
cgctatggcc tggaaaccat gtgcatcggc ggcggccagg gtattgccgc ggtcttcgaa   1200
cgctactga                                                          1209
```

<210> SEQ ID NO 69
<211> LENGTH: 1185
<212> TYPE: DNA
<213> ORGANISM: Escherichia coli

<400> SEQUENCE: 69

```
atgaaaaatt gtgtcatcgt cagtgcggta cgtactgcta tcggtagttt taacggttca    60
ctcgcttcca ccagcgccat cgacctgggg gcgacagtaa ttaaagccgc cattgaacgt    120
gcaaaaatcg attcacaaca cgttgatgaa gtgattatgg gtaacgtgtt acaagccggg   180
ctggggcaaa atccgcgcg tcaggcactg ttaaaaagcg gctggcaga acggtgtgc     240 ggattcacgg tcaataaagt atgtggttcg ggtcttaaaa gtgtggcgct tgccgcccag   300
gccattcagg caggtcaggc gcagagcatt gtggcggggg gtatggaaaa tatgagttta   360
gccccctact actcgatgc aaaagcacgc tctggttatc gtcttggaga cggacaggtt    420
tatgacgtaa tcctgcgcga tggcctgatg tgcgccaccc atggttatca tatggggatt   480
```

| | |
|---|---|
| accgccgaaa acgtggctaa agagtacgga attacccgtg aaatgcagga tgaactggcg | 540 |
| ctacattcac agcgtaaagc ggcagccgca attgagtccg gtgcttttac agccgaaatc | 600 |
| gtcccggtaa atgttgtcac tcgaaagaaa accttcgtct tcagtcaaga cgaattcccg | 660 |
| aaagcgaatt caacggctga agcgttaggt gcattgcgcc cggccttcga taaagcagga | 720 |
| acagtcaccg ctgggaacgc gtctggtatt aacgacggtg ctgccgctct ggtgattatg | 780 |
| gaagaatctg cggcgctggc agcaggcctt accccctgg ctcgcattaa agttatgcc | 840 |
| agcggtggcg tgccccccgc attgatgggt atggggccag tacctgccac gcaaaaagcg | 900 |
| ttacaactgg cggggctgca actgcggat attgatctca ttgaggctaa tgaagcattt | 960 |
| gctgcacagt tccttgccgt tgggaaaaac ctgggctttg attctgagaa agtgaatgtc | 1020 |
| aacggcgggg ccatcgcgct cgggcatcct atcggtgcca gtggtgctcg tattctggtc | 1080 |
| acactattac atgccatgca ggcacgcgat aaaacgctgg ggctggcaac actgtgcatt | 1140 |
| ggcggcggtc agggaattgc gatggtgatt gaacggttga attaa | 1185 |

<210> SEQ ID NO 70
<211> LENGTH: 1179
<212> TYPE: DNA
<213> ORGANISM: Clostridium acetobutylicum

<400> SEQUENCE: 70

| | |
|---|---|
| atgaaagaag ttgtaatagc tagtgcagta agaacagcga ttggatctta tggaaagtct | 60 |
| cttaaggatg taccagcagt agatttagga gctacagcta taaggaagc agttaaaaaa | 120 |
| gcaggaataa aaccgagga tgttaatgaa gtcatttag gaatgttct tcaagcaggt | 180 |
| ttaggacaga atccagcaag acaggcatct tttaaagcag gattaccagt tgaaattcca | 240 |
| gctatgacta ttaataaggt ttgtggttca ggacttagaa cagttagctt agcagcacaa | 300 |
| attataaaag caggagatgc tgacgtaata atagcaggtg gtatggaaaa tatgtctaga | 360 |
| gctccttact tagcgaataa cgctagatgg ggatatagaa tgggaaacgc taaatttgtt | 420 |
| gatgaaatga tcactgacgg attgtgggat gcatttaatg attaccacat gggaataaca | 480 |
| gcagaaaaca tagctgagag atggaacatt tcaagagaag aacaagatga gtttgctctt | 540 |
| gcatcacaaa aaaagctga agaagctata aaatcaggtc aatttaaaga tgaaatagtt | 600 |
| cctgtagtaa ttaaaggcag aaagggagaa actgtagttg atacagatga gcaccctaga | 660 |
| tttggatcaa ctatagaagg acttgcaaaa ttaaaacctg ccttcaaaaa agatggaaca | 720 |
| gttacagctg gtaatgcatc aggattaaat gactgtgcag cagtacttgt aatcatgagt | 780 |
| gcagaaaaag ctaaagagct tggagtaaaa ccacttgcta agatagtttc ttatggttca | 840 |
| gcaggagttg acccagcaat aatgggatat ggaccttct atgcaacaaa agcagctatt | 900 |
| gaaaaagcag gttggacagt tgatgaatta gatttaatag aatcaaatga agcttttgca | 960 |
| gctcaaagtt tagcagtagc aaaagatta aaatttgata tgaataaagt aaatgtaaat | 1020 |
| ggaggagcta ttgcccttgg tcatccaatt ggagcatcag gtgcaagaat actcgttact | 1080 |
| cttgtacacg caatgcaaaa aagagatgca aaaaaggct tagcaacttt atgtataggt | 1140 |
| ggcggacaag aacagcaat attgctagaa aagtgctag | 1179 |

<210> SEQ ID NO 71
<211> LENGTH: 1179
<212> TYPE: DNA
<213> ORGANISM: Clostridium acetobutylicum

<400> SEQUENCE: 71

```
atgagagatg tagtaatagt aagtgctgta agaactgcaa taggagcata tggaaaaaca    60
ttaaaggatg tacctgcaac agagttagga gctatagtaa taaaggaagc tgtaagaaga   120
gctaatataa atccaaatga gattaatgaa gttattttg gaaatgtact tcaagctgga   180
ttaggccaaa acccagcaag acaagcagca gtaaaagcag gattaccttt agaaacacct   240
gcgtttacaa tcaataaggt ttgtggttca ggtttaagat ctataagttt agcagctcaa   300
attataaaag ctggagatgc tgataccatt gtagtaggtg tatggaaaa tatgtctaga   360 tcaccatatt tgattaacaa tcagagatgg ggtcaaagaa tgggagatag tgaattagtt   420
gatgaaatga taaaggatgg tttgtgggat gcatttaatg gatatcatat gggagtaact   480
gcagaaaata ttgcagaaca atggaatata acaagagaag agcaagatga attttcactt   540
atgtcacaac aaaaagctga aaaagccatt aaaaatggag aatttaagga tgaaatagtt   600
cctgtattaa taaagactaa aaaaggtgaa atagtctttg atcaagatga atttcctaga   660
ttcggaaaca ctattgaagc attaagaaaa cttaaaccta ttttcaagga aaatggtact   720
gttacagcag gtaatgcatc cggattaaat gatggagctg cagcactagt aataatgagc   780
gctgataaag ctaacgctct cggaataaaa ccacttgcta agattacttc ttacggatca   840 tatgggtag atccatcaat aatgggatat ggagcttttt atgcaactaa agctgcctta   900
gataaaatta atttaaaacc tgaagactta gatttaattg aagctaacga ggcatatgct   960
tctcaaagta tagcagtaac tagagattta aatttagata tgagtaaagt taatgttaat  1020
ggtggagcta tagcacttgg acatccaata ggtgcatctg gtgcacgtat tttagtaaca  1080
ttactatacg ctatgcaaaa aagagattca aaaaaaggtc ttgctactct atgtattggt  1140
ggaggtcagg gaacagctct cgtagttgaa agagactaa                         1179
```

<210> SEQ ID NO 72
<211> LENGTH: 1197
<212> TYPE: DNA
<213> ORGANISM: Saccahromyces cerevisiae

<400> SEQUENCE: 72

```
atgtctcaga acgtttacat tgtatcgact gccagaaccc caattggttc attccagggt    60
tctctatcct ccaagacagc agtggaattg ggtgctgttg ctttaaaagg cgccttggct   120
aaggttccag aattggatgc atccaaggat tttgacgaaa ttattttgg taacgttctt   180 tctgccaatt tgggccaagc tccggccaga caagttgctt ggctgccgg tttgagtaat   240 catatcgttg caagcacagt taacaaggtc tgtgcatccg ctatgaaggc aatcattttg   300
ggtgctcaat ccatcaaatg tggtaatgct gatgttgtcg tagctggtgg ttgtgaatct   360
atgactaacg caccatacta catgccagca gcccgtgcgg gtgccaaatt tggccaaact   420
gttcttgttg atggtgtcga aagagatggg ttgaacgatg cgtacgatgg tctagccatg   480
ggtgtacacg cagaaaagtg tgcccgtgat tgggatatta ctagagaaca acaagacaat   540
tttgccatcg aatcctacca aaaatctcaa aaatctcaaa aggaaggtaa attcgacaat   600
gaaattgtac tgttaccat taagggattt agaggtaagc ctgatactca agtcacgaag   660
gacgaggaac ctgctagatt acacgttgaa aaattgagat ctgcaaggac tgttttccaa   720
aaagaaaacg gtactgttac tgccgctaac gcttctccaa tcaacgatgg tgctgcagcc   780
gtcatcttgg tttccgaaaa agttttgaag gaaaagaatt tgaagccttt ggctattatc   840
aaaggttggg gtgaggccgc tcatcaacca gctgatttta catgggctcc atctcttgca   900
```

```
gttccaaagg ctttgaaaca tgctggcatc gaagacatca attctgttga ttactttgaa      960
ttcaatgaag cctttcggt tgtcggtttg gtgaacacta agattttgaa gctagaccca     1020
tctaaggtta atgtatatgg tggtgctgtt gctctaggtc acccattggg ttgttctggt     1080
gctagagtgg ttgttacact gctatccatc ttacagcaag aaggaggtaa gatcggtgtt     1140
gccgccattt gtaatggtgg tggtggtgct tcctctattg tcattgaaaa gatatga        1197
```

<210> SEQ ID NO 73
<211> LENGTH: 2283
<212> TYPE: DNA
<213> ORGANISM: Escherichia coli

<400> SEQUENCE: 73

```
atgtccgagc ttaatgaaaa gttagccaca gcctgggaag gttttaccaa aggtgactgg       60
cagaatgaag taaacgtccg tgacttcatt cagaaaaact acactccgta cgagggtgac      120
gagtccttcc tggctggcgc tactgaagcg accaccaccc tgtgggacaa agtaatggaa      180
ggcgttaaac tggaaaaccg cactcacgcg ccagttgact ttgacaccgc tgttgcttcc      240
accatcacct ctcacgacgc tggctacatc aacaagcagc ttgagaaaat cgttggtctg      300
cagactgaag ctccgctgaa acgtgctctt atcccgttcg gtggtatcaa aatgatcgaa      360
ggttcctgca agcgtacaa ccgcgaactg gatccgatga tcaaaaaaat cttcactgaa      420
taccgtaaaa ctcacaacca gggcgtgttc gacgtttaca ctccggacat cctgcgttgc      480
cgtaaatctg gtgttctgac cggtctgcca gatgcatatg gccgtggccg tatcatcggt      540
gactaccgtc gcgttgcgct gtacggtatc gactacctga tgaaagacaa actggcacag      600
ttcacttctc tgcaggctga tctggaaaac ggcgtaaacc tggaacagac tatccgtctg      660
cgcgaagaaa tcgctgaaca gcaccgcgct ctgggtcaga tgaaagaaat ggctgcgaaa      720
tacggctacg acatctctgg tccggctacc aacgctcagg aagctatcca gtggactt ac      780 ttcggctacc tggctgctgt taagtctcag aacggtgctg caatgtcctt cggtcgtacc      840
tccaccttcc tggatgtgta catcgaacgt gacctgaaag ctggcaagat caccgaacaa      900
gaagcgcagg aaatggttga ccacctggtc atgaaactgc gtatggttcg cttcctgcgt      960
actccggaat acgatgaact gttctctggc gacccgatct gggcaaccga atctatcggt     1020
ggtatgggcc tcgacggtcg taccctggtt accaaaaaca gcttccgttt cctgaacacc     1080
ctgtacacca tgggtccgtc tccggaaccg aacatgacca ttctgtggtc tgaaaaactg     1140
ccgctgaact tcaagaaatt cgccgctaaa gtgtccatcg acacctcttc tctgcagtat     1200
gagaacgatg acctgatgcg tccggacttc aacaacgatg actacgctat tgcttgctgc     1260
gtaagcccga tgatcgttgg taaacaaatg cagttcttcg gtgcgcgtgc aaacctggcg     1320
aaaaccatgc tgtacgcaat caacggcggc gttgacgaaa aactgaaaat gcaggttggt     1380
ccgaagtctg aaccgatcaa aggcgatgtc ctgaactatg atgaagtgat ggagcgcatg     1440
gatcacttca tggactggct ggctaaacag tacatcactg cactgaacat catccactac     1500
atgcacgaca agtacagcta cgaagcctct ctgatggcgc tgcacgaccg tgacgttatc     1560
cgcaccatgg cgtgtggtat cgctggtctg tccgttgctg ctgactccct gtctgcaatc     1620
aaatatgcga agttaaaccc gattcgtgac gaagacggtc tggctatcga cttcgaaatc     1680
gaaggcgaat accgcagtt tggtaacaat gatccgcgtg tagatgacct ggctgttgac     1740
ctggtagaac gtttcatgaa gaaaattcag aaactgcaca cctaccgtga cgctatcccg     1800
actcagtctg ttctgaccat cacttctaac gttgtgtatg gtaagaaaac gggtaacacc     1860
```

```
ccagacggtc gtcgtgctgg cgcgccgttc ggaccgggtg ctaacccgat gcacggtcgt    1920
gaccagaaag gtgcagtagc ctctctgact tccgttgcta aactgccgtt tgcttacgct    1980
aaagatggta tctcctacac cttctctatc gttccgaacg cactgggtaa agacgacgaa    2040
gttcgtaaga ccaacctggc tggtctgatg gatggttact ccaccacga agcatccatc    2100 gaaggtggtc agcacctgaa cgttaacgtg atgaaccgtg aaatgctgct cgacgcgatg    2160 gaaaaccgg aaaatatcc gcagctgacc atccgtgtat ctggctacgc agtacgtttc    2220
aactcgctga ctaaagaaca gcagcaggac gttattactc gtaccttcac tcaatctatg    2280
taa                                                                  2283

<210> SEQ ID NO 74
<211> LENGTH: 741
<212> TYPE: DNA
<213> ORGANISM: Escherichia coli

<400> SEQUENCE: 74
atgtcagtta ttggtcgcat tcactccttt gaatcctgtg gaaccgtaga cggcccaggt      60
attcgcttta tcacctttt ccagggctgc ctgatgcgct gcctgtattg tcataaccgc     120
gacacctggg acacgcatgg cggtaaagaa gttaccgttg aagatttgat gaaggaagtg     180
gtgacctatc gccactttat gaacgcttcc ggcggcggcg ttaccgcatc cggcggtgaa     240
gcaatcctgc aagctgagtt tgttcgtgac tggttccgcg cctgcaaaaa agaaggcatt     300
catacctgtc tggacaccaa cggttttgtt cgtcgttacg atccggtgat tgatgaactg     360
ctggaagtaa ccgacctggt aatgctcgat ctcaaacaga tgaacgacga gatccaccaa     420
aatctggttg gagtttccaa ccaccgcacg ctggagttcg ctaaatatct ggcgaacaaa     480
aatgtgaagg tgtggatccg ctacgttgtt gtcccaggct ggtctgacga tgacgattca     540
gcgcatcgcc tcggtgaatt tacccgtgat atgggcaacg ttgagaaaat cgagcttctc     600
ccctaccacg agctgggcaa acacaaatgg gtggcaatgg gtgaagagta caaactcgac     660
ggtgttaaac caccgaagaa agagaccatg aacgcgtga aaggcattct tgagcagtac     720
ggtcataagg taatgttcta a                                              741

<210> SEQ ID NO 75
<211> LENGTH: 2364
<212> TYPE: DNA
<213> ORGANISM: Lactococcus lactis

<400> SEQUENCE: 75
atgaaaaccg aagttacgga aaatatcttt gaacaagctt gggatggttt taaaggaacc      60
aactggcgcg ataaagcaag cgttactcgc tttgtacaag aaaactacaa accatatgat     120
ggtgatgaaa gctttcttgc tgggccaaca gaacgtacac ttaaagtaaa gaaaattatt     180
gaagatacaa aaaatcacta cgaagaagta ggatttccct tcgatactga ccgcgtaacc     240
tctattgata aaatccctgc tggatatatc gatgctaatg ataaagaact tgaactcatc     300
tatgggatgc aaaatagcga acttttccgc ttgaatttca tgccaagagg tggacttcgt     360
gttgctgaaa gatttttgac agaacacggt ctctcagttg acccaggctt gcatgatgtt     420
ttgtcacaaa caatgacttc tgtaaatgat ggaatctttc gtgcttatac ttcagcaatt     480
cgtaaagcac gtcatgctca tactgtaaca ggtttgccag atgcttactc tcgtggacgt     540
atcattggtg tctatgcacg tcttgccctt tacggtgctg attaccttat gaaggaaaaa     600
```

| | | |
|---|---|---|
| gcaaaagaat gggatgcaat cactgaaatt aacgaagaaa acattcgtct taaagaagaa | 660 | |
| attaatatgc aataccaagc tttgcaagaa gttgtaaact ttggtgcttt atatggtctt | 720 | |
| gatgtttcac gtccagctat gaacgtaaaa gaagcaatcc aatgggttaa catcgcttat | 780 | |
| atggcagtat gtcgtgtcat taatggagct gcaacttcac ttggacgtgt tccaatcgtt | 840 | |
| cttgatatct ttgcagaacg tgaccttgct cgtggaacat ttactgaaca agaaattcaa | 900 | |
| gaatttgttg atgatttcgt tttgaagctt cgtacaatga aatttgcgcg tgcagctgct | 960 | |
| tatgatgaac tttattctgg tgacccaaca ttcatcacaa catctatggc tggtatgggt | 1020 | |
| aatgacggac gtcaccgtgt cactaaaatg gactaccgtt tcttgaacac acttgataca | 1080 | |
| atcggaaatg ctccagaacc aaacttgaca gtcctttggg attctaaact tccttactca | 1140 | |
| ttcaaacgtt attcaatgtc tatgagccac aagcattctt ctattcaata tgaaggtgtt | 1200 | |
| gaaacaatgg ctaaagatgg atatggcgaa atgtcatgta tctcttgttg tgtctcacca | 1260 | |
| cttgatccag aaaatgaaga aggacgtcat aacctccaat actttggtgc gcgtgtaaac | 1320 | |
| gtcttgaaag caatgttgac tggtttgaac ggtggttatg atgacgttca taagattat | 1380 | |
| aaagtattcg acatcgaacc tgttcgtgac gaaattcttg actatgatac agttatggaa | 1440 | |
| aactttgaca atctctcga ctggttgact gatacttatg ttgatgcaat gaatatcatt | 1500 | |
| cattacatga ctgataaata taactatgaa gcagttcaaa tggccttctt gcctactaaa | 1560 | |
| gttcgtgcta acatgggatt tggtatctgt ggattcgcaa atacagttga ttcactttca | 1620 | |
| gcaattaaat atgctaaagt taaaacattg cgtgatgaaa atggctatat ctacgattac | 1680 | |
| gaagtagaag gtgatttccc tcgttatggt gaagatgatg atcgtgctga tgatattgct | 1740 | |
| aaacttgtca tgaaaatgta ccatgaaaaa ttagcttcac acaaacttta caaaaatgct | 1800 | |
| gaagctactg tttcacttt gacaattaca tctaacgttg cttactctaa acaaactggt | 1860 | |
| aattctccag tacataaagg agtattcctc aatgaagatg gtacagtaaa taaatctaaa | 1920 | |
| cttgaattct tctcaccagg tgctaaccca tctaataaag ctaagggtgg ttggttgcaa | 1980 | |
| aatcttcgct cattggctaa gttggaattc aaagatgcaa atgatggtat ttcattgact | 2040 | |
| actcaagttt cacctcgtgc acttggtaaa actcgtgatg aacaagtgga taacttggtt | 2100 | |
| caaattcttg atggatactt cacaccaggt gctttgatta atggtactga atttgcaggt | 2160 | |
| caacacgtta acttgaacgt aatggaccct taaagatgttt acgataaaat catgcgtggt | 2220 | |
| gaagatgtta tcgttcgtat ctctggttac tgtgtcaata ctaaatacct cacaccagaa | 2280 | |
| caaaaacaag aattaactga acgtgtcttc catgaagttc tttcaaacga tgatgaagaa | 2340 | |
| gtaatgcata cttcaaacat ctaa | 2364 | |

<210> SEQ ID NO 76
<211> LENGTH: 2325
<212> TYPE: DNA
<213> ORGANISM: Streptococcus equinus

<400> SEQUENCE: 76

| | | |
|---|---|---|
| atggcgactg ttaaaacaaa tgcagatgtt tttgaaaaag cctgggaagg ctttaaaggt | 60 | |
| actgactgga agaaaaagc cagcgtttct cgcttcgttc aagctaacta cacaccatat | 120 | |
| gatggtgatg aaagcttctt agcaccagct actgaacgct ctcttaaaat caagaaaatc | 180 | |
| attgaagaca ctaaagctga atacgaagca actcgtttcc caatggacac tcgtccaaca | 240 | |
| tcaatcgcag atattcctgc cggctatatt caaaaagacg atgaattaat ctacggtatt | 300 | |
| caaaatgatg agttgttcaa attgaatttc atgccaaaag gtggtatccg tatggcagaa | 360 | |

```
acagcactta aagaacatgg ttatgaacca gatcctgctg ttcatgaaat tttcacaaaa      420
tacactacta cagtaaatga cggaattttc cgcgcttata catctaatat ccgccgtgcc      480
cgtcacgctc acacagtaac tggtcttcca gatgcttact cacgcggacg tatcatcggt      540
gtttatgctc gtcttgctct ttatggtgca gactacttga tgcaagaaaa agttaacgac      600
tggaacgcta tcacagaaat cgacgaagaa tctattcgtc ttcgcgaaga agttaacatg      660
caataccaag ctcttggtga agttgttaaa cttggtgacc tttacggact tgatgtccgt      720
aaaccagcca tgaacgttaa agaagctatc caatgggtaa acatcgcctt catggccgta      780
tgtcgtgtta tcaacggtgc tgctacttct cttggacgtg tgccaatcgt tcttgatatc      840
tttgctgaac gtgaccttgc tcgtggtact ttcacagaat cagaaatcca agaatttgtc      900
gatgactttg tcttgaaact tcgtactgta aaatttgctc gtactaaagc ttacgacgaa      960
ctttactctg gtgacccaac attcatcact acatctatgg ctggtatggg tgctgacggt     1020
cgtcaccgtg ttactaaaat ggactaccgt ttcttgcaca cacttgataa tatcggtaac     1080
gctccagaac caaacttgac agttctttgg actgataaat tgccatattc attccgtcgc     1140
tactgtatga aaatgtcaca caaacactcg tcaatccaat acgaaggtgt gacaacaatg     1200
gctaaagatg gttacggtga atgtcatgt atctcatgtt gtgtatcacc acttgaccca     1260
gaaaacgaag aacaacgtca caacatccaa tactttggtg ctcgtgtaaa cgtccttaaa     1320
gctcttctta ctggtttgaa cggtggttat gacgacgtcc acaaagacta caaagtattt     1380
gatatcgaac cagttcgtga tgaaatcctt gatttcgaaa cggttaaagc taatttcgaa     1440
aaatctcttg attggttgac ttcaacttac gtagatgccc ttaacatcat tcactacatg     1500
actgataaat acaactacga agctgttcaa atggcattct tgccaactaa caacgtgcc     1560 aacatgggat tcggtatctg tggtttcgct aataccgttg atactttatc agcaatcaaa     1620
tacgctactg ttaaaccaat ccgtgacgaa gatggttaca tctacgacta cgaaacaact     1680
ggtgacttcc ctcgttgggg tgaagatgac cctcgttcta acgaacttgc tgaatggttg     1740
gtagaagctt acactactcg tcttcgtagc cacaaacttt acaagaacgc tgaagctact     1800
gtatcacttc ttacaatcac ttcaaacgtt gcttattcta aacaaactgg taactctcca     1860
gttcacaaag tgtttacct taacgaagat ggtactgtaa acctttctaa acttgaattc     1920
ttctcaccag gtgccaaccc atctaacaaa gctcgtggtg gttggttgca aaacttgaac     1980
tctcttgcaa gccttgactt ctcatatgct gcagatggta tctcacttac aactcaagtt     2040
tctccacgcg ctcttggtaa gacatttgat gaacaagttg ataacttggt aactatcctt     2100
gatggttact tcgaaaacgg tggacaacac gttaacttga acgtcatgga ccttaaagat     2160
gtttatgaca agattatgaa tggtgaagat gttatcgttc gtatatcagg ttactgtgtc     2220
aacactaaat accttactaa agaacaaaag acagaattga cacaacgcgt cttccacgaa     2280
gttctttcaa tggatgatgt tgctgaaact gttgctgcta aataa                    2325
```

<210> SEQ ID NO 77
<211> LENGTH: 789
<212> TYPE: DNA
<213> ORGANISM: Streptococcus equinus

<400> SEQUENCE: 77

```
atgactgaaa tagattacgg aaaagtgaca ggaatgattc attcaacaga aagtttggt       60 tctgtggatg ggcctggtgt tcgctttgtc atttttatgc aaggctgcaa gatgcgttgc      120
```

```
caatattgtc acaatccaga tacttgggca ttagagacaa ataattctcg tgaacgcact      180
gttgatgatg ttttagcaga agctttgcgt tatcgacatt tctggggtga aaatggtggg      240
attaccgttt caggtggtga agccatgttg caaattgagt ttgtaacagc ccttttacc       300 aaggctaaag aattaggaat tcattgcacg cttgatacgt gtggttttac gttccgagat      360
acgcctgaat atcacgaaat tgtggataag ttactagctg tgacggattt agttctttta      420
gatttaaaag aaatcaatcc taaacaacac attgttgtaa cacgtcaacc caatactaat      480
attctagctt ttgctcgtta tttgtctgat aagggtgttc cagtctggat tcgtcatgtc      540
ttggttccag gattgaccga tttttgatgaa gacttaattg agctagggaa atttgttgaa      600
acgttaaaaa acgtggataa atttgaaatt ttgccttatc ataccttggg tgaattcaag      660
tggcgtgaat tgggaattcc ttatacccctt gaagggggtta aaccaccgac tagagaacgt      720
gtccaaaatg ctaaaaagct tatgcataca gagtcttaca cagactacat gaaacgcatt      780
catcactag                                                              789
```

<210> SEQ ID NO 78
<211> LENGTH: 717
<212> TYPE: DNA
<213> ORGANISM: Clostridium thermocellum

<400> SEQUENCE: 78

```
atgacattaa agggcaggat acactcattt gaatcttttg ggacactgga cggaccgggt       60
ataagatttg tggttttcat gcagggctgt cccttgcgtt gtatatattg ccacaacagg      120
gatacctggg atgttaatgc ggggagtgag tacactcccc ggcaagtaat tgatgaaatg      180
atgaaataca tagactatat aaaggtctcc ggaggcggaa taactgttac cggcggggag      240
cctgttctcc aggccgattt tgtggccgag gtgttcagac ttgcaaaaga gcagggagtg      300
catacggcgc tggataccaa tggatttgct gacatagaga aggttgaaag gcttataaaa      360
tacaccgatc ttgtattgct ggatataaag catgcccggg aggataaaca taagataatt      420
accggtgtgt ccaacgaaaa aatcaagcgt tttgcgctgt atctttcgga ccagggagtg      480
cctatctgga taagatatgt cccttgtcccc ggatataccg acgatgaaga tgaccttaaa      540
atggcggctg atttcataaa aaagcttaaa acggtggaaa aaatcgaagt tcttccttat      600
cacaacatgg gagcatacaa atgggaaaaa cttggtcaga aatacatgct tgaaggagta      660
aaggggccga gtgcgcaaga ggtggaaaaa gcaaagagga ttctgtcagg caaataa       717
```

<210> SEQ ID NO 79
<211> LENGTH: 1269
<212> TYPE: DNA
<213> ORGANISM: Jeotgalicoccus sp; ATCC8456

<400> SEQUENCE: 79

```
atggcaacac ttaagaggga taagggctta gataatactt tgaaagtatt aaagcaaggt       60
tatctttaca caacaaatca gagaaatcgt ctaaacacat cagttttcca aactaaagca      120
ctcggtggta aaccattcgt agttgtgact ggtaaggaag cgcctgaaat gttctacaac      180
aatgatgttg ttcaacgtga aggcatgtta ccaaaacgta tcgttaatac gcttttttggt      240 aaaggtgcaa tccatacggt agatggtaaa aaacacgtag acagaaaagc attgttcatg      300
agcttgatga ctgaaggtaa cttgaattat gtacgagaat taacgcgtac attatggcat      360
gcgaacacac aacgtatgga aagtatggat gaggtaaata tttaccgtga atctatcgta      420
ctacttacaa aagtaggaac acgttgggca ggcgttcaag caccacctga agatatcgaa      480
```

```
agaatcgcaa cagacatgga catcatgatc gattcattta gagcacttgg tggtgccttt      540
aaaggttaca aggcatcaaa agaagcacgt cgtcgtgttg aagattggtt agaagaacaa      600
attattgaga ctcgtaaagg gaatattcat ccaccagaag gtacagcact ttacgaattt      660
gcacattggg aagactactt aggtaaccca atggactcaa gaacttgtgc gattgactta      720
atgaacacat tccgcccatt aatcgcaatc aacagattcg tttcattcgg tttacacgcg      780
atgaacgaaa acccaatcac acgtgaaaaa attaaatcag aacctgacta tgcatataaa      840
ttcgctcaag aagttcgtcg ttactatcca ttcgttccat tcttccagg taaagcgaaa       900 gtagacatcg acttccaagg cgttacaatt cctgcaggtg taggtcttgc attagatgtt      960
tatggtacaa cgcatgatga atcactttgg gacgatccaa atgaattccg cccagaaaga     1020
ttcgaaactt gggacggatc accatttgac cttattccac aaggtggtgg agattactgg     1080
acaaatcacc gttgtgcagg tgaatggatc acagtaatca tcatggaaga aacaatgaaa     1140
tactttgcag aaaaaataac ttatgatgtt ccagaacaag atttagaagt ggacttaaac     1200
agtatcccag gatacgttaa gagtggcttt gtaatcaaaa atgttcgcga agttgtagac     1260
agaacataa                                                             1269

<210> SEQ ID NO 80
<211> LENGTH: 684
<212> TYPE: DNA
<213> ORGANISM: Aspergillus niger

<400> SEQUENCE: 80
atgttcaact cacttctatc cggtactact acaccaaact ccggccgtgc atctcctccc       60
gccagcgaaa tgcccatcga taatgatcac gtggccgttg cccgtccagc tccccgccgc      120
cgccgcattg tagtagccat gacgggtgcc actggagcca tgctcggcat caaagtccta      180
attgctctgc gccgtctaaa tgtggagaca cacctggtga tgagtaaatg ggcggaggct      240
acgatcaaat acgagactga ctaccatccc tcaaacgtgc gagcgctggc cgactacgtg      300
cacaacatca tgacatggc cgccccagta tccagcggct cattccgcgc ggacggaatg      360
attgtggtac cgtgcagcat gaaaacattg gctgctatcc actcgggctt ttgcgacgat      420
ctcatttcaa ggacagcaga tgtgatgctc aaggagcgca ggcggttggt gctagtagcg      480
cgggagacgc cattgagcga gatccatctg cgaaacatgt tggaggttac acgcgctggg      540
gcagtcatct tccccccagt accggcgttc tacatcaagg ccggaagtat cgaggacctc      600
atcgaccaga gtgttggacg aatgttggat ttatttgacc tcgacacggg ggattttgaa      660
cgttggaatg gatgggaaaa ataa                                            684

<210> SEQ ID NO 81
<211> LENGTH: 1555
<212> TYPE: DNA
<213> ORGANISM: Aspergillus niger

<400> SEQUENCE: 81
atgtctgcgc aacctgctca cctgtgtttc cgctccttcg tcgaagccct caaggtcgac       60
aacgaccttg ttgaaatcaa taccccaatt gaccccaatc tcgaagctgc tgctattacc      120
cgccgagtat gtgagaccaa cgacaaggct cctttattca acaacctcat cggcatgaaa      180
aatggcctct tccgtatact tggggctcct ggctctctca ggaagtcgtc tgctgatcgc      240
tacggccgcc ttgctcgtca cctagccctc ccacctacgg cctcaatgcg tgagattctc      300
```

```
gataagatgc tctccgccag cgatatgcct cccatccctc cgaccattgt tcccaccggg    360
ccatgcaagg agaacagctt agatgactct gaattcgacc ttaccgaact ccccgttcct    420
cttattcaca aatcggatgg tggtaaatac atccaaacct atggcatgca cattgtgcag    480
tctccggatg gaacctggac caactggtct attgcccgtg cgatggtcca tgacaagaac    540
catctgaccg gcctggttat tccccctcag cacatctggc agattcacca gatgtggaag    600
aaggaaggcc gcagtgacgt tccctgggct ttggcctttg tgtcccacc cgctgccatt    660
atggcctcta gcatgcctat tcccgatggt gtcaccgaag ctgggtacgt gggagctatg    720
acgggatcct ccctggagct tgttaaatgt gatacgaacg atctatatgt ccccgctacc    780
tcagaaatcg ttctcgaggg cacactctct atcagcgaga caggcccaga gggacctttc    840
ggtgagatgc atggttacat cttccccggg gatactcacc tcggcgccaa atacaaggtt    900
aaccggatca cctaccgcaa caacgccatc atgcccatgt cttcttgtgg ccgcttgacg    960
gatgaaacgg taagtttagt ccctgtcctg ccatttatag ccaaggacta acacggtcta   1020
gcacaccatg atcggctctc tggctgcggc ggagatccgt aagctctgcc agcagaatga   1080
cctccctatc actgatgcct tcgctccttt cgagtctcaa gttacctggg ttgctctgcg   1140
ggtcgatact gagaagctac gtgccatgaa gacaacgtct gagggattcc gcaagagagt   1200
gggagacgtc gtcttcaacc acaaggccgg atacaccatt catcgtctgg tgttggtcgg   1260
tgacgacatt gatgtctatg aaggaaagga tgtgctctgg gcgttctcca cccgttgccg   1320
tcctggtatg gacgagactt tgtttgagga tgttcgtggg ttccccttga ttccgtatat   1380
gggacacggg aatgggcccg cccaccgcgg cggaaaggtt gtgtccgacg ctcttatgcc   1440
gactgagtac accactggtc gcaactggga ggctgctgac ttcaaccaat cttatcccga   1500
ggatctgaag cagaaggtgt tggacaactg gacgaagatg ggtttcagca actaa        1555
```

<210> SEQ ID NO 82
<211> LENGTH: 2224
<212> TYPE: DNA
<213> ORGANISM: Aspergillus niger

<400> SEQUENCE: 82

```
atgggcaccc cgataaatcg tgaagagatt gaccgcgtgc tgcgaatgaa acgcaatcag     60
cgcgaggctc gagcgtgtta tccttgccgc cagcgcaagg tgaaatgcga cagcactcag    120
ccgtgtcgaa catgtcgccg acgaggccat ccccaaatat gtgtgtatga ccaagattcg    180
tctgggtcta aaaaggctcg tagcaccggc caaagacgtt cctctgctgc ttctcgtgga    240
acaaatcaga caccaaccgc cgagcaggca ttcgatgccg aaccacaatc tctgccctca    300
gcgcgcagtt taccagaagt ccagccaaaa acaagacagt actatagtac tcgaatcccg    360
tcttccgatg gccccgataa tgatcttatc tactcgggcg acaactcggt attgtcttat    420
ttgcgcaacc ggacgcaaga taccaatggc tccatgaccc gtgaggtggg ctctgttcta    480
ggcctgcaaa atacctacgg cagttatcca tttatggact tcggacaccc caggaccgg    540
tggaaggagc ttctacgtat tattccgcag cgagcggaac tgttgaagta agcacatctt    600
attgttgttt tgataaacct ctaacggata gcaggttctt ccattctac agaatatcag    660
cttacccttt caatccgatc atacttgaca ttgagagatt tgagcaagat gtgtgttcat    720
acctcaatga tcttgcagca ggagagctgc agaacacttc aaagatttgc gaacgttggg    780
ccactgatcg gtctgtcggg ctgatcagcc tgctacttgc ggccttggct tccggtgcgc    840
attattctga cctggattac atgcaaagaa cagagctatg ccaggatttt ggtacgtaac    900
```

```
cagtatctttt acctatgcat gtttgactaa acaggagaag caaaacgatc ctttcaagct      960
cttcgactag ccaattttct tttccgtccg acgatggata taatacaagc acttctaatc     1020
ataggaaaca ctctgcaaaa caatggccag tctgatgcag catgggtttt gttagggaca     1080
acagtccgtc tcgcgcagac attaggtctt cacacagaaa agagtgtagc acgcctaccg     1140
gatcatgtca aatacaaagc acgaaagcta tggtacataa accatgctac aggtaacgac     1200
acaagctgac gcggctacag gtacactgtc gtttggcaag attgcctgct ctgtttatgt     1260
tacgaccggc ctcgcgtagt ctctatgacc gggtgggctc cagattattc aatcctctcg     1320
agcagcgaac tatctttcac agaagctatg tattttctat gccaaactgc cttaaatatg     1380
atcacaacag acggaccgga gatatcggaa aatgcgcgac agcttgacat tttggccacg     1440
attgatagcc tcaaccaacg cactcagcca tatctgcgtg accgccagga atgcaaaacc     1500
ctccaacaca atctggagca cctggcgtta cgaatgcaca tgtctctagt tatttccgtc     1560
ctgacacgtc cagcactgaa gcgcactgta atgcaagacg cgtcctatga catcttgcgc     1620
acccgcgcca aattgagcct gatcgacgcc tctagggcct ttttggattt tcaggctctg     1680
agtgtggtac ccctccgaag ctggtcaatg gtgcacacgg tgcttagttc cactttactt     1740
ctctgcattt gggaggagac ccgaaacgat cccgagtgtc gtgatttaca gcaaaaggtg     1800
attgaggtct tttctgccgc tggcacagtg ggcacagtgg agaacacagc atcggagaat     1860
gggcaatggc tatcggaacg gcatatacga gcgctaatca cactgcgcaa ttcggtccga     1920
acggcagtcg aacgtgaaaa gggggaggca agcgttggga cagaacgcgc ggagcagccc     1980
cagccttttt ttcctgtcta tgggtatgtg cacccgctat tgtctgataa gtggagctgt     2040
gcgatggatg ctgattttgc agtatgccga acgggatccc ggatgacttc ggtcaagact     2100
tctcaccagc aagctatctt gactccatta tgaacggtat gctgaggctc ccgactattt     2160
atcgatcgaa ctaaccgtcg tagtacccat gtttgactta tcccaagagc tgggttttct     2220
ttga                                                                  2224

<210> SEQ ID NO 83
<211> LENGTH: 723
<212> TYPE: DNA
<213> ORGANISM: Aspergillis oryzae

<400> SEQUENCE: 83
atgctctcct ccttccttcc ttccggcacc aacacatcaa actccggtca tcacagcccc      60
gacaatgcat ccgaaacaca atcaaccaca cagtccgcac cactcgagca catatccacc     120
gcaatgccac cagtcccaac caaaggtcga cgcaaacgaa tcgtcgtagc catgaccgga     180
gccaccggct caatcctggg aatcaaagtc ctcatcgccc ttcgccgcct caacatcgaa     240
acccacctcg taatcagcaa atgggccgaa gcaaccataa aatacgaaac agactatcac     300
ccgcggaatt ttcgtgccct agccgactac gtccacaaca taaacgacat ggcggcaccc     360
atatccagcg ggtccttcaa gaccgacggc atgatcgtcg tcccatgttc catgaaaaca     420
ctcgccgcta tcaactccgg gttctgtgaa gatctcatct cccggactgc agacgtcatg     480
ctcaaggagc gcaggaagct ggttcttgtt gctagggaaa cgcctcttag tgatattcat     540
cttcgcaata tgcttttctgt gtctcaggct ggggctatta tcttcccgcc tgtgccggcg     600
tactatatca aggcggcgtc tgtggatgaa cttgtggatc agagtgttgg gcgcatgttg     660
gatctgtttg atctggatac ggctgatttt gctagatggg agggttggaa gaaggataac     720
``` tga                                                                    723

<210> SEQ ID NO 84
<211> LENGTH: 1512
<212> TYPE: DNA
<213> ORGANISM: Aspergillis oryzae

<400> SEQUENCE: 84
atggccgcga ttaacgaagt cgatcattcc ttccgcgcct tgtcgaagc cctcaaggcc        60 gacgatgact tggtcgagat caacaccgag atcgactcta acctggaagc cgccgcgatc       120
actcgtcttg tctgcgagac cgatgacaaa gcccccctct tcaataacct caaaggcatg       180
ggaaagaatg gcctcttccg tatcctgggc gctccgggct ctctcagaaa gtccaaacgt       240
gaccgctacg gccggctcgc ccgccacctg gcgctgcctc ctactgccag catgaaggaa       300
atccttgaca agatgctctc cgcctctcag ctacctccca ttgaccctaa gattgtagag       360
actggtcctg tgaaggacaa ttcccttgaa ggcgacgaaa tcgacctcac tgcgctccca       420
gtgcccatgg tgcacaagtc tgacggcggc aaatatctac aaacatacgg aatgcatgtc       480
gtgcagtctc ctgatggaaa gtggacgaac tggtctatcg cccgtgcgat ggtcaaggac       540
aagaaccatt tgacaggcct ggttattgag ccccagcata tttggcaaat ccaccagatg       600
tggaaaaagg agggaaagga tgtcccgtgg gctctatgct tcggagttcc tcctgccgct       660
atcatggcat catcgatgcc catcccggat ggtgtaactg aggctggcta cgttggtgcc       720
atgactggtc gcgccttgga gctcgtcaag tgcgacacca accatctcta cgtccctgcc       780
aatgcggaga ttgtcctcga gggtaccctc tccatcactg aaaccgccga tgaaggcccc       840
ttcggtgaga tgcacggcta cgtcttcccc ggcgatagcc acaagtgtcc cgtttacaaa       900
gttaacaaga tcacctaccg caccgatgct atcctgccca tgtccgcctg cggtcgtctt       960
accgacgaga cccatactat gattggctcg ttggctgccg ctgagattcg taaaatttgc      1020
caactggccg gcctccccat caccgacacc ttttctccct tcgaggcaca ggttacctgg      1080
gtggctctca agttgacac cgcaaagctt cgtcaaatga agctagcccc taaagagctt      1140
cagaaatggg tcggagacgt ggtctttaac cacaaggctg gtacactat ccaccgcctg      1200 gtcctggttg gcgatgatat tgacccgtat gagtggaagg atgtcatgtg gctttcgca      1260 acacggtgtc gacccaatgc tgatgaaatg ttctttgaag acgtccgtgg ttttcccctt      1320
atcccgtata tgggtcacgg cacggggtcg cccaccaagg gtggtaaggt ggtttccgac      1380
gctctgatgc ccacagagta taccacaggt gctgattggg aagctgctga ctttgagcac      1440
tcctatccgg aggagatcaa ggccaaggtg agggccaact gggaggcttt gggattcaga      1500
aaacaggatt aa                                                         1512

<210> SEQ ID NO 85
<211> LENGTH: 723
<212> TYPE: DNA
<213> ORGANISM: Aspergillis oryzae

<400> SEQUENCE: 85
atgctctcct ccttccttcc ttccggcacc aacacatcaa actccggtca tcacagcccc        60
gacaatgcat ccgaaacaca atcaaccaca cagtccgcac cactcgagca catatccacc       120
gcaatgccac cagtcccaac caaaggtcga cgcaaacgaa tcgtcgtagc catgaccgga       180
gccaccggct caatcctggg aatcaaagtc ctcatcgccc ttcgccgcct caacatcgaa       240
acccacctcg taatcagcaa atgggccgaa gcaaccataa aatacgaaac agactatcac       300

```
ccgcggaatg ttcgtgccct agccgactac gtccacaaca taaacgacat ggcggcaccc      360
atatccagcg ggtccttcaa gaccgacggc atgatcgtcg tcccatgttc catgaaaaca      420
ctcgccgcta tcaactccgg gttctgtgaa gatctcatct cccggactgc agacgtcatg      480
ctcaaggagc gcaggaagct ggttcttgtt gctagggaaa cgcctcttag tgatattcat      540
cttcgcaata tgctttctgt gtctcaggct ggggctatta tcttcccgcc tgtgccggcg      600
tactatatca aggcggcgtc tgtggatgaa cttgtggatc agagtgttgg gcgcatgttg      660
gatctgtttg atctggatac ggctgatttt gctagatggg agggttggaa gaaggataac      720
tga                                                                    723
```

<210> SEQ ID NO 86
<211> LENGTH: 1050
<212> TYPE: DNA
<213> ORGANISM: Picrophilus torridus

<400> SEQUENCE: 86

```
ttgaatgatc ttaatgttta tggtgaaaaa ataagaaata tgcttcttga acttggcatt       60
tataataaat cagatgatta ttcacctgat attaaataca ataaaacgtt ccacgcaaat      120
ggatacccaa taacaggtct ttataaattc cttggatact atgatagggga taataacata     180 gccaactttc catcgatatc gttcacaacg aactttcat catgtgatgt acatgcagg       240 gtattaagat caggcaatga caggatcata ttcaacggga aaaacaatga aaagtattac      300
aaaagggctg aaaaggccct gtcatttctc aggaaaaaat atagaataga tgcagcattt      360
gagtttaaca tcaggataaa tagaagatac agggatgcca aaggccttgg agaatcggca      420
gccgtggcat cggcaaccgc cagggccgtt gccgcagcag tctttggcat ggatgctgca      480
aaagacaggg gttttgtatc ataccctggcc aggcatgtct ctggctccgg taccagatct     540
gcggcaggaa ccttttcaat gtggctttca tatcctggaa tagacgattt atcttcaatt      600
ggcttcgaaa taagaaaaga cgatttattc catttctatg ccataccaat gagatcaaga      660
atagagacat taaatgcaca tgattatgca tcctcatcaa tttttttataa tgcatgggtc     720 aaatcaaaat tttttgatat aatagacatc attgaaaaca aattcaatac aaggatgatg     780
cttgaatact ccatgaagga tatgtacagg ctgcaggcgc ttttaatatc ctctggatat      840
atcatatatg aaaagcatta tttagacatt ataagaaaat taagatcatc attaaataac      900
tacaaaaacg tttattttcac atctgataca ggaacaagca ttgttgttat gtcaacatca     960
atgaatgagc tttcaaggtt cgttaacgat cttgatcttg atggtataag cggcaatttt     1020
ccagagaaga tcattataga ggaactatga                                      1050
```

<210> SEQ ID NO 87
<211> LENGTH: 975
<212> TYPE: DNA
<213> ORGANISM: Picrophilus torridus

<400> SEQUENCE: 87

```
atggaaaatt acaatgttaa gacaagggcg ttcccaacaa taggcataat actgcttggt       60
gggatctcgg ataaaagaa caggataccg ctgcatacaa cggcaggcat agcatatact       120
ggtataaaca atgatgttta cactgagaca aagctttatg tatcaaaaga tgaaaaatgc      180
tatattgatg aaaggaaat tgatttaaat tcagatagat caccatcgaa ggttattgat      240
aaattcaagc atgaaatact tatgagagta atcttgatg atgaaaataa cctttcaatt      300
```

```
gattcaagga actttaatat attaagtggc agctcagatt ctggggccgc tgcactggga      360
gagtgcatag aatcaatttt tgaatacaat ataaatatat ttacatttga aaacgatctt      420
cagaggatat cagaaagtgt tggaagaagc ctttacggtg gtttaacagt aaactatgcc      480
aatggcaggg aatcattaac agagccatta cttgagcctg aggcatttaa aactttaca       540 ataattggtg cacattttaa cattgataga aaccatcaa atgagattca tgaaaatatc      600
ataaaacatg aaaattacag ggaaagaata aaaagtgctg agagaaaggc gaaaaaactt      660
gaggagctat caaggaatgc aaacataaag ggtatctttg aacttgcaga atccgataca      720
gtggaatacc ataaaatgct ccatgatgtt ggcgttgaca taataaatga tagaatggag      780
aacctcattg aaagggtaaa agaaatgaaa ataacttct ggaattcata catagttacc       840
ggcggcccga acgttttgt aataacagag aaaaaggacg ttgataaggc aatggaagga       900
ttaaatgatc tgtgcgatga tataagatta ttaaaagttg caggaaagcc acaggtcatt      960
tcaaaaaact tttaa                                                       975
```

<210> SEQ ID NO 88
<211> LENGTH: 1191
<212> TYPE: DNA
<213> ORGANISM: Saccharomyces cerevisiae

<400> SEQUENCE: 88

```
atgaccgttt acacagcatc cgttaccgca cccgtcaaca tcgcaaccct taagtattgg       60
gggaaaaggg acacgaagtt gaatctgccc accaattcgt ccatatcagt gactttatcg      120
caagatgacc tcagaacgtt gacctctgcg gctactgcac ctgagtttga acgcgacact      180
ttgtggttaa atggagaacc acacagcatc gacaatgaaa gaactcaaaa ttgtctgcgc      240
gacctacgcc aattaagaaa ggaaatggaa tcgaaggacg cctcattgcc acattatct      300 caatggaaac tccacattgt ctccgaaaat aactttccta cagcagctgg tttagcttcc      360
tccgctgctg gctttgctgc attggtctct gcaattgcta agttatacca attaccacag      420
tcaacttcag aaatatctag aatagcaaga aaggggtctg gttcagcttg tagatcgttg      480
tttggcggat acgtggcctg ggaaatggga aaagctgaag atggtcatga ttccatggca      540
gtacaaatcg cagacagctc tgactggcct cagatgaaag cttgtgtcct agttgtcagc      600
gatattaaaa aggatgtgag ttccactcag ggtatgcaat tgaccgtggc aacctccgaa      660
ctatttaaag aaagaattga acatgtcgta ccaaagagat ttgaagtcat gcgtaaagcc      720
attgttgaaa aagatttcgc caccctttgca aaggaaacaa tgatggattc caactctttc      780
catgccacat gtttggactc tttccctcca atattctaca tgaatgacac ttccaagcgt      840
atcatcagtt ggtgccacac cattaatcag ttttacggag aaacaatcgt tgcatacacg      900
tttgatgcag gtccaaatgc tgtgttgtac tacttagctg aaaatgagtc gaaactcttt      960
gcatttatct ataaattgtt tggctctgtt cctggatggg acaagaaatt tactactgag     1020
cagcttgagg ctttcaacca tcaatttgaa tcatctaact ttactgcacg tgaattggat     1080
cttgagttgc aaaaggatgt tgccagagtg attttaactc aagtcggttc aggcccacaa     1140
gaaacaaacg aatctttgat tgacgcaaag actggtctac caaaggaata a             1191
```

<210> SEQ ID NO 89
<211> LENGTH: 1182
<212> TYPE: DNA
<213> ORGANISM: Schizosaccharomyces pombe

<400> SEQUENCE: 89

```
atggacaaaa aggtttatca atgcaccgtt agtgcgcctg ttaatattgc agtaattaaa     60
tactggggaa agagagatgt ggcattgaac ttgcctacca atagctcgat cagtgtgacc    120
ctttctcaag atgacttacg tactgttact acagctagtt gtagcgagaa gtttgagaat    180
gatacactgt ggttaaatgg aaacgctgag gaaatctttg ccaataaacg acttcgtgtc    240
tgtgtagagg aactgcgtaa agctagatta gatctcgaag aggaaaatga tgatcttgac    300
aagattggtg cattgaagct tcatgtcgtt tcagaaaaca acttccctac tgctgctggt    360
ttggcatctt cagctgctgg ttatgctgct ttttgtgaag caatcgctag attgtacgat    420
ttaccatgga cacccactca attatctcgc attgctagac aggggtctgg aagtgccttgt    480 cgtagcttgt ttgggggcta tgtagcctgg gagatgggcg agcttcatag cggtgctgat    540
agtgtagcag ttcaagttga acctgttgaa aattggcccg aaatacgtgt tgctgtttta    600
gtagcgtccg ctgccaaaaa aggggtttcc tcaacagctg gcatgcaagc tacagttgca    660
tcttctacct tgttccaaca tcgtattcaa aacatcgttc cacaacgtat ccaagaaatg    720
aagaccgcca ttcgtgagcg tgattttgag acttttgcga agcttaccat gactgattcc    780
aatcaattcc atgcgtgctg ccttgatact tttccccta tcttttactt gaacgatact    840
tcacgtgcgg ttatccgagt tgttgagaat ataaatgcta ctgctggaaa gaccattgct    900
gcctatacat ttgatgctgg cccaaatgct gttatttact tcttggaaga aaactccgag    960
attgtattaa atacactta tgctgttact aaaaatgctg aaggatggag caagcagtat   1020
ggctcttccc ccgttactgt tgattctgct gcagccaata ttgtatcatc tggtataagc   1080
cgagttatct taactcgagt gggtaatggg cctcgagttt tgacgattga cgaatctttg   1140
atcgatgcat ctggcaaccc taaatttata ggaagtcatt aa                     1182

<210> SEQ ID NO 90
<211> LENGTH: 972
<212> TYPE: DNA
<213> ORGANISM: Halorhabdus utahensis

<400> SEQUENCE: 90
atgaaagcga cagcgacggc ccacccgatc cagggggctgg tgaagtacca cgggatacgc     60
gaccccgaac tccggacgcc gtatcacgat tcgatcagcc tctgcactgc gccgagtaac    120
tccacgacga cggtcgcctt cgaacccgag cgtcccgagg acgagtacgt catcgacggc    180
gaacacatcg acgggcgcgg ggccgagcgc atccggaccg tcgtcgataa cgttcgcgaa    240
cgggccgatc tcgacgagcg cgtccgcgtc gcaagtgaga caacttccc gtcgaacgtc    300 ggctttggct cctcggcgtc gggattcgcg gcgctggcga ctgctctcgt tgaggccgct    360
ggcctggacc tctcacgccc ggagatctcg acgattgccc gcgcggctc gacctcggcg    420 gcgcgggcgg tcacgggtgg ctttttcggat ctgcgggcgg gcagtaacga cgccgactgc    480
cgttcgaagc gactcgacgt cccccttggag gatgacgttc gcatcgtcgg cgcagtgatt    540
cctgcataca aagagaccga ggcggcccac gaggaggccg ccgagagcca catgttcgag    600
ggccgactcg cccacgtcca cgagcaactc gcggacatgc gcgacgcgct cggtcgcggg    660
gacttcgagc ggtccttcga gatcgccgaa cacgacacac tctcgctggc ggcgacgacg    720
atgaccggac cgagcggctg ggtctactgg caacccgaga gcctcgaagt cttcgagacg    780
gttcgggacc ttcgcgacga cggggttccc gtctacttct ccggggatac cggcgcaagc    840
atctacgtca acaccacggc cgagtacgtc gaccgcgtcg aatcggcgat cgaaaccctc    900
```

```
gggatcgaga cgctcacctg gcgcgtcggt ggccccgcgc gcgtccgtga tcccgagaag    960
gcactgttct ga                                                        972
```

<210> SEQ ID NO 91
<211> LENGTH: 984
<212> TYPE: DNA
<213> ORGANISM: Haloterrigena turkmenica

<400> SEQUENCE: 91

```
atgaaagcga ccgccatggc ccacccgatt caggggctgg tcaagtatca cgggatgcga     60
gacgagatcg agcgcctgcc gtatcacgac agtatcagtc tctgtacggc cccgagccac    120
actcgcacga ccgtggagtt ctcgatggac tacgaggagg acacgttcgt cgtcgacggc    180
gaggaactcg acggcgggc ctacgagcgc gtcgaagccg tcgtcgagaa ggctcgttcg     240
aagtccgacg cggcccacac cgtctatccg gttcgcctcg agagcgagaa cagtttcccg    300
tcgaacgtcg gctgggctc ctcttcctcg gcttcgccg ccgccgcgat ggcgctggcc      360
gaggccgccg aactcgacgc ctcccgccag gagatttcga cgatcgctcg cgtcggctcg    420
gcgtcggccg cccgcgcggt caccggcgcg ttttcgcaac tgcacacggg tctgaacgac    480
gaggattgtc gctcgcggcg catcccgagt gaccttcacg aggacctgaa gatcgtcgtc    540
ggcctcgtcc cctaccacaa ggagaccgag gacgcccacc gcgaggccgc cgacagccac    600
atgttccagg cccgcaacgc ccacatccac ggccagatcg ccgagatgcg cgacgccctg    660
cggaacaacg agttcgaccg cgccttcgaa ctcgccgagc aggactccct ctcgctggcc    720
gcgacgacga tgaccggccc ctccgggtgg gtctactggc agcccgctac cctgaagatc    780
ttcaatacgg tgcgggaact ccgcgaggag gaggacatcc ccgtctactt ctcgacggac    840
accggcgcca cgtctacgt caacaccacc gaggaacacg tcgacgaggt cgaggaggcg    900
gtctcggatt gcggcgtctc caccaccgtc tgggacgtcg gcggccctgc gaagctgcta    960
gacgaggaaa agcacctgtt ctag                                           984
```

<210> SEQ ID NO 92
<211> LENGTH: 951
<212> TYPE: DNA
<213> ORGANISM: Leuconostoc kimchii

<400> SEQUENCE: 92

```
atgcctacaa cagccacagc acatactaat attgcattta ttaaatattg gggtaaaaaa     60
gatgcgcgct taaatttacc gacaaccagt tctttatccc taacactctc acaatttat    120 acaacaacaa cagtcacaca aaacaccgac aaagatcaac ttgttttaaa cggtgagcta    180
gccgacccta ctagaataca tcatttttta aatacaatac gtgatatcct tggtgatttt    240
cctgctgtga cagtcacttc agaaaaccat gtgccaacca gtgcaggtct agcctcttcg    300
gcttcatctt tcgctgcgct aacaggtgca gtaacaagag aaatgggatt tgatttgtct    360
aatcaatcct tatctcggtt agcacgccgt ggatctggtt ccgcctcacg atcgttttac    420
agtcactttg ctatctggca tgctggtatg gatgatgcct catcttttgc tgaaagttta    480
aatgcccctg acatgccgat tgccttgtc gttgccgaag tgtccacttc agcaaagaaa    540
gtgagctcaa gtgatggcat gcaacgtgca atcacttcac caaactacga tgattggctc    600
aaccgcagcg cgacacaatt tatggatatg cagtctgcca ttcaacaatc agacatcgaa    660
aaaattggta cgcttgctga agaaaacgct ttagctatgc atgcgcttaa tctcactgca    720
cgccataaac cattcaccta tttcacgcaa gaaacccaac aaatacttgc cctagtatca    780
```

| | |
|---|---|
| gatttacgac gacaagggat cctagccttc gcaacaatgg atgctggtcc aaacgtcaaa | 840 |
| attataacga ctttaaatga tgcaccaaaa attgttacag cactacattc tgctttacca | 900 |
| tatatccatc tcgaaactgc tacaagcgga tcaggtatta cctatgacta a | 951 |

<210> SEQ ID NO 93
<211> LENGTH: 1005
<212> TYPE: DNA
<213> ORGANISM: Halobacterium salinarum

<400> SEQUENCE: 93

| | |
|---|---|
| atgcgcgcga caccccccgca tcgacgtatg aaagcaaccg cgcgcgcaca ccccatccag | 60 |
| ggcctcgtga ataccacgg gatgcgcgac gagtcgcttc gcatgccgta ccacgactcc | 120 |
| atcagcgtct gcaccgcgcc cagcaacacc acgacgaccg tcgagttcga tcccgaccgc | 180 |
| gacgccgacc agtacgtcgt cgacggcgac acggtcaccg gtcacggcgc ggaccgcatc | 240 |
| cgcagtgtgg tcgatgcggt ccgcgaccgc gccgggttcg accaccgcgt gcgcctggag | 300 |
| agccagaaca gcttccccac gaacatcggc ctggggtcgt cgtcgtcggg gttcgcggcg | 360 |
| gccgcgctgg cgtgcgtccg cgccgccggc ctggatctgg acctcccgac ggtgtcgacg | 420 |
| gtcgcgcgcc gcggatcggc gtcggcggcc cgcgccgtca cgggcgggtt ctcggatctg | 480 |
| cacgcgggat tgaacgacgc cgactgccgc agcgaacgcc tcgacgcccc cgcggagttc | 540 |
| gcgtccgatc tgcgcatcgt cgtgggcgaa gtgcccgcgt acaaggagac ggagtctgcc | 600 |
| cacgccgagg ccgccgacag ccacatgttc gacgcgcggc tggcacacgt ccagggccaa | 660 |
| ctcgcggaga tgcgtgacgc cgtccgcgcg ggcgacttcc agcgcgtctt cgagaccgcc | 720 |
| gaacacgact cgctgtcgct cgcggcgacg acgatgacgg ggccgtccgg gtgggtgtac | 780 |
| tggaagcccg agacgctctc gatattcgag accgtgcggg agctccgggc ggacggcgtg | 840 |
| ccgacgtact tctcgacgga taccggcgcg acagtgtacg tgaacaccac tgcgagtcac | 900 |
| gccgacgagg tcgaggctgc ggtcgccgac tgcggcgtcg acaccgccgt ctgggaggtc | 960 |
| ggcgggcctg cccacgaact cgacgagcgc gacgcgatct tctga | 1005 |

<210> SEQ ID NO 94
<211> LENGTH: 1300
<212> TYPE: DNA
<213> ORGANISM: Aspergillus clavatus

<400> SEQUENCE: 94

| | |
|---|---|
| atggcggctg cggactcttc ggtctatagg gccaccacta ctgcccctgt caatattgct | 60 |
| gtcatcaagt aagttgactg cccccccccc ctaaataaac caaccgcctc cttttcttct | 120 |
| atcattaaat ttgtactaac gctgggactt ctctagatac tggggaaaac gggacgcaac | 180 |
| tctgaacctg cccaccaatt cttccctctc tgtgacccCT tcccagcgtt cgctccgcac | 240 |
| cctcaccacc gcctcctgtt ctgctatcta ccccaccgca gatgagctta tcctcaatgg | 300 |
| caagcctcaa gatatccaat cctccaagcg tacgctcgcc tgtctctcca gctgcgctc | 360 |
| tcttcgccag gcgctggaat ctacagactc atcgttgccg aaattatcta cacttccctt | 420 |
| gcggattgtt tccgagaaca atttccccac ggccgctggt cttgctagct cagctgctgg | 480 |
| gtttgcagcc ctcgttcgtg ctgtagcgaa cctctaccaa cttccgcaat cacctcggga | 540 |
| gctcagccgt atcgctcgtc agggatctgg ctctgcttgc cggtctctga tgggcggcta | 600 |
| cgtggcttgg cgcgctggag agttggagga cggcagcgat agtcttgctg aggaggttgc | 660 |

```
acctgcctca cactggcctg agatgcgtgc cattgtcctg gtggtcagcg ccgagaagaa      720
ggatgtcccc agtaccgagg gcatgcagac gacggtcgct acctcgagtc tcttcgctac      780
cagagcgaca tctgttgttc ccgagcggat ggctgccatt gagacagcaa tcctgaacaa      840
ggactttcct gccttcgccg aactcaccat gcgcgactct aacggcttcc acgccacctg      900
ccttgactcc tggcccccaa ttttctatat gaacgacgtt tcccgggctg ctgtcagaat      960
tgtccacgat atcaaccgtg ctattggccg aactgtgtgt gcgtacacct ttgatgctgg     1020
accgaatgct gttatctatt atctggaaaa ggattcggag ctggtcgcag aactgtcaa     1080 ggcaatcttg accaccaaca ctgacggctg gaatggtcct ttctacgata ttctgaagga     1140
cgtcactgcc ccgggtgttt ctttggataa gattgactct agagccgttg aagttctcaa     1200
ggagggagtc agccgcgtga ttctgaccgg tgttggtgag ggtcctgtca gtgtagaaga     1260
ccacctggtc agcgcaactg gagatgttct ttcgcactaa                           1300

<210> SEQ ID NO 95
<211> LENGTH: 1283
<212> TYPE: DNA
<213> ORGANISM: Neosartorya fischeri

<400> SEQUENCE: 95
atggcggcta cttctgatca taccgtctat cgtgctacca ctaccgcccc ggtcaatatt      60
gctgttatta agtgagttga ctatcgcccc ctaatccgtc ctgtggtgat tcttgtttcc     120
tcctaacagg gtcctctagg tattggggta aaagagatgc gtctctgaat ctgccaacca     180
attcctccct ctctgttacc ctctctcagc gctcccctcg aaccctcact accgcctcct     240
gctcagctat ctaccccgcc gcagacgagc tcatcttgaa cggcaagcca caggatattc     300
agtcctccaa acgcacactc gcttgtctct ccaacctacg ttccctccgt caggctctcg     360
aaaatgccga cccctcattg cctaaactgt ctgctctccc attgcgaatt gtttccgaga     420
acaacttccc caccgctgct ggtctcgcga gctcagctgc tggtttcgca gcccttgtcc     480
gtgctatagc agatctttat cagcttccac aatctcctct ggagctcagc cgtattgccc     540
gtcagggttc cggctctgct tgtcggtctc tgatgggcgg ttatgttgcc tggcgtgctg     600
gcgagcggga agatggtagc gacagtctgg ctgaggaagt cgctcccgca tctcattggc     660
ctgagatgcg tgcaattatc ctggtggtta gtgccgagaa gaaagacgtc cccagtacag     720
agggtatgca gactacagtt gctacctcga gtctcttttgc tacccgggcc gcatctgttg     780
tccctgagcg gatggccgcc attgagacgg caatccagaa caaggacttc gctacctttg     840
cggaaatcac catgcgtgac tctaacagtt ccacgcaac ttgcctcgac tcctggcctc     900
cgatcttcta catgaacgac gtctccagag ctgccgtgag actcgtccac gacatcaacc     960
gtgctgttgg ccggactgtg tgtgcttaca cattcgacgc tggcccgaat gccgttatct     1020
actaccttga gaaagactcg gaggtggtcg caggaaccgt caaggctatt ttgggcccca     1080
acaccgaagg gttcgacggc ccattctatg atatcttgaa gaatgtcact gcttcagtcg     1140
tgcctctgga gaatgttgac tctagagctg tagaagtctt gaagaacggc atcagccgcg     1200
tcattctgac tggtgtcggg gagggtccta tcagcgtgga ggatcacctt gtgagcgcga     1260
cgggtgatat cctcgcttct tga                                             1283

<210> SEQ ID NO 96
<211> LENGTH: 954
<212> TYPE: DNA
<213> ORGANISM: Streptococcus pseudopneumoniae
```

<400> SEQUENCE: 96

```
atggatagag agcctgtaac agtacgttcc tacgcaaata ttgctattat caaatattgg      60
ggaaagaaaa aagaaaaaga gatagtgcct gctactagca gtatttctct aactttggaa    120
aatatgtata cagagacgac cttgtcgcct ttaccagcca atgtaacagc tgacgaattt    180
tacatcaatg ctcagctaca aaatgaggtc gagcatgcca agatgagtaa gattattgac    240
cgttatcgtc cagctggtga gggctttgtc cgtatcgata ctcaaaataa tatgcctacg    300
gcagcgggcc tgtcctcaag ttctagtggt ttgtccgccc tggtcaaggc ttgtaatgct    360
tatttccagc ttggtttgtc tcggagtcag ttggcacagg aggctaagtt tgcctcaggt    420
tcttcttctc ggagttttta tggaccacta ggtgcctggg acaaggatag tgggggaatt    480
taccctgtag acaaaactt gaaactagct atgatcatgt tggtgctaga ggacaagaaa     540
aaaccaatct ctagccgtga cgggatgaaa ctttgtgtgg agacttcgac gacttttgac    600
gactgggttc gtcagtctga aaggactat caggatatgc tgatttatct caaggaaaat     660
gactttgcca agattggaga attaacggag aaaaatgctc ttgctatgca cgctacgaca    720
aaaacagcat caccagcctt ttcttatctg accgattcat cttatgaagc gatggacttt    780
gttcgtcaac ttcgcgagca aggagaggcc tgctacttta ctatggatgc cggtcctaat    840
gtcaaagttc tttgtcaaga gaaagacttg gagcattat caaaaatctt cggtcaacgt      900
taccgcttga ttgtgtcaaa aacaaaggat ttgagtcaag atgattgctg ttaa            954
```

<210> SEQ ID NO 97
<211> LENGTH: 1005
<212> TYPE: DNA
<213> ORGANISM: Lactobacillus rhamnosus

<400> SEQUENCE: 97

```
atgacaactt atgcacgtgc gcacactaac attgcattga tcaaatattg gggcaaagca      60
aataagcaac tgatgctgcc ggcaaccagc agtatttcgc ttaccttgaa tgacttttac    120
acggacacgg cggtaacttt tgaccctgca ctcgatcagg atcaattcac gttaaatcac    180
caaatgcagt cgcctactgc tgtcagccgc ttttttggatc atgttcggca cctggcccaa    240
attgatacac gcgctcgggt caactcgttg aatcatgtac cgactgctgc cggtttggcc    300
agttcggctt ctgcgtttgc ggcactggca ctggctacaa gtcgcgcggc tggcctaaat    360
ttaaccccta ccgctttgtc acggttggca cgtcgcggct cagggtcggc cacccgttca    420
atctttggcg gagcggtaat ttggcaccgt ggcagcgatg atcaatcctc gtttgccgaa    480
cccttaacca ttcagccaac tctgccgctg cggatgttgg tcgtcacggt ttccgatcag    540
aaaaaggcag tcagctcccg caccggcatg gccaacacgg ttgcgaccag cccttattac    600
caggcatggg tacaatcgaa tgaagcgtta atttcaccta tgatcacggc attggccgaa    660
aatgatctga cgacgattgg tgcactcacc gaattatcga gtatgcgcat gcacgctgcc    720
attatggctg aggagccgcc gttcacctac ttttttgccgg aaactttacg cgcctggcaa    780
ttggtgcaag aacaacgggc actcggcatt ccggcgtttg ccacgatgga tgccggaccc    840
aacgtcaaga tcctcacaac cgcaccgtac gtggatgttc tcatgaccgc cttgcagcct    900
gttttttggcg accggatttt gagcacccgc ctcggcccgg acgcgcaagt gattacaaag    960
gagcaattta tgacacaga gtcagcaatc acatcgcaag gatga                    1005
```

<210> SEQ ID NO 98

<211> LENGTH: 939
<212> TYPE: DNA
<213> ORGANISM: Borrelia afzelii

<400> SEQUENCE: 98

```
atgaaagtaa agtgtaaagc caatgcaagc ttggctttaa ttaaatattg gggaaagaag     60
gatgtttttt taaacattcc agcgacttct agtcttgctg ttagtgttga taaattttat    120
tcaataagtg agcttgaact ttcagatcga gatgaaataa ttttaaattc aaagccagtt    180
atattgcaaa atagagaaaa ggtgtttttt gattatgcaa gaaaaattct tagtgaaccg    240
aatgttagat ttaaaattaa aagtgaaaac aattttccaa cagcagcagg ccttgcaagt    300
tcaagttcag gatttgcttc tattgctgct tgtattttga aatattttga taaatattct    360
tttaatagtg catctaatct tgcaagagta ggatcagctt ctgcagcaag ggctatttac    420
ggagggttta ctattttgaa agaaggttca aaagaatctt ttcaattaag agatgaatct    480
tattttaatg atttgcgcat aatatttgcc ataattgata gtagtgaaaa agaattgtcc    540
tcaagagccg caatgaatat ttgcaaacac catggatttt attatgatgc ttggattgct    600
tctagtaaaa agatttttaa agatgcttta tatttttttt taaaaaaaga ttttgtgcat    660
tttggagcaa ctattgtaaa aagttatcag aatatgtttg ctttaatgtt tgcatcttct    720
atttttattt ttaaaaatag cacaatagat ttaattaaat atgccgctta tttaagaaat    780
aaaggaattt tggtatttga gacaatggat gcgggccccc aagtgaagtt tctttgtttg    840
gagaaaaatt taaatactat tttaaaagga cttaagcaga attttactga cattgagttt    900
attgtttcaa aggttggatg tgacttagaa tggatttga                           939
```

<210> SEQ ID NO 99
<211> LENGTH: 549
<212> TYPE: DNA
<213> ORGANISM: Escherichia coli

<400> SEQUENCE: 99

```
atgcaaacgg aacacgtcat tttattgaat gcacagggag ttcccacggg tacgctggaa     60
aagtatgccg cacacacggc agacacccgc ttacatctcg cgttctccag ttggctgttt    120
aatgccaaag gacaattatt agttacccgc cgcgcactga gcaaaaaagc atggcctggc    180
gtgtggacta actcggtttg tgggcaccca caactgggag aaagcaacga agacgcagtg    240
atccgccgtt gccgttatga gcttggcgtg gaaattacgc ctcctgaatc tatctatcct    300
gactttcgct accgcgccac cgatccgagt ggcattgtgg aaaatgaagt gtgtccggta    360
tttgccgcac gcaccactag tgcgttacag atcaatgatg atgaagtgat ggattatcaa    420
tggtgtgatt tagcagatgt attacacggt attgatgcca cgccgtgggc gttcagtccg    480
tggatggtga tgcaggcgac aaatcgcgaa gccagaaaac gattatctgc atttacccag    540
cttaaataa                                                            549
```

<210> SEQ ID NO 100
<211> LENGTH: 867
<212> TYPE: DNA
<213> ORGANISM: Saccharomyces cerevisiae

<400> SEQUENCE: 100

```
atgactgccg acaacaatag tatgccccat ggtgcagtat ctagttacgc caaattagtg     60
caaaaccaaa cacctgaaga cattttggaa gagtttcctg aaattattcc attacaacaa    120
agacctaata cccgatctag tgagacgtca aatgacgaaa gcggagaaac atgtttttct    180
```

```
ggtcatgatg aggagcaaat taagttaatg aatgaaaatt gtattgtttt ggattgggac    240
gataatgcta ttggtgccgg taccaagaaa gtttgtcatt taatgaaaaa tattgaaaag    300
ggtttactac atcgtgcatt ctccgtcttt attttcaatg aacaaggtga attacttta    360 caacaaagag ccactgaaaa aataactttc cctgatcttt ggactaacac atgctgctct    420
catccactat gtattgatga cgaattaggt ttgaagggta agctagacga taagattaag    480
ggcgctatta ctgcggcggt gagaaaacta gatcatgaat taggtattcc agaagatgaa    540
actaagacaa ggggtaagtt tcactttta aacagaatcc attacatggc accaagcaat    600
gaaccatggg gtgaacatga aattgattac atcctatttt ataagatcaa cgctaaagaa    660
aacttgactg tcaacccaaa cgtcaatgaa gttagagact caaatgggt ttcaccaaat    720 gatttgaaaa ctatgtttgc tgacccaagt tacaagttta cgccttggtt taagattatt    780
tgcgagaatt acttattcaa ctggtgggag caattagatg acctttctga agtggaaaat    840
gacaggcaaa ttcatagaat gctataa                                       867
```

```
<210> SEQ ID NO 101
<211> LENGTH: 996
<212> TYPE: DNA
<213> ORGANISM: Streptococcus mutans

<400> SEQUENCE: 101
atgacaaata gaaaagatga tcatataaaa tatgccttag actatcgttc gccatataat     60
agtttcgatg acatagaact cattcatcat tctttaccag attatgattt agccgagatt    120
gatttgtcta cacattttgc tggtcaggat tttgatttc cttttatat caacgctatg    180 acaggcggaa gccaaaaagg gaaagaagtt aatgaaaaat tagctcaggt agcggacacc    240
tgtggtcttc ttttttgtaac aggttcttac agcacagctc ttaaaaatcc agacgatact    300
tcttatcagg taaaaaaatc cagacctcat ttattactag caaccaatat cggccttgac    360
aaaccttatc aggctggctt acaggcagtt agggatttac agcctttatt tcttcaagtt    420
catattaatc ttatgcaaga gctccttatg ccagagggg aacgcgaatt taggtcttgg    480
aagaaacatt tatctgacta tgcgaagaaa ctacaacttc cttttatttt aaaagaagtt    540
ggttttggta tggacgttaa aacaatccaa actgctattg acctaggggt taaaactgtc    600
gatatttctg gccgaggcgg aactagtttt gcttatatcg aaaatagacg tggcggaaat    660
cgttcttatc ttaatcaatg gggacaaacc acagcgcaag ttctattaaa tgctcagccg    720
cttatggata aggtagaaat cctggctagc ggcgggattc gtcatccatt ggacataata    780
aaagctttgg tccttggagc caaagcggtc ggtttatctc gaacgatgtt agaattagtt    840
gaacagcatt ctgttcatga agtcattgct attgtaaatg gttggaaaga agatttgcgc    900
ctgatcatgt gcgcccttaa ctgtcaaacg attgcagaac ttcgaaatgt tgactatctt    960
ttatatgggc gcttaagaga aggacagaga caataa                             996
```

```
<210> SEQ ID NO 102
<211> LENGTH: 1050
<212> TYPE: DNA
<213> ORGANISM: Bacillus subtilis

<400> SEQUENCE: 102
gtgactcgag cagaacgaaa aagacaacac atcaatcatg ccttgtccat cggccagaag     60
cgggaaacag gtcttgatga tattacgttt gttcacgtca gtctgcccga tcttgcatta    120
```

```
gaacaagtag atatttccac aaaaatcggc gaactttcaa gcagttcgcc gattttatc      180 aatgcaatga ctggcggcgg cggaaaactt acatatgaga ttaataaatc gcttgcgcga      240
gcggcttctc aggctggaat tccccttgct gtgggatcgc aaatgtcagc attaaaagat      300
ccatcagagc gtctttccta tgaaattgtt cgaaaggaaa acccaaacgg gctgattttt      360
gccaacctgg gaagcgaggc aacggctgct caggcaaagg aagccgttga gatgattgga      420
gcaaacgcac tgcagatcca cctcaatgtg attcaggaaa ttgtgatgcc tgaaggggac      480
agaagcttta gcggcgcatt gaaacgcatt gaacaaattt gcagccgggt cagtgtaccg      540
gtcattgtga aagaagtcgg cttcggtatg agcaaagcat cagcaggaaa gctgtatgaa      600
gctggtgctg cagctgttga cattggcggt tacggggaa caaatttctc gaaaatcgaa      660
aatctccgaa gacagcggca aatctccttt tttaattcgt ggggcatttc gacagctgca      720
agtttggcgg aaatccgctc tgagtttcct gcaagcacca tgatcgcctc tggcggtctg      780
caagatgcgc ttgacgtggc aaaggcaatt gcgctggggg cctcttgcac cggaatggca      840
gggcattttt taaaagcgct gactgacagc ggtgaggaag gactgcttga ggagattcag      900
ctgatccttg aggaattaaa gttgattatg accgtgctgg gtgccagaac aattgccgat      960
ttacaaaagg cgccccttgt gatcaaaggt gaaacccatc attggctcac agagagaggg     1020
gtcaatacat caagctatag tgtgcgataa                                      1050
```

<210> SEQ ID NO 103
<211> LENGTH: 939
<212> TYPE: DNA
<213> ORGANISM: Escherichia coli

<400> SEQUENCE: 103

```
atgaaagtcg cagtcctcgg cgctgctggc ggtattggcc aggcgcttgc actactgtta       60
aaaacccaac tgccttcagg ttcagaactc tctctgtatg atatcgctcc agtgactccc      120
ggtgtggctg tcgatctgag ccatatccct actgctgtga aaatcaaagg tttttctggt      180
gaagatgcga ctccggcgct ggaaggcgca gatgtcgttc ttatctctgc aggcgtagcg      240
cgtaaaccgg gtatggatcg ttccgacctg tttaacgtta acgccggcat cgtgaaaaac      300
ctggtacagc aagttgcgaa aacctgcccg aaagcgtgca ttggtattat cactaacccg      360
gttaacacca cagttgcaat tgctgctgaa gtgctgaaaa agccggtgt ttatgacaaa      420 aacaaactgt tcggcgttac cacgctggat atcattcgtt ccaacacctt tgttgcggaa      480
ctgaaaggca acagccagg cgaagttaa gtgccggtta ttggcggtca ctctggtgtt      540
accattctgc cgctgctgtc acaggttcct ggcgttagtt ttaccgagca ggaagtggct      600
gatctgacca aacgcatcca gaacgcgggt actgaagtgg ttgaagcgaa ggccggtggc      660
gggtctgcaa ccctgtctat gggccaggca gctgcacgtt ttggtctgtc tctggttcgt      720
gcactgcagg gcgaacaagg cgttgtcgaa tgtgcctacg ttgaaggcga cggtcagtac      780
gcccgtttct tctctcaacc gctgctgctg gtaaaaacg gcgtggaaga gcgtaaatct      840
atcggtaccc tgagcgcatt tgaacagaac gcgctggaag gtatgctgga tacgctgaag      900
aaagatatcg ccctgggcga agagttcgtt aataagtaa                             939
```

<210> SEQ ID NO 104
<211> LENGTH: 990
<212> TYPE: DNA
<213> ORGANISM: Escherichia coli

<400> SEQUENCE: 104

```
atgaaactcg ccgtttatag cacaaaacag tacgacaaga agtacctgca acaggtgaac    60
gagtccttg gctttgagct ggaattttt gactttctgc tgacggaaaa aaccgctaaa   120
actgccaatg gctgcgaagc ggtatgtatt ttcgtaaacg atgacggcag ccgcccggtg   180
ctggaagagc tgaaaaagca cggcgttaaa tatatcgccc tgcgctgtgc cggtttcaat   240
aacgtcgacc ttgacgcggc aaaagaactg gggctgaaag tagtccgtgt tccagcctat   300
gatccagagg ccgttgctga acacgccatc ggtatgatga tgacgctgaa ccgccgtatt   360
caccgcgcgt atcagcgtac ccgtgacgct aacttctctc tggaaggtct gaccggcttt   420
actatgtatg gcaaaacggc aggcgttatc ggtaccggta aaatcggtgt ggcgatgctg   480
cgcattctga aggttttgg tatgcgtctg ctggcgttcg atccgtatcc aagtgcagcg   540
gcgctggaac tcgtgtgga gtatgtcgat ctgccaaccc tgttctctga atcagacgtt   600
atctctctgc actgcccgct gacaccggaa aactaccatc tgttgaacga agccgccttc   660
gatcagatga aaaatggcgt gatgatcgtc aataccagtc gcggtgcatt gattgattct   720
caggcagcaa ttgaagcgct gaaaaatcag aaaattggtt cgttgggtat ggacgtgtat   780
gagaacgaac gcgatctgtt ctttgaagat aaatccaacg acgtgatcca ggatgacgta   840
ttccgtcgcc tgtctgcctg ccacaacgtg ctgtttaccg ggcaccaggc attcctgaca   900
gcagaagctc tgaccagtat ttctcagact acgctgcaaa acttaagcaa tctggaaaaa   960
ggcgaaacct gcccgaacga actggtttaa                                    990

<210> SEQ ID NO 105
<211> LENGTH: 1050
<212> TYPE: DNA
<213> ORGANISM: Ralstonia eutropha

<400> SEQUENCE: 105
atgaagatct ccctcaccag cgcccgccag cttgcccgcg acatcctcgc cgcgcagcag    60
gtgcccgccg acatcgctga cgacgtggcc gagcacctgg tcgaatccga ccgctgcggc   120
tatatcagcc acggcctgtc gatcctgccc aactaccgca ccgccctcga cggccacagc   180
gtcaacccgc aaggccgcgc caaatgcgtg ctggaccagg gcacgctgat ggtgttcgac   240
ggcgacggcg gcttcggcca gcacgtgggc aagtccgtga tgcaagcagc gatcgagcgc   300
gtgcgccagc atggccactg catcgtcact ctgcgccgct cgcaccatct cggccgcatg   360
ggccactacg gcgagatggc ggccgccgcc ggctttgtgc tgctgagctt caccaacgtg   420
atcaaccgcg cgccggtggt ggcgccgttc ggcggccgcg tggcgcggct caccaccaac   480
ccgctgtgtt cgccggccc gatgcccaac gggcggccgc ctctggtggt ggacatcgcc   540
accagcgcga ttgccatcaa caaggcccgt gtgctggccg agaaaggcga gccggcgccc   600
gaaggcagca tcatcggcgc cgacggcaac cccaccaccg acgcgtcaac catgttcggc   660
gaacaccccg gcgcgctgct gcccttggc ggccacaagg ctacgcact gggcgttgtg   720
gccgagctgc tggcgggcgt gctgtccggc ggcggtacca tccagccaga caatccgcgc   780
ggcggcgtgg ccaccaacaa cctgttcgcg gtgctgctca atcccgcgct ggacctgggc   840
ctggactgga gagcgccga ggtcgaggcg ttcgtgcgct acctgcacga cacaccgccg   900
gcgccgggcg tcgaccgcgt gcagtacccc ggcgagtacg aggccgccaa ccgggcgcag   960
gccagcgaca cgctaaacat caacccgccc atctggcgca atcttgagcg cctggcgcag  1020
tcgctcaacg tggccgtccc cacggcctga                                   1050
```

<210> SEQ ID NO 106
<211> LENGTH: 1056
<212> TYPE: DNA
<213> ORGANISM: Clostridium beijerinckii

<400> SEQUENCE: 106

| | | | | | |
|---|---|---|---|---|---|
| atgaaaggtt | ttgcaatgct | aggtattaat | aagttaggat | ggatcgaaaa | agaaaggcca | 60 |
| gttgcgggtt | catatgatgc | tattgtacgc | ccattagcag | tatctccgtg | tacatcagat | 120 |
| atacatactg | tttttgaggg | agctcttgga | gataggaaga | atatgatttt | agggcatgaa | 180 |
| gctgtaggtg | aagttgttga | agtaggaagt | gaagtgaagg | attttaaacc | tggtgacaga | 240 |
| gttatagttc | cttgtacaac | tccagattgg | agatctttgg | aagttcaagc | tggttttcaa | 300 |
| cagcactcaa | acggtatgct | cgcaggatgg | aaattttcaa | atttcaagga | tggagttttt | 360 |
| ggtgaatatt | ttcatgtaaa | tgatgcggat | atgaatcttg | cgattctacc | taaagacatg | 420 |
| ccattagaaa | atgctgttat | gataacagat | atgatgacta | ctggatttca | tggagcagaa | 480 |
| cttgcagata | ttcaaatggg | ttcaagtgtt | gtggtaattg | cattggagc | tgttggctta | 540 |
| atgggaatag | caggtgctaa | attacgtgga | gcaggtagaa | taattggagt | ggggagcagg | 600 |
| ccgatttgtg | ttgaggctgc | aaaatttat | ggagcaacag | atattctaaa | ttataaaaat | 660 |
| ggtcatatag | ttgatcaagt | tatgaaatta | acgaatggaa | aaggcgttga | ccgcgtaatt | 720 |
| atggcaggcg | gtggttctga | acattatcc | caagcagtat | ctatggttaa | ccaggagga | 780 |
| ataatttcta | atataaatta | tcatggaagt | ggagatgctt | tactaatacc | acgtgtagaa | 840 |
| tggggatgtg | aatggctca | caagactata | aaggaggtc | tttgtcctgg | ggacgtttg | 900 |
| agagcagaaa | tgttaagaga | tatggtagta | tataatcgtg | ttgatctaag | taaattagtt | 960 |
| acacatgtat | atcatggatt | tgatcacata | gaagaagcac | tgttattaat | gaaagacaag | 1020 |
| ccaaaagact | taattaaagc | agtagttata | ttataa | | | 1056 |

<210> SEQ ID NO 107
<211> LENGTH: 1059
<212> TYPE: DNA
<213> ORGANISM: Thermoanaerobacter brockii

<400> SEQUENCE: 107

| | | | | | |
|---|---|---|---|---|---|
| atgaaaggtt | ttgcaatgct | cagtatcggt | aaagttggct | ggattgagaa | ggaaaagcct | 60 |
| gctcctggcc | catttgatgc | tattgtaaga | cctctagctg | tggccccttg | cacttcggac | 120 |
| attcataccg | tttttgaagg | cgccattggc | gaaagacata | acatgatact | cggtcacgaa | 180 |
| gctgtaggtg | aagtagttga | agtaggtagt | gaggtaaaag | attttaaacc | tggtgatcgc | 240 |
| gttgttgtgc | cagctattac | ccctgattgg | cggacctctg | aagtacaaag | aggatatcac | 300 |
| cagcactccg | gtggaatgct | ggcaggctgg | aaattttcga | atgtaaaaga | tggtgttttt | 360 |
| ggtgaatttt | ttcatgtgaa | tgatgctgat | atgaatttag | cacatctgcc | taaagaaatt | 420 |
| ccattggaag | ctgcagttat | gattcccgat | atgatgacca | ctggttttca | cggagctgaa | 480 |
| ctggcagata | tagaattagg | tgcgacggta | gcagttttgg | gtattggccc | agtaggtctt | 540 |
| atggcagtcg | ctggtgccaa | attgcgtgga | gccggaagaa | ttattgccgt | aggcagtaga | 600 |
| ccagtttgtg | tagatgctgc | aaaatactat | ggagctactg | atattgtaaa | ctataaagat | 660 |
| ggtcctatcg | aaagtcagat | tatgaatcta | actgaaggca | aggtgtcga | tgctgccatc | 720 |
| atcgctggag | gaaatgctga | cattatggct | acagcagtta | agattgttaa | acctggtggc | 780 |
| accatcgcta | atgtaaatta | ttttggcgaa | ggagaggttt | tgcctgttcc | tcgtcttgaa | 840 |

```
tggggttgcg gcatggctca taaaactata aaaggcgggc tatgcccgg tggacgtcta    900 agaatggaaa gactgattga ccttgttttt tataagcgtg tcgatccttc taagctcgtc    960
actcacgttt tccggggatt tgacaatatt gaaaaagcct ttatgttgat gaaagacaaa   1020
ccaaaagacc taatcaaacc tgttgtaata ttagcataa                          1059

<210> SEQ ID NO 108
<211> LENGTH: 2537
<212> TYPE: DNA
<213> ORGANISM: Rhodococcus ruber

<400> SEQUENCE: 108
ctgcagggct tcaccctcgg ccactacacc cacgtcttcc ccgagttcgc ggcgaagatg     60
gggccgtggc tcgcggccgg cgacgtggtg ttcgacgaga cgatcgtcga cggcatcggc    120
aactcggtcg atgccttcct cgacctcatg cgcgggcgca acgtcggcaa gatgctcgtc    180
cgaaccgcct gacgtccgga gccggaacgg ccggcgtcgt gcagcggaag attcgctcca    240
gtgccgggcg ggcgcacctt cccggccgta gagtcgggcg catgaaagcc ctccagtaca    300
ccgagatcgg ctccgagccg gtcgtcgtcg acgtccccac cccggcgccc gggccgggtg    360
agatcctgct gaaggtcacc gcggccggct tgtgccactc ggacatcttc gtgatggaca    420
tgccggcaga gcagtacatc tacggtcttc ccctcaccct cggccacgag ggcgtcggca    480
ccgtcgccga actcggcgcc ggcgtcaccg gattcgagac ggggacgcc gtcgccgtgt     540 acgggccgtg ggggtgcggt gcgtgccacg cgtgcgcgcg cggccgggag aactactgca    600
cccgcgccgc cgagctgggc atcaccccgc ccggtctcgg ctcgcccggg tcgatggccg    660
agtacatgat cgtcgactcg gcgcgccacc tcgtcccgat cggggacctc gaccccgtcg    720
cggcggttcc gctcaccgac gcgggcctga cgccgtacca cgcgatctcg cgggtcctgc    780
ccctgctggg acccgctcg accgcggtcg tcatcgggt cggcggactc gggcacgtcg     840
gcatccagat cctgcgcgcc gtcagcgcgg cccgcgtgat cgccgtcgat ctcgacgacg    900
accgactcgc gctcgcccgc gaggtcggcc ccgacgcggc ggtgaagtcg ggcgccgggg    960
cggcggacgc gatccgggag ctgaccggcg gtgagggcgc gacggcggtg ttcgacttcg   1020
tcggcgccca gtcgacgatc gacacggcgc agcaggtggt cgcgatcgac gggcacatct   1080
cggtggtcgg catccatgcc ggcgccacg ccaaggtcgg cttcttcatg atcccgttcg    1140
gcgcgtccgt cgtgacgccg tactggggca cgcggtccga gctgatggac gtcgtggacc   1200
tggcccgtgc cggccggctc gacatccaca ccgagacgtt caccctcgac gagggaccca   1260
cggcctaccg gcggctacgc gagggcagca tccgcggccg cggggtggtc gtcccgggct   1320
gacacgacga cgaaggctcc gcactcggat cgagtgcgga gccttcgtcg ggtacgggga   1380
tcagcgagcg aacagcagcg cgcgcttgac ctcctggatc gccttcgtca cctggatgcc   1440
gcgcgggcac gcgtcggtgc agttgaaggt ggtgcggcag cgccacacgc cctcgacgtc   1500
gttgaggatg tcgagacgct cggcggcgcc ctcgtcacgg ctgtcgaaga tgaaccggtg   1560
cgcgttgacg atggcggcgg gaccgaagta gctgccgtcg ttccagtaca ccgggcacga   1620
ggtggtgcag cacgcgcaca ggatgcactt ggtggtgtcg tcgaaccggg cacggtcggc   1680
ctgcgactgg atccgctcgc gggtgggctc gttgcccgtg gcgatgagga acggcttcac   1740
ggcgcggaac gcgtcgaaga agggctccat gtcgacgacg aggtccttct cgaccggcag   1800
gccgcggatc ggctcgacgg tgatggtcac cggcttgccg tccttgggca gcatgtcctt   1860
```

| | |
|---|---|
| catcaggatc ttgcaggcca ggcggttgac gccgttgatc cgcatggcgt ccgagccgca | 1920 |
| caccccgtgc gcgcagctgc ggcggaacgt gagggtgccg tcgaggtagc ccttcacgta | 1980 |
| gagcagcagg ttgagcatgc ggtccgacgg cagcgccgga acctggaagc tgtcccagtg | 2040 |
| ctgacccttg ccgtcctcgg ggttgaaccg cgcgatcttg agggtgacca tcgtggcgcc | 2100 |
| ctcgggcacg ggtggcaggt tcgagacgtc ggcttcgttc ttctcgaggg ttgtcatcaa | 2160 |
| gtacttccgc tccatcggct cgtagcgggt ctgcaccacc ggcttgtagt ccaggcggat | 2220 |
| gggggagatc agctccgtcc cctccttgta ggccatggtg tgcttgagga acttctcgtc | 2280 |
| gtcgcgcttc gggaagtcct cgcggcgtg accgccgcgc gattccttcc ggttgagcgc | 2340 |
| accggcgacg gtgacctcgg ccatctcgag caggaagccc agctcgacgg cctcgagcag | 2400 |
| gtcgctgttg tagcgcttgc ccttgtcctg gacggtgatg ttcttgtacc gctccttcag | 2460 |
| cgcgtggatg tcctcgagcg ccttggtgag cgtctcctcg gtgcggaaca ccgaggcgtt | 2520 |
| gttgtccatg gactgca | 2537 |

<210> SEQ ID NO 109
<211> LENGTH: 1173
<212> TYPE: DNA
<213> ORGANISM: Pyrococcus furiosus

<400> SEQUENCE: 109

| | |
|---|---|
| atgtttgaga tatcaattta tcttcccaca gaaatagttt ttggtcctgg gaagcttgaa | 60 |
| atgcttccta aactagtgaa gaagcatggg ctttctggga aggccctaat agtaactgga | 120 |
| aggagaagca caaaggaaac tggagttctt tatagagttc aagaactact taagcaagct | 180 |
| ggggtagaga gcatagtttt tgacaaaatt attccaaatc caatatctac tcatgtggat | 240 |
| gaaggggcag agatagcgag aaaagaaaat gttagctttg ttgttggctt gggtggtgga | 300 |
| agtgcgatag atagtgcaaa agctatagca atgactgccg ccagtggagg taaatattgg | 360 |
| gactatgttc cagctgtggg aggaggaaag aagcctactg gagcgcttcc aatagttgca | 420 |
| attccaacaa cccacgggac tggaacggag gctgatcctt atgctgttat aactaatcct | 480 |
| gaaacaaagg agaagcaggg aattggatat gatgttctct tccccaaatt ctctatagtt | 540 |
| gatccagaac ttatgcttac tcttccaaaa gatcaaacag tgtacacttc aatggatgct | 600 |
| ttctaccact ccattgaggc cttttcttaat gttagagcaa atccatattc ggatgttctg | 660 |
| gctctcgact caatgaggcg cattgttaca taccttccat ggcctacga aaacttgaga | 720 |
| aatcttgaag caagaacgca acttgcctgg gcaagtactg aggctggaat aacgaaaacg | 780 |
| gtaacgggag ttgtggcaaa tcatgcactt gagcatggtc taagtggatt ctatcctgaa | 840 |
| gtgcctcatg gtctgggcct ctgcattcta ggaccctacc tctttgaata cattctcgac | 900 |
| tatgcctatg aaaagttggc gatagtcgga agagaggtat ttggagttta cgagccaaat | 960 |
| gacagaaagg cagcagagct agctattaag aagctacgtg acttccagag cctctttgga | 1020 |
| gtaaacaaga agctcagaga attaggggtt aaagaggaag acattccaga gatggctagg | 1080 |
| actgcttata gaatgatgaa acctgttata gaggcaacac cgggagattt gaaagttgaa | 1140 |
| gacttggaag agatctatag aagagcatac taa | 1173 |

<210> SEQ ID NO 110
<211> LENGTH: 2676
<212> TYPE: DNA
<213> ORGANISM: Escherichia coli

<400> SEQUENCE: 110

-continued

| | |
|---|---|
| atggctgtta ctaatgtcgc tgaacttaac gcactcgtag agcgtgtaaa aaaagcccag | 60 |
| cgtgaatatg ccagtttcac tcaagagcaa gtagacaaaa tcttccgcgc cgccgctctg | 120 |
| gctgctgcag atgctcgaat cccactcgcg aaaatggccg ttgccgaatc cggcatgggt | 180 |
| atcgtcgaag ataaagtgat caaaaaccac tttgcttctg aatatatcta caacgcctat | 240 |
| aaagatgaaa aaacctgtgg tgttctgtct gaagacgaca cttttggtac catcactatc | 300 |
| gctgaaccaa tcggtattat ttgcggtatc gttccgacca ctaacccgac ttcaactgct | 360 |
| atcttcaaat cgctgatcag tctgaagacc cgtaacgcca ttatcttctc cccgcacccg | 420 |
| cgtgcaaaag atgccaccaa caaagcggct gatatcgttc tgcaggctgc tatcgctgcc | 480 |
| ggtgctccga agatctgat cggctggatc gatcaacctt ctgttgaact gtctaacgca | 540 |
| ctgatgcacc acccagacat caacctgatc ctcgcgactg gtggtccggg catggttaaa | 600 |
| gccgcataca gctccggtaa accagctatc ggtgtaggcg cgggcaacac tccagttgtt | 660 |
| atcgatgaaa ctgctgatat caaacgtgca gttgcatctg tactgatgtc caaaaccttc | 720 |
| gacaacggcg taatctgtgc ttctgaacag tctgttgttg ttgttgactc tgtttatgac | 780 |
| gctgtacgtg aacgttttgc aacccacggc ggctatctgt tgcagggtaa agagctgaaa | 840 |
| gctgttcagg atgttatcct gaaaaacggt gcgctgaacg cggctatcgt tggtcagcca | 900 |
| gcctataaaa ttgctgaact ggcaggcttc tctgtaccag aaaacaccaa gattctgatc | 960 |
| ggtgaagtga ccgttgttga tgaaagcgaa ccgttcgcac atgaaaaact gtccccgact | 1020 |
| ctggcaatgt accgcgctaa agatttcgaa gacgcggtag aaaaagcaga gaaactggtt | 1080 |
| gctatgggcg gtatcggtca tacctcttgc ctgtacactg accaggataa ccaaccggct | 1140 |
| cgcgtttctt acttcggtca gaaaatgaaa acggcgcgta tcctgattaa cacccccagcg | 1200 |
| tctcagggtg gtatcggtga cctgtataac ttcaaactcg caccttccct gactctgggt | 1260 |
| tgtggttctt ggggtggtaa ctccatctct gaaaacgttg gtccgaaaca cctgatcaac | 1320 |
| aagaaaaccg ttgctaagcg agctgaaaac atgttgtggc acaaacttcc gaaatctatc | 1380 |
| tacttccgcc gtggctccct gccaatcgcg ctggatgaag tgattactga tggccacaaa | 1440 |
| cgtgcgctca tcgtgactga ccgcttcctg ttcaacaatg ttatgctga tcagatcact | 1500 |
| tccgtactga aagcagcagg cgttgaaact gaagtcttct tcgaagtaga agcggacccg | 1560 |
| accctgagca tcgttcgtaa aggtgcagaa ctggcaaact ccttcaaacc agacgtgatt | 1620 |
| atcgcgctgg gtggtggttc cccgatggac gccgcgaaga tcatgtgggt tatgtacgaa | 1680 |
| catccggaaa ctcacttcga agagctggcg ctgcgcttta tggatatccg taacgtatc | 1740 |
| tacaagttcc cgaaaatggg cgtgaaagcg aaaatgatcg ctgtcaccac cacttctggt | 1800 |
| acaggttctg aagtcactcc gtttgcggtt gtaactgacg acgctactgg tcagaaatat | 1860 |
| ccgctggcag actatgcgct gactccggat atggcgattg tcgacgccaa cctggttatg | 1920 |
| gacatgccga agtccctgtg tgctttcggt ggtctggacg cagtaactca cgccatggaa | 1980 |
| gcttatgttt ctgtactggc atctgagttc tctgatggtc aggctctgca ggcactgaaa | 2040 |
| ctgctgaaag aatatctgcc agcgtcctac cacgaagggt ctaaaaatcc ggtagcgcgt | 2100 |
| gaacgtgttc acagtgcagc gactatcgcg ggtatcgcgt ttgcgaacgc cttcctgggt | 2160 |
| gtatgtcact caatggcgca caaactgggt tcccagttcc atattccgca cggtctggca | 2220 |
| aacgccctgc tgatttgtaa cgttattcgc tacaatgcga acgacaaccc gaccaagcag | 2280 |
| actgcattca gccagtatga ccgtccgcag gctcgccgtc gttatgctga aattgccgac | 2340 |

| | | | | |
|---|---|---|---|---|
| cacttgggtc | tgagcgcacc | gggcgaccgt | actgctgcta | agatcgagaa actgctggca | 2400 |
| tggctggaaa | cgctgaaagc | tgaactgggt | attccgaaat | ctatccgtga agctggcgtt | 2460 |
| caggaagcag | acttcctggc | gaacgtggat | aaactgtctg | aagatgcatt cgatgaccag | 2520 |
| tgcaccggcg | ctaacccgcg | ttacccgctg | atctccgagc | tgaaacagat tctgctggat | 2580 |
| acctactacg | gtcgtgatta | tgtagaaggt | gaaactgcag | cgaagaaaga agctgctccg | 2640 |
| gctaaagctg | agaaaaaagc | gaaaaaatcc | gcttaa | | 2676 |

<210> SEQ ID NO 111
<211> LENGTH: 3015
<212> TYPE: DNA
<213> ORGANISM: Clostridium acetobutylicum

<400> SEQUENCE: 111

| | | | | |
|---|---|---|---|---|
| attttacttt | attctaataa | tacgtaatac | acccacttat | aactagtatt tggcaataaa | 60 |
| aatagttata | atcattaatt | attgttaaat | gtttgacaat | ctttaattac tgttatataa | 120 |
| taatattata | gaaaataaaa | tgactgcata | attttactat | agaaatacaa gcgttaaata | 180 |
| tgtacatatc | aacggtttat | cacattagaa | gtaaataatg | taaggaaacc acactctata | 240 |
| atttataagg | catcaaagtg | tgttatataa | tacaataagt | tttatttgca atagtttgtt | 300 |
| aaatatcaaa | ctaataataa | attttataaa | ggagtgtata | taaatgaaag ttacaaatca | 360 |
| aaaagaacta | aaacaaaagc | taaatgaatt | gagagaagcg | caaagaagt ttgcaaccta | 420 |
| tactcaagag | caagttgata | aaatttttaa | acaatgtgcc | atagccgcag ctaaagaaag | 480 |
| aataaactta | gctaaattag | cagtagaaga | aacaggaata | ggtcttgtag aagataaaat | 540 |
| tataaaaaat | cattttgcag | cagaatatat | atacaataaa | tataaaaatg aaaaaacttg | 600 |
| tggcataata | gaccatgacg | attctttagg | cataacaaag | gttgctgaac caattggaat | 660 |
| tgttgcagcc | atagttccta | ctactaatcc | aacttccaca | gcaattttca atcattaat | 720 |
| ttctttaaaa | acaagaaacg | caatattctt | ttcaccacat | ccacgtgcaa aaaaatctac | 780 |
| aattgctgca | gcaaaattaa | ttttagatgc | agctgttaaa | gcaggagcac ctaaaaatat | 840 |
| aataggctgg | atagatgagc | catcaataga | actttctcaa | gatttgatga gtgaagctga | 900 |
| tataatatta | gcaacaggag | gtccttcaat | ggttaaagcg | gcctattcat ctggaaaacc | 960 |
| tgcaattggt | gttggagcag | gaaatacacc | agcaataata | gatgagagtg cagatataga | 1020 |
| tatggcagta | agctccataa | ttttatcaaa | gacttatgac | aatggagtaa tatgcgcttc | 1080 |
| tgaacaatca | atattagtta | tgaattcaat | atacgaaaaa | gttaaagagg aatttgtaaa | 1140 |
| acgaggatca | tatatactca | atcaaaatga | aatagctaaa | ataaagaaa ctatgtttaa | 1200 |
| aaatggagct | attaatgctg | acatagttgg | aaaatctgct | tatataattg ctaaaatggc | 1260 |
| aggaattgaa | gttcctcaaa | ctacaaagat | acttataggc | gaagtacaat ctgttgaaaa | 1320 |
| aagcgagctg | ttctcacatg | aaaaactatc | accagtactt | gcaatgtata agttaagga | 1380 |
| ttttgatgaa | gctctaaaaa | aggcacaaag | gctaatagaa | ttaggtggaa gtggacacac | 1440 |
| gtcatcttta | tatatagatt | cacaaaacaa | taaggataaa | gttaaagaat tggattagc | 1500 |
| aatgaaaact | tcaaggacat | ttattaacat | gccttcttca | cagggagcaa gcggagattt | 1560 |
| atacaatttt | gcgatagcac | catcatttac | tcttggatgc | ggcacttggg gaggaaactc | 1620 |
| tgtatcgcaa | aatgtagagc | ctaaacattt | attaaatatt | aaagtgttg ctgaagaag | 1680 |
| ggaaaatatg | ctttggttta | agtgccaca | aaaaatatat | tttaaatatg gatgtcttag | 1740 |
| atttgcatta | aaagaattaa | aagatatgaa | taagaaaaga | gcctttatag taacagataa | 1800 |

```
agatctttttt aaacttggat atgttaataa aataacaaag gtactagatg agatagatat      1860
taaatacagt atatttacag atattaaatc tgatccaact attgattcag taaaaaaagg      1920
tgctaaagaa atgcttaact ttgaacctga tactataatc tctattggtg gtggatcgcc      1980
aatggatgca gcaaaggtta tgcacttgtt atatgaatat ccagaagcag aaattgaaaa      2040
tctagctata aacttatgg atataagaaa gagaatatgc aatttcccta aattaggtac       2100
aaaggcgatt tcagtagcta ttcctacaac tgctggtacc ggttcagagg caacaccttt      2160
tgcagttata actaatgatg aaacaggaat gaaatacct ttaacttctt atgaattgac       2220
cccaaacatg gcaataatag atactgaatt aatgttaaat atgcctagaa attaacagc       2280 agcaactgga atagatgcat tagttcatgc tatagaagca tatgtttcgg ttatggctac      2340
ggattatact gatgaattag ccttaagagc aataaaaatg atatttaaat atttgcctag      2400
agcctataaa aatgggacta acgacattga agcaagagaa aaaatggcac atgcctctaa      2460
tattgcgggg atggcatttg caaatgcttt cttaggtgta tgccattcaa tggctcataa      2520
acttggggca atgcatcacg ttccacatgg aattgcttgt gctgtattaa tagaagaagt      2580
tattaaatat aacgctacag actgtccaac aaagcaaaca gcattccctc aatataaatc      2640
tcctaatgct aagagaaaat atgctgaaat tgcagagtat ttgaatttaa agggtactag      2700
cgataccgaa aaggtaacag ccttaataga agctatttca aagttaaaga tagatttgag      2760
tattccacaa aatataagtg ccgctggaat aaataaaaaa gatttttata atacgctaga      2820
taaaatgtca gagcttgctt ttgatgacca atgtacaaca gctaatccta ggtatccact      2880
tataagtgaa cttaaggata tctatataaa atcatttaa aaaataaaga atgtaaaata       2940
gtctttgctt cattatatta gcttcatgaa gcacatagac tattttacat tttactcttg      3000 tttttttatct ttcaa                                                      3015
```

<210> SEQ ID NO 112
<211> LENGTH: 2685
<212> TYPE: DNA
<213> ORGANISM: Leuconostoc mesenteroides

<400> SEQUENCE: 112

```
atgagcaagt aaaggagcaa agattatggc agaagcaatt gcaaagaaac ccgcaaaaaa       60
ggttttgacc cctgaagaaa aagcggaatt acaaacacaa gctgagaaga tgactgttgt      120
attgattgaa aaatcacaaa aggcattgtc tgaattttca acattttcgc aagaacaagt      180
tgataaaatt gttgcagcta tggccttggc aggttctgag aattcacttc tgttagccca      240
tgctgctcac gacgagactg gacgtggggt tgtggaagat aaggatacga aaaatcgttt      300
cgcctcagaa tcagtttata cgctattaa gtttgataag actgtgggtg ttattagtga       360
agacaagatt caaggtaagg tagaattagc agccccactt ggtattttgg ctggaatcgc      420
tccaacgaca aatccaacgt cgacaactat tttcaaatca atgttgacag caaagacacg      480
taacacaatt atctttgctt tccatcccca gcctcaaaaa gcatcggttc ttgctgcaaa      540
aattgtttat gatgctgctg ttaaagcagg cgcaccggaa aactttatcc aatggattga      600
aaagccttca ctttatgcaa caagtgcgct gatacaaaat cctcacattg cttcaattct      660
agctactggt gggccatcaa tggttaatgc agctttgaag tcaggaaatc catccatggg      720
tgtcggtgct ggaaacggtg cagttttatat tgatgcaact gttgacacag atcgtgccgt      780
gtctgatttg ttgttatcaa agcgtttcga taatggcatg atttgtgcca cagaaaactc      840
```

```
agccgttatt caagcaccaa tctatgacga aattttaact aagttacaag aacaaggtgc    900 atacettgtt cctaagaaag actacaagaa aattgctgat tatgtcttta agcctaacgc    960
agagggattt ggtattgctg gtcctgttgc tggtatgtca ggacgttgga ttgctgagca   1020
agcaggcgta aagattcctg atggtaaaga tgtacttttg ttcgaattag atcagaagaa   1080
cataggtgaa gcgttatctt ctgaaaagtt atcgccatta ctttcaattt ataaagttga   1140
gaagcgtgaa gaagctattg agactgttca atccttgtta aactatcaag gcgcagggca   1200
caacgcagca attcaaattg gttcacaaga tgatccattc attaaagagt atgctgacgc   1260
tattggtgca tcacgtattt tggttaacca acctgactca atcggtggcg ttggggatat   1320
ttatacagat gctatgcgtc catcgttgac acttggtacc ggatcatggg ggaagaattc   1380
attgtctcat aacttatcaa catacgactt acttaatatt aagaccgtgg ctcgccgccg   1440
taatcgtcct caatgggttc gtttacctaa ggaagtttac tacgaaacca atgccattac   1500
ttacttacaa gacttgccta ctataaaccg tgcatttatt gtcgctgatc ctggtatggt   1560
tcagttcgga tttgttggca gagtactagg tcaacttaag ttacgtcaag aacaggttga   1620
aacaaatatc tatggttcag ttaagcctga cccaactttg tcacaagctg ttgaaattgc   1680
tcgccaaatg gcagacttca aaccagatac agttatttta cttggcggtg gttcggcact   1740
tgacgctggt aaaattggtc ggttcttgta cgaatactcg acacgccatg aaggaatttt   1800
agaagatgac gaggcgatta agagctatt cttagaacta caacaaaagt ttatggatat   1860
tcgtaagcga atcgttaagt tttaccacgc acgtttgaca caaatggttg cgattccaac   1920
aacttcaggt actggatcag aagtcacacc atttgccgtt attacagatg atgaaacaca   1980
tgtaaagtat ccactagccg attatgaatt gacaccggaa gttgctattg ttgatccaga   2040
atttgttatg accgtaccac aacacacggt atcttggtca ggattagatg ctttgtcaca   2100
tgctttggaa tcgtatgtct cagtgatggc ttctgaattc tcacgtcctt gggcattaca   2160
agctattaag ttgattttg ataacttaac aaattcatac aattatgatc ctaaacaccc   2220
aactaaggaa ggtcagaatg cacgcacaaa gatgcactat gcgtcaacat ggctggtat   2280 gtcatttgcg aatgccttct tgggacttaa ccactcacta gcacacaaaa ctggtggaga   2340
attcggacta cctcacggta tggcaatcgc tattgcaatg ccacatgtga ttaagtttaa   2400
tgcggtaaca ggaaatgtaa agcgcacacc atcccacga tacgaaacct atacagcaca   2460
aaaagattat gctgatattg cacgttactt aggtttgaaa ggtgaaacag atgctgaatt   2520
ggtcgatgta ttgattgcag aaatcaagaa gttggctgca tcagtgggtg tcaatcaaac   2580
actatctggc aacggtgttt caagcatga ctttgataca aagttagaaa agatgattga   2640
cttagtttac aatgaccaat gcacgccggg aaaccctcgc caacc             2685
```

<210> SEQ ID NO 113
<211> LENGTH: 3164
<212> TYPE: DNA
<213> ORGANISM: Saccharomyces cerevisiae

<400> SEQUENCE: 113

```
atgccgccgc tattcaaggg actgaaacag atggcaaagc caattgccta tgtttcaaga     60
ttttcggcga aacgaccaat tcatataata cttttttctc taatcatatc cgcattcgct    120
tatctatccg tcattcagta ttacttcaat ggttggcaac tagattcaaa tagtgttttt    180
gaaactgctc caaataaaga ctccaacact ctatttcaag aatgttccca ttactacaga    240
gattcctctc tagatggttg ggtatcaatc accgcgcatg aagctagtga gttaccagcc    300
```

```
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagtgttt ccaaagaaat ttcttctact gatggaacga aatggaggtt aagaagtgac    480
agaaaaagtc ttttcgacgt aaagacgtta gcatattctc tctacgatgt attttcagaa    540
aatgtaaccc aagcagaccc gtttgacgtc cttattatgg ttactgccta cctaatgatg    600
ttctacacca tattcggcct cttcaatgac atgaggaaga ccgggtcaaa ttttttggttg    660 agcgcctcta cagtggtcaa ttctgcatca tcactttttct tagcattgta tgtcacccaa    720
tgtattctag gcaaagaagt ttccgcatta actcttttttg aaggtttgcc tttcattgta    780
gttgttgttg gtttcaagca caaaatcaag attgcccagt atgccctgga gaaatttgaa    840
agagtcggtt tatctaaaag gattactacc gatgaaatcg tttttgaatc cgtgagcgaa    900
gagggtggtc gtttgattca agaccatttg ctttgtattt ttgcctttat cggatgctct    960
atgtatgctc accaattgaa gactttgaca aacttctgca tattatcagc atttatccta   1020 attttttgaat tgattttaac tcctacatt tattctgcta tcttagcgct tagactggaa   1080
atgaatgtta tccacagatc tactattatc aagcaaacat tagaagaaga cggtgttgtt   1140
ccatctacag caagaatcat tttaaagcag aaaagaaatc cgtatcttct ttcttaaatc   1200
tcagtgtggt tgtcattatc atgaaactct ctgtcatact gttgtttgtc ttcatcaact   1260
tttataactt tggtgcaaat tgggtcaatg atgccttcaa ttcattgtac ttcgataagg   1320
aacgtgtttc tctaccagat tttattacct cgaatgcctc tgaaaacttt aaagagcaag   1380
ctattgttag tgtcaccccca ttattatatt acaaacccat taagtcctac caacgcattg   1440
aggatatggt tcttctattg cttcgtaatg tcagtgttgc cattcgtgat aggttcgtca   1500
gtaaattagt tctttccgcc ttagtatgca gtgctgtcat caatgtgtat ttattgaatg   1560
ctgctagaat tcataccagt tatactgcag accaattggt gaaaactgaa gtcaccaaga   1620
agtcttttac tgctcctgta caaaaggctt ctacaccagt tttaaccaat aaaacagtca   1680
tttctggatc gaaagtcaaa agtttatcat ctgcgcaatc gagctcatca ggaccttcat   1740
catctagtga ggaagatgat tcccgcgata ttgaaagctt ggataagaaa atacgtcctc   1800
tagaagaatt agaagcatta ttaagtagtg gaaatacaaa acaattgaag aacaaagagg   1860
tcgctgcctt ggttattcac ggtaagttac ctttgtacgc tttggagaaa aaattaggtg   1920
atactacgag agcggttgcg gtacgtagga aggctctttc aattttggca gaagctcctg   1980
tattagcatc tgatcgttta ccatataaaa attatgacta cgaccgcgta tttggcgctt   2040
gttgtgaaaa tgttataggt tacatgcctt tgcccgttgg tgttataggc cccttggtta   2100
tcgatggtac atcttatcat ataccaatgg caactacaga gggttgtttg gtagcttctg   2160
ccatgcgtgg ctgtaaggca atcaatgctg gcggtggtgc aacaactgtt ttaactaagg   2220
atggtatgac aagaggccca gtagtccgtt tcccaacttt gaaagatct ggtgcctgta   2280 agatatggtt agactcagaa gagggacaaa acgcaattaa aaaagctttt aactctacat   2340
caagatttgc acgtctgcaa catattcaaa cttgtctagc aggagattta ctcttcatga   2400
gatttagaac aactactggt gacgcaatgg gtatgaatat gatttctaaa ggtgtcgaat   2460
actcattaaa gcaaatggta gaagagtatg gctgggaaga tatggaggtt gtctccgttt   2520
ctggtaacta ctgtaccgac aaaaaaccag ctgccatcaa ctggatcgaa ggtcgtggta   2580
agagtgtcgt cgcagaagct actattcctg gtgatgttgt cagaaaagtg ttaaaaagtg   2640
```

```
atgtttccgc attggttgag ttgaacattg ctaagaattt ggttggatct gcaatggctg    2700
ggtctgttgg tggatttaac gcacatgcag ctaatttagt gacagctgtt ttcttggcat    2760
taggacaaga tcctgcacaa aatgttgaaa gttccaactg tataacattg atgaaagaag    2820
tggacggtga tttgagaatt tccgtatcca tgccatccat cgaagtaggt accatcggtg    2880
gtggtactgt tctagaacca caaggtgcca tgttggactt attaggtgta agaggcccgc    2940
atgctaccgc tcctggtacc aacgcacgtc aattagcaag aatagttgcc tgtgccgtct    3000
tggcaggtga attatcctta tgtgctgccc tagcagccgg ccatttggtt caaagtcata    3060
tgacccacaa caggaaacct gctgaaccaa caaaacctaa caatttggac gccactgata    3120
taaatcgttt gaaagatggg tccgtcacct gcattaaatc ctaa                     3164

<210> SEQ ID NO 114
<211> LENGTH: 1290
<212> TYPE: DNA
<213> ORGANISM: Comamonas testosteroni

<400> SEQUENCE: 114
atggccgtcg attcgcgtct tcccaatttc cgagctctca cccccgcaca gcgctgggag     60
catgtcgcca ccgcatgcaa tctcagcgcc gaagaacgac atctactgac ccaggcgggc    120
gccctgcccg ccaccttggc tgacggcatg atcgaaaatg tggtgggcac gttcgagcta    180
cccatgggca tcgcaggcaa cttccgcatc aacggtcgcg atgtgctgat tccgctcgca    240
gtggaagagc cctccatcat cgctgctgct tcgtatatgg ccaagctggc ccgtgaagac    300
ggaggctttg aaacgtcgag caccttgccg ctgatgcgtg cgcaggtgca atcgtcggc    360 atcagcgacc cctatggtgc aagactggcg ttgttcaagg cccgcgatga gatcctcgcg    420
caagccaata gccgagacaa ggtgctgatc agcctgggcg gtggctgcaa ggacatcgaa    480
atccacgtct cccagattc tccgcgcggc cctatggtcg tgatgcactt gatcgtggac    540
gtgcgcgatg ccatgggtgc caacaccgtg aacaccatgg ccgaatcagt ctcgccactg    600
gtggaaaaga ttaccggtgg ttcggtgcgc ctgcgcattc tctcgaacct ggcagacctg    660
cgcctggccc gtgctcgtgt acgcctgaca ccgcaaacct tggccaccaa agagcgcagc    720
ggcgaagcaa ttattgaagg cgtgctcgac gcctacactt tcgccgccat tgacccctac    780
cgcgccgcta cccacaacaa gggcatcatg aacggtatcg accccgtcat cgtcgctaca    840
ggcaacgatt ggcgcgcggt cgaagccggt gcccatgcct atgccagccg caacggccaa    900
tacacctcgc tgacgcactg gaaaaagac aatgccggcg ccttggtggg aacgatcgag    960
ctacccatgc ccgtgggctt ggtgggcggt gccaccaaga cccatccgct ggcgcgcctg   1020
gcgctcaaga tcatggaggt gaagtctgcc caggaactgg gcgagattgc cgccgcagtg   1080
ggtctggccc agaacctggg tgctttgcgc gcgctggcca ccgaaggcat tcagcgcggc   1140
catatggcac ttcatgctcg caatattgcg caggtcgcag gagccgtggg tgaagaagta   1200
gagatcgtcg ccaagcgcct ggctaccgag catgacgtgc gcaccgatcg cgcactggaa   1260
gtgctgcaag aaattcgcgc ccagcgctaa                                    1290

<210> SEQ ID NO 115
<211> LENGTH: 1284
<212> TYPE: DNA
<213> ORGANISM: Desulfurococcus kamchatkensis

<400> SEQUENCE: 115
atggagaaga caagccgtat acagggcttc tacaagcttc cccttgaaga aagacggagg     60
```

```
atagtctgcg agtgggctgg gctaacagag gaagagtgca ggacactgag cgaattcggt    120
aatctaccag ttaagatagg ggacagcatg attgagaacg ttataggcgc gatgagctat    180
cccttcgcag tagcgacaaa cttcctgatc aatgggaggg attaccttgt cccaatggtt    240
atagaggaga caagcgtcgt agcggctgca agcaatgcgg ccaggatgct taggcatggg    300
aaagggatac ttgcaaatgc tgagagacag gagatgatca gccaaataca cctggttaaa    360
gtaaactccc cacgctttaa agccatgaag attatcgagg ccaagaagga gctactggac    420
tacgcggcac agcaggatcc aaccctgcta aagtacggcg ggggtcccag ggacctcgag    480
gtaagagcaa tggagcaccc tgctttaggc ggggtcataa tagtccacct agtagtagac    540
gtcagagacg ccatgggtgc taacactgtt aacacgatgg ctgaagcgat agccccgctt    600
ctagagaaga taacgggtgg ggaagcaagg ctcagaatag tttcaaacca cgcagtatac    660
agggttacac gggcatgggc tgcgacacct gtcgaagaag tgggaggcct tgaagtagcc    720
aggaggataa tggaggcatc tatactcgcc gagatagatc cctataggc ggtaacccat    780 aacaagggca taatgaatgg agtaatagca gtagccctcg cgacgggaca ggatcaccgc    840
gccatagagc tggagcccca tgcatacgcc tctagaacgg gggtctacaa gccctcagc    900 tactgggagg taacaagcga taactatctt gcgggaagcc ttgagatacc tctccaaata    960
ggcgttgttg gaggagcagt caaggtacac cctgtggcaa agatagcatt gaagatccta   1020
ggggtaaaca cggctaggga gctcgccgag gtaatggctg cggtagggct agcccagaac   1080
ctagccgctc taagagccct cgtgacagag ggtattcaga aaggccatat gaggctccac   1140
gccagaaacc tcgctataat ggctggtgca tcaggagatc taatagataa gatagccgag   1200
aaaatgatca gggacggtag aataagatac gactacgcta acaactagt agagaaagca   1260 ctacagggcg agccattaga ctag                                         1284
```

<210> SEQ ID NO 116
<211> LENGTH: 1281
<212> TYPE: DNA
<213> ORGANISM: Staphylococcus aureus

<400> SEQUENCE: 116

```
atgcaaaatt tagataagaa ttttcgacat ttatctcgta aagaaaagtt acaacaattg     60
gttgataagc aatggttatc agaagaacaa ttcgacattt tactgaatca tccattaatc    120
gatgaagaag tagccaatag tttaattgaa aatgtcatcg cgcaaggtgc attacccgtt    180
ggattattac cgaatatcat tgtggacgat aaggcatatg ttgtacctat gatggtggaa    240
gagccttcag ttgtcgctgc agctagttat ggtgcaaagc tagtgaatca gactggcgga    300
tttaaaacgg tatcttctga acgtattatg ataggtcaaa tcgtctttga tggcgttgac    360
gatactgaaa aattatcagc agacattaaa gctttagaaa agcaaattca taaaattgcg    420
gatgaggcat atccttctat taagcgcgt ggtggtggtt accaacgtat agcgattgat    480
acatttcctg agcaacagtt actatcttta aaagtatttg ttgatacgaa agatgctatg    540
ggcgctaata tgcttaatac gattttagag gccataactg cattttttaaa aaatgaattt    600 ccgcaaagcg acattttaat gagtatttta tccaatcatg caacagcgtc cgttgttaaa    660
gttcaaggcg aaattgatgt taaagattta gcaaggggcg agagaactgg agaagaggtt    720
gccaaacgaa tggaacgtgc ttctgtattg cacaagtag atattcatcg tgcagcaaca    780
cataataaag gtgttatgaa tggcatacat gctgttgttt tagcaacagg aaatgatacg    840
```

```
cgtggtgcag aagcaagtgc gcatgcatac gcaagtcgtg acggacagta tcgtggtatt      900
gctacatggc gttacgatca agatcgtcaa cgattgattg gtacaattga agtgcctatg      960
acattggcaa ttgttggggg tggtacgaaa gtattaccaa tagctaaagc ttcattagag     1020
ctactaaatg tagagtcagc acaagaatta ggtcatgtag ttgctgccgt tggtttagcg     1080
caaaactttg cagcatgtcg cgcgcttgtg tcagaaggta ttcaacaagg tcatatgagt     1140
ttacaatata atcattagc tattgttgta ggagcaaaag gtgatgaaat tgctaaagta     1200
gctgaagctt tgaaaaaga accccgtgca atacacaag cagcggaacg tattttacaa      1260
gatttaagaa gccaacaata g                                               1281

<210> SEQ ID NO 117
<211> LENGTH: 1236
<212> TYPE: DNA
<213> ORGANISM: Lactobacillus johnsonii

<400> SEQUENCE: 117
atgaaattag aagaatcatc taaaaagaaa ttttatcaat ggttaccaga ggaaagaaga       60 gtcttttttaa ctgaaaaagg aattaaacta agtgagattg agtctgaaac tttggaaaga     120
ctagataaac ttagtgaaaa tgtaattggt caagtccgtc ttcctcttgg tgtgcttcct     180
aagttaatag ttaacgggaa agattatcaa gtaccaatgg ccgtagaaga accatcggtt     240
gttgcagcag caaaccatgc agctaaaatt tttaatcaaa atggtggagc agtagctgat     300
agtagacgaa atggaatata tggtcaaatt gttttagagg taactgataa ttttgattta     360
actaagttta ctactgaatt tcctcaatta attagcttag ctaataaaaa attcgttagc     420
ttagtcaagc atggtggagg agttcgtaaa attgaagctt ctcaaaaaga aaatttagtt     480
tttcttagag ttttggttga cccagcagaa gctatgggag ctaataaaac aaatgctatt     540
ttagaatttt taggaaatga attagagaag cagccagata ttgaacaaac tctgtatgca     600
attttgtcta attatcctac gcaattgact agtgctaaag taagtctttc aattgacagt     660
gtaggaggat taaagttgc taaaagata gctttattga gtaaaatagg acaaactgat     720
atttaccggg cagtgactaa taataaagga attatgaatg gtattgatag tgtattggtt     780
gcaactggta atgattatcg tggagttgaa gcagcaactg ctgtttgggc taataaaaat     840
ggtgcctata catctttgag taagtggaaa attgaagaag atagactagt ggggactgta     900
acagttccct tagcaatcgg tgtagtaggt ggctcaatta aggctcgtcg agacgttcaa     960
caaagcttta gtttatttagg taatatatct gccaagcaac tagcagaagt tattgcgaca    1020
actggcttag caaataactt ttcagctctt ttagcaattt ctactaaggg aattcaagct    1080
gggcatatga aattgcaggc gagaaattta gtagcaacct aaaagctag tgaaggtgaa    1140 aaagcaatag ttttaaaaaa attgcaggaa agtaaaaat atactcaaga agcagcttt     1200 gaattttaa gcgaaataag aaaggatcaa aaataa                                1236

<210> SEQ ID NO 118
<211> LENGTH: 912
<212> TYPE: DNA
<213> ORGANISM: Acinetobacter sp. ADP1

<400> SEQUENCE: 118
ttgatatcaa tcagggaaaa acgcgtgaac aaaaaacttg aagctctctt ccgagagaat       60
gtaaaaggta agtggctttt gatcactggt gcatctagtg gaatcggttt gacgattgca     120
aaaagaattg ctgcggcagg tgctcatgta ttattggttg cccgaaccca agaaacactg      180
```

```
gaagaagtga aagctgcaat tgaacagcaa gggggacagg cctctatttt tccttgtgac      240
ctgactgaca tgaatgcgat tgaccagtta tcacaacaaa ttatggccag tgtcgatcat      300
gtcgatttcc tgatcaataa tgcagggcgt tcgattcgcc gtgccgtaca cgagtcgttt      360
gatcgcttcc atgattttga acgcaccatg cagctgaatt actttggtgc ggtacgttta      420
gtgttaaatt tactgccaca tatgattaag cgtaaaaatg ccagatcat caatatcagc       480 tctattggtg tattggccaa tgcgacccgt ttttctgctt atgtcgcgtc taaagctgcg      540
ctggatgcct tcagtcgctg tctttcagcc gaggtactca agcataaaat ctcaattacc      600
tcgatttata tgccattggt gcgtacccca atgatcgcac ccaccaaaat ttataaatac      660
gtgcccacgc tttccccaga agaagccgca gatctcattg tctacgccat tgtgaaacgt      720
ccaaaacgta ttgcgacgca cttgggtcgt ctggcgtcaa ttacctatgc catcgcacca      780
gacatcaata atattctgat gtcgattgga tttaacctat tcccaagctc aacggctgca      840
ctgggtgaac aggaaaaatt gaatctgcta acgtgcct atgcccgctt gttcccaggc        900
gaacactggt aa                                                          912

<210> SEQ ID NO 119
<211> LENGTH: 1670
<212> TYPE: DNA
<213> ORGANISM: Acinetobacter baylyi

<400> SEQUENCE: 119
cagaagatat ggttcggtta tcggttggga ttgaacatat tgatgatttg attgcagatc       60
tggaacaagc attggccaca gtttgagcgt aaatttata aaaaacctct gcaatttcag      120
aggttttttt atatttgctt tattatcgta tgatgttcat aattgatcta gcaaataata      180
aaaattagag caattactct aaaaacattt gtaatttcag atacttaaca ctagattttt      240
taaccaaatc actttagatt aactttagtt ctggaaattt tatttccctt taaccgtctt      300
caatccaaat acaataatga cagcctttac agtttgatat caatcaggga aaaacgcgtg      360
aacaaaaaac ttgaagctct cttccgagag aatgtaaaag gtaaagtggc tttgatcact      420
ggtgcatcta gtggaatcgg tttgacgatt gcaaaaagaa ttgctgcggc aggtgctcat      480
gtattattgg ttgcccgaac ccaagaaaca ctggaagaag tgaaagctgc aattgaacag      540 caaggggggac aggcctctat ttttccttgt gacctgactg acatgaatgc gattgaccag      600
ttatcacaac aaattatggc cagtgtcgat catgtcgatt tcctgatcaa taatgcaggg      660
cgttcgattc gccgtgccgt acacgagtcg tttgatcgct tccatgattt tgaacgcacc      720
atgcagctga attactttgg tgcggtacgt ttagtgttaa atttactgcc acatatgatt      780
aagcgtaaaa atgccagat catcaatatc agctctattg gtgtattggc caatgcgacc      840 cgttttctg cttatgtcgc gtctaaagct gcgctggatg ccttcagtcg ctgtctttca      900
gccgaggtac tcaagcataa aatctcaatt acctcgattt atatgccatt ggtgcgtacc      960
ccaatgatcg cacccaccaa aatttataaa tacgtgccca cgctttcccc agaagaagcc     1020
gcagatctca ttgtctacgc cattgtgaaa cgtccaaaac gtattgcgac gcacttgggt     1080
cgtctggcgt caattaccta tgccatcgca ccagacatca ataatattct gatgtcgatt     1140
ggatttaacc tattcccaag ctcaacggct gcactgggtg aacaggaaaa attgaatctg     1200
ctacaacgtg cctatgcccg cttgttccca ggcgaacact ggtaaaattt ataaagaag      1260 cctctcatac cgagaggctt ttttatggtt acgaccatca gccagattta gaggaaattg     1320
```

```
acttttcctg tttttacatc ataaatcgca ccaacaatat caatttcttt gcgatccagc   1380
atatctttaa gtacagaact atgctgaata atgtattgaa tattatagtg aacattcata   1440
gcagtcacct gatcaataaa tgctttgctt aattcacgcg gttgcataat atcaaataca   1500
ctgccaaccg aatgcatgag tggcccaagc acgtattgga tgtgtggcat ttcctgaata   1560
tcggaaatct gcttatgttg caatcttaac tggcatgcgc tggtgaccgc accacagtcg   1620
gtatgtccca aaaccagaat cactttggaa cctttggctt gacaggcaaa              1670
```

<210> SEQ ID NO 120
<211> LENGTH: 1362
<212> TYPE: DNA
<213> ORGANISM: Clostridium kluyveri

<400> SEQUENCE: 120

```
atgagtaatg aagtatctat aaagaattta attgaaaagg caaaggtggc acaaaaaaaa    60
ttggaagcct atagtcaaga acaagttgat gtactagtaa agcactagg aaaagtggtt   120 tatgataatg cagaaatgtt tgcaaaagaa gcagttgaag aaacagaaat gggtgtttat   180
gaagataaag tagctaaatg tcatttgaaa tcaggagcta tttggaatca tataaaagac   240
aagaaaactg taggcataat aaaagaagaa cctgaaaggg cacttgttta tgttgctaag   300
ccaaagggag ttgtggcagc tactacgcct ataactaatc cagtggtaac tcctatgtgt   360
aatgcaatgg ctgctataaa gggcagaaat acaataatag tagcaccaca tcctaaagca   420
aagaaagttt cagctcatac tgtagaactt atgaatgctg agcttaaaaa attgggagca   480
ccagaaaata tcatacagat agtagaagca ccatcaagag aagctgctaa ggaacttatg   540
gaaagtgctg atgtagttat tgctacaggc ggtgctggaa gagttaaagc tgcttactcc   600
agtggaagac cagcttatgg cgttggacct ggaaattcac aggtaatagt tgataaggga   660
tacgattata caaagctgc acaggatata ataacaggaa gaaatatga caatggaatt   720 atatgttctt cagagcaatc agttatagct cctgctgaag attatgataa ggtaatagca   780
gcttttgtag aaaatggggc attctatgta gaagatgagg aaacagtaga aaagtttaga   840
tcaactttat ttaaagatgg aaaaataaac agcaagatta taggtaaatc cgtccaaatt   900
attgcggatc ttgcaggagt aaaagtacca gaaggtacta aggttatagt acttaagggt   960
aaaggtgcag gagaaaaaga tgtactttgt aaagaaaaaa tgtgtccagt tttagtagca  1020
ttgaaatatg atacttttga agaagcagtt gaaatagcta tggctaatta tatgtatgaa  1080
ggagctggtc atacagcagg catacattct gacaatgacg agaacataag atatgcagga  1140
actgtattac ctataagcag attagttgta atcagcctg caactactgc tggaggaagt  1200
ttcaataatg gatttaaccc tactactaca ctaggctgcg gatcatgggg cagaaacagt  1260
atttcagaaa atcttactta cgagcatctt ataaatgttt caagaatagg gtatttcaat  1320
aaagaagcaa aagttcctag ctatgaggaa atatggggat aa                     1362
```

<210> SEQ ID NO 121
<211> LENGTH: 1356
<212> TYPE: DNA
<213> ORGANISM: Porphyromonas gingivalis

<400> SEQUENCE: 121

```
atggaaatca agaaatggt gagccttgca cgcaaggctc agaaggagta tcaagctacc    60
cataaccaag aagcagttga caacatttgc cgagctgcag caaagttat ttatgaaaat   120 gcagctattc tggctcgcga agcagtagac gaaaccggca tgggcgttta cgaacacaaa   180
```

```
gtggccaaga atcaaggcaa atccaaaggt gtttggtaca acctccacaa taaaaaatcg         240
attggtatcc tcaatataga cgagcgtacc ggtatgatcg agattgcaaa gcctatcgga         300
gttgtaggag ccgtaacgcc gacgaccaac ccgatcgtta ctccgatgag caatatcatc         360
tttgctctta agacctgcaa tgccatcatt attgcccccc accccagatc aaaaaatgc          420 tctgcacacg cagttcgtct gatcaaagaa gctatcgctc cgttcaacgt accggaaggt         480
atggttcaga tcatcgaaga acccagcatc gagaagacgc aggaactcat gggcgccgta         540
gacgtagtag ttgctacggg tggtatgggc atggtgaagt ctgcatattc ttcaggaaag         600
ccttctttcg tgttggagc cggtaacgtt caggtgatcg tggatagcaa catcgatttc          660
gaagctgctg cagaaaaaat catcaccggt cgtgctttcg acaacggtat catctgctca         720
ggcgaacaga gcatcatcta caacgaggct gacaaggaag cagttttcac agcattccgc         780
aaccacggtg catatttctg tgacgaagcc aaggagatc gggctcgtgc agctatcttc         840
gaaaatggag ccatcgcgaa agatgtagta ggtcagagcg ttgccttcat tgccaagaaa        900
gcaaacatca atatccccga gggtacccgt attctcgttg ttgaagctcg cggcgtagga        960
gcagaagacg ttatctgtaa ggaaaagatg tgtcccgtaa tgtgcgccct cagctacaag       1020
cacttcgaag aaggtgtaga atcgcacgt acgaacctcg ccaacgaagg taacggccac        1080
acctgtgcta tccactccaa caatcaggca cacatcatcc tcgcaggatc agagctgacg       1140
gtatctcgta tcgtagtgaa tgctccgagt gccactacag caggcggtca catccaaaac       1200
ggtcttgccg taaccaatac gctcggatgc ggatcatggg gtaataactc tatctccgag       1260
aacttcactt acaagcacct cctcaacatt tcacgcatcg caccgttgaa ttcaagcatt       1320
cacatccccg atgacaaaga aatctgggaa ctctaa                                 1356
```

<210> SEQ ID NO 122
<211> LENGTH: 1407
<212> TYPE: DNA
<213> ORGANISM: Clostridium saccharoperbutylacetonicum

<400> SEQUENCE: 122

```
atgattaaag acacgctagt ttctataaca aaagatttaa aattaaaaac aaatgttgaa          60
aatgccaatc taaagaacta caaggatgat tcttcatgtt tcggagttt t cgaaaatgtt       120 gaaaatgcta taagcaatgc cgtacacgca caaaagatat tatcccttca ttatacaaaa        180
gaacaaagag aaaaaatcat aactgagata agaaaggccg cattagaaaa taaagagatt        240
ctagctacaa tgattcttga agaaacacat atgggaagat atgaagataa aatattaaag        300
catgaattag tagctaaata cactcctggg acagaagatt taactactac tgcttggtca        360
ggagataacg gcttacagt tgtagaaatg tctccatatg cgttataggg tgcaataact        420
ccttctacga atccaactga aactgtaata tgtaatagta taggcatgat agctgctgga        480
aatactgtgg tatttaacgg acatccaggc gctaaaaaat gtgttgcttt tgctgtcgaa        540
atgataaata aagctattat ttcatgtggt ggtcctgaga atttagtaac aactataaaa        600
aatccaacta tggactctct agatgcaatt attaagcacc cttcaataaa actactttgc        660
ggaactggag ggccaggaat ggtaaaaacc ctcttaaatt ctggtaagaa agctataggt        720
gctggtgctg gaaatccacc agttattgta gatgatactg ctgatataga aaaggctggt        780
aagagtatca ttaaggctg ttcttttgat aataatttac cttgtattgc agaaaaagaa         840
gtatttgttt ttgagaacgt tgcagatgat ttaatatcta acatgctaaa aaataatgct        900
```

```
gtaattataa atgaagatca agtatcaaag ttaatagatt tagtattaca aaaaaataat    960
gaaactcaag aatactctat aaataagaaa tgggtcggaa aagatgcaaa attattctta   1020
gatgaaatag atgttgagtc tccttcaagt gttaaatgca taatctgcga agtaagtgca   1080
aggcatccat ttgttatgac agaactcatg atgccaatat taccaattgt aagagttaaa   1140
gatatagatg aagctattga atatgcaaaa atagcagaac aaaatagaaa acatagtgcc   1200
tatatttatt caaaaaatat agacaaccta aataggtttg aaagagaaat cgatactact   1260
atctttgtaa agaatgctaa atcttttgcc ggtgttggtt atgaagcaga aggctttaca   1320
actttcacta ttgctggatc cactggtgaa ggaataaactt ctgcaagaaa ttttacaaga   1380
caaagaagat gtgtactcgc cggttaa                                      1407
```

<210> SEQ ID NO 123
<211> LENGTH: 1407
<212> TYPE: DNA
<213> ORGANISM: Clostridium beijerinckii

<400> SEQUENCE: 123

```
atgaataaag acacactaat acctacaact aaagatttaa agtaaaaac aaatggtgaa     60 aacattaatt taaagaacta caaggataat tcttcatgtt tcggagtatt cgaaaatgtt   120
gaaaatgcta aagcagcgc tgtacacgca caaaagatat tatcccttca ttatacaaaa   180
gagcaaagag aaaaaatcat aactgagata agaaaggccg cattacaaaa taagagggtc   240
ttggctacaa tgattctaga agaaacacat atgggaagat atgaggataa aatattaaaa   300
catgaattgg tagctaaata tactcctggt acagaagatt taactactac tgcttggtca   360
ggtgataatg gtcttacagt tgtagaaatg tctccatatg gtgttatagg tgcaataact   420
ccttctacga atccaactga aactgtaata tgtaatagca taggcatgat agctgctgga   480
aatgctgtag tatttaacgg acacccatgc gctaaaaaat gtgttgcctt tgctgttgaa   540
atgataaata aggcaattat ttcatgtggc ggtcctgaaa atctagtaac aactataaaa   600
aatccaacta tggagtctct agatgcaatt attaagcatc cttcaataaa acttctttgc   660
ggaactgggg gtccaggaat ggtaaaaacc ctcttaaatt ctggtaagaa agctataggt   720
gctggtgctg gaaatccacc agttattgta gatgatactg ctgatataga aaaggctggt   780
aggagcatca ttgaaggctg ttctttttgat aataatttac cttgtattgc agaaaaagaa   840
gtatttgttt ttgagaatgt tgcagatgat ttaatatcta acatgctaaa aaataatgct   900
gtaattataa atgaagatca agtatcaaaa ttaatagatt tagtattaca aaaaaataat   960
gaaactcaag aatactttat aaacaaaaaa tgggtaggaa aagatgcaaa attattctta  1020
gatgaaatag atgttgagtc tccttcaaat gttaaatgca taatctgcga agtaaatgca  1080
aatcatccat ttgttatgac agaactcatg atgccaatat tgccaattgt aagagttaaa  1140
gatatagatg aagctattaa atatgcaaag atagcagaac aaaatagaaa acatagtgcc  1200
tatatttatt ctaaaaatat agacaaccta aatagatttg aaagagaaat agatactact  1260
atttttgtaa agaatgctaa atcttttgct ggtgttggtt atgaagcaga aggatttaca  1320
actttcacta ttgctggatc tactggtgag ggaataaacct ctgcaaggaa ttttacaaga  1380
caaagaagat gtgtacttgc cggctaa                                       1407
```

<210> SEQ ID NO 124
<211> LENGTH: 999
<212> TYPE: DNA
<213> ORGANISM: Metallosphaera sedula

<400> SEQUENCE: 124

```
atgaaagctg tcgtagtgaa aggacataaa cagggttatg aggtcaggga agttcaggac    60
ccgaaacctg cttcaggaga agtaatcatc aaggtcagga gagcagccct gtgttatagg   120
gaccttctcc agctacaggg gttctaccct agaatgaagt accctgtggt tctaggacat   180
gaggttgttg gggagatact ggaggtaggt gagggagtga ccggtttctc tccaggagac   240
agagtaattt cactcctcta tgcgcctgac ggaacctgcc actactgcag acagggtgaa   300
gaggcctact gccactctag gttaggatac tctgaggaac tagatggttt cttctctgag   360
atggccaagg tgaaggtaac cagtctcgta aaggttccaa cgagagcttc agatgaggga   420
gccgttatgg ttccctgcgt cacaggcatg gtgtacagag ggttgagaag gccaatcta   480
agagagggtg aaactgtgtt agttacggga gcaagcggtg gagttggaat acatgccctg   540
caagtggcaa aggccatggg agccagggta gtgggtgtca cgacgtcgga ggagaaggca   600
tccatcgttg gaaagtatgc tgatagggtc atagttggat cgaagttctc ggaggaggca   660
aagaaagagg acattaacgt ggtaatagac accgtgggaa cgccaacctt cgatgaaagc   720
ctaaagtcgc tctggatggg aggtaggata gtccaaatag gaaacgtgga cccaaccca   780
tcctatcagc tgaggttagg ttacaccatt ctaaaggata tagccataat tgggcacgcg   840
tcagccacaa ggagggatgc agagggagca ctaaagctga ctgctgaggg gaagataaga   900
ccagtggttg cgggaactgt tcacctggag gagatagaca agggatatga aatgcttaag   960
gataagcaca aagtggggaa agtactcctt accacgtaa                          999
```

<210> SEQ ID NO 125
<211> LENGTH: 1005
<212> TYPE: DNA
<213> ORGANISM: Sulfolobus tokodaii

<400> SEQUENCE: 125

```
atgaaagcaa ttgtagttcc aggacctaag caagggtata aacttgaaga ggtacctgat    60
cctaagccgg aaaagatgac agtaataatt agggtagata gagctgctct tgttataga   120
gatttgcttc aactacaagg atattatcca agaatgaaat acccagttat actagggcat   180
gaagttgtag gaaccataga agaagtcgga gaaaatataa agggatttga agtaggtgat   240
aaagtaattt ctttattata tgcaccagat ggtacatgcg aatattgcca aataggtgag   300
gaagcatatt gtcatcatag gttaggctac tcagaagagc tagacggatt ttttgcagag   360
aaagctaaaa ttaaagtaac tagcttagta aaggttccaa aaggtacccc agatgaggga   420
gcagtacttg taccttgtgt aaccggaatg atatatagag gtattagaag ggctggtggt   480
atacgtaaag gggagctagt gttagttact ggtgccagtg gtggagtagg aatacatgca   540
attcaagttg ctaaggcctt aggtgctaaa gttataggg taacaacatc agaagaaaaa   600
gcaaagataa ttaagcagta tgcggattat gtcatcgttg gtacaaagtt ttctgaagaa   660
gcaaagaaga taggtgatgt tactttagtt attgatactg tgggtactcc tactttcgat   720
gaaagcttaa agtcattgtg gatgggcgga aggattgttc aaatagggaa tgtcgaccct   780
tctcaaatct ataatttaag attgggctac ataatattaa aagatttaaa gatagttggt   840
catgcctcag ctaccaaaaa agatgctgaa gatacactaa aattaacaca gagggaaaa   900
attaaaccag ttattgcagg aacagtcagt cttgaaaata ttgatgaagg ttataaaatg   960
ataaaggata agaataaagt aggcaaagtc ttagtaaaac cataa                  1005
```

<210> SEQ ID NO 126
<211> LENGTH: 999
<212> TYPE: DNA
<213> ORGANISM: Metallosphaera cuprina

<400> SEQUENCE: 126

| | | |
|---|---|---|
| atgaaagctg ttatcgttaa gggagccaaa caaggttatg aagtcagaga cgttcaagat | 60 |
| ccgaaacctc aacctgatga ggtagtaata aaggttaaca gagctgccct atgttacaga | 120 |
| gatctccttc aacttcaggg gttttacccc aggatgaaat acccagtggt tctgggacac | 180 |
| gaagtgatag gcgaaatcgt tgacgtaggt agagacgtga aggggttcgc catagggggat | 240 |
| agagtcatat ccttacttta cgctcctgac ggtagctgtc actactgtaa aaggggagag | 300 |
| gaggcatact gtcactctag actgggctat tctgaggagc ttgatggatt cttcgcggag | 360 |
| atggcaaggg ttaaagtaag tagcctcgtt aaggtaccct ctggagtttc cgatgagggg | 420 |
| ggagtcatgg taccttgcgt aaccgggatg atatatagag gtttaagaag agctaactta | 480 |
| agcgaagggg agaccgtttt agtgacaggg gccagtggag gagtcggaat acacgccctg | 540 |
| caagtcgcga aaggaatggg ggccagagtg attggggtga cgacttcaga ggagaagagt | 600 |
| tcgattatag cgaagtactc tgacagggta atagtaggtt ccaagttctc ggaagaggcc | 660 |
| aagaaagagg acgtcaacgt gatcattgat accgttggaa ctcctacgtt tgaggaaagc | 720 |
| ctcagatcgt tatggatggg aggtagaata gtccagattg gtaacgtaga tcctacacag | 780 |
| gcttaccaat tgagattagg ctacacgatt ctcaaagata ttgccataat tgggcatgcc | 840 |
| tcagctacca aacgcgatgc tgaagccgct ttaaaactaa cttcagaagg caaggtaagg | 900 |
| ccgatagtag ctggaaccgt cagcttagag gagatagata agggttacga aatcctcaag | 960 |
| gacaaacaca agtagggaa ggtattgcta aagccttag | 999 |

<210> SEQ ID NO 127
<211> LENGTH: 1788
<212> TYPE: DNA
<213> ORGANISM: Streptomyces clavuligerus

<400> SEQUENCE: 127

| | | |
|---|---|---|
| atgggacagt acgctgcacc gttgcgcgac atgcaattcg tcttgcacga attgctgaac | 60 |
| gtcgaagccg aactgaagca actgcctaag cacgcggatc tggatgccga tacgatcaat | 120 |
| gcggtgctgc aggaggcggg caagttctgc tccgaggtcc tgtttccgtt gaaccaggtt | 180 |
| ggcgaccagc agggttgtac gtatgtcggc gacggcgtgg tgaccacgcc cgagggcttc | 240 |
| aagcaagcgt accagcagta tatcgaggcc ggctggccgg cgttgggctg cgatccggcc | 300 |
| tatggcggcc agggcttgcc cgcgttcgtg aacaacgcgc tgtacgagat gctcaattcg | 360 |
| gcgaaccagg catggaccat gtatcctggc ctgtcgcacg gcgcgtacga atgcctgcac | 420 |
| gcgcacggca cgccggagct tcaacagcgg tatctaccga agctggtatc cggtcagtgg | 480 |
| accggcacga tgtgcttgac cgagccgcat tgcggcaccg accttgggat cttgcgcacg | 540 |
| cgggccgagc ccaacggcga cggctcgtac tcgattaccg gcacgaagat ctttattcg | 600 |
| agcggcgagc acgacctcgc cgacaacatc gtccacctgg tgctcgcgcg gttgccggac | 660 |
| gcgccggcgg ggaccaaggg catttcattg ttcatcgtgc ccaagttcat cccggacgac | 720 |
| aacggcgagc ctgggcagcg caacggcgtc aagtgtggct cgatcgagca caagatgggc | 780 |
| atccatggca atgcgacgtg cgtaatcaat ctggatgatg ccaggggctg gctggtcggc | 840 |
| gagccgaaca agggcttgaa tgcgatgttc gtgatgatga atgcggcgcg gctcggcgtg | 900 |

```
ggcatgcaag gcctggggct gaccgaagtc gcgtaccaga actcgctcgc ctacgcgagg    960
cagcggctgc agatgcgctc gcttagcggt cctaaggcgc cggacaaggc ggccgacccg   1020
atcatcgtgc acccggatgt gcgacgcatg ttgttgacgc agaaggccta cgtcgaggcg   1080
gggcgcgcgt tcacgtactg ggcggctctg cagatcgaca aggaactgtc gcacgaggac   1140
gaggcggtgc gccgggatgc ggccgacctg gttgcgttgc tcacaccggt catcaaggcg   1200
ttcctgaccg acaacgcgtt cgaggcgacc aacaacgcca tgcaggtgtt gggcggccat   1260
ggctatatcg ctgagtgggg catcgagcaa tatgtgcgtg atgcgcgcat caacatgatt   1320
tacgaaggca ctaacacgat tcagtcgctg gacctgctgg ggcgcaaggt gctcggcgac   1380
atgggcgcga agctgaagaa gtttggcaag ctcgtgcagg attttgtcca ggccgagggc   1440
atcaaccccg acatgcagga gttcgtcaat ccgctggcgg acatcggcga aaaggtacag   1500
aagctgacga tggaaatcgg catgaaggcg atgcagagcc cggacgaagt tggcgccgcg   1560
gcggtaccgt acctgcgcac ggtcgggcat ttagtgttct cgtacttttg ggcgcgcatg   1620
gcccgtctgg cgctggacaa gcaaggtagc ggcgacccat tctaccggtc caagctcgcg   1680
accgcgcggt tctactttgc gaagctgtta cccgagacgg ccttcacgat ccgcgccgcg   1740
cgtgccggag ccaagccgct gaccgagatc gacgaagcgc tgttttaa               1788
```

<210> SEQ ID NO 128  
<211> LENGTH: 981  
<212> TYPE: DNA  
<213> ORGANISM: Rhodobacter sphaeroides
<400> SEQUENCE: 128

```
gtgagagccg ttctgataga gaaatccgac gatacgcagt ccgtttcggt gacggagctt     60
gccgaggacc agctgcccga gggcgacgtt ctggtcgacg tcgcctattc gaccttgaac    120
tacaaggacg cgctggcgat caccggcaag gcgccggtcg tgcggcgctt ccccatggtg    180
ccgggcatcg acttcacggg cacggtggca caaagcagcc atgccgattt caagcccggc    240
gaccgggtca tcctgaatgg ctggggcgtg ggggaaaaac actggggcgg gctggccgaa    300
cgggcacggg tccgcggcga ctggctggtt ccgctgccgg cgcccctcga cttgcggcag    360
gcggcgatga tcggcacggc gggctatacg gccatgctct gcgttctggc gctcgagcgg    420
cacggggtcg tgcccggcaa tggcgagatc gtcgtgagcg cgccgctgg cggtgtcggc     480
agcgttgcga cgacacttct tgccgcgaag ggctacgaag ttgctgcggt caccggccgt    540
gcctccgagg cggagtatct gcgcggtctg ggcgccgcgt cggtgatcga ccgcaacgaa    600
ctgaccggca aggtccgtcc gctggggcag gagcgttggg ccggcggcat cgatgttgcg    660
ggcagcacgg tgctggcgaa catgctctcg atgatgaaat accggggcgt cgtcgcggcc    720
tgcggtcttg ccgcgggaat ggatctgccc gcgtcggtgg cgcccttcat cctgcgcggt    780
atgaccctgg ccggggtcga cagcgtcatg tgcccgaaaa ccgaccgcct tgcggcctgg    840
gctcggctcg ccagcgatct cgatccggca aagctcgagg agatgacgac cgaactgccc    900
ttctccgagg tcatcgagac cgccccgaag ttccttgacg ggaccgtccg aggacgcatc    960
gtcattccgg tcaccccctg a                                             981
```

<210> SEQ ID NO 129  
<211> LENGTH: 1104  
<212> TYPE: DNA  
<213> ORGANISM: Clostridium propionicum

<400> SEQUENCE: 129

```
atggctttta acagtgctga tataaattcg tttcgagata tttgggtatt ttgcgaacag      60
agagaaggca agcttattaa tacagatttt gagctgattt cagaaggaag aaagctcgct     120
gatgagcggg gctcaaaatt ggttggtatt ttattaggac atgaggtaga agagattgca     180
aaagagctag gtggatatgg tgcagataaa gtgattgttt gcgaccatcc cgaattaaaa     240
ttttatacca cagatgctta tgccaaggta ctttgtgatg tggttatgga ggagaaaccc     300
gaggttattt tgattggtgc aacaaatatt ggccgtgatt taggccccag atgtgcagca     360
cgcttacata cgggtttaac agcagattgt acccatttgg atattgatat gaacaaaatat    420
gtggactttc tttccacctc ctcaacattg gatatatcat ccatgacctt tcctatggag     480
gacacaaatt taaaaatgac ccgtcctgcc tttggcggac atttgatggc aactatcatt     540
tgccctagat tccgcccttg tatgtctact gtaagacccg gggttatgaa aaaagcagag     600
tttagccagg aaatggctca ggcttgtcag gttgttacac gccatgtaaa tttatctgat     660
gaggacttaa agacgaaagt aatcaatatt gtgaaagaaa ctaaaaaaat tgttgattta     720
atcggcgccg aaattattgt ttctgttgga cgtggaatca gcaaggatgt gcaaggggc     780
attgccctag cagaaaagct tgccgatgcg tttgggaatg tgttgttgg cggttctcgt      840
gcggttattg attccggttg gctccctgcg gatcatcagg ttgggcagac gggaaaaacc     900
gtgcatccta aggtatatgt tgcccttggt atttccggcg ccattcagca taaggcaggt     960
atgcaggatt cagagttgat tattgcggta aataagacg agactgctcc tattttcgat    1020
tgtgctgatt atggtataac aggggatttg tttaaaattg taccaatgat gattgatgca    1080
attaaggaag gtaaaaatgc ttga                                           1104
```

<210> SEQ ID NO 130
<211> LENGTH: 804
<212> TYPE: DNA
<213> ORGANISM: Clostridium propionicum

<400> SEQUENCE: 130

```
atgagaattt atgtttgtgt aaaacaagtt ccggatacat cgggaaaggt tgctgtaaac      60
cccgatggaa ccttaaaccg tgcatctatg gcggctatta ttaatcccga tgatatgagt     120
gccattgagc aggccttaaa gttgaaggat gaaacaggct gtcaagttac agcccttacc     180
atggggccac ctcctgcgga gggaatgttg cgggaaatta tcgcaatggg cgcagatgat     240
ggcgttttaa tttccgccag agagttcggt ggttccgata ccttcgcaac ctctcaaatt     300
atatcggcgg cgatacataa attagggctt tccaatgagg atatgatttt tgcggtagg     360
caggcaattg atgcagatac agcacaggta ggaccgcaaa ttgcagaaaa attaagcatt     420
cctcaggtga cttatggggc agggattaaa aaaagcggag atttggtttt ggtaaagcgc     480
atgctgaaag atggatatat gatgatagag gtggaaacac cctgcttgat tacttgcatt     540
caggataagg ctgtaaaacc acgctatatg actttgaatg gaattatgga atgctatagc     600
aagcctcttt tggtattaga ttatgaagcc cttaaggatg aacccctaat cgaattggat     660
acgatcggtc tgaaaggttc tcctacaaat atatttaaat cctttacgcc gccacaaaag     720
ggtgtaggcg ttatgcttca aggaacagac aaagaaaaag ttgaagattt ggtggacaaa     780
ttgatgcaga agcatgtcat ttaa                                           804
```

<210> SEQ ID NO 131
<211> LENGTH: 1562

<212> TYPE: DNA
<213> ORGANISM: Candida boidinii

<400> SEQUENCE: 131

```
ttcaactaaa aattgaacta tttaaacact atgatttcct tcaattatat taaaatcaat      60
ttcatatttc cttacttctt tttgctttat tatacatcaa taactcaatt aactcattga     120
ttatttgaaa aaaaaaaaca tttattaact taactccccg attatatatt atattattga     180
ctttacaaaa tgaagatcgt tttagtctta tatgatgctg gtaagcacgc tgctgatgaa     240
gaaaaattat atggttgtac tgaaaataaa ttaggtattg ctaattggtt aaaagatcaa     300
ggtcatgaac taattactac ttctgataaa gaaggtgaaa caagtgaatt ggataaacat     360
atcccagatg ctgatattat catcaccact cctttccatc ctgcttatat cactaaggaa     420
agacttgaca aggctaagaa cttaaaatta gtcgttgtcg ctggtgttgg ttctgatcac     480
attgatttag attatattaa tcaaacaggt aagaaaatct cagtcttgga agttacaggt     540
tctaatgttg tctctgttgc tgaacacgtt gtcatgacca tgcttgtctt ggttagaaat     600
ttcgttccag cacatgaaca aattattaac cacgattggg aggttgctgc tatcgctaag     660
gatgcttacg atatcgaagg taaaactatt gctaccattg gtgctggtag aattggttac     720
agagtcttgg aaagattact ccctttaat ccaaaagaat tattatacta cgattatcaa     780
gctttaccaa aagaagctga agaaaaagtt ggtgctagaa gagttgaaaa tattgaagaa     840
ttagttgctc aagctgatat cgttacagtt aatgctccat acacgcagg tacaaaaggt     900
ttaattaata aggaattatt atctaaattt aaaaaggtg cttggttagt caataccgca     960
agaggtgcta tttgtgttgc tgaagatgtt gcagcagctt tagaatctgg tcaattaaga    1020
ggttacggtg gtgatgttg gttcccacaa ccagctccaa aggatcaccc atggagagat    1080
atgagaaata aatatggtgc tggtaatgcc atgactcctc actactctgg tactactta     1140
gatgctcaaa caagatacgc tgaaggtact aaaaatatct tggaatcatt ctttactggt    1200
aaatttgatt acagaccaca agatattatc ttattaaatg gtgaatacgt tactaaagct    1260
tacggtaaac acgataagaa ataaattttc ttaacttgaa aactataatt gctataacaa    1320
ttcttcaatt tctctttttc ttccttttt tgaagaattt ttaacaatca aaattttgac    1380
tctttgattt cccgcaatct ctgagctcag catactcatt attatttat tattattatt    1440
attattactt ttattattat tatatttty cttctttaac gatatcgttt gtgttttatc    1500
ttttatgatt taaattttat acgaatttat gaatacaaca aaatatttaa gtttacacaa    1560
tg                                                                  1562
```

<210> SEQ ID NO 132
<211> LENGTH: 1131
<212> TYPE: DNA
<213> ORGANISM: Saccharomyces cerevisiae

<400> SEQUENCE: 132

```
atgtcgaagg gaaaggtttt gctggttctt tacgaaggtg gtaagcatgc tgaagagcag      60
gaaaagttat tggggtgtat tgaaaatgaa cttggtatca gaaatttcat tgaagaacag    120
ggatacgagt tggttactac cattgacaag gaccctgagc aacctcaac ggtagacagg      180
gagttgaaag acgctgaaat tgtcattact acgcccttt tccccgccta catctcgaga      240
aacaggattg cagaagctcc taacctgaag ctctgtgtaa ccgctggcgt cggttcagac      300
catgtcgatt tagaagctgc aaatgaacgg aaaatcacgg tcaccgaagt tactggttct      360
```

```
aacgtcgttt ctgtcgcaga gcacgttatg ccacaatttt tggttttgat aagaaactat    420
aatggtggtc atcaacaagc aattaatggt gagtgggata ttgccggcgt ggctaaaaat    480
gagtatgatc tggaagacaa aataatttca acggtaggtg ccggtagaat tggatatagg    540
gttctggaaa gattggtcgc atttaatccg aagaagttac tgtactacga ctaccaggaa    600
ctacctgcgg aagcaatcaa tagattgaac gaggccagca agcttttcaa tggcagaggt    660
gatattgttc agagagtaga gaaattggag gatatggttg ctcagtcaga tgttgttacc    720
atcaactgtc cattgcacaa ggactcaagg ggtttattca ataaaaagct tatttcccac    780
atgaaagatg gtgcatactt ggtgaatacc gctagaggtg ctatttgtgt cgcagaagat    840
gttgccgagg cagtcaagtc tggtaaattg gctggctatg tggtgatgt ctgggataag    900 caaccagcac caaaagacca tccctggagg actatggaca ataaggacca cgtgggaaac    960
gcaatgactg ttcatatcag tggcacatct ctggatgctc aaaagaggta cgctcaggga   1020
gtaaagaaca tcctaaatag ttacttttcc aaaaagtttg attaccgtcc acaggatatt   1080
attgtgcaga atggttctta tgccaccaga gcttatggac agaagaaata a            1131

<210> SEQ ID NO 133
<211> LENGTH: 438
<212> TYPE: DNA
<213> ORGANISM: Saccharomyces cerevisiae

<400> SEQUENCE: 133
atgtcgaagg gaaaggtttt gctggttctt tatgaaggtg gtaagcatgc tgaagagcag     60
gaaaagttat ggggtgtat tgaaaatgaa cttggtatca gaaatttcat tgaagaacag    120
ggatacgagt tggttactac cattgacaag gaccctgagc caacctcaac ggtagacagg    180
gagttgaaag acgctgaaat tgtcattact acgccctttt tccccgccta catctcgaga    240
aacaggattg cagaagctcc taacctgaag ctctgtgtaa ccgctggcgt cggttcagac    300
catgtcgatt tagaagctgc aaatgaacgg aaaatcacgg tcaccgaagt tactggttct    360
aacgtcgttt ctgtcgcaga gcacgttatg ccacaatttt tggttttgat aagaaactat    420
aatggtggtc atcaataa                                                  438

<210> SEQ ID NO 134
<211> LENGTH: 867
<212> TYPE: DNA
<213> ORGANISM: Cupriavidus necator

<400> SEQUENCE: 134
atgatgcgct gcatgcagtc accggaggtg catccggccg cggccggaga cgccgagccg     60
cccactcaca gcaccttcgc cgtcagccgc tggcgccgcg cgagctgat gctgagcccc    120 gatgaagtgg ccgaggaagt gccggtcgcg ctggtgtaca acggcatctc gcacgcggtg    180
atgctggcga cgccggccga cctggaggac ttcgcactcg gcttcagcct gagcgaaggc    240
atcgttaccc gtgccagcga cgtctatgac atcgagatcg acacgcgcga gcacggcatc    300
gccgtgcagc tggagatcgc atcggaagcc ttcatgcggc tcaaggaccg ccgccgctcg    360
ctggccgggc gcaccggctg cgggctgtgc ggcaccgaat cgctggaaca ggtgatgcgc    420
ctgccggcac cggtgcgcag cgatgccagc ttccataccg acgtgatcca ggccgcgttc    480
gtgcaactgc aactgcggca ggaactgcag caacacacgg tgcgacgca cgctgccgca    540 tggctgcgtg ccgatggcca tgtatcactg gtgcgtgaag acgtgggccg ccacaacgcg    600
ctggacaagc tggcgggcgc gctcgccagc agcggcgagg acatctccag cggcgcggtg    660
```

```
ctggtgacca gccgcgccag ctatgaaatg gtgctgaaga ccgccgccat cggcgccggc      720
gtgctcgccg cagtgtccgc accgacggcg ctggccgtgc ggcttgccga acaagccagc      780
atcaccctgg ccggcttcgt gcgcgccggc gcgcacgtgg tctatgccca tccccaacgc      840
ctgcagcacg aagcgagcct ggcatga                                          867

<210> SEQ ID NO 135
<211> LENGTH: 2880
<212> TYPE: DNA
<213> ORGANISM: Cupriavidus necator

<400> SEQUENCE: 135
atgaacgccc gcaacgagat cgatttcggc acgcccgcca gcccatccac cgaactggtc       60
accctggagg tcgatggcgt cagcgtcacc gtgcccgccg gcacctcggt gatgcgcgcc      120
gcgatggaag cgcagatcgc cgtccccaag ctgtgcgcca ccgacagcct cgaagccttc      180
ggctcgtgcc ggctgtgcct ggtcgagatc gaagggcgcc gcggctatcc ggcatcgtgc      240
accacgccgg tcgaagccgg catgaaggtc aagacccaga gcgacaagct ggccgacctg      300
cgccgcggcg tgatggagct gtatatctcc gaccacccgc tcgattgcct gacctgcccg      360
accaacggca actgcgagct gcaggacatg gccggcgtgg tcggcctgcg tgaagtgcgc      420
tacaacgacg gcgccccgga agctgcgccg atcgcgaccc acacgcagat gaagaaggac      480
gaatccaatc cttacttcac ctacgacccc tccaagtgca tcgtctgcaa ccgctgcgtg      540
cgcgcctgcg aggaaacgca gggcaccttc gccctgacca tcagcggccg cggcttcgat      600
tcccgcgtct cgcccggaac cagccagtcg ttcatggaat cggactgcgt ctcgtgcggc      660
gcctgcgtgc aggcgtgccc gaccgcgacg ctgaccgaga cctcggtgat caagttcggc      720
cagccctcgc acagcaccgt gaccacctgt gcctattgcg gcgtgggctg ttcgttcaag      780
gccgagatga agggcaatga agtggtgcgc atggtgccgt acaaggacgg caaggccaat      840
gaaggccacg cctgcgtcaa gggccgcttt gcctggggct acgccacgca caaggaccgc      900
atcctcaagc cgatgatccg cgccaagatc accgatccgt ggcgcgaggt gtcgtgggaa      960
gaggcgatcg actatgccgc gtcgcagttc aagcgtatcc aggccgagca cggcaaggac     1020
tccatcggcg gcatcgtgtc gtcgcgctgc accaatgaag agggctacct ggtgcagaag     1080
ctggtgcgcg cagccttcgg caacaacaac gtcgacacct gcgcgcgcgt gtgccattcg     1140
ccgaccggct acggcctgaa gcagaccctg ggcgaatcgg ccggcacgca gaccttcaag     1200
tcggtggaga aggccgacgt gatcatggtg atcggtgcca cccgaccga cggccacccg     1260 gtctttgcgt cgcgcatgaa gaagcgcctg cgcgccggcg ccaggctgat cgtggtcgat     1320
ccgcgccgca tcgacctggt cgactccccg catatccgtg ccgactatca cctgcaactg     1380
cgcccgggca ccaacgtggc gctggtgacc tcgctggccc acgtgatcgt caccgaaggc     1440
ctgctcaacg aagctttcat cgccgagcgc tgcgaggacc gcgccttcca gcaatgcgc     1500 gatttcgtct cgctgccgga gaactcgccg gaggcgatgg aaagcgtgac cggcattccg     1560
gcggaacagc tgcgcggtgc cgcacgcctg tatgccaccg gcggcaacgc tgcgatctac     1620
tacggcctgg gcgtgaccga gcatgcgcaa ggctcaacca ccgtgatggg cattgccaac     1680
ctcgccatgg ccaccggcaa tatcggccgc gaaggcgtgg tgtgaaccc gctgcgcggg     1740 cagaacaatg tgcagggctc gtgcgacatc ggttcgttcc gcatgagct gccgggctat     1800 cgccacgtgt cggactcgac cacgcgcggt ctgttcgaag ccgcgtggaa tgtcgagatc     1860
```

```
agccccgagc cgggcctgcg catccccaat atgtttgaag ccgcgctggc cggcagcttc     1920
aagggcctct actgccaggg cgaggacatt gtccagtccg acccgaacac gcagcacgtg     1980
tccgaggcgc tgtcatcgat ggaatgcatc gtggtgcagg acatcttcct gaacgagacc     2040
gccaagtacg cgcacgtgtt cctgccgggc tcgtccttcc tggaaaagga cggcaccttc     2100
accaacgccg agcgccgcat ctcgcgcgtg cgcaaggtga tgccgcccaa ggcgcgctat     2160
gccgactggg aagccaccat cctgctggcc aatgcgctgg gctacccgat ggactacaag     2220
catccgtcgg agatcatgga cgagatcgcg cgcctgacgc cgaccttcgc cggtgtcagc     2280
tacaagcgcc tggaccagct cggcagcatc cagtggccgt gcaacgccga cgcgccggaa     2340
ggcacgccga ccatgcatat cgacaccttc gtgcgcggca agggcaagtt catcatcacc     2400
aagtacgtgc ccaccaccga agagatcacg cgcgccttcc cgctgatcct gaccaccggc     2460
cgcatcctgt cgcaatacaa cgtcggcgcg cagacgcgcc gtaccgacaa cgtctactgg     2520
catgccgagg accggctcga gatccatccg cacgatgccg aggagcgcgg catcaaggac     2580
ggcgactggg tcggggtgca gagccgtgcc ggcgacacgg tgctgcgcgc gatcgtcagc     2640
gagcgcatgc agccgggcgt ggtctacacc accttccact tcccggaatc cggcgccaac     2700
gtgatcacca ccgacaactc cgactgggcc accaactgcc cggagtacaa ggtgaccgcg     2760
gtgcaggtgc tgccggtggc gcagccgtcg gcgtggcagc gggagtacca ggagttcaac     2820
gcccagcagc tgcaactgct ggaagccgcc agcgccgacc cggcgcaggc cgtacgctga     2880

<210> SEQ ID NO 136
<211> LENGTH: 1563
<212> TYPE: DNA
<213> ORGANISM: Cupriavidus necator

<400> SEQUENCE: 136
atgatcacga tcaccaccat cttcgtgccg cgcgattcca ccgcgctggc actgggcgcc       60
gacgacgtcg cccgcgccat cgcgcgtgaa gccgcggcgc gcaacgagca cgtgcgcatt      120
gtgcgcaatg gctcgcgcgg catgttctgg ctggagccgc tggtcgaggt gcagaccgga      180 gccgccgcg tggcctatgg cccggtcagc gccgcagacg tgccggggct gttcgacgcc       240
ggcttgctgc aaggcggcga gcacgcgctg tcgcagggcg tcaccgaaga gatccccttc      300
ctgaagcagc aggagcgcct gaccttcgcc cgcgtcggca tcaccgatcc gctgtcgctg      360
gacgactacc gcgcgcatga gggctttgcc ggcctggagc gcgcgctggc gatgcagccc      420
gccgagatcg tgcaggaggt caccgactcc ggcctgcgcg ccgcggcgg cgggcgttc       480 ccgaccggca tcaagtggaa gaccgtgctg ggcgcgcagt ccgcggtcaa gtacatcgtc      540
tgcaatgccg acgagggcga ctcgggcacg ttctccgatc gcatggtgat ggaagacgac      600
ccgttcatgc tgatcgaagg catgaccatt gccgcgcttg cggtgggtgc ggagcagggc      660
tacatctact gccgttccga atacccgcac gcgattgccg tgctggaaag cgcgattggt      720
atcgccaacg ccgccggctg gctcggcgac gacatccgcg gcagcggcaa cgcttccac       780 ctcgaagtgc gcaagggcgc cggcgcctat gtctgcggcg aggaaaccgc gctgctggaa      840
agcctggaag acggcgcgg cgtggtgcgc gccaagccgc cgctgccggc gctgcagggg      900
ctgttcggca agcccacggt gatcaacaac gtgatctcgc tggccaccgt gccggtgatc      960
ctggcgcgcg gcgcgcagta ctaccgcgac tacggcatgg ccgttcgcg cggcacgctg     1020 ccgttccagc ttgccggcaa catcaagcag ggcggactgg tggaaaaggc gttcggcgtg     1080
acgctgcgcg agctgctggt cgactacggc ggcggcacgc gcagcggccg cgccatccgc     1140
```

| | |
|---|---|
| gcggtgcagg tgggcgggcc gctgggcgcc tacctgcccg agtcgcgctt cgacgtgccg | 1200 |
| ctggactatg aagcctatgc cgcgttcggc ggcgtggtcg gccacggcgg catcgtggtg | 1260 |
| ttcgatgaaa ccgtcgacat ggcaaagcag gcccgctacg cgatggagtt ctgcgcgatc | 1320 |
| gaatcgtgcg gcaagtgcac cccgtgccgg atcggctcga cccgcggcgt cgaagtgatg | 1380 |
| gaccgcatca tcgccggcga gcagccggtc aagcacgtcg ccctggtgcg cgacctgtgc | 1440 |
| gacaccatgc tcaacggctc gctgtgcgcg atgggcggca tgaccccgta cccggtgctg | 1500 |
| tccgcgctga tgaattcccc gaggacttc ggcctcgcct ccaacccagc caaggccgcc | 1560 |
| tga | 1563 |

<210> SEQ ID NO 137
<211> LENGTH: 225
<212> TYPE: DNA
<213> ORGANISM: Cupriavidus necator

<400> SEQUENCE: 137

| | |
|---|---|
| atgaagatcg acaacctcat caccatggcc aaccagatcg gcagcttctt cgaggccatg | 60 |
| ccggatcggg aagaggccgt ctctgatatt gcagggcata tcaagcggtt ttgggagccg | 120 |
| cgcatgcgca aggccttgct ggggcatgtg gatgccgagg cagggagcgg gctgctggac | 180 |
| atcgtgcgcg aggcgctggg gcggcatcgg gcgatgctgg agtag | 225 |

<210> SEQ ID NO 138
<211> LENGTH: 531
<212> TYPE: DNA
<213> ORGANISM: Cupriavidus necator

<400> SEQUENCE: 138

| | |
|---|---|
| atgccagaaa tttccccccca cgcaccggca tccgccgatg ccacgcgcat cgccgccatc | 60 |
| gtggccgcgc gccaggacat accgggcgcc ttgctgccga tcctgcatga gatccaggac | 120 |
| acacagggct atatccccga cgccgccgtg cccgtcattg cccgcgcgct gaacctgtcg | 180 |
| cgcgccgagg tgcacggcgt gatcaccttc taccaccatt tccgcagca gccggccggg | 240 |
| cgccacgtgg tgcaggtctg ccgcgccgaa gcctgccagt cggtcggcgc cgaagcgctg | 300 |
| gccgagcatg cgcagcgcgc acttggctgt ggctttcatg aaaccaccgc ggacgggcag | 360 |
| gtgacgctgg agcggtttta ttgcctgggc cagtgcgcct gcggcccgc cgtgatggtc | 420 |
| ggcgagcagc tgcacggcta tgtcgatgcc aggcgcttcg acgcgctggt gcgctcgctg | 480 |
| cgcgagtcgt ccgcggaaaa gaccacggaa gccgcggagg cacaggcatg a | 531 |

<210> SEQ ID NO 139
<211> LENGTH: 1095
<212> TYPE: DNA
<213> ORGANISM: Cupriavidus necator

<400> SEQUENCE: 139

| | |
|---|---|
| atgattcgca tctcgatcca cccgcacctg cagatccggg acgacgccag ccccggtggc | 60 |
| gaggccctgg acgtgtcccg cctggtggcc ctgctcggcc atatcgagga atccggcagc | 120 |
| atcagccact cggcgcaggc ggtatcgctg tcctaccgct acgcctgggg catcctgcgc | 180 |
| gatgccgagg cgctgttcgg cggcccgctg atcgacaaga cccgcgggcg cggcagcgcg | 240 |
| ctgacgccgc tggcgcagca gttggtgtgg ccagcaagc ggatcggcgc gcggctgtcg | 300 |
| ccgacgctgg acagcctggc gtccgagctg gagatcgagt tgaagaagct gatggaccag | 360 |

-continued

```
cccgaagcca cggcgcggct gcatgccagc cacggcttcg cggtggcggc gctgcgcgac      420
ttcctcgacg agcagcaggt gcggcacgac ctgaagtact gcggcagcgt cgaggccgtg      480
gcggcactgg ccgaaggcgc ctgcgatatc gccggcttcc atgtgccggt gggcgagttc      540
gagcacggca tgtggcggca tttcaccacc tggctcaagc cggacaccca ctgcctggtg      600
cacctggcgg tgcgcagcca gggactgttc gtgcggccgg acaacccgct tggcatccac      660
acgctggaag acctgacccg gcgcgaggtg cgcttcgtca accgccaggt gggctcgggc      720
acgcgcctgc tgctggacct gatgctggcc gcgcgcggca tcgacacggc ccgcatcgag      780
ggctacagca acggtgaatt cacccacgcc gcggtggccg cgtatatcgg cagcggcatg      840
gccgacgtgg gctttggcgt ggaaaccgcg gcgcggcgct tcgggctggc gttcgtgccg      900
gtgatcaagg agcgctactt ctttgcgatc gagcgcgcca agctgcgcag cgcggcactg      960
gccggcgcgg tggacgcgct taccagcgaa gccttccgcc agcgcgtcaa tgcactgccc     1020
ggctacgacg gcacgctgac cggcaccgtg ctgacgctgg aagaagcgtt cccggattac     1080
gctgaggcgc gctag                                                      1095
```

MODIFIED MICROORGANISMS AND METHODS OF MAKING BUTADIENE USING SAME

CROSS-REFERENCE TO RELATED APPLICATIONS

This application is a continuation of U.S. application Ser. No. 14/365,441, filed Jun. 13, 2014, which is a 371 National Stage Application of International Application No. PCT/US2012/70161, filed Dec. 17, 2012, which claims priority to and the benefit of U.S. Provisional Application No. 61/606,035, filed on Mar. 2, 2012, and U.S. Provisional Application No. 61/576,788, filed Dec. 16, 2011, the disclosures of each of which are incorporated by reference herein in their entirety.

BACKGROUND

Butadiene (1,3-butadiene, $CH_2=CH-CH=CH_2$, CAS 106-99-0) is a linear, conjugated 4-carbon hydrocarbon typically manufactured (along with other 4-carbon molecules) by steam cracking petroleum-based hydrocarbons. This process involves harsh conditions and high temperatures (at least about 850° C.). Other methods of butadiene production involve toxic and/or expensive catalysts, highly flammable and/or gaseous carbon sources, and high temperatures. Globally, several million tons of butadiene-containing polymers are produced annually. Butadiene can be polymerized to form polybutadiene, or reacted with hydrogen cyanide (prussic acid) in the presence of a nickel catalyst to form adiponitrile, a precursor to nylon. More commonly, however, butadiene is polymerized with other olefins to form copolymers such as acrylonitrile-butadiene-styrene (ABS), acrylonitrile-butadiene (ABR), or styrene-butadiene (SBR) copolymers.

SUMMARY

The present disclosure generally relates to microorganisms (e.g., non-naturally occurring microorganisms, also referred to herein as modified microorganisms) that comprise one or more polynucleotides coding for enzymes in one or more pathways that catalyze a conversion of a carbon source to butadiene and the uses of such microorganisms in industrial processes including, for use in the production of butadiene and products derived therefrom.

The present disclosure provides methods of producing butadiene from a fermentable carbon source, comprising: providing a fermentable carbon source; contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media; and expressing the one or more polynucleotides coding for the enzymes in the pathway that catalyzes a conversion of the fermentable carbon source to one or more intermediates in a pathway for the production of butadiene and the one or more polynucleotides coding for enzymes in a pathway that catalyze a conversion of the one or more intermediates to butadiene in the microorganism to produce butadiene.

In some embodiments which may be combined with any of the above or below mentioned embodiments, the enzymes that catalyze the conversion of the fermentable carbon source to one or more intermediates in the pathway for the production of butadiene are set forth in any one of Tables 1-3.

In some embodiments which may be combined with any of the above or below mentioned embodiments, the enzymes that catalyze the conversion of the one or more intermediates to butadiene are set forth in any one of Tables 1-3.

In some embodiments which may be combined with any of the above or below mentioned embodiments, butadiene is produced via an acetyl-CoA and propionyl-CoA intermediate; a crotonyl-CoA intermediate; and/or a formic acid intermediate.

In some embodiments which may be combined with any of the above or below mentioned embodiments, the one or more polynucleotides coding for enzymes in a pathway that catalyze a conversion of acetyl-CoA and propionyl-CoA to ketovaleryl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of ketovaleryl-CoA to (R) or (S) 3-hydroxyaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S) hydroxyaleryl-CoA to 2-pentenoyl-CoA code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of 2-pentenoyl-CoA to 2-pentenoic acid code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 2-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of 2-pentenoic acid to 4-pentenoic acid code for an isomerase including, for example, and isomerase encoded by a polynucleotide as set forth in any one of SEQ ID NOs: 99-102.

In some embodiments which may be combined with any of the above or below mentioned embodiments, the one or more polynucleotides coding for enzymes in a pathway that catalyze a conversion of 4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of 2-pentenoyl-CoA to pent-2,4-dienoyl-CoA code for a dehydrogenase including, for example, a dehydrogenase encoded by a polynucleotide as set forth in any one of SEQ ID NOs: 124-139.

In some embodiments which may be combined with any of the above or below mentioned embodiments, the one or more polynucleotides coding for enzymes in a pathway that catalyze a conversion of pent-2,4-dienoyl-CoA to pent-2,4-dienoic code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 2,4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of crotonyl-CoA to crotonyl alcohol code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of crotonyl-CoA to crotonaldehyde code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of crotonaldehyde to crotonyl alcohol code for an oxidoreductase or CoA synthetase including, for example, an oxidoreductase or synthetase encoded by a polynucleotide as set forth in any one of SEQ ID NOs: 103-123 or SEQ ID NOs: 34-36, respectively.

In some embodiments which may be combined with any of the above or below mentioned embodiments, the one or more polynucleotides coding for enzymes in a pathway that catalyze a conversion of crotonyl alcohol to butadiene code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of $CO_2$ to formic acid code for a dehydrogenase including, for example, a dehydrogenase encoded by a polynucleotide as set forth in any one of SEQ ID NOs: 124-139.

In some embodiments which may be combined with any of the above or below mentioned embodiments, the one or more polynucleotides coding for enzymes in a pathway that catalyze a conversion of pyruvate and CoA to acetyl-CoA and formic acid code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of formic acid to formyl-CoA code for a transferase or a CoA synthetase including, for example, a transferase or a CoA synthetase encoded by a polynucleotide as set forth in any one of SEQ ID NOs: 1-28 or 34-36, respectively.

In some embodiments which may be combined with any of the above or below mentioned embodiments, the one or more polynucleotides coding for enzymes in a pathway that catalyze a conversion of 2 acetyl-CoA to acetoacetyl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of acetoacetyl-CoA and formyl-CoA to 3,5-ketovaleryl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of 3,5-ketovaleryl-CoA to (R) or (S)-5-hydroxy-3-ketovaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S)-5-hydroxy-3-ketovaleryl-CoA to (R) or (S)-3,5-dihydroxyaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S)-3,5-dihydroxyaleryl-CoA to (R) or (S) 3-hydroxy-4-pentenoyl-CoA code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of (R) or (S)-3-hydroxy-4-pentenoyl-CoA to 3-hydroxy-4-pentenoic acid code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 3-hydroxy-4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the microorganism is a bacterium is selected from the genera consisting of: *Burkholderia, Propionibacterium, Propionispira, Clostridium, Bacillus, Escherichia, Pelobacter*, or *Lactobacillus*.

In some embodiments which may be combined with any of the above or below mentioned embodiments, the microorganism is a eukaryote is a yeast, filamentous fungi, protozoa, or algae.

In some embodiments which may be combined with any of the above or below mentioned embodiments, the yeast is *Saccharomyces cerevisiae, Zymomonas mobilis*, or *Pichia pastoris*.

In some embodiments which may be combined with any of the above or below mentioned embodiments, the carbon source is sugarcane juice, sugarcane molasses, hydrolyzed starch, hydrolyzed lignocellulosic materials, glucose, sucrose, fructose, lactate, lactose, xylose, pyruvate, or glycerol in any form or mixture thereof.

In some embodiments which may be combined with any of the above or below mentioned embodiments, the carbon source is a monosaccharide, oligosaccharide, or polysaccharide.

In some embodiments which may be combined with any of the above or below mentioned embodiments, the butadiene is secreted by the microorganism into the fermentation media.

In some embodiments which may be combined with any of the above or below mentioned embodiments, the methods may further comprise recovering the butadiene from the fermentation media.

In some embodiments which may be combined with any of the above or below mentioned embodiments, the microorganism has been genetically modified to express the one or more polynucleotides coding for enzymes in a pathway that catalyzes a conversion of the fermentable carbon source to one or more intermediates in the pathway for the production of butadiene and the one or more polynucleotides coding for enzymes in a pathway that catalyze a conversion of one or more intermediates to butadiene.

In some embodiments which may be combined with any of the above or below mentioned embodiments, the conversion of the fermentable carbon source to butadiene is ATP positive (e.g., generates a net of ATP per mol of butadiene produced) and may be additionally combined with a NADH consuming pathway to provide an anaerobic process for butadiene production.

The present disclosure also provides microorganisms comprising one or more polynucleotides coding for enzymes in a pathway that catalyzes a conversion of a fermentable carbon source to one or more intermediates in a pathway for the production of butadiene and one or more polynucleotides coding for enzymes in a pathway that catalyze a conversion of the one or more intermediates to butadiene.

In some embodiments which may be combined with any of the above or below mentioned embodiments, the enzymes that catalyze the conversion of the fermentable carbon source to one or more intermediates in the pathway for the production of butadiene are set forth in any one of Tables 1-3.

In some embodiments which may be combined with any of the above or below mentioned embodiments, the enzymes that catalyze the conversion of the one or more intermediates to butadiene are set forth in any one of Tables 1-3.

In some embodiments which may be combined with any of the above or below mentioned embodiments, butadiene is produced via an acetyl-CoA and propionyl-CoA intermediate; a crotonyl-CoA intermediate; and/or a formic acid intermediate.

In some embodiments which may be combined with any of the above or below mentioned embodiments, the microorganism is a bacterium is selected from the genera consisting of: *Burkholderia, Propionibacterium, Propionispira, Clostridium, Bacillus, Escherichia, Pelobacter*, or *Lactobacillus*.

In some embodiments which may be combined with any of the above or below mentioned embodiments, the microorganism is a eukaryote is a yeast, filamentous fungi, protozoa, or algae.

In some embodiments which may be combined with any of the above or below mentioned embodiments, the yeast is *Saccharomyces cerevisiae, Zymomonas mobilis*, or *Pichia pastoris*.

In some embodiments which may be combined with any of the above or below mentioned embodiments, the microorganism has been genetically modified to express the one or more polynucleotides coding for enzymes in a pathway that catalyzes a conversion of the fermentable carbon source to one or more intermediates in the pathway for the production of butadiene and the one or more polynucleotides coding for enzymes in a pathway that catalyze a conversion of one or more intermediates to butadiene.

The present disclosure also provides a method for producing butadiene, the method comprising: catalyzing a conversion of crotonyl alcohol to butadiene with an enzyme having an amino acid sequence at least 70% identical to linalool dehydratase (GI: 302064203).

In some embodiments, which may be combined with any of the above or below mentioned embodiments, the enzyme is at least 80% identical to linalool dehydratase (GI: 302064203).

In some embodiments, which may be combined with any of the above or below mentioned embodiments, the enzyme is at least 95% identical to linalool dehydratase (GI: 302064203).

In some embodiments, which may be combined with any of the above or below mentioned embodiments, the enzyme is linalool dehydratase (GI: 302064203).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity In some embodiments, which may be combined with any of the above or below mentioned embodiments, the enzyme has dehydratase and isomerase activity.

In some embodiments, which may be combined with any of the above or below mentioned embodiments, the method is performed in a microorganism.

The present disclosure also provides a method for producing butadiene, the method comprising: catalyzing a conversion of crotonyl alcohol to butadiene with an enzyme having an amino acid sequence at least 70% identical to a linalool dehydratase (EC 4.2.1.127).

In some embodiments, which may be combined with any of the above or below mentioned embodiments, the enzyme is at least 80% identical to a linalool dehydratase (EC 4.2.1.127).

In some embodiments, which may be combined with any of the above or below mentioned embodiments, the enzyme is at least 95% identical to a linalool dehydratase (EC 4.2.1.127).

In some embodiments, which may be combined with any of the above or below mentioned embodiments, the enzyme is a linalool dehydratase (EC 4.2.1.127).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity.

In some embodiments, which may be combined with any of the above or below mentioned embodiments, the enzyme has dehydratase and isomerase activity.

In some embodiments, which may be combined with any of the above or below mentioned embodiments, the method is performed in a microorganism.

The present disclosure also provides a modified microorganism comprising a polynucleotide coding for an enzyme that catalyzes a conversion of crotonyl alcohol to butadiene, wherein enzyme has an amino acid sequence at least 70% identical to linalool dehydratase (GI: 302064203).

In some embodiments, which may be combined with any of the above or below mentioned embodiments, the enzyme has an amino acid sequence at least 80% identical to linalool dehydratase (GI: 302064203).

In some embodiments, which may be combined with any of the above or below mentioned embodiments, the enzyme has an amino acid sequence at least 95% identical to linalool dehydratase (GI: 302064203).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity.

In some embodiments, which may be combined with any of the above or below mentioned embodiments, the enzyme has dehydratase and isomerase activity.

The present disclosure also provides a modified microorganism comprising a polynucleotide coding for an enzyme that catalyzes a conversion of crotonyl alcohol to butadiene, wherein the enzyme has an amino acid sequence at least 70% identical to a linalool dehydratase (EC 4.2.1.127).

In some embodiments, which may be combined with any of the above or below mentioned embodiments, the enzyme has an amino acid sequence at least 80% identical to linalool dehydratase (EC 4.2.1.127).

In some embodiments, which may be combined with any of the above or below mentioned embodiments, the enzyme has an amino acid sequence at least 95% identical to linalool dehydratase (EC 4.2.1.127).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity.

In some embodiments, which may be combined with any of the above or below mentioned embodiments, the enzyme has dehydratase and isomerase activity.

These and other embodiments of the present disclosure will be disclosed in further detail herein below.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1:
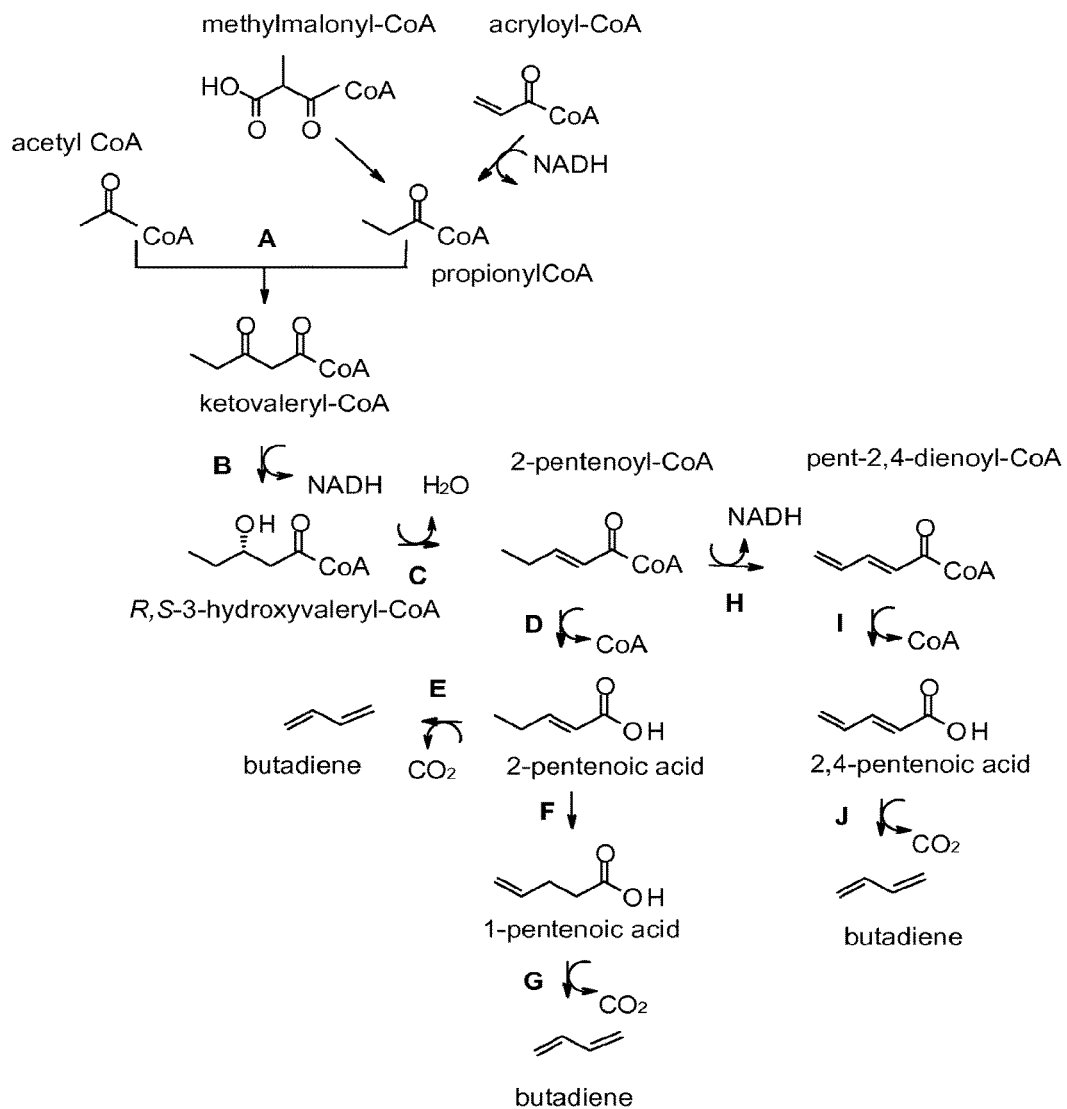
FIG. 1 depicts an exemplary pathway for the production of butadiene from a fermentable carbon source via an acetyl-CoA and propionyl-CoA intermediate.
Figure 2:
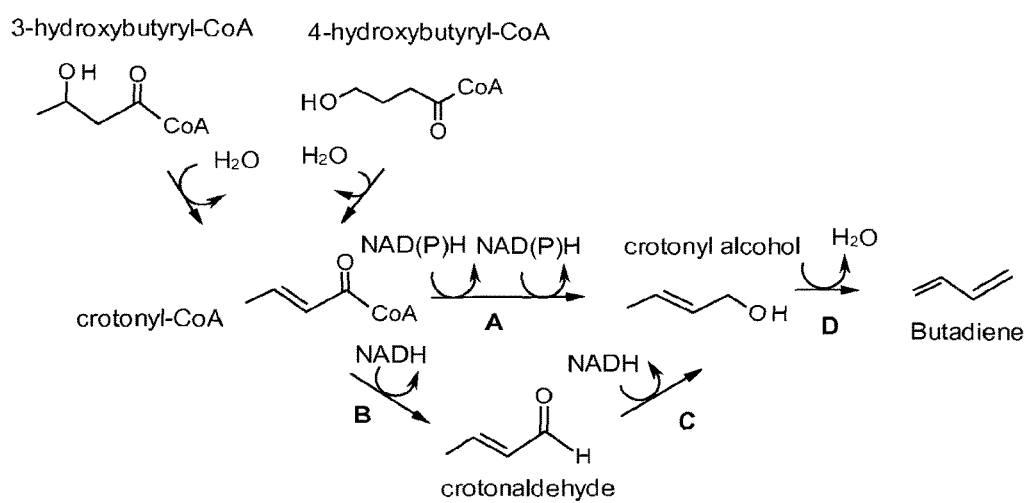
FIG. 2 depicts an exemplary pathway for the production of butadiene from a fermentable carbon source via a crotonyl-CoA intermediate.
Figure 3:
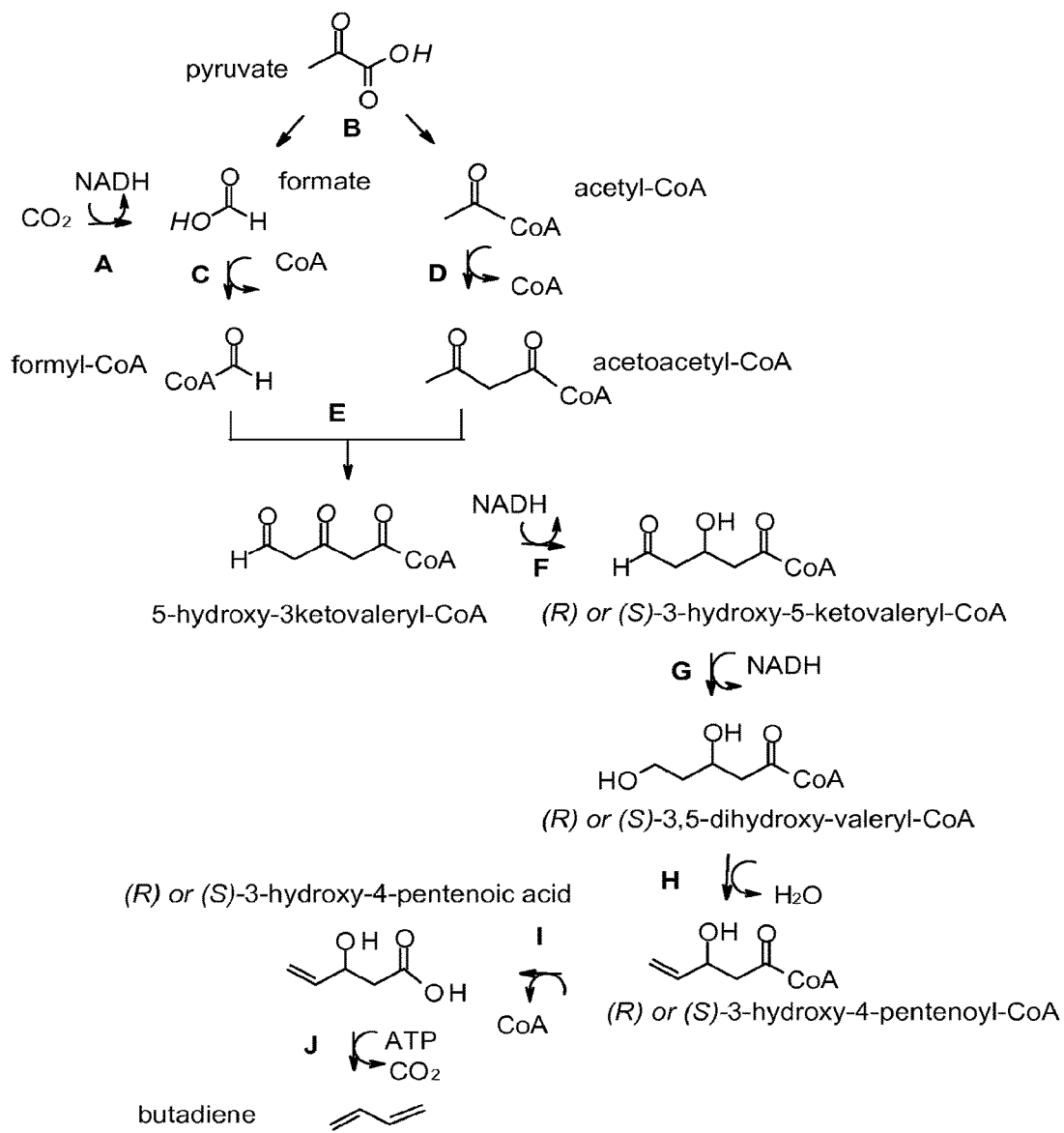
FIG. 3 depicts an exemplary pathway for the production of butadiene from a fermentable carbon source via a formic acid intermediate.

The present disclosure generally relates to microorganisms (e.g., non-naturally occurring microorganisms; modified microorganisms) that comprise a genetically modified pathway and uses of the microorganisms for the conversion of a fermentable carbon source to butadiene (see, FIGS. 1-3). Such microorganisms comprise one or more polynucleotides coding for enzymes that catalyze a conversion of a fermentable carbon source to butadiene via novel enzymatic pathways. Optionally, the produced butadiene may subsequently be converted to polybutadiene or any number of other butadiene-containing polymers.

This disclosure provides, in part, the discovery of novel enzymatic pathways including, for example, novel combinations of enzymatic pathways, for the production of butadiene from a carbon source (e.g., a fermentable carbon source). The enzymatic pathways disclosed herein permit the enzymatic production of butadiene via: an acetyl-CoA and propionyl-CoA intermediate; a crotonyl-CoA intermediate; and/or a formic acid intermediate.

The methods provided herein provide end-results similar to those of sterilization without the high capital expenditure and continuing higher management costs that are typically required to establish and maintain sterility throughout a production process. In this regard, most industrial-scale butadiene production processes are operated in the presence of measurable numbers of bacterial contaminants due to the aerobic nature of their processes. It is believed that bacterial contamination of a butadiene production processes causes a reduction in product yield and an inhibition of growth of the microorganism producing butadiene. Such drawbacks of prior methods are avoided by the presently disclosed methods as the toxic nature of the produced butadiene reduces contaminants in the production process.

The enzymatic pathways disclosed herein are advantageous over prior known enzymatic pathways for the production of butadiene in that the enzymatic pathways disclosed herein are ATP positive and when combined with a NADH consuming pathway it can provide an anaerobic pathway for butadiene. While it is possible to use aerobic processes to produce butadiene, anaerobic processes are preferred due to the risk incurred when olefins (which are by nature are explosive) are mixed with oxygen during the fermentation process, especially for butadiene fermentation. Moreover, the supplementation of oxygen and nitrogen in a fermenter requires an additional investment for air compressor, fermenters (bubble column or air-lift fermenter), temperature control and nitrogen. The presence of oxygen can also catalyze the polymerization of butadiene and can promote the growth of aerobic contaminants in the fermenter broth. Additionally, aerobic fermentation processes for the production of butadiene present several drawbacks at industrial scale (where it is technically challenging to maintain aseptic conditions) such as the fact that: (i) greater biomass is obtained reducing overall yields on carbon for the desired products; (ii) the presence and oxygen favors the growth of contaminants (Weusthuis et al., 2011, *Trends in Biotechnology*, 2011, Vol. 29, No. 4, 153-158) and (iii) the mixture of oxygen and gaseous compounds such as butadiene, poses serious risks of explosion, (iv) the oxygen can catalyze the unwanted reaction of polymerization of the olefin and, finally, (v) higher costs of fermentation and purification in aerobic conditions. Additionally, the butadiene produced by the processes disclosed herein is not diluted by $O_2$ and $N_2$ thus preventing both costly and time-consuming purification of the produced butadiene.

It will be understood that the steps involved in any and all of the methods described herein may be performed in any order and are not to be limited or restricted to the order in which they are particularly recited. For example, the present disclosure provides methods of producing butadiene from a fermentable carbon source, comprising: providing a fermentable carbon source; contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media; and expressing the one or more polynucleotides coding for the enzymes in the pathway that catalyzes a conversion of the fermentable carbon source to one or more intermediates in a pathway for the production of butadiene and one or more polynucleotides coding for enzymes in a pathway that catalyze a conversion of the one or more intermediates to butadiene in the microorganism to produce butadiene. As such, expression of the one or more polynucleotides coding for the enzymes in the pathway that catalyzes a conversion of the fermentable carbon source to one or more intermediates in a pathway for the production of butadiene and one or more polynucleotides coding for enzymes in a pathway that catalyze a conversion of the one or more intermediates to butadiene in the microorganism to produce butadiene may be performed prior to or after contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media.

It will also be understood that the microorganisms disclosed herein may comprise the entire pathway disclosed in any of FIGS. 1-3 including, comprising all of the polynucleotides that code for enzymes that catalyze a conversion of a fermentable carbon source to butadiene. Alternatively, it will also be understood that the microorganisms disclosed herein may comprises one or more of the polynucleotides coding for enzymes that catalyze a conversion of a fermentable carbon source to butadiene in any of FIGS. 1-3 (e.g., a microorganism may comprise 2, 3, 4, 5, 6, 7, 8, 9, 10 or more polynucleotides that code for enzymes that catalyze a conversion of a fermentable carbon source to butadiene as disclosed in any of FIGS. 1-3.

In some embodiments, the ratio of grams of the produced butadiene to grams of the fermentable carbon source is 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or 1.00.

In some embodiments, a number of moles of carbon in the produced butadiene comprises 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of a number of moles of carbon in the fermentable carbon source.

As used herein, "butadiene" is intended to mean buta-1, 3-diene or 1,3-butadiene (CAS 106-99-0), with a general formula $CH_2=CH-CH=CH_2$, and a molecular mass of 54.09 g/mol.

As used herein, the term "biological activity" or "functional activity," when referring to a protein, polypeptide or peptide, may mean that the protein, polypeptide or peptide exhibits a functionality or property that is useful as relating to some biological process, pathway or reaction. Biological or functional activity can refer to, for example, an ability to interact or associate with (e.g., bind to) another polypeptide or molecule, or it can refer to an ability to catalyze or regulate the interaction of other proteins or molecules (e.g., enzymatic reactions).

As used herein, the term "culturing" may refer to growing a population of cells, e.g., microbial cells, under suitable conditions for growth, in a liquid or on solid medium.

As used herein, the term "derived from" may encompass the terms originated from, obtained from, obtainable from, isolated from, and created from, and generally indicates that one specified material finds its origin in another specified material or has features that can be described with reference to the another specified material.

As used herein, the term "an expression vector" may refer to a DNA construct containing a polynucleotide or nucleic acid sequence encoding a polypeptide or protein, such as a DNA coding sequence (e.g., gene sequence) that is operably linked to one or more suitable control sequence(s) capable of affecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome (e.g., independent vector or plasmid), or may, in some instances, integrate into the genome itself (e.g., integrated vector). The plasmid is the most commonly used form of expression vector. However, the disclosure is intended to include such other forms of expression vectors that serve equivalent functions and which are, or become, known in the art.

As used herein, the term "expression" may refer to the process by which a polypeptide is produced based on a nucleic acid sequence encoding the polypeptides (e.g., a gene). The process includes both transcription and translation.

As used herein, the term "gene" may refer to a DNA segment that is involved in producing a polypeptide or protein (e.g., fusion protein) and includes regions preceding and following the coding regions as well as intervening sequences (introns) between individual coding segments (exons).

As used herein, the term "heterologous," with reference to a nucleic acid, polynucleotide, protein or peptide, may refer to a nucleic acid, polynucleotide, protein or peptide that does not naturally occur in a specified cell, e.g., a host cell. It is intended that the term encompass proteins that are encoded by naturally occurring genes, mutated genes, and/or synthetic genes. In contrast, the term homologous, with reference to a nucleic acid, polynucleotide, protein or peptide, refers to a nucleic acid, polynucleotide, protein or peptide that occurs naturally in the cell.

As used herein, the term a "host cell" may refer to a cell or cell line, including a cell such as a microorganism which a recombinant expression vector may be transfected for expression of a polypeptide or protein (e.g., fusion protein). Host cells include progeny of a single host cell, and the progeny may not necessarily be completely identical (in morphology or in total genomic DNA complement) to the original parent cell due to natural, accidental, or deliberate mutation. A host cell may include cells transfected or transformed in vivo with an expression vector.

As used herein, the term "introduced," in the context of inserting a nucleic acid sequence or a polynucleotide sequence into a cell, may include transfection, transformation, or transduction and refers to the incorporation of a nucleic acid sequence or polynucleotide sequence into a eukaryotic or prokaryotic cell wherein the nucleic acid sequence or polynucleotide sequence may be incorporated into the genome of the cell (e.g., chromosome, plasmid, plastid, or mitochondrial DNA), converted into an autonomous replicon, or transiently expressed.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Non-naturally occurring microbial organisms of the disclosure can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely. Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

As used herein, "butadiene" is intended to mean a conjugated linear diene with the molecular formula C4H6, a general formula of $CH_2=CH-CH=CH_2$ and a molecular mass of 54.09 g/mol. Butadiene is also known in the art as 1,3-butadiene, but-1,3-diene, biethylene, erythrene, divinyl, and vinylethylene.

As used herein, the term "operably linked" may refer to a juxtaposition or arrangement of specified elements that allows them to perform in concert to bring about an effect. For example, a promoter may be operably linked to a coding sequence if it controls the transcription of the coding sequence.

As used herein, the term "a promoter" may refer to a regulatory sequence that is involved in binding RNA polymerase to initiate transcription of a gene. A promoter may be an inducible promoter or a constitutive promoter. An inducible promoter is a promoter that is active under environmental or developmental regulatory conditions.

As used herein, the term "a polynucleotide" or "nucleic acid sequence" may refer to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Such polynucleotides or nucleic acid sequences may encode amino acids (e.g., polypeptides or proteins such as fusion proteins). Because the genetic code is degenerate, more than one codon may be used to encode a particular amino acid, and the present disclosure encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms polynucleotide, nucleic acid, and oligonucleotide are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S (thioate), P(S)S (dithioate), (O)NR$_2$ (amidate), P(O)R, P(O)OR', COCH$_2$ (formacetal), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, the term a "protein" or "polypeptide" may refer to a composition comprised of amino acids and recognized as a protein by those of skill in the art. The conventional one-letter or three-letter code for amino acid residues is used herein. The terms protein and polypeptide are used interchangeably herein to refer to polymers of amino acids of any length, including those comprising linked (e.g., fused) peptides/polypeptides (e.g., fusion proteins). The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, related proteins, polypeptides or peptides may encompass variant proteins, polypeptides or peptides. Variant proteins, polypeptides or peptides differ from a parent protein, polypeptide or peptide and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "recovered," "isolated," "purified," and "separated" may refer to a material (e.g., a protein, peptide, nucleic acid, polynucleotide or cell) that is removed from at least one component with which it is naturally associated. For example, these terms may refer to a material which is substantially or essentially free from components which normally accompany it as found in its native state, such as, for example, an intact biological system.

As used herein, the term "recombinant" may refer to nucleic acid sequences or polynucleotides, polypeptides or proteins, and cells based thereon, that have been manipulated by man such that they are not the same as nucleic acids, polypeptides, and cells as found in nature. Recombinant may also refer to genetic material (e.g., nucleic acid sequences or polynucleotides, the polypeptides or proteins they encode, and vectors and cells comprising such nucleic acid sequences or polynucleotides) that has been modified to alter its sequence or expression characteristics, such as by mutating the coding sequence to produce an altered polypeptide, fusing the coding sequence to that of another coding sequence or gene, placing a gene under the control of a different promoter, expressing a gene in a heterologous organism, expressing a gene at decreased or elevated levels, expressing a gene conditionally or constitutively in manners different from its natural expression profile, and the like.

As used herein, the term "selective marker" or "selectable marker" may refer to a gene capable of expression in a host cell that allows for ease of selection of those hosts containing an introduced nucleic acid sequence, polynucleotide or vector. Examples of selectable markers include but are not limited to antimicrobial substances (e.g., hygromycin, bleomycin, or chloramphenicol) and/or genes that confer a metabolic advantage, such as a nutritional advantage, on the host cell.

As used herein, the term "substantially similar" and "substantially identical" in the context of at least two nucleic acids, polynucleotides, proteins or polypeptides may mean that a nucleic acid, polynucleotide, protein or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) nucleic acid, polynucleotide, protein or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

As used herein, the term "transfection" or "transformation" may refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into host cells. Examples of transfection techniques include, but are not limited to, calcium phosphate precipitation, DEAE-dextran-mediated transfection, lipofection, electroporation, and microinjection.

As used herein, the term "transformed," "stably transformed," and "transgenic" may refer to a cell that has a non-native (e.g., heterologous) nucleic acid sequence or polynucleotide sequence integrated into its genome or as an episomal plasmid that is maintained through multiple generations.

As used herein, the term "vector" may refer to a polynucleotide sequence designed to introduce nucleic acids into one or more cell types. Vectors include cloning vectors, expression vectors, shuttle vectors, plasmids, phage particles, single and double stranded cassettes and the like.

As used herein, the term "wild-type," "native," or "naturally-occurring" proteins may refer to those proteins found in nature. The terms wild-type sequence refers to an amino acid or nucleic acid sequence that is found in nature or naturally occurring. In some embodiments, a wild-type sequence is the starting point of a protein engineering project, for example, production of variant proteins.

Unless defined otherwise herein, all technical and scientific terms used herein have the same meaning as commonly understood by one of ordinary skill in the art to which this disclosure belongs. Singleton, et al., Dictionary of Microbiology and Molecular Biology, second ed., John Wiley and Sons, New York (1994), and Hale & Markham, The Harper Collins Dictionary of Biology, Harper Perennial, NY (1991) provide one of skill with a general dictionary of many of the terms used in this disclosure. Further, it will be understood that any of the substrates disclosed in any of the pathways herein may alternatively include the anion or the cation of the substrate.

Numeric ranges provided herein are inclusive of the numbers defining the range.

Unless otherwise indicated, nucleic acids sequences are written left to right in 5' to 3' orientation; amino acid sequences are written left to right in amino to carboxyl orientation, respectively.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Modification of Microorganism

A microorganism may be modified (e.g., genetically engineered) by any method known in the art to comprise and/or express (e.g., including over express) one or more polynucleotides (e.g., heterologous polynucleotides and/or non-heterologous polynucleotides) coding for enzymes in one or more pathways that are capable of converting a fermentable carbon source to butadiene. The microorganism may naturally express all of the enzymes in one or more pathways needed to convert a fermentable carbon source to butadiene or may be modified to express including, for example, over express, one or more enzymes in the one or more pathways. In some embodiments, the microorganism may comprise fewer than all of the enzymes in such pathway and polynucleotides coding for the missing enzymes may be genetically introduced into the microorganism. For example, the modified microorganism may be modified to comprise one or more polynucleotides coding for enzymes that catalyze a conversion of a fermentable carbon source (e.g., glucose) to one or more intermediates (e.g., acetyl-CoA and propionyl-CoA; crotonyl-CoA; and/or formic acid) in a pathway for the production of butadiene. Additionally or alternatively, the modified microorganism may be modified to comprise one or more polynucleotides coding for enzymes that catalyze a conversion of the one or more intermediates (e.g., acetyl-CoA and propionyl-CoA; crotonyl-CoA; and/or formic acid) to butadiene. In some embodiments, a polynucleotide may code for an enzyme that catalyzes a conversion of one or more intermediates in a pathway for the production of butadiene. In some embodiments, polynucleotides may be modified (e.g., genetically engineered) to modulate (e.g., increase or decrease) the substrate specificity of the encode enzyme, or the polynucleotides may be modified to change the substrate specificity of the encoded enzyme (e.g., a polynucleotide that codes for an enzyme with specificity for a substrate may be modified such that the enzyme has specificity for another substrate). Preferred microorganisms may comprise polynucleotides coding for one or more of the enzymes as set forth in any one of Tables 1-3 and FIG. 1-3.

A microorganism may comprise one or more polynucleotides coding for enzymes in a pathway that catalyze a conversion of acetyl-CoA and propionyl-CoA to butadiene. In some embodiments, the one or more polynucleotides coding for enzymes in a pathway that catalyze a conversion of acetyl-CoA and propionyl-CoA to butadiene may include, but are not limited to:

one or more polynucleotides coding for enzymes in a pathway that catalyze a conversion of acetyl-CoA and propionyl-CoA to ketovaleryl-CoA (e.g., a thiolase);

one or more polynucleotides coding for enzymes in a pathway that catalyze a conversion of ketovaleryl-CoA to (R) or (S) 3-hydroxyvaleryl-CoA (e.g., a hydroxyvaleryl-CoA dehydrogenase);

one or more polynucleotides coding for enzymes in a pathway that catalyze a conversion of (R) or (S) hydroxyaleryl-CoA to 2-pentenoyl-CoA (e.g., a hydroxyvaleryl-CoA dehydratase);

one or more polynucleotides coding for enzymes in a pathway that catalyze a conversion of 2-pentenoyl-CoA to 2-pentenoic acid (e.g., a pentenoyl-CoA hydrolase or transferase);

one or more polynucleotides coding for enzymes in a pathway that catalyze a conversion of 2-pentenoic acid to butadiene (e.g., a 2-pentenoic acid decarboxylase);

one or more polynucleotides coding for enzymes in a pathway that catalyze a conversion of 2-pentenoic acid to 4-pentenoic acid (e.g., a transposing C=C bonds isomerase);

one or more polynucleotides coding for enzymes in a pathway that catalyze a conversion of 4-pentenoic acid to butadiene (e.g., a 4-pentenoic acid decarboxylase);

one or more polynucleotides coding for enzymes in a pathway that catalyze a conversion of 2-pentenoyl-CoA to pent-2,4-dienoyl-CoA (e.g., a pentenoyl-CoA dehydrogenase);

one or more polynucleotides coding for enzymes in a pathway that catalyze a conversion of pent-2,4-dienoyl-CoA to pent-2,4-dienoic (e.g., a pent-2,4-dienoyl-CoA hydrolase, or transferase); and/or one or more polynucleotides coding for enzymes in a pathway that catalyze a conversion of 2,4-pentenoic acid to butadiene (e.g., a pent,2,4-dienoic acid decarboxylase).

In some embodiments, the microorganism further comprises one or more polynucleotides coding for enzymes in a pathway that catalyze a conversion of a fermentable carbon source (e.g., glucose) to methylmalonyl-CoA and/or acryloyl-CoA.

In some embodiments, a microorganism is provided that comprises one or more of the above polynucleotides including, all, of the polynucleotides above.

Exemplary enzymes which convert acetyl-CoA and propionyl-CoA to butadiene are presented in Table 1 below, as well as, the substrates that they act upon and product that they produce. The enzyme number represented in Table 1 correlates with the enzyme numbering used in FIG. 1 which schematically represents the enzymatic conversion of a fermentable carbon source to butadiene through an acetyl-CoA and propionyl-CoA intermediate.

TABLE 1

Production of butadiene via acetyl-CoA and propionyl-CoA intermediates.

| Enzyme No. | Enzyme Name | E.C. number | Mediated Conversion |
|---|---|---|---|
| A | thiolase | 2.3.1. | acetyl-CoA + propionyl-CoA → ketovaleryl-CoA |
| B | hydroxyvaleryl-CoA dehydrogenase | 1.1.1. 1.1.1. | ketovaleryl-CoA + NADH→ (R) or (S) 3-hydroxyaleryl-CoA |
| C | hydroxyvaleryl-CoA dehydratase | 4.2.1. | (R) or (S) hydroxyaleryl-CoA→ 2-pentenoyl-CoA |
| D | pentenoyl-CoA hydrolase or transferase | 3.1.2, 2.8.3 or 2.3.3 | 2-pentenoyl-CoA → 2-pentenoic acid |
| E | 2-pentenoic acid decarboxylase | 4.1.1. | 2-pentenoic acid → butadiene |
| F | transposing C=C bonds isomerase | 5.3.3 | 2-pentenoic acid → 4-pentenoic acid |
| G | 4-pentenoic acid decarboxylase | 4.1.1.33 | 4-pentenoic acid → butadiene |
| H | pentenoyl-CoA dehydrogenase | 1.3.1. | 2-pentenoyl-CoA → pent-2,4-dienoyl-CoA |
| I | pent-2,4-dienoyl-CoA hydrolase, or transferase | 3.1.2, 2.8.3 or 2.3.3 | pent-2,4-dienoyl-CoA → pent-2,4-dienoic |
| J | pent,2,4-dienoic acid decarboxylase | 4.1.1. | 2,4-pentenoic acid → butadiene |

A microorganism may comprise one or more polynucleotides coding for enzymes in a pathway that catalyze a conversion of crotonyl-CoA to butadiene. In some embodiments, the one or more polynucleotides coding for enzymes in a pathway that catalyze a conversion of crotonyl-CoA to butadiene may include, but are not limited to:

one or more polynucleotides coding for enzymes in a pathway that catalyze a conversion of crotonyl-CoA to crotonyl alcohol (e.g., a crotonyl-CoA reductase (bifunctional));

one or more polynucleotides coding for enzymes in a pathway that catalyze a conversion of crotonyl-CoA to crotonaldehyde (e.g., a crotonaldehyde dehydrogenase);

one or more polynucleotides coding for enzymes in a pathway that catalyze a conversion of crotonaldehyde to crotonyl alcohol (e.g., a crotonyl alcohol dehydrogenase); and/or one or more polynucleotides coding for enzymes in a pathway that catalyze a conversion of crotonyl alcohol to butadiene (e.g., a crotonyl alcohol dehydratase).

In some embodiments, a microorganism is provided that comprises one or more of the above polynucleotides including, all, of the polynucleotides above.

In preferred embodiments, the microorganism further comprises one or more polynucleotides coding for enzymes in a pathway that catalyze a conversion of a fermentable carbon source (e.g., glucose) to crotonyl-CoA.

In some embodiments, the microorganism may further comprise one or more polynucleotides coding for enzymes in a pathway that catalyze a conversion of a fermentable carbon source (e.g., glucose) to 3-hydroxybutyryl-CoA and/or 4-hydroxybutyryl-CoA. In such embodiments, the microorganism further comprises one or more polynucleotides coding for enzymes in a pathway that catalyze a conversion of 3-hydroxybutyryl-CoA to crotonyl-CoA and/or one or more polynucleotides coding for enzymes in a pathway that catalyze a conversion of 4-hydroxybutyryl-CoA to crotonyl-CoA.

Exemplary enzymes which convert crotonyl-CoA to butadiene are presented in Table 1 below, as well as, the substrates that they act upon and product that they produce.

The enzyme number represented in Table 1 correlates with the enzyme numbering used in FIG. 1 which schematically represents the enzymatic conversion of a fermentable carbon source to butadiene through a crotonyl-CoA intermediate.

TABLE 2

Production of butadiene via a crotonyl-CoA intermediate.

| Enzyme No. | Enzyme Name | E.C. number | Mediated Conversion |
|---|---|---|---|
| A | crotonyl-CoA reductase (bifuncional) | 1.1.1 | crotonyl-CoA → crotonyl alcohol |
| B | crotonaldehyde dehydrogenase | 1.2.1 | crotonyl-CoA → crotonaldehyde |
| C | crotonyl alcohol dehydrogenase | 1.1.1 1.1.1.1 | crotonaldehyde → crotonyl alcohol |
| D | crotonyl alcohol dehydratase | 4.2.1 4.2.1.127 | crotonyl alcohol → butadiene |

A microorganism may comprise one or more polynucleotides coding for enzymes in a pathway that catalyze a conversion of formic acid to butadiene. In some embodiments, the one or more polynucleotides coding for enzymes in a pathway that catalyze a conversion of formic acid to butadiene may include, but are not limited to:

one or more polynucleotides coding for enzymes in a pathway that catalyze a conversion of $CO_2$ to formic acid (e.g., a formate dehydrogenase);

one or more polynucleotides coding for enzymes in a pathway that catalyze a conversion of pyruvate and CoA to acetyl-CoA and formic acid (e.g., an acetyl-CoA:formate C-acetyltransferase);

one or more polynucleotides coding for enzymes in a pathway that catalyze a conversion of formic acid to formyl-CoA (e.g., a formyl-CoA transferase or synthase);

one or more polynucleotides coding for enzymes in a pathway that catalyze a conversion of 2 acetyl-CoA to acetoacetyl-CoA (e.g., an acetoacetyl-CoA thiolase);

one or more polynucleotides coding for enzymes in a pathway that catalyze a conversion of acetoacetyl-CoA and formyl-CoA to 3,5-ketovaleryl-CoA (e.g., a 3,5-ketovaleryl-CoA thiolase);

one or more polynucleotides coding for enzymes in a pathway that catalyze a conversion of 3,5-ketovaleryl-CoA to (R) or (S)-5-hydroxy-3-ketovaleryl-CoA (e.g., a 3,5-ketovaleryl-CoA dehydrogenase);

one or more polynucleotides coding for enzymes in a pathway that catalyze a conversion of (R) or (S)-5-hydroxy-3-ketovaleryl-CoA to (R) or (S)-3,5-dihydroxyaleryl-CoA (e.g., a 5-hydroxy-3-ketovaleryl-CoA dehydrogenase);

one or more polynucleotides coding for enzymes in a pathway that catalyze a conversion of (R) or (S)-3,5-dihydroxyaleryl-CoA to (R) or (S) 3-hydroxy-4-pentenoyl-CoA (e.g., a 3,5-hydroxyvaleryl-CoA dehydratase);

one or more polynucleotides coding for enzymes in a pathway that catalyze a conversion of (R) or (S)-3-hydroxy-4-pentenoyl-CoA to 3-hydroxy-4-pentenoic acid (e.g., a 3-hydroxy-4-pentenoyl-CoA hydrolase, transferase or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase).

In some embodiments, the microorganism further comprises one or more polynucleotides coding for enzymes in a pathway that catalyze a conversion of a fermentable carbon source (e.g., glucose) to pyruvate.

In some embodiments, a microorganism is provided that comprises one or more of the above polynucleotides including, all, of the polynucleotides above.

Exemplary enzymes which convert formic acid to butadiene are presented in Table 3 below, as well as, the substrates that they act upon and product that they produce. The enzyme number represented in Table 3 correlates with the enzyme numbering used in FIG. 3 which schematically represents the enzymatic conversion of a fermentable carbon source to butadiene through a formic acid intermediate.

A microorganism is also provided that comprises one or more polynucleotides coding for enzymes in a pathway that catalyze a conversion of a fermentable carbon source to acetyl-CoA and propionyl-CoA and one or more polynucleotides coding for enzymes in a pathway that catalyze a conversion of acetyl-CoA and propionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to methylmalonyl-CoA; one or more polynucleotides coding for enzymes in a pathway that catalyze a conversion of methylmalonyl-CoA to propionyl-CoA; one or more polynucleotides coding for enzymes in a pathway that catalyze a conversion of pyruvate to acryloyl-CoA; one or more polynucleotides coding for enzymes in a pathway that catalyze a conversion of acryloyl-CoA to propionyl-CoA; one or more polynucleotides coding for enzymes in a pathway that catalyze a conversion of acetyl-CoA and propionyl-CoA to ketovaleryl-CoA (e.g., a thiolase); one or more polynucleotides coding for enzymes in a pathway that catalyze a conversion of ketovaleryl-CoA to (R) or (S) 3-hydroxyvaleryl-CoA (e.g., a hydroxyvaleryl-CoA dehydrogenase); one or more polynucleotides coding for enzymes in a pathway that catalyze a conversion of (R) or (S) 3-hydroxyvaleryl-CoA to 2-pentenoyl-CoA (e.g., a hydroxyvaleryl-CoA dehydratase); one or more polynucleotides coding for enzymes in a pathway that catalyze a conversion of 2-pentenoyl-CoA to 2-pentenoic acid (e.g., a pentenoyl-CoA hydrolase, a pentenoyl-CoA transferase or a pentenoyl-CoA synthase); one or more polynucleotides coding for enzymes in a pathway that catalyze a conversion of 2-pentenoic acid to 4-pentenoic acid (e.g., a transposing bonds C=C isomerase); and/or one or more polynucleotides coding for enzymes in a pathway that catalyze a conversion of 4-pentenoic acid to butadiene (e.g., a 4-pentenoic fatty acid decarboxylase or a 2-petenoic acid decarboxylase). In some embodiments, a microorgan-

TABLE 3

Production of butadiene via a formic acid intermediate.

| Enzyme No. | Enzyme Name | E.C. number | Mediated Conversion |
|---|---|---|---|
| A | formate dehydrogenase | 1.2.1.2 | $CO_2 \rightarrow$ Formate |
| B | acetyl-CoA:formate C-acetyltransferase | 2.3.1.54 | pyruvate + CoA $\rightarrow$ acetyl-CoA + formic acid |
| C | formyl-CoA transferase or synthase | 2.8.3.16 6.2.1 | formic acid $\rightarrow$ formyl-CoA |
| D | acetoacetyl-CoA thiolase | 2.3.1.16 | 2 acetyl-CoA $\rightarrow$ acetoacetyl-CoA |
| E | 3,5-ketovaleryl-CoA thiolase | 2.3.1. 2.3.1.16 | acetoacetyl-CoA + formyl-CoA $\rightarrow$ 3,5-ketovaleryl-CoA |
| F | 3,5-ketovaleryl-CoA dehydrogenase | | 3,5-ketovaleryl-CoA $\rightarrow$ (R) or (S)-5-hydroxy-3-Ketovaleryl-CoA |
| G | 5-hydroxy-3-ketovaleryl-CoA dehydrogenase | 1.1.1.35 1.1.1.36 | (R) or (S)-5-hydroxy-3-ketovaleryl-CoA $\rightarrow$ (R) or (S)-3,5-dihydroxyaleryl-CoA |
| H | 3,5-hydroxyvaleryl-CoA dehydratase | 4.2.1.17 4.2.1.54 | (R) or (S)-3,5-dihydroxyaleryl-CoA $\rightarrow$ (R) or (S) 3-hydroxy-4-pentenoyl-CoA |
| I | 3-hydroxy-4-pentenoyl-CoA hydrolase, transferase or synthase | 3.1.2, 2.8.3 or 2.3.3 | (R) or (S)-3-hydroxy-4-pentenoyl-CoA $\rightarrow$ 3-hydroxy-4-pentenoic acid |
| J | 3-hydroxy-4-pentenoic acid decarboxylase | 4.1.1.33 | 3-hydroxy-4-pentenoic acid $\rightarrow$ butadiene | ism is provided that comprises one or more of the above polynucleotides including, all, of the polynucleotides above.

A microorganism is also provided that comprises one or more polynucleotides coding for enzymes in a pathway that catalyze a conversion of a fermentable carbon source to ethyl-malonyl-CoA and one or more polynucleotides coding for enzymes in a pathway that catalyze a conversion of ethyl-malonyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyzes a conversion of pyruvate to acetyl-CoA; one or more polynucleotides coding for enzymes in a pathway that catalyzes a conversion of acetyl-CoA to acetoacetyl-CoA (e.g., an acetoacetyl-CoA thiolase); one or more polynucleotides coding for enzymes in a pathway that catalyzes a conversion of acetoacetyl-CoA to 3-hydroxybutyryl-CoA (e.g., a 3-hydroxybutyryl-CoA dehydrogenase); one or more polynucleotides coding for enzymes in a pathway that catalyzes a conversion of 3-hydroxybutyryl-CoA to crotonyl-CoA (e.g., a crotonase); one or more polynucleotides coding for enzymes in a pathway that catalyzes a conversion of crotonyl-CoA to ethyl-malonyl-CoA (e.g., a crotonyl-CoA carboxylase/reductase); one or more polynucleotides coding for enzymes in a pathway that catalyzes a conversion of crotonyl-CoA to butyric acid (e.g., butyryl-CoA dehydrogenase); one or more polynucleotides coding for enzymes in a pathway that catalyzes a conversion of butyric acid to ethyl-malonyl-CoA (e.g., a butanoyl-CoA:carbon-dioxide ligase); one or more polynucleotides coding for enzymes in a pathway that catalyze a conversion of ethyl-malonyl-CoA to 2-(formol)butanoic acid (e.g., an ethyl-malonyl-CoA reductase (aldehyde forming)); one or more polynucleotides coding for enzymes in a pathway that catalyze a conversion of 2-(formol)butanoic acid to 2-(hydroxymethyl)butanoic acid (e.g., a 2-(formyl)butanoic acid reducatase (alcohol forming)); one or more polynucleotides coding for enzymes in a pathway that catalyze a conversion of ethyl malonyl-CoA to 2-(hydroxymethyl)butanoic acid (e.g., an ethyl-malonyl-CoA reductase (alcohol forming)); one or more polynucleotides coding for enzymes in a pathway that catalyze a conversion of 2-(hydroxymethyl)butanoic acid to 2-(phosphanyloxymethyl)butanoic acid (e.g., a 2-(hydroxymethyl)butanoic acid kinase); one or more polynucleotides coding for enzymes in a pathway that catalyze a conversion of 2-(phosphanyloxymethyl)butanoic acid to 2-(diphosphanyloxymethyl)butanoic acid (e.g., a 2-(phosphanyloxymethyl)butanoic acid kinase); one or more polynucleotides coding for enzymes in a pathway that catalyze a conversion of 2-(diphosphanyloxymethyl)butanoic acid to [(E)-but-2-enoxy]-phosphanyl-phosphane (e.g., 2-(diphosphanyloxymethyl)butanoic acid decarboxylase); and/or one or more polynucleotides coding for enzymes in a pathway that catalyze a conversion of [(E)-but-2-enoxy]-phosphanyl-phosphane to butadiene (e.g., butadiene synthetase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to 4-hydroxybutyryl-CoA and 3-hydroxybutyryl-CoA and one or more polynucleotides coding for enzymes in a pathway that catalyze a conversion of 4-hydroxybutyryl-CoA and 3-hydroxybutyryl-CoA to butadiene including, but not limited to: one or more polynucleotides coding for enzymes in a pathway that catalyze a conversion of a fermentable carbon source (e.g., glucose) to PEP; one or more polynucleotides coding for enzymes in a pathway that catalyze a conversion of PEP to oxaloacetate (e.g., a PEP carboxykinase or PEP carboxylase); one or more polynucleotides coding for enzymes in a pathway that catalyze a conversion of PEP to pyruvate; one or more polynucleotides coding for enzymes in a pathway that catalyze a conversion of pyruvate to acetyl-CoA (e.g., a pyruvate dehydrogenase or a pyruvate ferrodoxin oxirreductase) or oxaloacetate (e.g., a PEP carboxykinase or PEP carboxylase); one or more polynucleotides coding for enzymes in a pathway that catalyze a conversion of acetyl-CoA to acetoacetyl-CoA (e.g., an acetoacetyl-CoA thiolase); one or more polynucleotides coding for enzymes in a pathway that catalyze a conversion of acetoacetyl-CoA to 3-hydroxybutyryl-CoA (e.g., 3-hydroxybutyryl-CoA dehydrogenase); one or more polynucleotides coding for enzymes in a pathway that catalyze a conversion of oxaloacetate to malate (e.g., a malate dehydrogenase); one or more polynucleotides coding for enzymes in a pathway that catalyze a conversion of malate to fumarate (e.g., a fumarase); one or more polynucleotides coding for enzymes in a pathway that catalyze a conversion of fumarate to succinate (e.g., a fumarate reductase); one or more polynucleotides coding for enzymes in a pathway that catalyze a conversion of succinate to succinyl-CoA (e.g., a succinyl-CoA transferase or a succinyl-CoA synthase); one or more polynucleotides coding for enzymes in a pathway that catalyze a conversion of succinyl-CoA to succinyl semialdehyde (e.g., a succinyl-CoA reductase); one or more polynucleotides coding for enzymes in a pathway that catalyze a conversion of succinyl semialdehyde to 4-hydroxybutyrate (e.g., a 4-hydroxybutyrate dehydrogenase); one or more polynucleotides coding for enzymes in a pathway that catalyze a conversion of succinate to 4-hydroxybutyrate (e.g., a succinate reductase, phosphopantatheinylase or 4-hydroxybutyrate dehydrogenase); one or more polynucleotides coding for enzymes in a pathway that catalyze a conversion of 4-hydroxybutyrate to 4-hydroxybutyryl-CoA (e.g., a 4-hydroxybutyryl-CoA transferase or a 4-hydroxybutyryl-CoA synthase); one or more polynucleotides coding for enzymes in a pathway that catalyze a conversion of 4-hydroxybutyryl-CoA to crotonyl-CoA (e.g., a 4-hydroxybutyryl-CoA dehydratase); one or more polynucleotides coding for enzymes in a pathway that catalyze a conversion of 3-hydroxybutyryl-CoA to crotonyl-CoA (e.g., a crotonase); one or more polynucleotides coding for enzymes in a pathway that catalyze a conversion of crotonyl-CoA to crotonaldehyde (e.g., a crotonaldehyde dehydrogenase); one or more polynucleotides coding for enzymes in a pathway that catalyze a conversion of crotonaldehyde to crotonyl alcohol (e.g., an alcohol dehydrogenase); one or more polynucleotides coding for enzymes in a pathway that catalyze a conversion of crotonyl-CoA to crotonyl alcohol (e.g., a crotonyl-CoA reductase (bifunctional); and/or one or more polynucleotides coding for enzymes in a pathway that catalyze a conversion of crotonyl alcohol to butadiene (e.g., a crotonyl alcohol dehydratase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to acryloyl-CoA and acetyl-CoA and one or more polynucleotides coding for enzymes in a pathway that catalyze a conversion of acryloyl-CoA and acetyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to lactate (e.g., a lactate dehydrogenase); one or more polynucleotides coding for enzymes in a pathway that catalyze a conversion of lactate to lactoyl-CoA (e.g., a lactoyl-CoA transferase or synthase); one or more polynucleotides coding for enzymes in a pathway that catalyze a conversion of lactoyl-CoA to acryloyl-CoA; one or more polynucleotides coding for enzymes in a pathway that catalyze a conversion of pyruvate to acetyl-CoA; one or more polynucleotides coding for enzymes in a pathway that catalyze a conversion of acryloyl-CoA and acetyl-CoA to 3-keto-4-pentenoyl-CoA (e.g., a thiolase); one or more polynucleotides coding for enzymes in a pathway that catalyze a conversion of 3-keto-4-pentenoyl-CoA to (R) or (S) 3-hydroxy-4-pentenoyl-CoA (e.g., a 3-keto-4-pentenoyl-CoA dehydrogenase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA transferase, a hydrolase, or a synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetyl-CoA and 3-hydroxypropionyl-CoA and one or more polynucleotides coding for enzymes in a pathway that catalyze a conversion of acetyl-CoA and 3-hydroxypropionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to lactate; one or more polynucleotides coding for enzymes in a pathway that catalyze a conversion of lactate to lactoyl-CoA (e.g., lactoyl-CoA transferase or synthase); one or more polynucleotides coding for enzymes in a pathway that catalyze a conversion of lactoyl-CoA to acryloyl-CoA (e.g., lactoyl-CoA dehydratase); one or more polynucleotides coding for enzymes in a pathway that catalyze a conversion of acryloyl-CoA to 3-hydroxypropionyl-CoA (e.g., acryloyl-CoA hydratase); one or more polynucleotides coding for enzymes in a pathway that catalyze a conversion of pyruvate to 3-hydroxypropionate; one or more polynucleotides coding for enzymes in a pathway that catalyze a conversion of 3-hydroxypropionate to 3-hydroxypropionyl-CoA; one or more polynucleotides coding for enzymes in a pathway that catalyze a conversion of acetyl-CoA and 3-hydroxypropionyl-CoA to 5-hydroxy-3-ketovaleryl-CoA (e.g., a thiolase); one or more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-ketovaleryl-CoA dehydrogenase); one or more polynucleotides coding for enzymes in a pathway that catalyze a conversion of (R) or (S) 3,5-dihydroxy-valeryl-CoA to (R) or (S) 3-hydroxy-4-pentenoyl-CoA (e.g., a 3,5-hydroxyvaleryl-CoA dehydratase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA hydrolase, transferase, or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetoacetyl-CoA and formyl-CoA and one or more polynucleotides coding for enzymes in a pathway that catalyze a conversion acetoacetyl-CoA and formyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to acetyl-CoA and formate (e.g., a pyruvate formate-lyase); one or more polynucleotides coding for enzymes in a pathway that catalyze a conversion of acetyl-CoA to acetoacetyl-CoA (e.g., thiolase); one or more polynucleotides coding for enzymes in a pathway that catalyze a conversion of $CO_2$ to formate (e.g., formate dehydrogenase); one or more polynucleotides coding for enzymes in a pathway that catalyze a conversion of formate to formyl-CoA (e.g., a formyl-CoA transferase, or formyl-CoA synthase); one or more polynucleotides coding for enzymes in a pathway that catalyze a conversion of formyl-CoA and acetoacetyl-CoA to 3,5-ketovaleryl-CoA (e.g., a thiolase); one or more polynucleotides coding for enzymes in a pathway that catalyze a conversion of 3,5-ketovaleryl-CoA to 5-hydroxy-3-ketovaleryl-CoA; one or more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-Ketovaleryl-CoA dehydrogenase); one or more polynucleotides coding for enzymes in a pathway that catalyze a conversion of (R) or (S) 3,5-dihydroxy-valeryl-CoA to (R) or (S) 3-hydroxy-4-pentenoyl-CoA (e.g., a 3,5-hydroxyvaleryl-CoA dehydratase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA hydrolase, transferase, or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetyl-CoA and 3-hydroxypropionyl-CoA and one or more polynucleotides coding for enzymes in a pathway that catalyze a conversion of acetyl-CoA and 3-hydroxypropionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to acryloyl-CoA; one or more polynucleotides coding for enzymes in a pathway that catalyze a conversion of acryloyl-CoA to 3-hydroxypropionyl-CoA; one or more polynucleotides coding for enzymes in a pathway that catalyze a conversion of pyruvate to 3-hydroxypropionate; one or more polynucleotides coding for enzymes in a pathway that catalyze a conversion of 3-hydroxypropionate to 3-hydroxypropionyl-CoA; one or more polynucleotides coding for enzymes in a pathway that catalyze a conversion of acetyl-CoA and 3-hydroxypropionyl-CoA to 5-hydroxy-3-ketovaleryl-CoA (e.g., a thiolase); one or of more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-ketovaleryl-CoA dehydrogenase); one or more polynucleotides coding for enzymes in a pathway that catalyze a conversion of (R) or (S) 3,5-dihydroxy-valeryl-CoA to 3,5-hydroxypentanoic acid (e.g., a 3,5-hydroxypentanoic acid kinase); one or more polynucleotides coding for enzymes in a pathway that catalyze a conversion of 3,5-hydroxypentanoic acid to 3,5-hydroxypentanoic acid phosphate (e.g., a 3,5-hydroxypentanoic acid kinase); one or more polynucleotides coding for enzymes in a pathway that catalyze a conversion of 3,5-hydroxypentanoic acid phosphate to 3,5-hydroxypentanoic acid diphosphate (e.g., a 3,5-hydroxypentanoic acid phosphate kinase); one or more polynucleotides coding for enzymes in a pathway that catalyze a conversion of 3,5-hydroxypentanoic acid diphosphate to 1-butenyl-4-diphosphate (e.g., a hydroxypentanoic acid diphosphate decarboxylase); and/or one or more polynucleotides coding for enzymes in a pathway that catalyze a conversion of 1-butenyl-4-diphosphate to butadiene (e.g., a butadiene synthase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to ethyl-malonyl-CoA and one or more polynucleotides coding for enzymes in a pathway that catalyze a conversion of ethyl-malonyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyzes a conversion of pyruvate to acetyl-CoA; one or more polynucleotides coding for enzymes in a pathway that catalyzes a conversion of acetyl-CoA to acetoacetyl-CoA (e.g., an acetoacetyl-CoA thiolase); one or more polynucleotides coding for enzymes in a pathway that catalyzes a conversion of acetoacetyl-CoA to 3-hydroxybutyryl-CoA (e.g., a 3-hydroxybutyryl-CoA dehydrogenase); one or more polynucleotides coding for enzymes in a pathway that catalyzes a conversion of 3-hydroxybutyryl-CoA to crotonyl-CoA (e.g., a crotonase); one or more polynucleotides coding for enzymes in a pathway that catalyzes a conversion of crotonyl-CoA to ethyl-malonyl-CoA (e.g., a crotonyl-CoA carboxylase/reductase); one or more polynucleotides coding for enzymes in a pathway that catalyzes a conversion of crotonyl-CoA to butyric acid (e.g., butyryl-CoA dehydrogenase); one or more polynucleotides coding for enzymes in a pathway that catalyzes a conversion of butyric acid to ethyl-malonyl-CoA (e.g., a butanoyl-CoA:carbon-dioxide ligase); one or more polynucleotides coding for enzymes in a pathway that catalyze a conversion of ethyl-malonyl-CoA to 2-hydroxymethyl-butanoic acid (e.g., an ethyl-malonyl-CoA reductase, an alcohol dehydrogenase, or a aldehyde dehydrogenase); one or more polynucleotides coding for enzymes in a pathway that catalyze a conversion of 2-hydroxymethyl-butanoic acid to 2-butenyl 4-diphosphate (e.g., a 2-hydroxymethyl-butanoate kinase, a hydroxymethyl butanoate-phosphate kinase, or a 2-hydroxymethyl butanoate-diphosphate decarboxylase); one or more polynucleotides coding for enzymes in a pathway that catalyze a conversion of 2-hydroxymethyl-butanoic acid to 2-butenyl 4-phosphate; one or more polynucleotides coding for enzymes in a pathway that catalyze a conversion of 2-butenyl 4-phosphate to butadiene, and/or one or more polynucleotides coding for enzymes in a pathway that catalyze a conversion of 2-butenyl 4-diphosphate to butadiene (e.g., butadiene synthetase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to lactate and acetyl-CoA and oxalacetate and one or more polynucleotides coding for enzymes in a pathway that catalyze a conversion of lactate and acetyl-CoA and oxalacetate to butadiene including, but are not limited to: one or more polynucleotides coding for enzymes in a pathway that catalyze a conversion of a fermentable carbon source (e.g., glucose) to PEP; one or more polynucleotides coding for enzymes in a pathway that catalyze a conversion of PEP to pyruvate; one or more polynucleotides coding for enzymes in a pathway that catalyze a conversion of pyruvate to acetyl-CoA; one or more polynucleotides coding for enzymes in a pathway that catalyze a conversion of lactate to lactoyl-CoA (e.g., a lactate CoA-transferase); one or more polynucleotides coding for enzymes in a pathway that catalyze a conversion of lactoyl-CoA to acryloyl-CoA (e.g., a lactoyl-CoA dehydratase); one or more polynucleotides coding for enzymes in a pathway that catalyze a conversion of acryloyl-CoA to propionyl-CoA (e.g., an acryloyl-CoA oxidoreductase); one or more polynucleotides coding for enzymes in a pathway that catalyze a conversion of propionyl-CoA to ketovaleryl-CoA (e.g., a thiolase); one or more polynucleotides coding for enzymes in a pathway that catalyze a conversion of ketovaleryl-CoA to 2-pentenoyl-CoA (e.g., a ketovaleryl-CoA dehydratase); one or more polynucleotides coding for enzymes in a pathway that catalyze a conversion of 2-pentenoyl-CoA to 2-pentenoic acid (e.g., a pentenoyl-CoA hydrolase, transferase, or synthase); one or more polynucleotides coding for enzymes in a pathway that catalyze a conversion of 2 pentenoic acid to butadiene (e.g., a 4-pentenoic acid decarboxylase); one or more polynucleotides coding for enzymes in a pathway that catalyze a conversion of 2-pentenoic acid to 4-pentenoic acid (e.g., a transposing C=C bonds isomerase); one or more polynucleotides coding for enzymes in a pathway that catalyze a conversion of 4-pentenoic acid to butadiene (e.g., a 4-pentenoic acid decarboxylase); one or more polynucleotides coding for enzymes in a pathway that catalyze a conversion of oxalacetate to malate (e.g., a malate dehydrogenase); one or more polynucleotides coding for enzymes in a pathway that catalyze a conversion of malate to fumarate (e.g., a fumarase); one or more polynucleotides coding for enzymes in a pathway that catalyze a conversion of fumarate to succinate (e.g., a fumarate reductase); one or more polynucleotides coding for enzymes in a pathway that catalyze a conversion of succinate to succynil-CoA (e.g., a succinyl-CoA transferase synthase); one or more polynucleotides coding for enzymes in a pathway that catalyze a conversion of succynil-CoA to succinate semialdehyde (e.g., a succinyl-CoA reducatase); one or more polynucleotides coding for enzymes in a pathway that catalyze a conversion of succinate semialdehyde to 4-hydroxybutyrate (e.g., a 4 hydroxybutyrate dehydrogenase); one or more polynucleotides coding for enzymes in a pathway that catalyze a conversion of 4-hydroxybutyrate to 4-hydroxybutyril-CoA (e.g., a 4-hydroxybutyryl-CoA transferase, or a 4-hydroxybutyryl-CoA synthase); one or more polynucleotides coding for enzymes in a pathway that catalyze a conversion of 4-hydroxybutyril-CoA to crotonyl-CoA (e.g., a 4-hydroxybutyryl-CoA dehydratase); one or more polynucleotides coding for enzymes in a pathway that catalyze a conversion of crotonyl-CoA to crotonaldehyde (e.g., a crotonaldehyde dehydrogenase); one or more polynucleotides coding for enzymes in a pathway that catalyze a conversion of crotonyl-CoA to crotonyl-alcohol (e.g., a crotonyl-CoA reductase or a bifunctional alcohol dehydrogenase); one or more polynucleotides coding for enzymes in a pathway that catalyze a conversion of crotonaldehyde to crotonyl-alcohol (e.g., an alcohol dehydrogenase); and/or one or more polynucleotides coding for enzymes in a pathway that catalyze a conversion of crotonyl-alcohol to butadiene (e.g., a crotonyl alcohol dehydratase).

Any of the microorganisms provided herein may optionally comprise one or more polynucleotides coding for enzymes that permit for a redox balanced conversion of a fermentable carbon source to butadiene.

The microorganism may be an archea, bacteria, or eukaryote. In some embodiments, the bacteria is a *Propionibacterium*, Propionispira, *Clostridium, Bacillus, Escherichia, Pelobacter*, or *Lactobacillus* including, for example, *Pelobacter propionicus, Clostridium propionicum, Clostridium acetobutylicum, Lactobacillus, Propionibacterium acidipropionici* or *Propionibacterium freudenreichii*. In some embodiments, the eukaryote is a yeast, filamentous fungi, protozoa, or algae. In some embodiments, the yeast is *Saccharomyces cerevisiae, Zymomonas mobilis*, or *Pichia pastoris*.

In some embodiments, the disclosure contemplates the modification (e.g., engineering) of one or more of the enzymes provided herein. Such modification may be performed to redesign the substrate specificity of the enzyme and/or to modify (e.g., reduce) its activity against others substrates in order to increase its selectivity for a given substrate. Additionally or alternatively, one or more enzymes as provided herein may be engineered to alter (e.g., enhance including, for example, increase its catalytic activity or its substrate specificity) one or more of its properties.

Any of the enzymes (e.g., the polynucleotide coding for the enzyme) may be modified (e.g., mutagenized or diversified) to expand or alter its substrate specificity (e.g., change the substrate specificity of an enzyme from one substrate to another substrate) by any method known in the art. Such methods include, but are not limited to EpPCR Pritchard et al., J. Theor. Biol. 234:497-509 (2005)); Error-prone Rolling Circle Amplification (epRCA) Fujii et al., Nucleic Acids Res. 32:e145 (2004); and Fujii et al., Nat. Protoc. 1:2493-2497 (2006)); DNA or Family Shuffling Stemmer, Proc. Natl. Acad. Sci. U.S.A. 91:10747-10751 (1994); and Stemmer, Nature 370:389-391 (1994)); Staggered Extension (StEP) Zhao et al., Nat. Biotechnol. 16:258-261 (1998)); and/or Random Priming Recombination (RPR) Shao et al., Nucleic Acids Res 26:681-683 (1998)).

Additional exemplary methods for mutagenesis of a polynucleotide include Heteroduplex Recombination (Volkov et al., Nucleic Acids Res. 27:e18 (1999); and Volkov et al., Methods Enzymol. 328:456-463 (2000)); Random Chimeragenesis on Transient Templates (RACHITT) (Coco et al., Nat. Biotechnol. 19:354-359 (2001)); Recombined Extension on Truncated templates (RETT) (Lee et al., J. Molec. Catalysis 26:119-129 (2003)); Degenerate Oligonucleotide Gene Shuffling (DOGS) (Bergquist and Gibbs, Methods Mol. Biol. 352:191-204 (2007); Bergquist et al., Biomol. Eng. 22:63-72 (2005); Gibbs et al., Gene 271:13-20 (2001)); Incremental Truncation for the Creation of Hybrid Enzymes (ITCHY) (Ostermeier et al., Proc. Natl. Acad. Sci. U.S.A. 96:3562-3567 (1999); and Ostermeier et al., Nat. Biotechnol. 17:1205-1209 (1999)); Thio-Incremental Truncation for the Creation of Hybrid Enzymes (THIO-ITCHY) (Lutz et al., Nucleic Acids Res. 29:E16 (2001)); SCRATCHY (Lutz et al., Proc. Natl. Acad. Sci U.S.A. 98:11248-11253 (2001)); Random Drift Mutagenesis (RNDM) (Bergquist et al., Biomol. Eng. 22:63-72 (2005)); Sequence Saturation Mutagenesis (SeSaM) (Wong et al., Biotechnol. J. 3:74-82 (2008); Wong et al., Nucleic Acids Res. 32:e26 (2004); and Wong et al., Anal. Biochem. 341:187-189 (2005)); Synthetic Shuffling (Ness et al., Nat. Biotechnol. 20:1251-1255 (2002)); Nucleotide Exchange and Excision Technology NexT (Muller et al., Nucleic Acids Res. 33:e117 (2005)). Additional exemplary methods include Sequence Homology-Independent Protein Recombination (SHIPREC) (Sieber et al., Nat. Biotechnol. 19:456-460 (2001)); Gene Site Saturation Mutagenesis™ (GSSM™) (Kretz et al., Methods Enzymol. 388:3-11 (2004)); Combinatorial Cassette Mutagenesis (CCM) (Reidhaar-Olson et al. Methods Enzymol. 208:564-586 (1991); and Reidhaar-Olson et al. Science 241:53-57 (1988)); Combinatorial Multiple Cassette Mutagenesis (CMCM) (Reetz et al., Angew. Chem. Int. Ed Engl. 40:3589-3591 (2001)); and the Mutator Strains technique (Selifonova et al., Appl. Environ. Microbiol. 67:3645-3649 (2001); Low et al., J. Mol. Biol. 260:359-3680 (1996)). Further exemplary methods include Look-Through Mutagenesis (LTM) (Rajpal et al., Proc. Natl. Acad. Sci. U.S.A. 102:8466-8471 (2005)); Gene Reassembly (Tunable GeneReassembly™ (TGR™) Technology supplied by Verenium Corporaiton), in Silico Protein Design Automation (PDA) (Hayes et al., Proc. Natl. Acad. Sci. U.S.A. 99:15926-15931 (2002)); and Iterative Saturation Mutagenesis (ISM) (Reetz et al., Nat. Protoc. 2:891-903 (2007); and Reetz et al., Angew. Chem. Int. Ed Engl. 45:7745-7751 (2006)).

In some embodiments, sequence alignment and comparative modeling of proteins may be used to alter one or more of the enzymes disclosed herein. Homology modeling or comparative modeling refers to building an atomic-resolution model of the desired protein from its primary amino acid sequence and an experimental three-dimensional structure of a similar protein. This model may allow for the enzyme substrate binding site to be defined, and the identification of specific amino acid positions that may be replaced to other natural amino acid in order to redesign its substrate specificity.

Variants or sequences having substantial identity or homology with the polynucleotides encoding enzymes as disclosed herein may be utilized in the practice of the disclosure. Such sequences can be referred to as variants or modified sequences. That is, a polynucleotide sequence may be modified yet still retain the ability to encode a polypeptide exhibiting the desired activity. Such variants or modified sequences are thus equivalents. Generally, the variant or modified sequence may comprise at least about 40%-60%, preferably about 60%-80%, more preferably about 80%-90%, and even more preferably about 90%-95% sequence identity with the native sequence.

In some embodiments, a microorganism may be modified to express including, for example, over express, one or more enzymes as provided herein. The microorganism may be modified by genetic engineering techniques (i.e., recombinant technology), classical microbiological techniques, or a combination of such techniques and can also include naturally occurring genetic variants to produce a genetically modified microorganism. Some of such techniques are generally disclosed, for example, in Sambrook et al., 1989, Molecular Cloning: A Laboratory Manual, Cold Spring Harbor Labs Press.

A microorganism may include a microorganism in which a polynucleotide has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, over expression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

Where desired, the expression of one or more of the enzymes provided herein are under the control of a regulatory sequence that controls directly or indirectly the expression of the enzyme in a time-dependent fashion during a fermentation reaction.

In some embodiments, a microorganism is transformed or transfected with a genetic vehicle such as, an expression vector comprising an exogenous polynucleotide sequence coding for the enzymes provided herein.

Polynucleotide constructs prepared for introduction into a prokaryotic or eukaryotic host may typically, but not always, comprise a replication system (i.e. vector) recognized by the host, including the intended polynucleotide fragment encoding the desired polypeptide, and may preferably, but not necessarily, also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

The manipulation of polynucleotides of the present disclosure including polynucleotides coding for one or more of the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector of use according to the disclosure may be selected to accommodate a protein coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the disclosure.

Vectors, including cloning and expression vectors, may contain nucleic acid sequences that enable the vector to replicate in one or more selected host cells. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

A cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in $E.$ $coli$ (e.g., strain TB1 or TG1, DH5$\alpha$, DH10$\beta$, JM110). An $E.$ $coli$-selectable marker, for example, the $\beta$-lactamase gene that confers resistance to the antibiotic ampicillin, may be of use. These selectable markers can be obtained from $E.$ $coli$ plasmids, such as pBR322 or a pUC plasmid such as pUC18 or pUC19, or pUC119.

Expression vectors may contain a promoter that is recognized by the host organism. The promoter may be operably linked to a coding sequence of interest. Such a promoter may be inducible or constitutive. Polynucleotides are operably linked when the polynucleotides are in a relationship permitting them to function in their intended manner.

Promoters suitable for use with prokaryotic hosts may include, for example, the $\alpha$-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Moreover, host constitutive or inducible promoters may be used. Promoters for use in bacterial systems will also generally contain a Shine-Dalgarno sequence operably linked to the coding sequence.

Viral promoters obtained from the genomes of viruses include promoters from polyoma virus, fowlpox virus, adenovirus (e.g., Adenovirus 2 or 5), herpes simplex virus (thymidine kinase promoter), bovine papilloma virus, avian sarcoma virus, cytomegalovirus, a retrovirus (e.g., MoMLV, or RSV LTR), Hepatitis-B virus, Myeloproliferative sarcoma virus promoter (MPSV), VISNA, and Simian Virus 40 (SV40). Heterologous mammalian promoters include, e.g., the actin promoter, immunoglobulin promoter, heat-shock protein promoters.

The early and late promoters of the SV40 virus are conveniently obtained as a restriction fragment that also contains the SV40 viral origin of replication (see, e.g., Fiers et al., Nature, 273:113 (1978); Mulligan and Berg, Science, 209:1422-1427 (1980); and Pavlakis et al., Proc. Natl. Acad. Sci. USA, 78:7398-7402 (1981)). The immediate early promoter of the human cytomegalovirus (CMV) is conveniently obtained as a Hind III E restriction fragment (see, e.g., Greenaway et al., Gene, 18:355-360 (1982)). A broad host range promoter, such as the SV40 early promoter or the Rous sarcoma virus LTR, is suitable for use in the present expression vectors.

Generally, a strong promoter may be employed to provide for high level transcription and expression of the desired product. Among the eukaryotic promoters that have been identified as strong promoters for high-level expression are the SV40 early promoter, adenovirus major late promoter, mouse metallothionein-I promoter, Rous sarcoma virus long terminal repeat, and human cytomegalovirus immediate early promoter (CMV or CMV IE). In an embodiment, the promoter is a SV40 or a CMV early promoter.

The promoters employed may be constitutive or regulatable, e.g., inducible. Exemplary inducible promoters include jun, fos and metallothionein and heat shock promoters. One or both promoters of the transcription units can be an inducible promoter. In an embodiment, the GFP is expressed from a constitutive promoter while an inducible promoter drives transcription of the gene coding for one or more enzymes as disclosed herein and/or the amplifiable selectable marker.

The transcriptional regulatory region in higher eukaryotes may comprise an enhancer sequence. Many enhancer sequences from mammalian genes are known e.g., from globin, elastase, albumin, α-fetoprotein and insulin genes. A suitable enhancer is an enhancer from a eukaryotic cell virus. Examples include the SV40 enhancer on the late side of the replication origin (bp 100-270), the enhancer of the cytomegalovirus immediate early promoter (Boshart et al. Cell 41:521 (1985)), the polyoma enhancer on the late side of the replication origin, and adenovirus enhancers (see also, e.g., Yaniv, Nature, 297:17-18 (1982) on enhancing elements for activation of eukaryotic promoters). The enhancer sequences may be introduced into the vector at a position 5' or 3' to the gene of interest, but is preferably located at a site 5' to the promoter.

Yeast and mammalian expression vectors may contain prokaryotic sequences that facilitate the propagation of the vector in bacteria. Therefore, the vector may have other components such as an origin of replication (e.g., a nucleic acid sequence that enables the vector to replicate in one or more selected host cells), antibiotic resistance genes for selection in bacteria, and/or an amber stop codon which can permit translation to read through the codon. Additional eukaryotic selectable gene(s) may be incorporated. Generally, in cloning vectors the origin of replication is one that enables the vector to replicate independently of the host chromosomal DNA, and includes origins of replication or autonomously replicating sequences. Such sequences are well known, e.g., the ColE1 origin of replication in bacteria. Various viral origins (e.g., SV40, polyoma, adenovirus, VSV or BPV) are useful for cloning vectors in mammalian cells.

Generally, a eukaryotic replicon is not needed for expression in mammalian cells unless extrachromosomal (episomal) replication is intended (e.g., the SV40 origin may typically be used only because it contains the early promoter).

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

The plasmids may be propagated in bacterial host cells to prepare DNA stocks for subcloning steps or for introduction into eukaryotic host cells. Transfection of eukaryotic host cells can be any performed by any method well known in the art. Transfection methods include lipofection, electroporation, calcium phosphate co-precipitation, rubidium chloride or polycation mediated transfection, protoplast fusion and microinjection. Preferably, the transfection is a stable transfection. The transfection method that provides optimal transfection frequency and expression of the construct in the particular host cell line and type, is favored. Suitable methods can be determined by routine procedures. For stable transfectants, the constructs are integrated so as to be stably maintained within the host chromosome.

Vectors may be introduced to selected host cells by any of a number of suitable methods known to those skilled in the art. For example, vector constructs may be introduced to appropriate cells by any of a number of transformation methods for plasmid vectors. For example, standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used may depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or Lipo-Taxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation. Immortalized host cell cultures amenable to transfection and in vitro cell culture and of the kind typically employed in genetic engineering are preferred. Examples of useful mammalian host cell lines are monkey kidney CV1 line transformed by SV40 (COS-7, ATCC CRL 1651); human embryonic kidney line (293 or 293 derivatives adapted for growth in suspension culture, Graham et al., J. Gen Virol., 36:59 (1977); baby hamster kidney cells (BHK, ATCC CCL 10); DHFR-Chinese hamster ovary cells (ATCC CRL-9096); dp12.CHO cells, a derivative of CHO/DHFR-(EP 307,247 published 15 Mar. 1989); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); PEER human acute lymphoblastic cell line (Ravid et al. Int. J. Cancer 25:705-710 (1980)); MRC 5 cells; FS4 cells; human hepatoma line (Hep G2), human HT1080 cells, KB cells, JW-2 cells, Detroit 6 cells, NIH-3T3 cells, hybridoma and myeloma cells. Embryonic cells used for generating transgenic animals are also suitable (e.g., zygotes and embryonic stem cells).

Suitable host cells for cloning or expressing polynucleotides (e.g., DNA) in vectors may include, for example, prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), *E. coli* JM110 (ATCC 47,013) and *E. coli* W3110 (ATCC 27,325) are suitable.

In addition to prokaryotes, eukaryotic microbes such as filamentous fungi or yeast may be suitable cloning or expression hosts for vectors comprising polynucleotides coding for one or more enzymes. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia* pastors (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

When the enzyme is glycosylated, suitable host cells for expression may be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk moth) have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, tobacco, *lemna*, and other plant cells can also be utilized as host cells.

Examples of useful mammalian host cells are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for production of one or more enzymes as disclosed herein or with polynucleotides coding for one or more enzymes as disclosed herein and cultured in conventional nutrient media modified as appropriate for inducing promoters, selecting transformants, or amplifying the genes encoding the desired sequences.

Host cells containing desired nucleic acid sequences coding for the disclosed enzymes may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44, (1979); Barnes et al., Anal. Biochem. 102: 255 (1980); U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adeNOSine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polynucleotides and Encoded Enzymes

Any known polynucleotide (e.g., gene) that codes for an enzyme or variant thereof that is capable of catalyzing an enymatic conversion including, for example, an enzyme as set forth in any one of Tables 1-3 or FIGS. 1-3, is contemplated for use by the present disclosure. Such polynucleotides may be modified (e.g., genetically engineered) to modulate (e.g., increase or decrease) the substrate specificity of an encoded enzyme, or the polynucleotides may be modified to change the substrate specificity of the encoded enzyme (e.g., a polynucleotide that codes for an enzyme with specificity for a substrate may be modified such that the enzyme has specificity for an alternative substrate). Preferred microorganisms may comprise polynucleotides coding for one or more of the enzymes as set forth in any one of Tables 1-3 and FIG. 1-3.

In some embodiments, the microorganism may comprise an oxidoreductase such as a hydroxyvaleryl-CoA dehydrogenase, a crotonyl-CoA reductase (bifunctional), a crotonaldehyde dehydrogenase, a crotonyl alcohol dehydrogenase, a 3,5-ketovaleryl-CoA dehydrogenase, or an oxidoreductase as set forth in SEQ ID NOs: 103-123. In some embodiments, the microorganism may comprise a transferase such as a pentenoyl-CoA transferase, a pent-2,4-dienoyl-CoA transferase, a formyl-CoA transferase, a 3-hydroxy-4-pentenoyl-CoA transferase, or a transferase as set forth in SEQ ID NOs: 1-28. In some embodiments, the microorganism may comprise a hydrolase such as a pentenoyl-CoA hydrolase, a pent-2,4-dienoyl-CoA hydrolase, a 3-hydroxy-4-pentenoyl-CoA hydrolase, or a hydrolase as set forth in SEQ ID NOs: 29-33. In some embodiments, the microorganism may comprise a CoA synthetase such as a formyl-CoA synthase or a CoA synthase as set forth in SEQ ID NOs: 34-36. In some embodiments, the microorganism may comprise a ketothiolase such as a thiolase, an acetyl-CoA:formate C-acetyltransferase, an acetoacetyl-CoA thiolase, a 3,5-ketovaleryl-CoA thiolase, or a ketothiolase as set forth in SEQ ID NOs: 58-78. In some embodiments, the microorganism may comprise a dehydrogenase such as a pentenoyl-CoA dehydrogenase, a formate dehydrogenase, or a dehydrogenase as set forth in SEQ ID NOs: 124-139. In some embodiments, the microorganism may comprise a dehydratase such as a hydroxyvaleryl CoA dehydratase, a crotonyl alcohol dehydratase, a 3,5-hydroxyvaleryl-CoA dehydratase, or a dehydratase as set forth in SEQ ID NOs: 37-55. In some embodiments, the microorganism may comprise an isomerase such as a transposing C=C bonds isomerase, or an isomerase as set forth in SEQ ID NOs: 99-102. In some embodiments, the microorganism may comprise a decarboxylase such as a 2-pentenoic acid decarboxylase, a 4-pentenoic acid decarboxylase, a pent,2,4-dienoic acid decarboxylase, a 3-hydroxy-4-pentenoic acid decarboxylase, or a decarboxylase as set forth in SEQ ID NOs: 79-98.

Enzymes for catalyzing the conversions in FIGS. 1-3 are categorized in Table 4 by Enzyme Commission (EC) number, function, and the step in FIGS. 1-3 in which they catalyze a conversion (Table 4).

TABLE 4

EC number for employed enzymes

| EC Number | Function | FIG. (Number) and Step (Letter) |
|---|---|---|
| 1.1.1. | Oxidoreductase | 1B, 2A, 2B, 2C, 3F, 3G |
| 2.8.3. | Transferase | 1D, 1I, 3C, 3I |

TABLE 4-continued

EC number for employed enzymes

| EC Number | Function | FIG. (Number) and Step (Letter) |
|---|---|---|
| 3.1.2. | Hydrolase | 1D, 1I, 3I |
| 6.2.1 | CoA Synthetase | 3C |
| 2.3.1. | Ketothiolase | 1A, 3B, 3D, 3E |
| 1.3.1. or 1.2.99 | Dehydrogenase | 1H, 3A |
| 4.2.1. | Dehydratase | 1C, 2D, 3H |
| 5.3.3. | Isomerase | 1F |
| 4.1.1. | Decarboxylase | 1E, 1G, 1J, 3J |

Steps D and I of FIG. 1, and steps C and I in FIG. 3 can be catalyzed by transferases in EC 2.8.3 including, for example, a transferase that catalyzes the reversible transfer of a CoA moiety from one molecule to another. Any known polynucleotide coding for a CoA transferase enzyme including, for example, those polynucleotides set forth in Table 5 below, is contemplated for use by the present disclosure.

TABLE 5

Exemplary genes coding for enzymes in EC 2.8.3

| Gene | Gene ID | Organism | SEQ ID NO: |
|---|---|---|---|
| atoA | 2492994 | Escherichia coli K12 | 1 |
| atoD | 2492990 | Escherichia coli K12 | 2 |
| actA | 62391407 | Corynebacterium glutamicum ATCC 13032 | 3 |
| Cg0592 | 62289399 | Corynebacterium glutamicum ATCC 13032 | 4 |
| ctfA | 15004866 | Clostridium acetobutylicum | 5 |
| ctfB | 15004867 | Clostridium acetobutylicum | 6 |
| Ach1 | 60396828 | Roseburia sp. A2-183 | 7 |
| Pct | 7242549 | Clostridium propionicum | 8 |
| Cbei_4543 | 150019354 | Clostridium beijerinchii | 9 |
| pcaI | 50084858 | Acinetobacter sp. ADP1 | 10 |
| PcaJ | 141776 | Acinetobacter sp. ADP1 | 11 |
| pcaI | 24985644 | Pseudomonas putida | 12 |
| pcaJ | 141776 | Pseudomonas putida | 13 |
| ScoA | 16080950 | Bacillus subtilis | 14 |
| ScoB | 16080949 | Bacillus subtilis | 15 |
| Cat1 | 729048 | Clostridium kluyveri | 16 |
| Cat2 | 172046066 | Clostridium kluyveri | 17 |
| Cat3 | 146349050 | Clostridium kluyveri | 18 |
| gctA | 559392 | Acidaminococcus fermentans | 19 |
| gctB | 559393 | Acidaminococcus fermentans | 20 |
| frc | 12931869 | Escherichia coli | 21 |
| BBta_3113 | 5149017 | Bradyrhizobium sp. | 22 |
| RPA1945 | 2688995 | Rhodopseudomonas palustris | 23 |
| SDY_2572 | 3797090 | Shigella dysenteriae | 24 |
| RPB_3427 | 3911229 | Rhodopseudomonas palustris | 25 |
| frc | 8191935 | Methylobacterium extorquens | 26 |
| H16_B1711 | 4455693 | Ralstonia eutropha H16 | 27 |
| Bxe_B2760 | 4006524 | Burkholderia xenovorans | 28 |

Steps D and I of FIG. 1, and step I of FIG. 3 can be catalyzed by hydrolases in EC 3.1.2 including, for example, hydrolases with broad substrate ranges capable of hydrolyzing 2-petentenoyl-CoA, 2,4-pentenoyl-CoA, and 3-hydroxypentenoyl-CoA to their corresponding acids. Any known polynucleotide coding for a hydrolase including, for example, those polynucleotides set forth in Table 6 below, is contemplated for use by the present disclosure.

TABLE 6

Exemplary genes coding for enzymes in EC 3.1.2.

| Gene | Gene ID | Organism | SEQ ID NO: |
|---|---|---|---|
| Orf1 | 23664428 | Azoarcus evansii | 29 |
| COG0824 | 46200680 | Magnetospirillum magnetotacticum | 30 |

TABLE 6-continued

Exemplary genes coding for enzymes in EC 3.1.2.

| Gene | Gene ID | Organism | SEQ ID NO: |
|---|---|---|---|
| Jann_0674 | 89052491 | *Jannaschia* sp. CCS1 | 31 |
| SSE37_24444 | 126729407 | *Sagittula stellata* | 32 |
| entH | 1786813 | *Escherichia coli* | 33 |

Step C in FIG. 3 may be catalyzed by a CoA synthetase in EC 6.2.1., including, for example, a CoA synthetase with a broad substrate range capable of activating formic acid to formyl-CoA. Any known polynucleotide coding for a CoA synthetase including, for example, those polynucleotides set forth in Table 7 below, is contemplated for use by the present disclosure.

TABLE 7

Exemplary genes coding for enzymes in EC 6.2.1.

| Gene | Gene ID (GI) | Organism | SEQ ID NO: |
|---|---|---|---|
| acs | 8434601 | *Acetobacter pasteurianus* | 34 |
| Avin_10660 | 7760010 | *Azotobacter vinelandii* | 35 |
| acs | 8657923 | *Dehalococcoides* sp. | 36 |

The hydration of a double bond can be catalyzed by hydratase enzymes in EC 4.2.1 and the removal of water to form a double bond can be catalyzed by dehydratase enzymes in EC 4.2.1. Hydratase enzymes are sometimes reversible and may also catalyze dehydration. Likewise, dehydratase enzymes are sometimes reversible and may also catalyze hydration. The addition or removal of 7 water from a given substrate is required by step C in FIG. 1, step D in FIG. 2, and step H in FIG. 3. Any known polynucleotide coding for a hydratase or dehydratase including, for example, those polynucleotides set forth in Table 8 below, is contemplated for use by the present disclosure.

For example, the linalool dehydratase-isomerase from *Castellaniella defragrans* strain 65Phen (E.C. 4.2.1.127; SEQ ID NO: 55) catalyzes the stereospecific hydration of beta-myrcene to (3S)-linalool, the isomerization of (3S)-linalool to geraniol, and is involved in the initial steps of the anaerobic degradation of the monoterpene beta-myrcene. Additionally, this linalool dehydratase-isomerase catalyzes the reverse reactions, i.e. the isomerization of geraniol to linalool and the dehydration of linalool to myrcene. In this direction, the formation of myrcene from geraniol may be seen as a detoxification process for the monoterpene alcohol. Thus, linalool dehydratase represents a suitable candidate for step D in FIG. 2 below.

TABLE 8

Exemplary genes coding for enzymes in EC 4.2.1.

| Gene | Gene ID | Organism | SEQ ID NO: |
|---|---|---|---|
| mhpD | 87081722 | *Escherichia coli* | 37 |
| ctmF | 1263188 | *Pseudomonas putida* | 38 |
| todG | 1263188 | *Pseudomonas putida* | 39 |
| hpaH | 7150958100 | *Klebsiella pneumoniae* | 40 |
| hpaH | 8178258 | *Escherichia coli* | 41 |
| cnbE | 6386628 | *Comamonas testosteroni* | 42 |
| leuD | 2122345 | *Methanocaldococcus jannaschii* | 43 |
| dmdA | 9884634 | *Eubacterium limosum* | 44 |
| dmdB | 9884633 | *Eubacterium limosum* | 45 |

TABLE 8-continued

Exemplary genes coding for enzymes in EC 4.2.1.

| Gene | Gene ID | Organism | SEQ ID NO: |
|---|---|---|---|
| Olhyd_maccj | 7390838 | *Macrococcus caseolyticus* | 46 |
| ech | 1047000 | *Pseudomonas putida* | 47 |
| crt | 1118895 | *Clostridium acetobutylicum* | 48 |
| phaB | 1046931 | *Pseudomonas putida* | 49 |
| fadA | 12934462 | *Escherichia coli* | 50 |
| fadB | 12934454 | *Escherichia coli* | 51 |
| fadI | 12933009 | *Escherichia coli* | 52 |
| fadJ | 12931539 | *Escherichia coli* | 53 |
| fadR | 12931108 | *Escherichia coli* | 54 |
| ldi | 302064203 | *Castellaniella defragrans* | 55 |

In some embodiments, a dehydratase-isomerase including, 4-hydroxybutyryl-CoA dehydratase/vinylacetyl-CoA-Delta-isomerase may be engineered by standard methods to increase its selectivity for crotonyl-alcohol. Exemplary genes that can be engineered to increase its selectivity for crotonyl-alcohol are set forth in Table 9 below and represent a suitable candidate for step D in FIG. 2 below:

TABLE 9

Exemplary genes that can be engineered to increase its selectivity for crotonyl-alcohol.

| Gene | Gene ID | Organism | SEQ ID NO: |
|---|---|---|---|
| ldi | 302064203 | *Castellaniella defragrans* | 56 |
| abdD | 1453964 | *Sulfolobus solfataricus* | 57 |

Step A of FIG. 1, and steps C, D and E of FIG. 3 require condensation of either acetyl-CoA or acetoacetyl-CoA with formyl-CoA or propionyl-CoA. Such a condensation can be catalyzed with a ketothiolase set forth in EC 2.3.1. However, any known polynucleotide coding for a ketothiolase including, for example, those polynucleotides set forth in Table 10 below, is contemplated for use by the present disclosure.

TABLE 10

Exemplary genes coding for enzymes in EC 2.3.1.

| Gene | Gene ID | Organism | SEQ ID NO: |
|---|---|---|---|
| paaJ | 12934018 | *Escherichia coli* | 58 |
| phaD | 1046928 | *Pseudomonas putida* | 59 |
| pcaF | 10441755 | *Pseudomonas putida* | 60 |
| pcaF | 11639550 | *Acinetobacter calcoaceticus* | 61 |
| fadA | 4490319 | *Aeromonas hydrophila* | 62 |
| AtoB | 4997503 | *Aeromonas salmonicida* | 63 |
| pcaF | 4383639 | *Pseudomonas aeroginosa* | 64 |
| bktB | 428815 | *Ralstonia eutropha* | 65 |
| pimB | 2692199 | *Rhodopseudomonas palustris* | 66 |
| syn_02642 | 3882984 | *Syntrophus aciditrophicus* | 67 |
| phaA | 10921806 | *Cupriavidus necator* | 68 |
| atoB | 12934272 | *Escherichia coli* | 69 |
| thlA | 1119056 | *Clostridium acetobutylicum* | 70 |
| thlB | 1116083 | *Clostridium acetobutylicum* | 71 |
| ERG10 | 856079 | *Saccharomyces cerevisiae* | 72 |
| pflB | 12931841 | *Escherichia coli* | 73 |
| pflA | 12930359 | *Escherichia coli* | 74 |
| pfl | 15671982 | *Lactococcus lactis* | 75 |
| pfl | 3168596 | *Streptococcus equinus* | 76 |
| act | 14141682 | *Streptococcus equinus* | 77 |
| Clo1313_1716 | 12421448 | *Clostridium thermocellum* | 78 |

Steps E, G, and J in FIG. 1, and step J in FIG. 2 can be catalyzed by a decarboxylase enzyme as set forth in EC class 4.1.1 Numerous decarboxylases have been characterized and shown to decarboxylate structurally similar substrates to 2-pentenoic acid, 2,4-pentedienoic acid (FIG. 1) and 3-hydroxypentenoic acid (FIG. 3). Exemplary enzymes for step J of FIG. 1 include sorbic acid decarboxylase and aconitate decarboxylase as set forth in EC 4.1.1.16. Exemplary enzymes for steps G and E of FIG. 1 may include p450 fatty acid decarboxylase from *Jeotgalicoccus*. Exemplary enzymes for step J of FIG. 3 may include those enzymes as set forth in EC 4.1.1.33 such as diphosphomevalonate decarboxylase. However, any known polynucleotide coding for a decarboxylase including, for example, those polynucleotides set forth in Table 11 below, is contemplated for use by the present disclosure.

TABLE 11

Exemplary genes coding for enzymes in EC 4.1.1.

| Gene | Gene ID | Organism | SEQ ID NO: |
|---|---|---|---|
| OleT$_{JE}$ | 320526717 XXX | *Jeotgalicoccus* sp; ATCC8456 | 79 |
| PadA1 | 145235767 | *Aspergillus niger* | 80 |
| ohbA1 | 145235771 | *Aspergillus niger* | 81 |
| sdrA | 145235769 | *Aspergillus niger* | 82 |
| padA1 | 169786362 | *Aspergillis oryzae* | 83 |
| ohbA1 | 169768360 | *Aspergillis oryzae* | 84 |
| sdrA | 169768362 | *Aspergillis oryzae* | 85 |
| Mvd | 2845318 | *Picrophilus torridus* | 86 |
| mvd | 2845209 | *Picrophilus torridus* | 87 |
| mvd | 855779 | *Saccharomyces cerevisiae* | 88 |
| mvd | 162312575 | *Schizosaccharomyces pombe* | 89 |
| mvd | 257051090 | *Halorhabdus utahensis* | 90 |
| mvd | 8741675 | *Haloterrigena turkmenica* | 91 |
| mvd | 9132821 | *Leuconostoc kimchii* | 92 |
| dvd | 1447408 | *Halobacterium salinarum* | 93 |
| dfd | 121708954 | *Aspergillus clavatus* | 94 |
|  | 4593483 | *Neosartorya fischeri* | 95 |
| mvaD | 11027973 | *Streptococcus pseudopneumoniae* | 96 |
| mvaD | 8433456 | *Lactobacillus rhamnosus* | 97 |
| mvaD | 12158799 | *Borrelia afzelii* | 98 |

Step F of FIG. 1 involves an isomerase enzyme as set forth in EC 5.3.3. Exemplary enzymes for the step include the isopentenyl-diphosphate delta-isomerase. However, any known polynucleotide coding for an isomerase including, for example, those polynucleotides set forth in Table 12 below, is contemplated for use by the present disclosure.

TABLE 12

Exemplary genes coding for enzymes in EC 5.3.3.

| Gene | Gene ID | Organism | SEQ ID NO: |
|---|---|---|---|
| Idi | 12930440 | *Escherichia coli* | 99 |
| Idi1 | 855986 | *Saccharomyces cerevisiae* | 100 |
| fni | 1028286 | *Streptococcus mutans* | 101 |
| fni | 938985 | *Bacillus subtilis* | 102 |

Step B of FIG. 1, steps A, B and C of FIG. 2, and steps F and G of FIG. 3 involve the reduction of a ketone to an alcohol and can be catalyzed by oxidoreductase enzymes in EC class 1.1.1. However, any known polynucleotide coding for an oxidoreductase including, for example, those polynucleotides set forth in Table 13 below, is contemplated for use by the present disclosure.

TABLE 13

Exemplary genes coding for enzymes in EC 1.1.1.

| Gene | Gene ID | Organism | SEQ ID NO: |
|---|---|---|---|
| mdh | 6059112 | *Escherichia coli* | 103 |
| idhA | 5591397 | *Escherichia coli* | 104 |
| idh | 113866693 | *Ralstonia eutropha* | 105 |
| adh | 60592974 | *Clostridium beijerinckii* | 106 |
| Adh | 113443 | *Thermoanaerobacter brockii* | 107 |
| Sadh | 21615552 | *Rhodococcus ruber* | 108 |
| adhA | 3288810 | *Pyrococcus furiosus* | 109 |
| adhE | 12930611 | *Escherichia coli* | 110 |
| adhE2 | 12958626 | *Clostridium acetobutylicum* | 111 |
| adhE | 55818563 | *Leuconostoc mesenteroides* | 112 |
| HMG1 | 854900 | *Saccharomyces cerevisiae* | 113 |
| CtCNB1_3119 | 8560791 | *Comamonas testosteroni* | 114 |
| DKAM_0720 | 7170894 | *Desulfurococcus kamchatkensis* | 115 |
| mvaA | 1004602 | *Staphylococcus aureus* | 116 |
| LJ1608 | 2742117 | *Lactobacillus johnsonii* | 117 |
| acrI | 2879608 | *Acinetobacter* sp. ADP1 | 118 |
| acrI | 1684885 | *Acinetobacter baylyi* | 119 |
| sucD | 5394466 | *Clostridium kluyveri* | 120 |
| sucD | 2551522 | *Porphyromonas gingivalis* | 121 |
| bld | 31075383 | *Clostridium saccharoperbutylacetonicum* | 122 |
| Cbei_3832 | 5294993 | *Clostridium beijerinckii* | 123 |

Step I of FIG. 1, and step A of FIG. 3 involve a dehydrogenase as set forth in EC 1.3.1 or 1.2.99. However, any known polynucleotide coding for a dehydrogenase including, for example, those polynucleotides set forth in Table 14 below, is contemplated for use by the present disclosure.

TABLE 14

Exemplary genes coding for enzymes in EC 1.3.1 or 1.2.99.

| Gene | Gene ID | Organism | SEQ ID NO: |
|---|---|---|---|
| Msed_1426 | 5104797 | *Metallosphaera sedula* | 124 |
| ST0480 | 1458422 | *Sulfolobus tokodaii* | 125 |
| Mcup_0809 | 10493000 | *Metallosphaera cuprina* | 126 |
| RBRH_02090 | 9986550 | *Streptomyces clavuligerus* | 127 |
| RSP_1434 | 3718801 | *Rhodobacter sphaeroides* | 128 |
| acrA | JN244654.1 | *Clostridium propionicum* | 129 |
| acrB | JN244655 | *Clostridium propionicum* | 130 |
| Fdh1 | 2276464 | *Candida boidinii* | 131 |
| Fdh1 | 854570 | *Saccharomyces cerevisiae* | 132 |
| Fdh2 | 1370568 | *Saccharomyces cerevisiae* | 133 |
| fdsC | 4248880 | *Cupriavidus necator* | 134 |
| fdsA | 4248878 | *Cupriavidus necator* | 135 |
| fdsB | 4248879 | *Cupriavidus necator* | 136 |
| fdsD | 4248881 | *Cupriavidus necator* | 137 |
| fdsG | 4248882 | *Cupriavidus necator* | 138 |
| fdsR | 4248883 | *Cupriavidus necator* | 139 |

Methods for the Production of Butadiene

Butadiene (e.g., fermentation product) may be produced by contacting one or more genetically modified microorganisms provided herein with a fermentable carbon source. Such methods may preferably comprise contacting a fermentable carbon source with a microorganism comprising one or more polynucleotides coding for enzymes in a pathway that catalyzes a conversion of the fermentable carbon source to any of the intermediates provided in Tables 1-3 or FIGS. 1-3 and one or more polynucleotides coding for enzymes in a pathway that catalyze a conversion of the one or more intermediates provided in Tables 1-3 or FIGS. 1-3 to butadiene in a fermentation media including, under sufficient conditions and for a suitable period of time; and expressing the one or more polynucleotides coding for the enzymes in the pathway that catalyzes a conversion of the fermentable carbon source to the one or more intermediates provided in Tables 1-3 or FIGS. 1-3 and one or more polynucleotides coding for enzymes in a pathway that catalyze a conversion of the one or more intermediates provided in Tables 1-3 or FIGS. 1-3 to butadiene in the microorganism to produce butadiene. In some embodiments, the conversion of the fermentable carbon source to butadiene is ATP positive (e.g., generates a net of ATP per mol of butadiene produced; produces ATP as a byproduct) and when combined with a NADH consuming pathway it can provide an anaerobic process for butadiene production. For example, the conversion of a fermentable carbon source such as glucose or fructose to butadiene may produce a net of 1 mol of ATP per mol of butadiene produced.

Exemplary fermentable carbon sources may include, but are not limited to, sugarcane juice, sugarcane molasses, hydrolyzed starch, hydrolyzed lignocellulosic materials, glucose, sucrose, fructose, lactate, lactose, xylose, pyruvate, or glycerol in any form or mixture thereof. In some embodiments, the carbon source is a monosaccharide, oligosaccharide, or polysaccharide.

Metabolic pathways that lead to the production of industrially important compounds such as butadiene involve oxidation-reduction (redox) reactions. For example, during fermentation, glucose is oxidized in a series of enzymatic reactions into smaller molecules with the concomitant release of energy. The electrons released are transferred from one reaction to another through universal electron carriers, such Nicotinamide Adenine Dinucleotide (NAD) and Nicotinamide Adenine Dinucleotide Phosphate (NAD (P)), which act as cofactors for oxidoreductase enzymes. In microbial catabolism, glucose is oxidized by enzymes using the oxidized form of the cofactors (NAD(P)+ and/or NAD+) as cofactor thus generating reducing equivalents in the form of the reduced cofactor (NAD(P)H and NADH). In order for fermentation to continue, redox-balanced metabolism is required, i.e., the cofactors must be regenerated by the reduction of microbial cell metabolic compounds. In some embodiment, the novel pathways disclosed herein are advantageous in that they provide for the conversion of a fermentable carbon source to butadiene through a pathway that redistributes the end products to achieve a redox balance.

Some key parameters for efficient fermentation of a fermentable carbon source by one or more modified microorganisms as disclosed herein include: the ability to grow microorganisms to a greater cell density, increased yield of desired products, increased amount of volumetric productivity, removal of unwanted co-metabolites, improved utilization of inexpensive carbon and nitrogen sources, adaptation to varying fermenter conditions, increased production of a primary metabolite, increased production of a secondary metabolite, increased tolerance to acidic conditions, increased tolerance to basic conditions, increased tolerance to organic solvents, increased tolerance to high salt conditions and increased tolerance to high or low temperatures. Inefficiencies in any of these parameters can result in high manufacturing costs, inability to capture or maintain market share, and/or failure to bring fermented end-products to market.

The methods of the present disclosure can be adapted to conventional fermentation bioreactors (e.g., batch, fed-batch, cell recycle, and continuous fermentation). In some embodiments, a microorganism (e.g., a genetically modified microorganism) as provided herein is cultivated in liquid fermentation media (i.e., a submerged culture) which leads to excretion of the fermented product(s) into the fermentation media. Fermentation may occur in a bioreactor configured as a stirred tank, a bubble column, an airlift reactor or any other suitable configuration known in the art. In one embodiment, the fermented end product(s) can be isolated from the fermentation media using any suitable method known in the art.

In some embodiments, formation of the fermented product may occur during an initial, fast growth period of the microorganism. In one embodiment, formation of the fermented product may occur during a second period in which the culture is maintained in a slow-growing or non-growing state. In one embodiment, formation of the fermented product may occur during more than one growth period of the microorganism. In such embodiments, the amount of fermented product formed per unit of time is generally a function of the metabolic activity of the microorganism, the physiological culture conditions (e.g., pH, temperature, medium composition), and the amount of microorganisms present in the fermentation process.

In some embodiments, the fermentation product is recovered from the periplasm or culture medium as a secreted metabolite. In one embodiment, the fermentation product is extracted from the microorganism, for example when the microorganism lacks a secretory signal corresponding to the fermentation product. In one embodiment, the microorganisms are ruptured and the culture medium or lysate is centrifuged to remove particulate cell debris. The membrane and soluble protein fractions may then be separated if necessary. The fermentation product of interest may then be purified from the remaining supernatant solution or suspension by, for example, distillation, fractionation, chromatography, precipitation, filtration, and the like. In one embodiment, fermentation products are extracted by one or more of: distillation, reactive distillation, azeotropic distillation and extractive distillation.

The methods of the present disclosure are preferably preformed under anaerobic conditions. Both the degree of reduction of a product as well as the ATP requirement of its synthesis determines whether a production process is able to proceed aerobically or anaerobically. To produce butadiene via anaerobic microbial conversion, or at least by using a process with reduced oxygen consumption, redox imbalances should be avoided. Several types of metabolic conversion steps involve redox reactions including some of the conversions as set forth in Table 1-3 or FIGS. 1-3. Such redox reactions involve electron transfer mediated by the participation of redox cofactors such as NADH, NADPH and ferredoxin. Since the amounts of redox cofactors in the cell are limited to permit the continuation of metabolic processes, the cofactors have to be regenerated. In order to avoid such redox imbalances, alternative ways of cofactor regeneration may be engineered, and in some cases additional sources of ATP generation may be provided. Alternatively, oxidation and reduction processes may be separated spatially in bioelectrochemical systems (Rabaey and. Rozendal, 2010, Nature reviews, Microbiology, vol 8: 706-716).

In some embodiment, redox imbalances may be avoided by using substrates (e.g., fermentable carbon sources) that are more oxidized or more reduced. for example, if the utilization of a substrate results in a deficit or surplus of electrons, a requirement for oxygen can be circumvented by using substrates that are more reduced or oxidized, respectively. For example, glycerol which is a major byproduct of biodiesel production is more reduced than sugars, and is therefore more suitable for the synthesis of compounds whose production from sugar results in cofactor oxidation, such as succinic acid. In some embodiments, if the conversion of a substrate to a product results in an electron deficit, co-substrates can be added that function as electron donors (Babel 2009, Eng. Life Sci. 9, 285-290). An important criterion for the anaerobic use of co-substrates is that their redox potential is higher than that of NADH (Geertman et al., 2006, FEMS Yeast Res. 6, 1193-1203). If the conversion of substrate to produce results in an electron surplus, co-substrates can be added that function as electron acceptors.

Methods for the Production of Polybutadiene and Other Compounds from Butadiene

Butadiene is gaseous at room temperature or in fermentative conditions (20-45° C.), and their production from a fermentation process results in a gas that could accumulate in the headspace of a fermentation tank, and be siphoned and concentrated. Butadiene may be purified from fermentation of gases, including gaseous alcohol, CO2 and other compound by solvent extraction, cryogenic processes, distillation, fractionation, chromatography, precipitation, filtration, and the like.

Butadiene produced via any of the processes or methods disclosed herein may be converted to polybutadiene. Alternatively, butadiene produced via methods disclosed herein may be polymerized with other olefins to form copolymers such as acrylonitrile-butadiene-styrene (ABS), acrylonitrile-butadiene (ABR), or styrene-butadiene (SBR) copolymers, BR butyl rubber (RB), poly butadiene rubber (PBR), nitrile rubber and polychloroprene (Neoprene). Those synthetic rubbers or plastic elastomers applications include productions of tires, plastic materials, sole, shoe hills, technical goods, home appliance, neoprene, paper coatings, gloves, gaskets and seals.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1: Modification of Microorganism for Production of Butadiene

A microorganism such as a bacterium may be genetically modified to produce butadiene from a fermentable carbon source including, for example, glucose.

In an exemplary method, a microorganism may be genetically engineered by any methods known in the art to comprise: i.) one or more polynucleotides coding for enzymes in a pathway that catalyze a conversion of the fermentable carbon source to acetyl-CoA and propionyl-CoA, and/or one or more polynucleotides coding for enzymes in a pathway that catalyze a conversion of acetyl-CoA and propionyl-CoA to butadiene; ii.) one or more polynucleotides coding for enzymes in a pathway that catalyze a conversion of the fermentable carbon source to crotonyl-CoA, and/or one or more polynucleotides coding for enzymes in a pathway that catalyze a conversion of crotonyl-CoA to butadiene; or iii.) one or more polynucleotides coding for enzymes in a pathway that catalyze a conversion of the fermentable carbon source to formic acid, and/or one or more polynucleotides coding for enzymes in a pathway that catalyze a conversion of formic acid to butadiene.

Alternatively, a microorganism that lacks one or more enzymes (e.g., one or more functional enzymes that are catalytically active) for the conversion of a fermentable carbon source to butadiene may be genetically modified to comprise one or more polynucleotides coding for enzymes (e.g., functional enzymes including, for example any enzyme disclosed herein) in a pathway that the microorganism lacks to catalyze a conversion of the fermentable carbon source to butadiene.

Example 2: Fermentation of a Carbon Source by a Genetically Modified Microorganism to Produce Butadiene A genetically modified microorganism, as produced in Example 1 above, may be used to ferment a carbon source, to produce butadiene.

In an exemplary method, a previously-sterilized culture medium comprising a fermentable carbon source (e.g., 9 g/L glucose, 1 g/L KH2PO4, 2 g/L (NH4)2HPO4, 5 mg/L FeSO4.7H2O, 10 mg/L MgSO4.7H2O, 2.5 mg/L MnSO4.120, 10 mg/L CaCl2.6H2O, 10 mg/L CoCl2.6H2O, and 10 g/L yeast extract) is charged in a bioreactor.

During fermentation, anaerobic conditions are maintained by, for example, sparging nitrogen through the culture medium. A suitable temperature for fermentation (e.g., about 30° C.) is maintained using any method known h the art. A near physiological pH (e.g., about 6.5) is maintained by, for example, automatic addition of sodium hydroxide. The bioreactor is agitated at, for example, about 50 rpm. Fermentation is allowed to run to completion.

The produced butadiene is then recovered from the culture medium using conventional methods. When the fermentation products are recovered by distillation, the butadiene fraction may be optionally polymerized to form polybutadiene. Distillation fractions containing other intermediates along the butadiene pathway (if any) may be subjected to a subsequent fermentation in a bioreactor to produce additional butadiene.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A genetically modified microorganism comprising a polynucleotide encoding an enzyme that catalyzes a conversion of crotonyl alcohol to butadiene, wherein the enzyme has an amino acid sequence at least 70% identical to the enzymes encoded by SEQ ID NOs: 37, 41, 43, 44, 46, 47, 48, 50, 51 and 55, and has a dehydratase activity; and wherein the microorganism further comprises a polynucleotide encoding a crotonaldehyde dehydrogenase and a polynucleotide encoding a crotonyl alcohol dehydrogenase.

2. The genetically modified microorganism of claim 1, wherein the enzyme has an amino acid sequence at least 80% identical to the enzymes encoded by SEQ ID NOs: 37, 41, 43, 44, 46, 47, 48, 50, 51 and 55.

3. The genetically modified microorganism of claim 1, wherein the enzyme has an amino acid sequence at least 95% identical to the enzymes encoded by SEQ ID NOs: 37, 41, 43, 44, 46, 47, 48, 50, 51 and 55.

4. The genetically modified microorganism of claim 1, wherein the enzyme accepts crotonyl alcohol as a substrate.

5. The genetically modified microorganism of claim 1, wherein the enzyme has isomerase activity.

6. The genetically modified microorganism of claim 1, wherein the enzyme has dehydratase and isomerase activity.

7. A genetically modified microorganism comprising a polynucleotide encoding an enzyme that catalyzes a conversion of crotonyl alcohol to butadiene, wherein the enzyme has an amino acid sequence at least 70% identical to a linalool dehydratase encoded by SEQ ID NOs: 37, 41, 43, 44, 46, 47, 48, 50, 51 and 55, and has a dehydratase activity; and wherein the microorganism further comprises a polynucleotide encoding a crotonaldehyde dehydrogenase and a polynucleotide encoding a crotonyl alcohol dehydrogenase.

8. The genetically modified microorganism of claim 7, wherein the enzyme has an amino acid sequence at least 80% identical to the enzymes encoded by SEQ ID NOs: 37, 41, 43, 44, 46, 47, 48, 50, 51 and 55.

9. The genetically modified microorganism of claim 7, wherein the enzyme has an amino acid sequence at least 95% identical to the enzymes encoded by SEQ ID NOs: 37, 41, 43, 44, 46, 47, 48, 50, 51 and 55.

10. The genetically modified microorganism of claim 7, wherein the enzyme accepts crotonyl alcohol as a substrate.

11. The genetically modified microorganism of claim 7, wherein the enzyme has isomerase activity.

12. The genetically modified microorganism of claim 7, wherein the enzyme has dehydratase and isomerase activity.

13. The genetically modified microorganism of claim 1, wherein the enzyme has an amino acid sequence at least 70% identical to the enzyme encoded by SEQ ID NO: 55.

14. The genetically modified microorganism of claim 1, wherein the enzyme has an amino acid sequence at least 95% identical to the enzyme encoded by SEQ ID NO: 55.

* * * * *